(12) United States Patent
Sinisi et al.

(10) Patent No.: US 10,633,542 B2
(45) Date of Patent: Apr. 28, 2020

(54) AZACYANINE DYES AND USE THEREOF

(71) Applicant: Ecole Polytechnique Fédérale de Lausanne (EPFL), Lausanne (CH)

(72) Inventors: Riccardo Sinisi, Lausanne (CH); Alma Rosa Morales Morales, Lausanne (CH); Elena A. Goun, Lausanne (CH); Rajendra Singh, Lausanne (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 0 days.

(21) Appl. No.: 15/928,074

(22) Filed: Mar. 21, 2018

(65) Prior Publication Data

US 2019/0292371 A1   Sep. 26, 2019

(51) Int. Cl.
*C09B 23/01* (2006.01)
*A61K 41/00* (2020.01)
*A61K 49/00* (2006.01)

(52) U.S. Cl.
CPC ...... *C09B 23/0075* (2013.01); *A61K 41/0057* (2013.01); *A61K 49/0032* (2013.01); *A61K 2123/00* (2013.01)

(58) Field of Classification Search
None
See application file for complete search history.

(56) References Cited

U.S. PATENT DOCUMENTS

| 5,217,846 A | 6/1993 | Smothers |
| 2003/0113755 A1 | 6/2003 | Nishigaki et al. |
| 2018/0079906 A1 | 3/2018 | Sinisi et al. |

OTHER PUBLICATIONS

International Search Report from International Patent Application No. PCT/IB2018/000390, 4 pages, dated Dec. 11, 2018.

*Primary Examiner* — James W Rogers
(74) *Attorney, Agent, or Firm* — McDermott Will & Emery LLP; Judy M. Mohr; Wen Li

(57) ABSTRACT

The application provides fluorescent dyes, which are cyanine dyes that incorporate additional aza moieties in the indolenium heterocycles and/or in the methine chains connecting them. Symmetrical and unsymmetrical chemically reactive azacyanine dyes are described for conjugation, as well as their bioconjugates for in-vitro and in-vivo assays and fluorescence imaging.

3 Claims, 22 Drawing Sheets

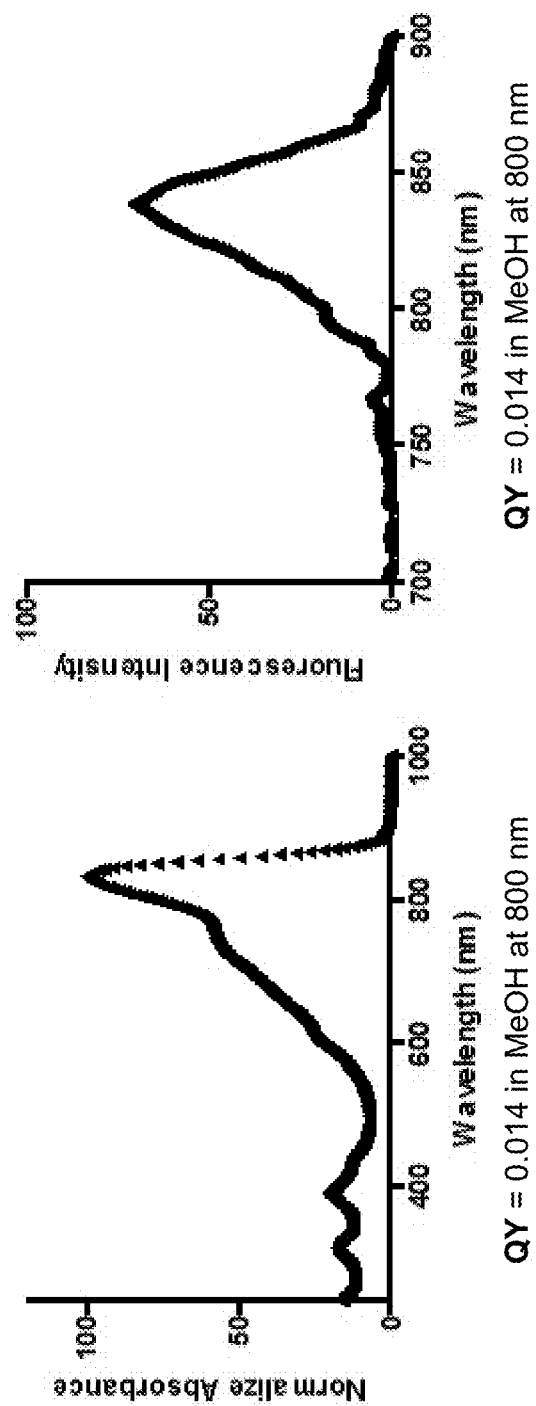

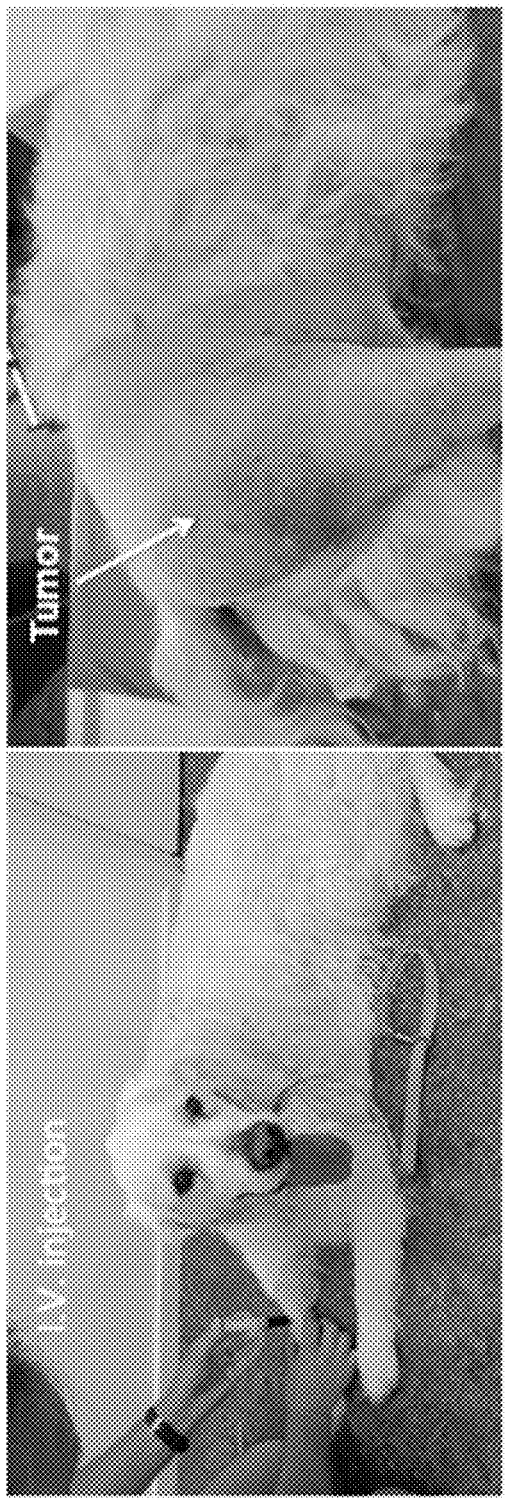

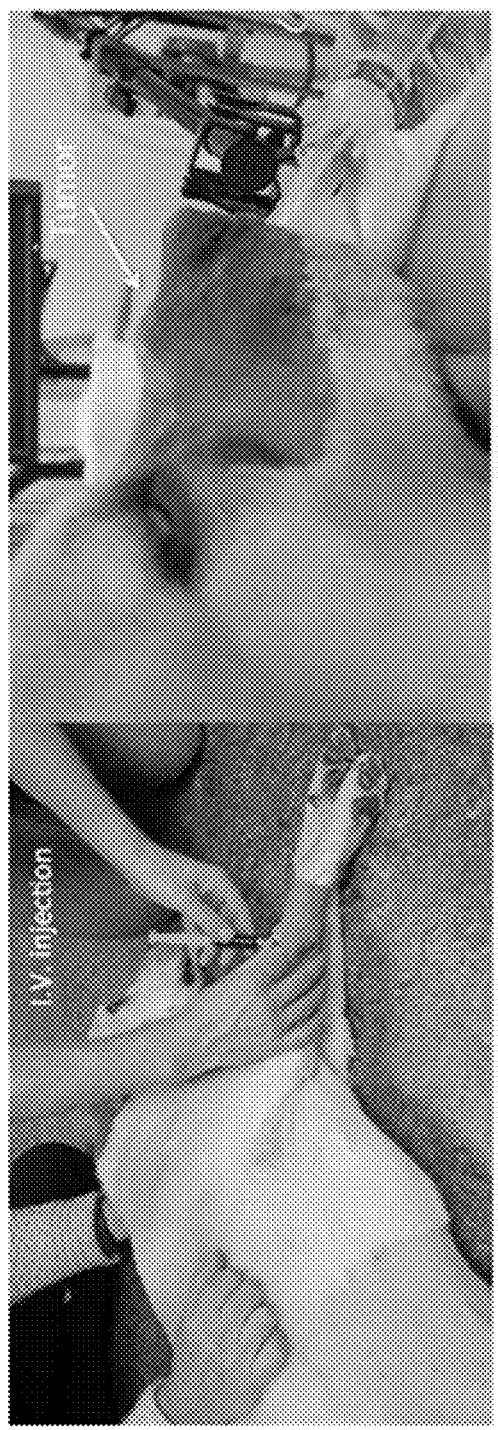

Signal (right thigh)/control (left thigh) ratio

AZACYANINE DYES AND USE THEREOF

TECHNICAL FIELD

This application relates to fluorescent dyes, which are cyanine dyes that incorporate additional aza moieties in the indolenium heterocycles and/or in the methine chains connecting them. Symmetrical and unsymmetrical chemically reactive azacyanine dyes are described for conjugation, as well as their bioconjugates for in-vitro and in-vivo assays and fluorescence imaging.

BACKGROUND

Fluorescent dyes form the building blocks of many reagents that are used in a myriad of bioanalytical applications such as nucleic acid detection and sequencing, flow cytometry for cellular characterization, fluorescence microscopy, enzymatic assays and increasingly in the field of optical imaging as probes to detect disease tissue and organ in vivo. There are a large number of fluorescent dyes available for use in microscopy, immunohistology, and other high technology research. These dyes have extended conjugated carbon chains embedded in their chemical structures. The molecules are able to absorb light energy and emit light of a different colour. The emission wavelengths of organic dyes are usually fine-tuned to emit light of longer wavelength by incorporation of an electron sink within the molecule that allows for delocalization of $\pi$ electrons along the unsaturated chain. Even though NIR dyes have been developed for many years for use in high technology fields, just a handful of them have found use for in vivo applications.

Optical imaging, in particular fluorescence offers several advantages that make it a powerful molecular imaging approach, both in the research and clinical settings. Specifically, optical imaging, besides being fast, safe, cost effective and highly sensitive, can be tailored for diagnostic as well as therapeutic outcomes. The organic dyes typically used as imaging reporters are amenable to design modifications through various linker chemistries to incorporate one or more targeting motifs. Fluorescence imaging is translational from the preclinical stage in small animals to human subjects as the same agent can be used without modifying the biological target. While bioluminescence has the sensitivity it is not translatable from preclinical small animal imaging to humans. Also the luciferin/luciferase based system cannot be multiplexed to interrogate multi mode based mechanism of binding to cell surface or of receptors in tumours for example in oncology applications. Fluorescence based methods are thus a natural choice to bridge the translation of imaging reagents used concurrently with the established PET, SPECT MRI and X-ray methods as the optical reporter dyes are amenable via multiple linker chemistry to carry similar or different recognition motifs. Molecular imaging involves the use of a "molecular" probe or agent that selectively targets a particular cellular receptor, nucleic acid sequences of a gene, amino acid sequences and post translational motifs within a protein, epigenetic modifications, cellular function and pathways, with the absence, presence or level of the specific target being indicative of a particular disease state.

The development of NIR fluorescent dyes has played a critical role in the optical imaging field, allowing it to become an increasingly important contributor to imaging science. In contrast to the classical application of fluorescent dyes in other technologies; the design of fluorescent dyes for in vivo applications needs to incorporate several important criteria including (1) water solubility, (2) structural and chemical stability, (3) NIR fluorescence, (4) high quantum yield and last but, not least (5) a functional group for bioconjugation.

Among the fluorescent dyes available for optical imaging the cyanine family of dyes have been the preferred class as they provide the wavelength range for in vivo fluorescence excitation and emission not compromised by the optical properties of the tissue of interest. Hemoglobin has a strong absorption at wavelengths lower than 600 nm and significant background fluorescence from endogenous biomolecules can be detected up to 650 nm. The heptamethine cyanine dyes, which absorb and emit beyond 750 nm, are classified as near infrared (NIR) dyes and are preferred labels for in vivo imaging as near infrared light can overcome the biological optical interference limitations by penetrating more deeply into tissue, because light scattering decreases with increasing wavelength.

Cyanine dyes are characterized as possessing two heterocyclic moieties, acting as both electron donors and acceptors, and are joined by a single or odd of number of methine groups in which (n+1) 2 electrons are distributed over n atoms producing a delocalized cation across the methine chain. This unique characteristic gives cyanine dyes a wider range of absorption than any other known class of dyes. A great number of synthetic cyanines are known to absorb between the visible and infrared regions of the electromagnetic spectrum. In addition, cyanines exhibit narrow absorption bands and high extinction coefficients. Due to these properties, cyanine dyes have been extensively employed in various applications such as photographic processes, laser printing, nonlinear optical materials, and more recently fluorescent probes for biomolecular labelling. For example, U.S. Pat. No. 5,571,388 discloses exemplary methods of identifying strands of DNA by means of cyanine dyes. More recently, they have been used for optical imaging of dye-labelled biomolecules, either in vivo or in vitro (U.S. Pat. No. 7,597,878, others). Cyanine dyes are the preferred labels in biological applications because, among other reasons, many of these dyes fluoresce in the near-infrared (NIR) region of the spectrum (600-1000 nm).

Development of polymethine cyanine dyes that absorb longer wavelengths for in vivo imaging applications, have focused on polyenes since each double bond enhancement in this region increases the bathochromic shift by ~100 nm. This feature shows the advantage of cyanines compared to other dyes where tuning is contingent upon the expansion of the aromatic rings. Several lines of research have demonstrated that addition of an aromatic 6-membered ring would shift the absorbance by approximately 20 nm. The major drawback to this approach is the increased hydrophobicity of the resulting compound.

Advantages of cyanine dyes include, for example: 1) strong absorption cross sections and ability to fluoresce after excitation; 2) they do not rapidly bleach under a fluorescence microscope or plate reader excitation sources; 3) the derivatives are amenable as effective coupling reagents without loss of photochemical properties; 4) many structures and synthetic procedures have been developed over the last sixty years, and the class of dyes are versatile reagents; 5) cyanine dyes are relatively small (a typical molecular weight is about 1,000 daltons), so they do not cause appreciable steric interference in a way that might reduce the ability of a labelled biomolecule to reach its binding site or carry out its function and 6) when appropriately derivatized are not pH sensitive.

However, many of the known cyanine dyes have a number of disadvantages, such as chemical instability in the presence of certain reagents that are commonly found in bioassays. Such reagents include ammonium hydroxide, dithiothreitol (DTT), primary and secondary amines, and ammonium persulfate (APS). Further, some cyanine dyes lack the thermal stability and photostability that is necessary for biological applications such as DNA sequencing and genotyping. Besides photostability, which arises due to the cis trans summarization or disruption of the extended conjugation, aqueous solubility and charge modification are sometimes needed to derive superior biomedical applications.

For these reasons, there is still a need for stable cyanine dyes for use in labelling biomolecules as well as in vivo imaging for the diagnosis and prognosis of diseases such as cancer, infectious disease imaging and metabolic activity. Such compositions and methods would aid in the analysis of responses to various therapies.

U.S. Pat. No. 5,217,846 photopolymerizable compositions containing initiator systems that absorb in the longer wavelength region of the visible spectrum. The photopolymerizable composition comprises at least one ethylenically unsaturated monomer capable of free radical initiated addition polymerization and an initiator system activatable by actinic radiation, wherein said initiator system comprises a hexaarylbisimidazole, a coinitiator, and a sensitizer.

TOLMACHEV et al report in a "KHIMIYA GETEROTSIKLICHESKIKH SOEDINENII"—"CHEMISTRY OF HETEROCYCLIC COMPOUNDS", LATVIJSKIJ INSTITUT ORGANICESKOGO SINTEZA, RIGA, LV, the syntheses of derivatives of glutaconaldehydedianil hydrochloride of general formula I, where α,α'-carbon atoms are included to dihydropyran, dihydrothiopyran, and N-methyltetrahydropyridine cycle.

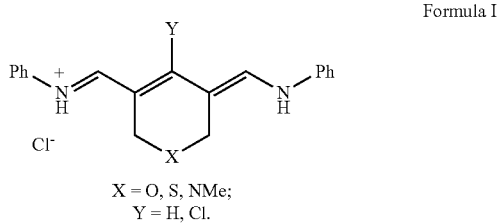

Formula I

X = O, S, NMe;
Y = H, Cl.

It was shown that synthesized dianils give the corresponding cyanine dyes on heating with 2-methyl-3-ethylbenzothiazolium or 2-methyl-3-ethylnaphtothiazolium tozylates under basic conditions (sodium acetate or triethylamine in dry ethanol) of the general formula below:

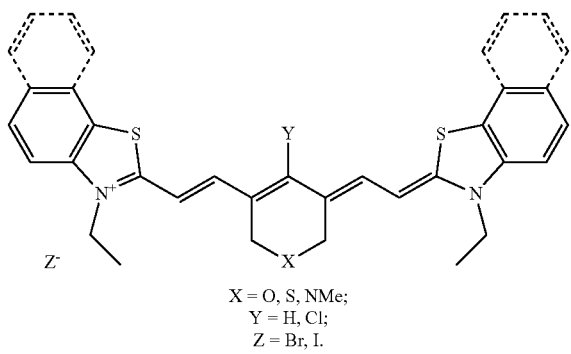

X = O, S, NMe;
Y = H, Cl;
Z = Br, I.

SUMMARY

In one aspect, the present application provides a fluorescent dye of formula A

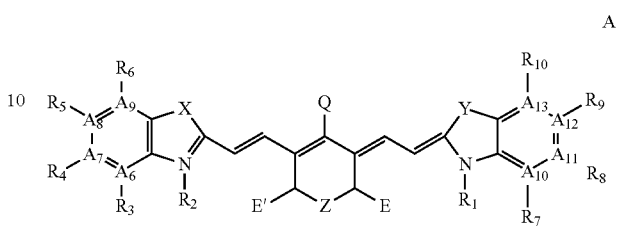

A or a salt thereof, wherein
Z is selected from the group consisting of $NR^{17}$ and $^+NR^{17}R^{18}$;
Q is independently H or selected from the groups a), b) and c) consisting of:
a) Halide selected from Cl, Br, I; $R^{19}U$, $-OR^{19}U$, $-SR^{19}U$ and $-NR^{19}R^{20}U$, wherein $R^{19}$ is a single bond; or wherein $R^{19}$ and $R^{20}$ each independently may be an optical properties modifying group, and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$ aromatic ring which can be substituted by a linear or branched $C_1$-$C_6$ alkyl group; and homocyclic and heterocyclic 5-, 6- and 7-membered aromatic rings which can be substituted by a linear or branched $C_1$-$C_6$ alkyl group, wherein preferably one of $R^{19}$ and $R^{20}$ is not aromatic in case of $-NR^{19}R^{20}U$; $-(CH_2-O-CH_2)_xCH_2-$ wherein x is an integer from 1 to 50; and U is a physiochemistry modifying group selected from the group consisting of: $-(CH_2)_mSO_3^-$, $-(CH_2)_mC(O)O^-$, $-(CH_2)_mP(O)O_2^{2-}$, $-(CH_2)_mNH_2$; $-(CH_2)_mNHR^{32}$; $-(CH_2)_mNR^{32}R^{33}$ wherein m is an integer from 0 to 6, and wherein $R^{32}$ and $R^{33}$ are independently of each other an alkyl group having from 1-12, preferably 1-8, more preferably 1-4 C atoms, in particular methyl or ethyl; and wherein in case of $-(CH_2)_mNH_2$; $-(CH_2)_mNHR^{32}$; $-(CH_2)_mNR^{32}R^{33}$ the N atom may be bond to a further substituent $R^3$ to form a quaternary N atom, and wherein $R^3$ is in all the above cases independently selected from H, and an alkyl group having from 1-12, preferably 1-8, more preferably 1-4 C atoms, in particular methyl or ethyl,
b) $R^{21}L$, $-OR^{21}L$, $-SR^{21}L$ and $-NR^{21}R^{22}L$ wherein $R^{21}$ and $R^{22}$ each independently may be are an optical properties modifying group and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic rings which can be substituted by a linear or branched $C_1$-$C_6$ alkyl group, wherein preferably one of $R^{21}$ and $R^{22}$ is not aromatic in case of $-NR^{21}R^{22}$; $-(CH_2-O-CH_2)_xCH_2-L$ wherein x is an integer from 1 to 50; and L is a linker which can form a covalent bond with a targeting agent;

c) $R^{19}$, $-OR^{19}$, $-SR^{19}$ and $-NR^{19}R^{20}$ wherein $R^{19}$ and $R^{20}$ each independently may be an optical properties modifying group and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic ring which can be substituted by a linear or branched $C_1$-$C_6$ alkyl group; and homocyclic and heterocyclic 5-, 6- and 7-membered aromatic rings which can be substituted by a linear of branched $C_1$-$C_6$ alkyl group, wherein preferably one of $R^{19}$ and $R^{20}$ is not aromatic in the case of $-NR^{19}R^{20}$; $-(CH_2-O-CH_2)_xCH_2-$ wherein x is an integer from 1 to 50; or wherein $R^{19}$ and $R^{20}$, together with the N atom to which they are attached, form a 5- or 6-membered heterocycle optionally containing one further heteroatom selected from O and N, wherein the heterocycle can be substituted by a linear or branched, cyclic or non cyclic $C_1$-$C_6$ alkyl group, in particular 4-cyclohexylpiperazinyl;

$R^1$ and $R^2$ are absent, H or independently selected from the group consisting of:
a) linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- and 7-membered aromatic rings which can be substituted by a linear of branched $C_1$-$C_6$ alkyl group; and $-(CH_2-O-CH_2)_xCH_2-$ wherein x is an integer from 1 to 50,
b) $R^2L$ wherein $R^{23}$ is selected from the group: linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$-aryl group which can be substituted by a linear or branched $C_1$-$C_6$ alkyl group; homocyclic and heterocyclic 5-, 6- and 7-membered aromatic rings which can be substituted by a linear or branched $C_1$-$C_6$ alkyl group; $-(CH_2-O-CH_2)_xCH_2-$ wherein x is an integer from 1 to 50; and L is a linker which can form a covalent bond with a targeting agent,
c) $R^{23}U$, wherein $R^{23}$ is a single bond; or wherein $R^{23}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic rings which can be substituted by a linear or branched $C_1$-$C_6$ alkyl group; $-(CH_2-O-CH_2)_xCH_2-$ wherein x is an integer from 1 to 50; and U is a physiochemistry modifying group selected from the group consisting of: $-(CH_2)_mSO_3^-$, $-(CH_2)_mC(O)O^-$, $-(CH_2)_mP(O)O_2^{2-}$ $-(CH_2)_mNR_2-$ $(CH_2)_mNH_2$; $-(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl. wherein m is an integer from 0 to 6;

$R^{17}$ and $R^{18}$ are independently H or selected from the group consisting of:
a) linear and branched, non-cyclic or cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- and 7-membered aromatic rings which can be substituted by a linear or branched $C_1$-$C_6$ alkyl group, wherein preferably one of $R^{17}$ and $R^{18}$ is not aromatic; and $-(CH_2-O-CH_2)_xCH_2-$ wherein x is an integer from 1 to 50,
b) $R^{24}L$ wherein $R^{24}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group, wherein preferably one of $R^{17}$ and $R^{20}$ is not aromatic; $-(CH_2-O-CH_2)_xCH_2-$ wherein x is an integer from 1 to 50; and L is a linker which can form a covalent bond with a targeting agent,
c) $R^{24}U$, wherein $R^{24}$ is a single bond; or wherein $R^{24}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group, wherein preferably one of $R^{17}$ and $R^{18}$ is not aromatic; $-(CH_2-O-CH_2)_xCH_2-$ wherein x is an integer from 1 to 50; and U is a physiochemistry modifying group selected from the group consisting of: $-(CH_2)_mSO_3$, $-(CH_2)_mC(O)O-(CH_2)_mNH_2$; $-(CH_2)_mP(O)O_2^{2-}$ $-(CH_2)_mNR_2$ $-(CH_2)_mNH_2$; $-(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl, wherein m is an integer from 0 to 6; $A^6, A^7, A^8, A^9, A^{10}, A^{11}, A^{12}$, and $A^{13}$ are C, N, or N, and either.

A)
form a 6-membered aromatic ring which together with the pyrrolin derived ring to which they are attached form an indol or an azaindol system, which indol system can comprise a total of 1 N atoms, and which azaindol system can comprise a total of 2 N atoms;
$R^3$, $R^4$, $R^5$, $R^6$, $R^7$, $R^8$ $R^9$ $R^{10}$ are independently H or selected from the group consisting of:
a) halide selected from Cl, Br, I; $R^2H$ and $OR^2H$, wherein $R^3$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; $-(CH_2-O-CH_2)_xCH_2-$ wherein x is an integer from 1 to 50,
b) $R^{25}L$ and $OR^{25}L$, wherein $R^{25}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; $-(CH_2-O-$ $CH_2)_xCH_2$— wherein x is an integer from 1 to 50; and L is a linker which can form a covalent bond with a targeting agent, and c) $R^2U$ and $OR^{23}U$ wherein $R^{25}$ is a single bond; or wherein $R^{25}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear or branched $C_1$-$C_6$ alkyl group; —$(CH_2$—O—$CH_2)_xCH_2$— wherein x is an integer from 1 to 50; and U is a physiochemistry modifying group selected from the group consisting of: —$(CH_2)_mSO_3^-$, —$(CH_2)_mC(O)O^-$, —$(CH_2)_mP(O)O_2^{2-}$ —$(CH_2)_mNR_2$; —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$ is an alkyl group having from 1-12, preferably 1-8, more preferably 1-4 C atoms, in particular methyl or ethyl. wherein m in an integer from 0 to 6; and wherein $OR^{25}H$, $OR^{23}L$ and $OR^{25}U$ are present only when O is attached to a C atom;

or

B) $A^6, A^7, A^8, A^9$, and $A^{10}, A^{11}, A^{12}, A^{13}$ are C, N, or N and form a 6-membered aromatic ring which together with the pyrrolin derived ring to which they are attached form an indol or an azaindol system, and to which indol or azaindol system a further 6-membered ring is annulated which is formed by at least two of the substituents $R^3, R^4, R^5, R^6$, or $R^7, R^8R^9$ $R^{10}$, resulting in a trinuclear ring in which 1, 2 or 3 C atoms may be replaced by N or N and which are substituted by $R^{11}$, $R^{12}$, $R^{13}$, $R^{14}$, $R^{15}$, $R^{16}$;

$R^{11}$, $R^{12}$, $R^{13}$, $R^{14}$, and $R^{15}$, $R^{16}$ are independently H or selected from the group consisting of:

a) halide selected from Cl, Br, I; $R^{26}H$ and $OR^{26}H$, wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; —$(CH_2$—O—$CH_2)_xCH_2$— wherein x is an integer from 1 to 50, b) $R^{26}L$ and $OR^{26}L$, wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$-aryl group which can be substituted by a linear or branched $C_1$-$C_6$ alkyl group, homocyclic and heterocyclic $C_5$-, $C_6$- or $C_7$-aromatic groups which can be substituted by a linear or branched $C_1$-$C_6$ alkyl group; —$(CH_2$—O—$CH_2)_xCH_2$— wherein x is an integer from 1 to 50; and L is a linker which can form a covalent bond with a targeting agent, c) $R^{26}U$ and $OR^{26}U$, wherein $R^{26}$ is a single bond; or wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; —$(CH_2$—O—$CH_2)_xCH_2$— wherein x is an integer from 1 to 50; and U is a physiochemistry modifying group selected from the group consisting of: —$(CH_2)_mSO_3^-$, —$(CH_2)_mC(O)O^-$, and d) —$(CH_2)_mP(O)O_2^{2-}$ —$(CH_2)_mNR_2$ —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$ is an alkyl group having from 1-12, preferably 1-8, more preferably 1-4 C atoms, in particular methyl or ethyl;

X and Y are selected from the group consisting of:
$CR^{29}R^{30}$, where $R^{29}$ and $R^{30}$ are each independently selected from H, unsubstituted and substituted linear or branched, cyclic or non-cyclic $C_1$-$C_6$ alkyl;

E and E' are independently selected from H, unsubstituted and substituted linear or branched, cyclic or non-cyclic $C_1$-$C_6$ alkyl.

The person skilled in the art is aware that in case that any of the groups $R^1$ to $R^{36}$ wherein a group $R^1, \ldots R^{36} \ldots$ is connected to a further group like L or U, the term "alkyl", refers to an alkyl group in which at least one H atom is substituted by L, U or an atom or functional group. In one embodiment of the invention, the compound according to formula A contains at least 1 linker and/or 1 physiochemistry modifying group as defined in the context of the present application.

In case the compound according to formula A does not contain at least 1 linker and/or 1 physiochemistry modifying group as defined in the context of the present application, then $R^{19}$ in —$OR^{19}$ is not H.

In a further embodiment of the invention, $R^{19}$ in —$OR^{19}$ is not H in all compounds according to formula A.

In an embodiment, it is conceivable that in any alkyleneoxy group —$(CH_2$—O—$CH_2)_xCH_2$— which is cited in the context with $R_1, R_2, R_3, R_4, R_5, R_6, R_7, R_8, R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{23}, R_{24}, R_{25}, R_{26}$, wherein x is an integer from 1 to 50, x is 2500.

In the most general embodiment of the subject matter of the present application, linkers L are selected from the group consisting of: —$NH_2$, —OH, —SH, —$C(O)O^-$, —$C(O)Cl$, —$(CO)O(CO)R^{27}$, —$C(O)NHNH_2$, —$C(O)$, —$C(O)OR^{28}$, wherein $R^{27}$ is selected from the group consisting of H, alkyl and aryl; wherein $R^{28}$ is derived from substituted and unsubstituted N-hydroxysuccinimide, substituted and unsubstituted N-hydroxysulfosuccinimide, nitrophenol, fluorophenol each bound via —O—; azide $N_3^-$, —NCO, —NCS, —CHO, —$COCH_2I$, phosphoramidityl, phthalamidyl, maleimide, an alkyne group in particular —C≡$CR^{31}$ wherein $R^{31}$ is H or a $C_1$-$C_8$ alkyl group, sulfonate esters, alkyl halides, acyl halides, propargylglycine, a pentanoyl group, in particular pentanoyl chloride, pentynoic acid, propargylic acid, 6-aminobenzo[d]thiazole-2-carbonitrile, 6-hydroxybenzo[d]thiazole-2-carbonitrile, a 1,2-aminothiol group, in particular L-cysteine or D-cysteine.

Further aspects, objects and advantages of the subject matter of the present application will become apparent upon consideration of the detailed description and figures that follow.

BRIEF DESCRIPTION OF THE FIGURES

FIG. 2A shows absorption and quantum yield QY of Compound II, FIG. 2B shows fluorescence spectra and quantum yield QY of Compound II.

FIG. 10 A shows mice imaged by IVIS Spectrum to show tumour localization and FIG. 10B shows NIR fluorescence images to show specific biomarker detection, after intravenously receiving 0.7 nmol of antibody conjugate XXVIII.

FIG. 13A shows I.V. catheter injection in a 30 kg dog 6 h before surgery with 180 nmol/kg of probe XXI, and FIG. 13B shows localization of mastocytoma tumour in dog's right leg.

FIG. 16A shows I.V. catheter injection in a 33 Kg dog 10 h before surgery with 92 nmol/kg of probe XXI, and FIG. 16B shows localization of mastocytoma tumour in dog's nose.

DETAILED DESCRIPTION

Figures 1A, 1B:
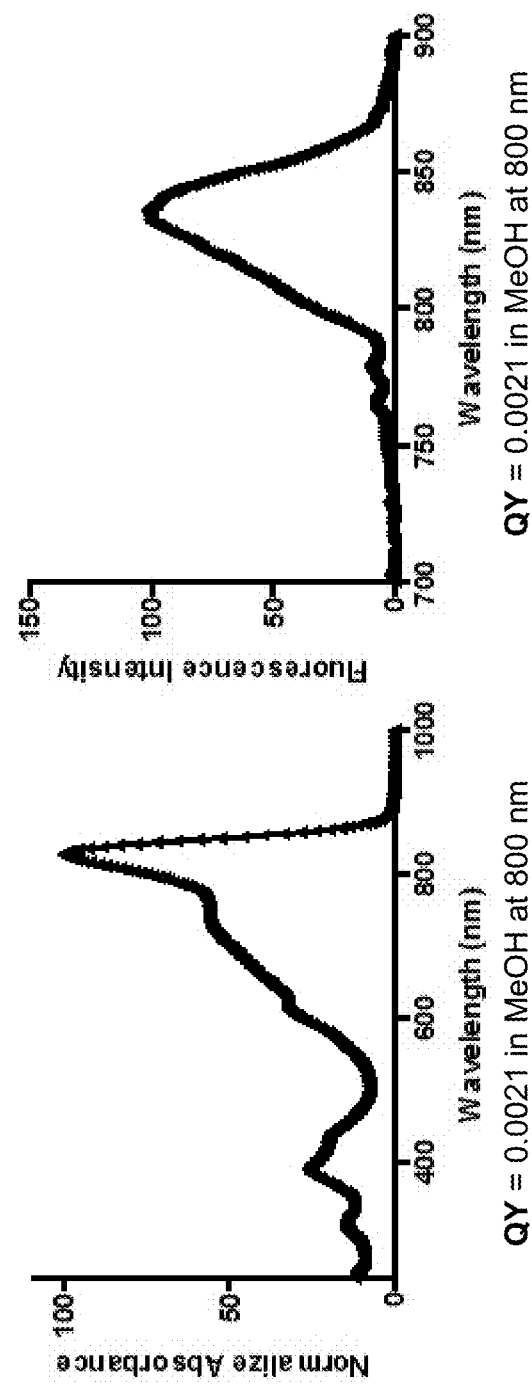
FIG. 1A shows absorption and quantum yield QY of Compound I.
FIG. 1B shows fluorescence spectra and quantum yield QY of Compound I.

All publications, patent applications, patents, and other references mentioned herein are incorporated by reference in their entirety. The publications and applications discussed herein are provided solely for their disclosure prior to the filing date of the present application. Nothing herein is to be construed as an admission that the present subject matter is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the subject matter of the present application.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular form "a", "an" and "the" include plural references unless the context clearly dictates otherwise.

As used in the specification and claims, the term "and/or" used in a phrase such as "A and/or B" herein is intended to include "A and B", "A or B", "A", and "B".

The dyes according to formula A can contain various substituents in various positions. The person skilled in the art is aware of some principle differences between these substituents, according to their chemical properties and to the impact on the physical and chemical properties of the respective dye in which they are present. The skilled artisan will differentiate between the following types of substituents:

Substituents Having an Impact on the Optical Properties of the Dye (Optical Properties Modulation Groups, Optical Properties Modifying Groups)

Substituents of this type are attached in position Q of the dye. Here, they are attached to the conjugated double bonds responsible for the optical properties and will, hence, influence them. In general, these substituents are inorganic or organic groups, which are known to the person skilled in the art as modulating optical properties in dyes having the structural characteristics of the dyes of the present application, in particular a conjugated double bond system. In the context of the present application, optical properties include: absorption, fluorescence, fluorescence quantum yield, stokes shift, lifetime, photostability and further properties known to the person skilled in the art. According to the subject matter of the present application, a fluorescence modulation is a change in the emission wavelength of a dye containing such fluorescence modifying substituent, with respect to the dye not containing the fluorescence modifying substituent.

Examples for this type of substituents (optical properties modifying group) include: Cl, Br, I; $R^{19}$, $-OR^{19}$, $-SR^{19}$ and $-NR^{19}R^{20}$ wherein $R^{19}$ and $R^{20}$ are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic ring which can be substituted by a linear or branched $C_1$-$C_6$ alkyl group; and homocyclic and heterocyclic 5-, 6- and 7-membered aromatic rings which can be substituted by a linear or branched $C_1$-$C_6$ alkyl group.

The above definition is not limited to $R^{19}$ and/or $R^{20}$ which is an organic residue in a substituent of the heterocycle being part of the conjugated double bond system, but of course applies to all other positions and substituents in the molecule which have been defined in connection with the dyes according to A, in the general and all preferred embodiments, to which an optical properties modifying substituent can be attached and/or at which position the substituent has an impact on the optical properties.

As the case may be, an optical properties modifying group as defined beforehand may also contain a physiochemistry modifying group and/or a linker, see below.

The person skilled in the art is furthermore aware that not all of the above cited groups will have an effect on the optical properties of the dyes of the subject matter of the present application in each and every case, as this depends on the chemical and/or fluorescent properties of the respective dye.

Examples for preferred optical properties modifying groups include: Cl, Br, I; 1-cyclohexylpiperazine, phenyl; —O-phenyl; —S-phenyl; —N(H)-phenyl; and wherein each of the groups phenyl, —O-phenyl, S-phenyl, —N(H)-phenyl can be single or multiple substituted by $C_1$-$C_6$ alkyl; and wherein the phenyl group can be substituted by a physiochemistry modifying group U selected from the group consisting of: $-(CH_2)_mSO_3^-$, $-(CH_2)_mC(O)O^-$, $-(CH_2)_mP(O)O_2^{2-}$ $-(CH_2)_mNR_2$ $-(CH_2)_mNH_2$; $-(CH_2)_mNHR^{32}$; $(CH_2)_mNR^{32}R^{33}$ wherein m is an integer from 0 to 6, i.e. 0, 1, 2, 3, 4, 5, and 6; and wherein $R^{32}$, $R^{33}$, is an alkyl group having from 1-12, preferably 1-8, i.e. 1, 2, 3, 4, 5, 6, 7 and 8; more preferably 1-4 C atoms, in particular methyl or ethyl; The above groups are preferred in combination with the general, preferred, and most preferred embodiments for the other substituents Z, Q, $R^1$-$R^{30}$, $A^6$-$A^{16}$ and X and Y.

Substituents Having an Impact on the Physiochemical Properties of the Dye ("Physiochemistry Modifiers", "Physiochemistry Modifying Group", "Physiochemical Properties Modifying Group", "Physiochemistry Modulating Group")

Substituents of this type, generally denoted U throughout this application, have an impact on various properties of the dye. These properties are in particular: solubility of the dye, stability of the dye, and, as the case may be, other properties known to the person skilled in the art. Thus, in particular these substituents render the respective dye more water soluble or more dispersible, in particular in media for administration. Furthermore, and depending on the case, a physiochemistry modifying group can increase binding specificity, increase or decrease net molecular charge, decrease immunogenicity or toxicity, or modify cellular uptake, pharmacokinetic or biodistribution profiles, compared to the unmodified bioconjugate targeting or imaging agents.

Further effects of physiochemistry modifiers may be enhancement of the binding selectivity of the targeting agent for receptors on the cell surface, negatively charged, apoptotic cell surfaces over other negatively charged endogenous cell surfaces, reduction of the nonspecific cell membrane permeability of the targeting agent, and reduction of non-specific tissue accumulation of the targeting agent when administered to a live animal.

The physiochemistry modifiers can have a pronounced impact on in vivo biodistribution and clearance, in particular when modulating solubility.

In general, physiochemistry modifiers are functional groups which are known to the person skilled in the art as having an influence on solubility. Examples include the groups $-SO_3^-$, $-C(O)O^-$, $-(CH_2)_mP(O)O_2^{2-}$ $-(CH_2)_mNR_2$ $-(CH_2)_mNH_2$; $-(CH_2)_mNHR^{32}$; $(CH_2)_mNR^{32}R^{33}$ wherein m is an integer from 0 to 6, and wherein $R^{32}$, $R^{33}$ is an alkyl group having from 1-12, preferably 1-8, more preferably 1-4 C atoms, in particular methyl or ethyl; and wherein in case of $-(CH_2)_mNH_2$; $-(CH_2)_mNHR^{32}$; $-(CH_2)_mNR^{32}R^{33}$ the N atom may be bond to a further substituent $R^3$ to form a quaternary N atom, and wherein $R^{34}$ is in all the above cases independently selected from H, and an alkyl group having from 1-12, preferably 1-8, more preferably 1-4 C atoms, in particular methyl or ethyl. In case $-(CH_2)_mNH_2$, $-(CH_2)_mNHR^{32}$ and $-(CH_2)_mNR^{32}R^{33}$ contain a further substituent $R^{34}$ connected to the N atom to form a quaternary N atom, this substituent $R^{34}$ is preferably identical with the other substituents, i.e. at least one of them if $R^{32}$ and $R^{33}$ are different, or with both in case $R^{32}$ and $R^{33}$ are the same. This means that $R^{32}$ and $R^{33}$ and $R^{34}$ are identical and form a group $-(CH_2)_mNR^{32}R^{33}R^{34}$, or a group $-(CH_2)_mNH_3$, with m being an integer from 0 to 6, and wherein $R^{32}$, $R^{33}$, and $R^{34}$ are an alkyl group having from 1-12, preferably 1-8, more preferably 1-4 C atoms, in particular methyl or ethyl.

The above-named functional groups can be attached directly to a C or N atom which is part of the basic structure of the dye according to A, or these groups can be attached to such N or C atom via an alkyl group, as expressed by the formulae $-(CH_2)_mSO_3^-$, $-(CH_2)_mC(O)O^-$, $-(CH_2)_mP(O)O_2^{2-}$ $-(CH_2)_mNR_2$ $-(CH_2)_mNH_2$; $-(CH_2)_mNHR^{32}$; $(CH_2)_mNR^{32}R^{33}$ wherein m is an integer from 0 to 6, i.e. 1, 2, 3, 4, 5, and 6; and wherein $R^{32}$, $R^{33}$, and $R^{34}$ are an alkyl group having from 1-12, preferably 1-8, i.e. 1, 2, 3, 4, 5, 6, 7 and 8; more preferably 1-4 C atoms, in particular methyl or ethyl; or these groups can be attached to a substituent of a C or a N atom which is part of the basic structure of the dye, as expressed by $-R^{19}U$, $-OR^{19}U$, $-SR^{19}U$ and $-NR^{19}UR^{20}$ wherein $R^{19}$ and $R^{20}$ are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic ring which can be substituted by a linear of branched $C_1$-$C_6$ alkyl group; and homocyclic and heterocyclic 5-, 6- and 7-membered aromatic rings which can be substituted by a linear of branched $C_1$-$C_6$ alkyl group;

or a group —(CH$_2$—O—CH$_2$)$_x$CH$_2$— wherein x is an integer from 1 to 50; and U is a physiochemistry modifying group selected from those as defined hereinabove. The groups attached to a C or N atom of the dye, on the one hand side, and to the physiochemistry modifying group, on the other hand side, are also referred to as "spacer" or "spacer group" in the present context. The above definition is not limited to R$^{19}$ which is an organic residue in a substituent of the heterocycle being part of the conjugated double bond system, but of course applies to all other positions and substituents in the molecule which have been defined in connection with the dyes according to S, in the general and all preferred embodiments, to which a physiochemistry modifying group can be attached.

Substituents Serving as "Linker" and being Converted into a "Linking Group"

Substituents of this type, generally denoted L throughout this application, serve to link the dye to the targeting agent. In general, these linkers are functional groups which are known to the person skilled in the art as being capable of linking a molecule to another molecule in a chemical reaction, under formation of a "linking group" between the dyes of the subject matter of the present application and a targeting agent. The chemical reaction preferably forms a covalent bond between the dye and the targeting agent. Examples for linkers include the groups —NH$_2$, —OH, —SH, —C(O)O$^-$, —C(O)Cl, —(CO)O(CO)R$^{27}$ wherein R$^{27}$ is selected from the group consisting of H, alkyl and aryl; —C(O)NHNH$_2$, —C(O)OR$^{28}$ wherein R$^{28}$ is derived from substituted and unsubstituted N-hydroxysuccinimide, substituted and unsubstituted N-hydroxysulfosuccinimide, nitrophenol, fluorophenol each bound via —O—; azide N$_3^-$, —NCO, —NCS, —CHO, —COCH$_2$I, phosphoramidityl, phthalamidyl, maleimide, an alkyne group in particular —C≡CR$^{31}$ wherein R$^{31}$ is H or a C$_1$-C$_8$ alkyl group. Examples for further functional groups which can serve as a linker include sulfonate esters, alkyl halides, acyl halides, propargylglycine, a pentanoyl group (like in pentanoyl chloride), pentynoic acid, propargylic acid, 6-aminobenzo[d]thiazole-2-carbonitrile, 6-hydroxybenzo[d]thiazole-2-carbonitrile, a 1,2-aminothiol group, in particular L-cysteine or D-cysteine. These linkers can react with complementary groups present on the targeting agent in reactions known as such to the skilled person.

These groups can be attached directly to a C or N atom which is part of the basic structure of the dye according to A, or these groups can be linked to the basic structure by a further group attached to a C or a N atom which is part of the basic structure of the dye, as expressed by R$^{23}$L wherein R$^{23}$ is selected from the group: linear and branched, non-cyclic and cyclic, substituted and unsubstituted C$_{1-20}$ alkyl, wherein the said alkyl group can be single or multiple substituted by a homocyclic or heterocyclic C$_5$-, C$_6$- or C$_7$-aryl group; homocyclic and heterocyclic 5-, 6- or 7-membered aromatic rings; —(CH$_2$—O—CH$_2$)$_x$CH$_2$— wherein x is an integer from 1 to 50; and L is a linker which can form a covalent bond with a targeting agent. The groups attached to a C or N atom of the dye, on the one hand side, and to the linker, on the other hand side, are also referred to as "spacer" or "spacer group" in the present context. The above definition is not limited to R$^{23}$ which is an organic residue in a substituent of the heterocycle being part of the conjugated double bond system, but of course applies to all other positions and substituents in the molecule which have been defined in connection with the dyes according to S, in the general and all preferred embodiments, to which a solubility modifying group can be attached.

"Click" chemistry provides one possible way for linking the fluorescent dyes of the subject matter of the present application to targeting agents. In a further embodiment of the application, "click chemistry" can be used to connect the dye to the targeting agent via a chemical reaction of the linker. "Click" chemistry uses simple, robust reactions, such as the copper-catalyzed cycloaddition of azides and alkynes, to create intermolecular linkages. For a review of "Click" chemistry, see Kolb, H. C; Finn, M. G.; Sharpless, K. B. Angew. Chem. 2001, 40, 2004. Connection (or ligation) of two fragments to make a larger molecule or structure is often achieved with the help of so-called "click chemistry" described by Sharpless et al. Angew. Chem, Int. Ed. 40: 2004 (2001).

This term is used to describe a set of bimolecular reactions between two different reactants such as azides and acetylenes. The formation of 1,2,3-triazoles in 1,3-dipolar cycloaddition of azides to a triple bond is known to the person skilled in the art, and it is known that the reaction can even be carried out under physiological conditions, see e.g., U.S. Pat. No. 7,807,619 to Bertozzi. Another novel thiol-based "click" reaction involves the efficient condensation between the cyano group of 2-cyano-6-aminobenzothiazole (CBT) (or 2-cyano-6-hydroxybenzothiazole) and 1,2-aminothiol group of L-cysteine (or D-cysteine) to yield a thiazole functionality, which can be controlled by pH, reduction and enzyme reported by White, et al. J. Am. Chem. Soc. 85 (1963). To date, this click condensation reaction has been successfully employed to design smart optical imaging probes.

Other Type Substituents

The definition of A cites other substituents, which do not have any of the above effects, or only to a minor extent. These other type substituents may e.g., be present in the molecule due to the availability of starting compounds, or they may facilitate the synthesis of the respective dye, or they are present due to other reasons known to the person skilled in the art. Groups, which do not have the above effects and thus belong into the present group, are known to the skilled person.

As a difference to other fields where a slight modification of the molecule will often have a pronounced effect on the molecule's property (e.g., in the field of pharmaceutically active compounds), the molecules of the present application (dyes) provide various possibilities for the attachment of various substituents, which do not or not substantially change the molecules' properties. It is contemplated that substituent Q is an exception to this, due to its proximity to the conjugated double bond system in the substituents Q, meaning that a modification of Q may have an impact on the optical properties of the molecule. This, however, depends on each single case.

In the other positions of the molecule where a substituent can be present, the effect of a modification of the substituent with respect to fluorescence properties will not be very pronounced, in the very most cases. As a consequence, and for example, a physiochemistry modifying group and/or a linker may be attached to a large number of positions, sometimes in practice even any position, in the molecules A which are synthetically accessible and which does not negatively affect the purpose of the respective substituent. For example, a linker (serving to attach a targeting agent to the dye) should not be attached to a position which is not easily accessible, e.g., due to sterical hindrance. Another example is that inert groups, like e.g., alkyl groups of various lengths, can often be attached to the dyes of the present application, and the dye still lends itself for its intended purposes with respect to its analogue not substituted in the respective position, as important properties like the solubility and/or the optical properties are not or not substantially effected. Thus, the skilled artisan is aware that a large number of groups can be attached to various sites without (substantially) changing the molecules' properties (namely physiochemistry, solubility, optical properties, e.g., fluorescence properties).

The above groups often serve as a "spacer".

When in the foregoing it has been quoted that "R" is a single bond (e.g., in connection with $R^{23}U$, where it is quoted that $R^{23}$, "$R^{23}U$ is a single bond"), this relates to the case that the group U is directly connected to the respective site of the dye via a chemical bond, in general via a single bond.

The skilled person is aware that he present application includes not only the case that the 1 linker L (generally attached via a spacer group) or 1 physiochemistry modifying group U (which may be attached via a spacer group or not) is/are present, but also to the case that 2, 3, 4 or more groups U and 2, 3, 4 or more groups L are present in the dye. In a preferred embodiment, 1 or 2 groups L are present in the dyes according to the subject matter of the present application.

The person skilled in the art knows that the dyes according to the application should be inert and stable under physiological conditions, as a reaction during monitoring or diagnosing a disease is not desirable, in particular when monitoring or diagnosing is carried out in vitro. This means that it should be avoided to prepare dyes carrying reactive groups under the conditions of monitoring/diagnosis (i.e. that these groups undrgo chemical reactions when exposed to the typical conditions applied during the monitoring or the diagnosis process), in particular physiological conditions. In general, the groups attached to the dyes according to the present subject matter, if not serving to modulate physiochemical properties and/or optical properties, are inert groups which show only a low reactivity at maximum, and which in general do not affect the physiochemical properties and/or optical properties. Often, these groups serve as a "spacer", holding a physiochemical properties modulating group and/or a linker in or at the end of their chain. In particular in case of a linker, a respective linker attached to the chain (where the chain is often linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic ring which can be substituted by a linear of branched $C_1$-$C_6$ alkyl group; and homocyclic and heterocyclic 5-, 6- and 7-membered aromatic rings which can be substituted by a linear of branched $C_1$-$C_6$ alkyl group, or a group —(CH$_2$—O—CH$_2$)$_x$CH$_2$— wherein x is an integer from 1 to 50) must not be too close to the basic structure, in order to avoid steric interactions between the dye and the targeting agent to be bound.

Accordingly, a spacer group must show no or only a low chemical reactivity (which also applies for the basic structure of the dye) and must not influence in particular the optical properties of the resulting dye, or only to a minor extent which has no practical relevance. Accordingly, a huge amount of spacers having various alkyl chain lengths and/or various sizes and various natures of the aromatic group may be used in the context of the present application, which do not or only minimally alter the optical properties of the dye.

With respect to the physiochemical properties of the dye, its relation to the spacer may be more delicate. As solubility is a component of physiochemical properties, and the solubility of a dye may change with the length and nature of the spacer (alkyl, aralkyl or aromatic group, alkyleneoxy group; chain length in case of alkyl, and ring size and presence of heteroatoms in an aromatic ring), these parameters may also affect physiochemical properties. Alkyleneoxy groups enhance water-solubility of a molecule in general, where aromatic groups reduce water-solubility, in general. However, the effect of these parameters, in general, will only be observed to a lesser extent than for physiochemical property modulating groups.

From the above, it follows that the nature of the spacers can be widely varied within the limits given by its respective definitions, without substantially affecting the optical and/or physiochemical properties of the dye. These latter are adjusted, in general, by the choice of the optical property modulators and/or the physiochemical property modulators. The person skilled in the art is aware how to adjust desired properties of a dye by selecting the above parameters.

The term "alkyl" refers to an aliphatic saturated hydrocarbon group which may be linear or branched, including methyl ($C_1$ alkyl), ethyl ($C_2$ alkyl), n-propyl, iso-propyl ($C_3$ alkyl), n-butyl, iso-butyl, sec.-butyl and tert.-butyl ($C_4$ alkyl), n-pentyl (amyl), 2-pentyl (sec-pentyl), 3-pentyl; 2-methylbutyl, 3-methylbutyl (iso-pentyl or iso-amyl), 3-methylbut-2-yl, 2-methylbut-2-yl; 2,2-dimethylpropyl (neopentyl) ($C_5$ alkyl), a hexyl group ($C_6$ alkyl) including all isomers, a heptyl group ($C_7$ alkyl) including all isomers, an octyl group ($C_8$ alkyl) including all isomers, a nonyl group including all isomers ($C_9$ alkyl), a decyl group including all isomers ($C_{10}$ alkyl), an undecyl group including all isomers ($C_{11}$ alkyl), a dodecyl group including all isomers ($C_{12}$ alkyl), a tridecyl group including all isomers ($C_{13}$ alkyl), a tetradecyl group including all isomers ($C_{14}$ alkyl), a pentadecyl group including all isomers ($C_{15}$ alkyl), a hexadecyl group including all isomers ($C_{16}$ alkyl), a heptadecyl group including all isomers ($C_{17}$ alkyl), a octadecyl group including all isomers ($C_{18}$ alkyl), a nonadecyl group including all isomers ($C_{19}$ alkyl), and a $C_{20}$ alkyl group including al isomers, as known to the person skilled in the art.

The term "alkyl" also refers to an aliphatic saturated cyclic hydrocarbon group, which may have alkyl substituents. Examples include cyclopropyl ($C_3$ cycloalkyl), cyclobutyl ($C_4$ cycloalkyl), cyclopentyl ($C_5$ cycloalkyl), cyclohexyl ($C_6$ cycloalkyl), cycloheptyl ($C_7$ cycloalkyl), and cyclooctyl ($C_8$ cycloalkyl). Each hydrogen of a cycloalkyl carbon may be replaced by an alkyl substituent.

The term "phenyl" refers to the group —$C_6H_5$ as known to the person skilled in the art. The aromatic ring of the phenyl group may be substituted 1 or 2 times by $C_1$-$C_4$ alkyl and/or 1 or 2 times by Cl, Br. I.

The term "homocyclic 5-, 6- or 7-membered aromatic group" is known to the person skilled in the art. Aromatic groups are known to the person skilled in the art, who is also aware that typical representatives have 5, 6 or 7 members in its cycle, and of the heteroatoms which may be present. Typical examples for heteroatoms in the context of the present application are N, O and A. In the context of the present application, N and O are preferred. Non-limiting examples include phenyl, pyridyl (6-membered), pyrrol, furyl, thiophen (5-membered), cycloheptatrienyl (7-membered). The aromatic heterocycle can be connected to the respective place in the dye via the heteroatom or via a C-atom.

A homocyclic 6-membered aromatic group is phenyl of pyridyl, preferably phenyl.

"Aryl" or "Ar" or "aromatic group" refers to a monovalent aromatic carbocyclic group of from 5 to 18 carbon atoms having a single ring such as C6 in phenyl or anion such as C5 cyclopentadienyl anion or a ring system having multiple condensed rings such as those in anthracenyl, napthyl, phenanthrenyl, the condensed rings may be bridged by a transition atom or ion such as iron with two cyclopentadienyl anions in ferrocene, the condensed rings may or may not be aromatic, provided that the point of attachment is through an atom of an aromatic ring such as dihydroindolyl, dihydrobenzthiazolyl and other partially hydrogenated aromatic groups. Unless otherwise constrained by the definition for the aryl substituent that are defined by groups obeying Huckels law of 4n+2 pi electrons (n being an integer), such aryl groups can optionally be substituted with from 1 to 5 substituents, or from 1 to 3 substituents, "Amino" refers to the group —$NH_2$.

"Substituted amino" refers to the group —NRR where each R is independently selected from the group consisting of hydrogen, $C_1$-$C_8$ alkyl, which can be substituted or unsubstituted, $C_5$-$C_7$ cycloalkyl which can be substituted or unsubstituted, and a homocyclic 5-, 6- or 7-membered aromatic group, provided that at least one R is not hydrogen.

"Azido" refers to the group —$N_3$.

"Carboxyl," "carboxy" or "carboxylate" refers to —C(O)OH or salts thereof derived from $CO_2^-$ "Cyano" or "nitrile" refers to the group —CN.

"Thiocyanate" refers to the group —SCN.

"Isothiocyante" refers to the group —NCS.

"Halo", halide" or "halogen" refers to F, Cl, Br and I, preferably Cl, Br and I.

"Hydroxy" or "hydroxyl" refers to the group —OH.

"Heteroaryl" refers to an aromatic group of from 2 to 15 carbon atoms, such as from 3 to 10 carbon atoms and 1 to 10 heteroatoms selected from the group consisting of oxygen, nitrogen (referred to as aza in the application) and sulfur within the ring. Such heteroaryl groups can have a single ring (such as, pyrrole, pyridyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocylooxy, aminoacyloxy, oxyacylamino, thioalkoxy, substituted thioalkoxy, thioaryloxy, thioheteroaryloxy, sulfinate and sulfonate esters-SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, —$SO_3$-M1, phosphate diesters exemplified by —$OPO_3$-(M)alkyl, —$OPO_3$-(M)aryl, —$OPO_3$-(M)heteroaryl, $OPO_3$-heteroaryloxy, phosphate triesters —$OPO_3$-dialkyl, —$OPO_3$-(alkyl)aryl, —$OPO_3$-diaryl, —$OPO_3$-(alkyl)heteroaryl, —$OPO_3$-(aryl)heteroaryl, —$OPO_3$-diheteroaryl, —$OPO_3$M2, —$OPO_3$-2M1 where M1 and M2 are monovalent and divalent cations.

"Hydroxylamino" refers to the group —NHOH.

"Nitro" refers to the group —$NO_2$.

"Thiol" refers to the group —SH.

"Thioxo" or the term "thioketo" refers to the atom (=S).

"Ureido" refers to the group NH—CO—NH—, and "thioureido" refers to the group —NH—CS—NH—.

The term "N-hydroxysuccinimide is the N-hydroxy derivative of succinimide.

The term substituted and unsubstituted N-hydroxysulfosuccinimide refers to the N-hydroxy derivative of succinimide which is substituted by a group —$SO_3^-$ at the 5-membered cycle.

The terms "phosphoramidityl" and "phosphoramidit", "phthalamidyl" and "phatilimide" and "maleimide" are known to the person skilled in the art.

The term "sulfonate ester", "alkyl halide" and "acyl halide" are current terms in the art and known to the skilled artisan.

The general and preferred embodiments of the application are defined hereinafter.

In the most general embodiment of the fluorescent dyes of the application, Z is selected from the group consisting of N, $NR^{17}$, $^+NR^{17}R^{18}$.

In a preferred embodiment of the application, Z is is N or $^+$N, $NR^{17}$, or $^+NR^{17}R^{18}$.

In a more preferred embodiment of the application, Z is N or $^+$N, $NR^{17}$, or $^+NR^{17}R^{18}$.

In the most general embodiment of the application, Q is independently H or selected from the groups a), b), and c) consisting of:

a) Halide selected from Cl, Br, I; $R^{19}U$, —$OR^{19}U$, —$SR^{19}U$ and —$NR^{19}R^{20}U$, wherein $R^{19}$ is a single bond; or wherein $R^{19}$ and $R^{20}$ may independently be an optical properties modifying group, and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$ aromatic ring which can be substituted by a linear or branched $C_1$-$C_6$ alkyl group; and homocyclic and heterocyclic 5-, 6- and 7-membered aromatic rings which can be substituted by a linear or branched $C_1$-$C_6$ alkyl group, wherein preferably one of $R^{19}$ and $R^{20}$ is not aromatic in case of —$NR^{19}R^{20}U$; —$(CH_2$—O—$CH_2)_xCH_2$— wherein x is an integer from 1 to 50; and U is a physiochemistry modifying group selected from the group consisting of: —$(CH_2)_mSO_3$—, —$(CH_2)_mC(O)O$—, —$(CH_2)_mP(O)O_2^{2-}$, —$(CH_2)_mNH_2$; —$(CH_2)_mNHR^{32}$; —$(CH_2)_mNR^{32}R^{33}$ wherein m is an integer from 0 to 6, and wherein $R^{32}$ and $R^{33}$ are independently of each other an alkyl group having from 1-12, preferably 1-8, more preferably 1-4 C atoms, in particular methyl or ethyl; and wherein in case of —$(CH_2)_mNH_2$; —$(CH_2)_mNHR^{32}$; —$(CH_2)_mNR^{32}R^{33}$ the N atom may be bond to a further substituent $R^{34}$ to form a quatemary N atom, and wherein $R^{34}$ is in all the above cases independently selected from H, and an alkyl group having from 1-12, preferably 1-8, more preferably 1-4 C atoms, in particular methyl or ethyl;

b) $R^{21}L$, —$OR^{21}L$, —$SR^{21}L$ and —$NR^{21}R^{22}L$ wherein $R^{21}$ and $R^{22}$ may be an optical properties modifying group and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic rings which can be substituted by a linear or branched $C_1$-$C_6$ alkyl group, wherein preferably one of $R^{21}$ and $R^2$ is not aromatic in case of —$NR^{21}R^{22}$; —$(CH_2$—O—$CH_2)_xCH_2$-L wherein x is an integer from 1 to 50; and L is a linker which can form a covalent bond with a targeting agent;
  c) $R^{19}$, —$OR^{19}$, —$SR^{19}$ and —$NR^{19}R^{20}$ wherein $R^{19}$ and $R^{20}$ wherein $R^{19}$ and $R^{12}$ may independently be an optical properties modifying group and are independently selected from the group consisting of: H, linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic ring which can be substituted by a linear or branched $C_1$-$C_6$ alkyl group; and homocyclic and heterocyclic 5-, 6- and 7-membered aromatic rings which can be substituted by a linear of branched $C_1$-$C_6$ alkyl group, wherein preferably one of $R^{19}$ and $R^{20}$ is not aromatic in case of —$NR^{19}R^{20}$; —$(CH_2$—O—$CH_2)_xCH_2$— wherein x is an integer from 1 to 50; or wherein $R^{19}$ and $R^{20}$, together with the N atom to which they are attached, form a 5- or 6-membered heterocycle optionally containing one further heteroatom selected from O and N, wherein the heterocycle can be substituted by a linear or branched, cyclic or non cyclic $C_1$-$C_6$ alkyl group, in particular 4-cyclohexylpiperazinyl.

In an embodiment within this most general embodiment of the invention, $R^{19}$ in —$OR^{19}$ is not H. This is in particular the case if the compound according to formula A does not contain at least 1 linker and/or 1 physiochemistry modifying group as defined in the context of the present application.

In a preferred embodiment of the application, Q is independently H or selected from the groups a), b), and c) consisting of:
  a) halide selected from Cl, Br, I; $R^{19}U$, —$OR^{19}U$, —$SR^{19}U$ and —$NR^{19}R^{20}U$; wherein $R^{19}$ is a single bond; or wherein $R^{19}$ and $R^{20}$ may independently be an optical properties modifying group, and are independently selected from the group consisting of: H, linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; and homocyclic 6-membered aromatic rings which can be substituted by a linear or branched $C_1$-$C_4$ alkyl group, wherein preferably one of $R^{19}$ and $R^{20}$ is not aromatic in case of —$NR^{19}R^{20}U$; —$(CH_2$—O—$CH_2)_xCH_2$— wherein x is an integer from 1 to 20; and U is a physiochemistry modifying group selected from the group consisting of: —$(CH_2)_mSO_3^-$, —$(CH_2)_mC(O)O$—$(CH_2)_mP(O)O_2^{2-}$ —$(CH_2)_mNR_2$—$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl; and wherein in case of —$(CH_2)_mNH_2$; —$(CH_2)_mNHR^{32}$; —$(CH_2)_mNR^{32}R^{33}$ the N atom may be bond to a further substituent $R^{34}$ to form a quaternary N atom, and wherein $R^3$ is in all the above cases independently selected from H, and an alkyl group having from 1-12, preferably 1-8, more preferably 1-4 C atoms, in particular methyl or ethyl;
  b) $R^{21}L$, —$OR^{21}L$, —$SR^{21}L$ and —$NR^{21}R^{22}L$ wherein $R^{21}$ and $R^{22}$ may independently be an optical properties modifying group and are independently selected from the group consisting of: H; linear, non-cyclic, substituted and unsubstituted $C_{1-12}$ alkyl, wherein the said alkyl group can be single or multiple substituted by a homocyclic $C_6$-aryl group which can be substituted by a linear or branched $C_1$-$C_4$ alkyl group; —$(CH_2$—O—$CH_2)_xCH_2$— wherein x is an integer from 1 to 20; and homocyclic 6-membered aromatic groups rings which can be substituted by a linear or branched $C_1$-$C_4$ alkyl group, wherein preferably one of $R^{21}$ and $R^{22}$ is not aromatic in case of —$NR^{21}R^{22}$; and L is a linker which can form a covalent bond with a targeting agent;
  c) $R^{19}$, —$OR^{19}$, —$SR^{19}$ and —$NR^{19}R^{20}$ wherein $R^{19}$ and $R^{20}$ may independently be an optical properties modifying group and are independently selected from the group consisting of: H; linear, non-cyclic, substituted and unsubstituted $C_{1-12}$ alkyl, wherein the said alkyl group can be single or multiple substituted by a homocyclic $C_6$-aryl group which can be substituted by a linear or branched $C_1$-$C_4$ alkyl group; and homocyclic 6-membered aromatic groups which can be substituted by a linear or branched $C_1$-$C_4$ alkyl group, wherein preferably one of $R^{19}$ and $R^{21}$ is not aromatic in case of —$NR^{19}R^{20}U$; —$(CH_2$—O—$CH_2)_xCH_2$— wherein x is an integer from 1 to 20; or wherein $R^{19}$ and $R^{20}$, together with the N atom to which they are attached, form a 5- or 6-membered heterocycle optionally containing one further heteroatom selected from O and N, wherein the heterocycle can be substituted by a linear or branched, cyclic. or non cyclic $C_1$-$C_6$ alkyl group, in particular 4-cyclohexylpiperazinyl.

In an embodiment within this preferred embodiment of the invention, $R^{19}$ in —$OR^{19}$ is not H. This is in particular the case if the compound according to formula A does not contain at least 1 linker and/or 1 physiochemistry modifying group as defined in the context of the present application.

In a more preferred embodiment of the application, Q is independently H or selected from the groups a), b), and c) consisting of:
  a) Halide selected from Cl, Br, I; $R^{19}U$, —$OR^{19}U$, —$SR^{19}U$ and —$NR^{19}R^{20}U$, wherein $R^{19}$ is a single bond; or wherein $R^{19}$ and $R^{20}$ may independently be an optical properties modifying group, and are independently selected from the group consisting of: H; linear, non-cyclic, substituted and unsubstituted $C_{1-8}$ alkyl, wherein the said alkyl group can be single substituted by a homocyclic 6-membered aromatic group; and homocyclic 6-membered aromatic groups wherein preferably one of $R^{19}$ and $R^{20}$ is not aromatic in case of —$NR^{19}R^{20}U$; —$(CH_2$—O—$CH_2)_xCH_2$— wherein x is an integer from 1 to 12; and U is a physiochemistry modifying group selected from the group consisting of: —$(CH_2)_mSO_3^-$, —$(CH_2)_mC(O)O^-$, —$(CH_2)_mP(O)O_2^{2-}$ —$(CH_2)_mNR_2$—$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl; and wherein in case of —$(CH_2)_mNH_2$; —$(CH_2)_mNHR^{32}$; —$(CH_2)NR^{32}R^{33}$ the N atom may be bond to a further substituent $R^{34}$ to form a quaternary N atom, and wherein $R^{34}$ is in all the above cases independently selected from H, and an alkyl group having from 1-12, preferably 1-8, more preferably 1-4 C atoms, in particular methyl or ethyl, b) $R^{21}L$, $—OR^{21}L$, $—SR^{21}L$ and $—NR^{21}R^{22}L$ wherein $R^{21}$ and $R^{22}$ may independently be an optical properties modifying group and are independently selected from the group consisting of: H; linear, non-cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{21}$ and $R^{22}$ is not aromatic in case of $—NR^{21}R^{22}$; $—(CH_2—O—CH_2)_xCH_2$-L wherein x is an integer from 1 to 12; and L is a linker which can form a covalent bond with a targeting agent; and L is a linker which can form a covalent bond with a targeting agent;

c) $R^{19}$, $—OR^{19}$, $—SR^{19}$ and $—NR^{19}R^{20}$ wherein $R^{19}$ and $R^{20}$ may independently be an optical properties modifying group and are independently selected from the group consisting of: H; linear, non-cyclic, substituted and unsubstituted $C_{1-8}$ alkyl, wherein the said alkyl group can be single substituted by a homocyclic 6-membered aromatic group; and homocyclic 6-membered aromatic groups, wherein preferably one of $R^{19}$ and $R^{20}$ is not aromatic in case of $—NR^{21}R^{22}$; $—(CH_2—O—CH_2)_xCH_2—$ wherein x is an integer from 1 to 12; or wherein $R^{19}$ and $R^{20}$, together with the N atom to which they are attached, form a 6-membered heterocycle optionally containing one further heteroatom selected from O and N, wherein the heterocycle can be substituted by a linear or branched, cyclic or non cyclic $C_1$-$C_6$ alkyl group, in particular 4-cyclohexylpiperazinyl.

In an embodiment within this more preferred embodiment of the invention, $R^{19}$ in $—OR^9$ is not H. This is in particular the case if the compound according to formula A does not contain at least 1 linker and/or 1 physiochemistry modifying group as defined in the context of the present application.

In a still more preferred embodiment of the application, Q is independently H or selected from the groups a), b), and c) consisting of:

a) Halide selected from Cl, Br, I; $R^{19}U$, $—OR^{19}U$, and $—NR^{19}R^{20}U$, wherein $R^{19}$ is a single bond; or wherein $R^{19}$ and $R^{20}$ may independently be an optical properties modifying group, and are independently selected from the group consisting of: H; linear, non-cyclic, substituted and unsubstituted $C_{1-8}$ alkyl, wherein the said alkyl group can be single substituted by a homocyclic 6-membered aromatic group; and homocyclic 6-membered aromatic groups wherein preferably one of $R^{19}$ and $R^{20}$ is not aromatic in case of $—NR^{19}R^{20}U$; $—(CH_2—O—CH_2)_xCH_2—$ wherein x is an integer from 1 to 6; and U is a physiochemistry modifying group selected from the group consisting of: $—(CH_2)_mSO_3^-$, $—(CH_2)_mC(O)O^-$, $—(CH_2)_mP(O)O_2^{2-}$ $—(CH_2)_mNR_2—(CH_2)_mNH_2$; $—(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl and wherein in case of $—(CH_2)_mNH_2$; $—(CH_2)_mNHR^{32}$; $—(CH_2)_mNR^{32}R^{33}$ the N atom may be bond to a further substituent $R^{34}$ to form a quaternary N atom, and wherein $R^{34}$ is in all the above cases independently selected from H, and an alkyl group having from 1-12, preferably 1-8, more preferably 1-4 C atoms, in particular methyl or ethyl;

b) $R^{21}L$, $—OR^{21}L$, and $—NR^{21}R^{22}L$ wherein $R^{21}$ and $R^{22}$ may independently be an optical properties modifying group and are independently selected from the group consisting of: H; linear, non-cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{2'}$ and $R^{22}$ is not aromatic in case of $—NR^{21}R^{22}$; $—(CH_2—O—CH_2)_xCH_2$-L wherein x is an integer from 1 to 6; and L is a linker which can form a covalent bond with a targeting agent; and L is a linker which can form a covalent bond with a targeting agent;

c) $R^{19}$, $—OR^{19}$, and $—NR^{19}R^{20}$ wherein $R^{19}$ and $R^{20}$ may independently be an optical properties modifying group and are independently selected from the group consisting of: H; linear, non-cyclic, substituted and unsubstituted $C_{1-8}$ alkyl, wherein the said alkyl group can be single substituted by a homocyclic 6-membered aromatic group; and homocyclic 6-membered aromatic groups, wherein preferably one of $R^{19}$ and $R^{20}$ is not aromatic in case of $—NR^{21}R^{22}$; $—(CH_2—O—CH_2)_xCH_2—$ wherein x is an integer from 1 to 6; or wherein $R^{19}$ and $R^{20}$, together with the N atom to which they are attached, form a 6-membered heterocycle optionally containing one further heteroatom selected from O and N, wherein the heterocycle can be substituted by a linear or branched, cyclic or non cyclic $C_1$-$C_6$ alkyl group, in particular 4-cyclohexylpiperazinyl.

In an embodiment within this still more preferred embodiment of the invention, $R^{19}$ in $—OR^{19}$ is not H. This is in particular the case if the compound according to formula A does not contain at least 1 linker and/or 1 physiochemistry modifying group as defined in the context of the present application.

In the most general embodiment of the application, $R^1$ and $R^2$ are absent?, H or independently selected from the group:

a) linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- and 7-membered aromatic rings which can be substituted by a linear or branched $C_1$-$C_6$ alkyl group; and $—(CH_2—O—CH_2)_xCH_2—$ wherein x is an integer from 1 to 50;

b) $R^{23}L$ wherein $R^{23}$ is selected from the group: linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$-aryl group which can be substituted by a linear or branched $C_1$-$C_6$ alkyl group; homocyclic and heterocyclic 5-, 6- and 7-membered aromatic rings which can be substituted by a linear or branched $C_1$-$C_6$ alkyl group; $—(CH_2—O—CH_2)_xCH_2—$ wherein x is an integer from 1 to 50; and L is a linker which can form a covalent bond with a targeting agent;

c) $R^{23}U$, wherein $R^{23}$ is a single bond; or wherein $R^{23}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic rings which can be substituted by a linear or branched $C_1$-$C_6$ alkyl group; —($CH_2$—O—$CH_2$)$_x$$CH_2$— wherein x is an integer from 1 to 50; and U is a physiochemistry modifying group selected from the group consisting of: —($CH_2$)$_m$$SO_3$, —($CH_2$)$_m$C(O)O$^-$, —($CH_2$)$_m$P(O)$O_2$$^{2-}$ —($CH_2$)$_m$NR$_2$—($CH_2$)$_m$$NH_2$; —($CH_2$)$_m$NHR$^{32}$; ($CH_2$)$_m$NR$^{32}$R$^{33}$ wherein m is an integer from 0 to 6, and wherein R$^{32}$, R$^{33}$ is an alkyl group having from 1-12, preferably 1-8, more preferably 1-4 C atoms, in particular methyl or ethyl.

In a preferred embodiment of the application, R$^1$ and R$^2$ are absent, independently H or selected from the group:
  a) linear, non-cyclic, substituted and unsubstituted $C_{1-12}$ alkyl, wherein the said alkyl group can be single or multiple substituted by a homocyclic $C_6$-aromatic group which can be substituted by a linear or branched $C_1$-$C_4$ alkyl group; homocyclic 6-membered aromatic rings which can be substituted by a linear or branched $C_1$-$C_4$ alkyl group; and —($CH_2$—O—$CH_2$)$_x$$CH_2$— wherein x is an integer from 1 to 20;
  b) R$^{23}$L wherein R$^{23}$ is selected from the group: linear, non-cyclic, substituted and unsubstituted $C_{1-12}$ alkyl, wherein the said alkyl group can be single or multiple substituted by a homocyclic $C_6$-aromatic group which can be substituted by a linear or branched $C_1$-$C_4$ alkyl group; homocyclic $C_6$ aromatic rings which can be substituted by a linear or branched $C_1$-$C_4$ alkyl group; —($CH_2$—O—$CH_2$)$_x$$CH_2$— wherein x is an integer from 1 to 20; and L is a linker which can form a covalent bond with a targeting agent;
  c) R$^{23}$U, wherein R$^{23}$ is a single bond; wherein R$^{23}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic $C_6$ aromatic rings which can be substituted by a linear or branched $C_1$-$C_4$ alkyl group; —($CH_2$—O—$CH_2$)$_x$$CH_2$— wherein x is an integer from 1 to 20; and U is a physiochemistry modifying group selected from the group consisting of: —($CH_2$)$_m$$SO_3$$^-$, —($CH_2$)$_m$C(O)O$^-$, —($CH_2$)$_m$P(O)$O_2$$^{2-}$—($CH_2$)$_m$NR$_2$ —($CH_2$)$NH_2$; —($CH_2$)$_m$NHR$^{32}$; ($CH_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl;

In a more preferred embodiment of the application, R$^1$ and R$^2$ are absent, H or independently selected from the group:
  a) linear, non-cyclic, substituted and unsubstituted $C_{1-8}$ alkyl, wherein the said alkyl group can be single substituted by a homocyclic 6-membered aromatic group; homocyclic 6-membered aromatic rings; and —($CH_2$—O—$CH_2$)$_x$$CH_2$— wherein x is an integer from 1 to 20;
  b) R$^{23}$L wherein R$^{23}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic group; —($CH_2$—O—$CH_2$)$_x$$CH_2$— wherein x is an integer from 1 to 12; and L is a linker which can form a covalent bond with a targeting agent;
  c) R$^{23}$U, wherein R$^{23}$ is a single bond; or wherein R$^{23}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic groups; —($CH_2$—O—$CH_2$)$_x$$CH_2$— wherein x is an integer from 1 to 12; and U is a physiochemistry modifying group selected from the group consisting of: —($CH_2$)$_m$$SO_3$$^-$, —($CH_2$)$_m$C(O)O$^-$, —($CH_2$)$_m$P(O)$O_2$$^{2-}$ —($CH_2$)$_m$NR$_2$ —($CH_2$)$_m$$NH_2$; —($CH_2$)$_m$NHR$^{32}$; ($CH_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl.

In a still more preferred embodiment of the application, R$^1$ and R$^2$ are absent, H or independently selected from the group:
  a) linear, non-cyclic, substituted and unsubstituted $C_{1-8}$ alkyl, wherein the said alkyl group can be single substituted by a homocyclic 6-membered aromatic group; homocyclic 6-membered aromatic rings; and —($CH_2$—O—$CH_2$)$_x$$CH_2$— wherein x is an integer from 1 to 6;
  b) R$^{23}$L wherein R$^{23}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic group; —($CH_2$—O—$CH_2$)$_x$$CH_2$— wherein x is an integer from 1 to 8; and L is a linker which can form a covalent bond with a targeting agent;
  c) R$^{23}$U, wherein R$^{23}$ is a single bond; or wherein R$^{23}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic groups; —($CH_2$—O—$CH_2$)$_x$$CH_2$— wherein x is an integer from 1 to 6; and U is a physiochemistry modifying group selected from the group consisting of: —($CH_2$)$_m$$SO_3$$^-$, —($CH_2$)$_m$C(O)O$^-$, —($CH_2$)$_m$P(O)$O_2$$^{2-}$ —($CH_2$)$_m$NR$_2$ —($CH_2$)$_m$$NH_2$; —($CH_2$)$_m$NHR$^{32}$; ($CH_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl.

In the most general embodiment of the application, R$^{17}$ and R$^{18}$ are independently H or selected from the group consisting of:
  a) linear and branched, non-cyclic or cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- and 7-membered aromatic rings which can be substituted by a linear or branched $C_1$-$C_6$ alkyl group, wherein preferably one of R$^{17}$ and R$^{18}$ is not aromatic; and —($CH_2$—O—$CH_2$)$_x$$CH_2$— wherein x is an integer from 1 to 50
  b) R$^{24}$L wherein R$^{24}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group, wherein preferably one of R$^{17}$ and R$^{20}$ is not aromatic; —($CH_2$—O—$CH_2$)$_x$$CH_2$— wherein x is an integer from 1 to 50; and L is a linker which can form a covalent bond with a targeting agent;

c) $R^{24}U$, wherein $R^{24}$ is a single bond; or wherein $R^{24}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group, wherein preferably one of $R^{17}$ and $R^{18}$ is not aromatic; —$(CH_2$—O—$CH_2)_xCH_2$— wherein x is an integer from 1 to 50; and U is a physiochemistry modifying group selected from the group consisting of: —$(CH_2)_mSO_3^-$, —$(CH_2)_mC(O)O$—$(CH_2)_mNH_2$; —$(CH_2)_mP(O)O_2^{2-}$ —$(CH_2)_mNR_2$ —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl, wherein m is an integer from 0 to 6.

In a preferred embodiment of the application, $R^{17}$ and $R^{18}$ are independently H or selected from the group consisting of:
a) linear, non-cyclic, substituted and unsubstituted $C_{1-12}$ alkyl, wherein the said alkyl group can be single or multiple substituted by a homocyclic 6-membered aromatic group; homocyclic 6-membered aromatic groups which can be substituted by a linear or branched $C_1$-$C_4$ alkyl group, wherein preferably one of $R^{17}$ and $R^{18}$ is not aromatic; —$(CH_2$—O—$CH_2)_xCH_2$— wherein x is an integer from 1 to 20; and
b) $R^{24}L$ wherein $R^{24}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic group which can be substituted by a linear or branched $C_1$-$C_4$ alkyl group, wherein preferably one of $R^{17}$ and $R^{18}$ is not aromatic; —$(CH_2$—O—$CH_2)_xCH_2$— wherein x is an integer from 1 to 20; and L is a linker which can form a covalent bond with a targeting agent;
c) $R^{24}U$, wherein $R^{24}$ is a single bond; or wherein $R^{24}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic groups which can be substituted by a linear or branched $C_1$-$C_4$ alkyl group, wherein preferably one of $R^{17}$ and $R^{18}$ is not aromatic; —$(CH_2$—O—$CH_2)_xCH_2$— wherein x is an integer from 1 to 20; and U is a physiochemistry modifying group selected from the group consisting of: —$(CH_2)_mSO_3^-$, —$(CH_2)_mC(O)O^-$, $(CH_2)P(O)O_2^{2-}$ —$(CH_2)_mNR_2$ —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl;

In a more preferred embodiment of the application, $R^{17}$ and $R^{18}$ are independently H or selected from the group consisting of:
a) linear, non-cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{17}$ and $R^{18}$ is not aromatic; and —$(CH_2$—O—$CH_2)_xCH_2$— wherein x is an integer from 1 to 12;
b) $R^{24}L$ wherein $R^{24}$ is selected from the group: linear and branched, non-cyclic and cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{17}$ and $R^{18}$ is not aromatic; —$(CH_2$—O—$CH_2)_xCH_2$— wherein x is an integer from 1 to 12; and L is a linker which can form a covalent bond with a targeting agent;
c) $R^{24}U$, wherein $R^{24}$ is a single bond; or wherein $R^{24}$ is selected from the group: linear and branched, non-cyclic and cyclic, substituted and unsubstituted $C_{1-8}$ alkyl, wherein the said alkyl group can be single substituted by a homocyclic 6-membered aromatic group; homocyclic 6-membered aromatic groups; wherein preferably one of $R^{17}$ and $R^{18}$ is not aromatic; —$(CH_2$—O—$CH_2)_xCH_2$— wherein x is an integer from 1 to 12; and U is a physiochemistry modifying group selected from the group consisting of: —$(CH_2)_mSO_3^-$, —$(CH_2)_mC(O)O^-$, —$(CH_2)_mP(O)O_2^{2-}$ —$(CH_2)_mNR_2$ —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl.

In a still more preferred embodiment of the application, $R^{17}$ and $R^{18}$ are independently H or selected from the group consisting of:
a) linear, non-cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{17}$ and $R^{18}$ is not aromatic; and —$(CH_2$—O—$CH_2)_xCH_2$— wherein x is an integer from 1 to 6;
b) $R^{24}L$ wherein $R^{24}$ is selected from the group: linear and branched, non-cyclic and cyclic, substituted and unsubstituted $C_{1-8}$ alkyl, wherein the said alkyl group can be single substituted by a homocyclic 6-membered aromatic group; homocyclic 6-membered aromatic groups, wherein preferably one of $R^{17}$ and $R^{18}$ is not aromatic; —$(CH_2$—O—$CH_2)_xCH_2$— wherein x is an integer from 1 to 6; and L is a linker which can form a covalent bond with a targeting agent;
c) $R^{24}U$, wherein $R^{24}$ is a single bond; or wherein $R^{24}$ is selected from the group: linear and branched, non-cyclic and cyclic, substituted and unsubstituted $C_{1-8}$-alkyl, wherein the said alkyl group can be single substituted by a homocyclic 6-membered aromatic group; homocyclic 6-membered aromatic groups; wherein preferably one of $R^{17}$ and $R^{18}$ is not aromatic; —$(CH_2$—O—$CH_2)_xCH_2$— wherein x is an integer from 1 to 6; and U is a physiochemistry modifying group selected from the group consisting of: —$(CH_2)_mSO_3^-$; —$(CH_2)_mC(O)O^-$, —$(CH_2)_mP(O)O_2^{2-}$ —$(CH_2)_mNR_2$ —$(CH_2)_mNH_2$; —$(CH_2)_mNHR^{32}$; $(CH_2)_mNR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl.

In the most general embodiment of the application, $A^6$, $A^7$, $A^8$, $A^9$, and $A^{10}$, $A^{11}$, $A^{12}$, $A^{13}$ are C, N or $^+$N, and either
A)
form a 6-membered aromatic ring which together with the pyrrolin derived ring to which they are attached form an indol or an azaindol system, which indol system can comprise a total of 1 N atoms, and which azaindol system can comprise a total of 2 N atoms; $R^3$, $R^4$, $R^5$, $R^6$, $R^7$, $R^8$ $R^9$ $R^{10}$ are independently H or selected from the group consisting of:
a) halide selected from Cl, Br, I; $R^{25}$H and OR$^{25}$H, wherein $R^{25}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_5$-$C_6$ alkyl group; —(CH$_2$—O—CH$_2$)$_x$CH$_2$— wherein x is an integer from 1 to 50;
b) $R^{25}$L and OR$^{25}$L, wherein $R^{25}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_5$-$C_6$ alkyl group; homocyclic and heterocyclic 5-, 6- or 7-membered aromatic groups which can be substituted by a linear of branched $C_1$-$C_6$ alkyl group; —(CH$_2$—O—CH$_2$)$_x$CH$_2$— wherein x is an integer from 1 to 50; and L is a linker which can form a covalent bond with a targeting agent; and
c) $R^{25}$U and OR$^{25}$U wherein $R^{25}$ is a single bond; or wherein $R^{25}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear or branched $C_1$-$C_6$ alkyl group; —(CH$_2$—O—CH$_2$)$_x$CH$_2$— wherein x is an integer from 1 to 50; and U is a physiochemistry modifying group selected from the group consisting of: —(CH$_2$)$_m$SO$_3^-$, —(CH$_2$)$_m$C(O)O$^-$, —(CH$_2$)$_m$P(O)O$_2^{2-}$ —(CH$_2$)$_m$NR$_2$—(CH$_2$)$_m$NH$_2$; —(CH$_2$)$_m$NHR$^{32}$; (CH$_2$)$_m$NR$^{32}$R$^{33}$ wherein m is an integer from 0 to 6, and wherein $R^{32}$, $R^{33}$, is an alkyl group having from 1-12, preferably 1-8, more preferably 1-4 C atoms, in particular methyl or ethyl, wherein m in an integer from 0 to 6; and wherein OR$^{25}$H, OR$^2$L and OR$^2$U are present only when O is attached to a C atom;
or
B)
$A^6$, $A^7$, $A^8$, $A^9$, and $A^{10}$, $A^{11}$, $A^{12}$, $A^{13}$ are C, N, or $^+$N and form a 6-membered aromatic ring which together with the pyrrolin derived ring to which they are attached form an indol or an azaindol system, and to which indol or azaindol system a further 6-membered ring is annulated which is formed by at least two of the substituents $R^3$, $R^4$, $R^5$, $R^6$, or $R^7$, $R^8$ $R^9$ $R^{10}$, resulting in a trinuclear ring in which 1, 2 or 3 C atoms may be replaced by N or $^+$N and which are substituted by $R^{11}$, $R^{12}$, $R^{13}$, $R^{14}$, and $R^{18}$, $R^6$, $R^{17}$; $R^{18}$;
$R^{11}$, $R^{12}$, $R^{13}$, $R^{14}$, and $R^{15}$, $R^{16}$, $R^{17}$, $R^{18}$ are independently H or selected from the group consisting of:

a) halide selected from Cl, Br, I; $R^{26}$H and OR$^{26}$H, wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; —(CH$_2$—O—CH$_2$)$_x$CH$_2$— wherein x is an integer from 1 to 50; and
b) $R^{26}$L and OR$^{26}$L, wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic $C_5$-, $C_6$- or $C_7$-aryl group which can be substituted by a linear or branched $C_1$-$C_6$ alkyl group; homocyclic and heterocyclic $C_5$-, $C_6$- or $C_7$-aromatic groups which can be substituted by a linear or branched $C_1$-$C_6$ alkyl group; —(CH$_2$—O—CH$_2$)$_x$CH$_2$— wherein x is an integer from 1 to 50; and L is a linker which can form a covalent bond with a targeting agent;
c) $R^{26}$U and OR$^{26}$U, wherein $R^{26}$ is a single bond; or wherein $R^{26}$ is selected from the group: linear and branched, non-cyclic and cyclic, substituted and unsubstituted $C_{1-20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic groups which can be substituted by a linear of branched $C_1$-$C_6$ alkyl group; —(CH$_2$—O—CH$_2$)$_x$CH$_2$— wherein x is an integer from 1 to 50; and U is a physiochemistry modifying group selected from the group consisting of: —(CH$_2$)$_m$SO$_3^-$, —(CH$_2$)$_m$C(O)O$^-$, —(CH$_2$)$_m$P(O)O$_2^{2-}$ —(CH$_2$)$_m$NR$_2$—(CH$_2$)$_m$NH$_2$; —(CH$_2$)$_m$NHR$^{32}$; (CH$_2$)$_m$NR$^{32}$R$^{33}$ wherein m is an integer from 0 to 6, and wherein $R^{32}$, $R^{33}$, is an alkyl group having from 1-12, preferably 1-8, more preferably 1-4 C atoms, in particular methyl or ethyl.

In a preferred embodiment of the application, $A^6$, $A^7$, $A^8$, $A^9$, and $A^{10}$, $A^{11}$, $A^{12}$, $A^{13}$ are C, N, $^+$N and either
A)
form a 6-membered aromatic ring which together with the pyrrolin derived ring to which they are attached form an indol or an azaindol system, which indol system can comprise a total of 1 N atoms and which azaindol system can comprise a total of 2 N atoms;
$R^3$, $R^4$, $R^5$, $R^6$, $R^7$, $R^8$ $R^9$ $R^{10}$ are independently H or selected from the group consisting of:
a) Halide selected from Cl, Br, I; $R^{25}$H and OR$^{25}$H, wherein $R^{25}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic groups which can be substituted by a linear or branched $C_1$-$C_4$ alkyl group; —(CH$_2$—O—CH$_2$)$_x$CH$_2$— wherein x is an integer from 1 to 20;
b) $R^{25}$L and OR$^{25}$L wherein $R^{25}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic groups which can be substituted by a linear or branched $C_1$-$C_4$ alkyl group; —($CH_2$—O—$CH_2$)$_x$$CH_2$— wherein x is an integer from 1 to 20; and L is a linker which can form a covalent bond with a targeting agent; and c) $R^{25}U$ and $OR^{25}U$, wherein $R^{25}$ is a single bond; or wherein $R^{25}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic groups which can be substituted by a linear or branched $C_1$-$C_4$ alkyl group; —($CH_2$—O—$CH_2$)$_x$$CH_2$— wherein x is an integer from 1 to 20; and U is a physiochemistry modifying group selected from the group consisting of: —($CH_2$)$_m$$SO_3^-$, —($CH_2$)$_m$C(O)O—($CH_2$)$_m$P(O)$O_2^{2-}$ —($CH_2$)$_m$$NR_2$—($CH_2$)$_m$$NH_2$; —($CH_2$)$_m$$NHR^{32}$; ($CH_2$)$_m$$NR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl; and wherein $OR^{25}H$, $OR^{25}L$ and $OR^{25}U$ are present only when O is attached to a C atom;

or

B)

form a 6-membered aromatic ring which together with the pyrrolin derived ring to which they are attached form an indol or an azaindol system, and to which indol or azaindol system a further 6-membered ring is annulated which is formed by at least two of the substituents $R^3$, $R^4$, $R^5$, $R^6$, or $R^7$, $R^8$ $R^9$ $R^{10}$, resulting in a trinuclear ring in which 1 or 2 C atoms may be replaced by N, and which are substituted by $R^{11}$, $R^{12}$, $R^{13}$, $R^{14}$, and $R^{15}$, $R^{16}$, $R^{17}$;

$R^{11}$, $R^{12}$, $R^{13}$, $R^{14}$, and $R^{15}$, $R^{16}$, $R^{17}$ are independently H or selected from the group consisting of:

a) Halide selected from Cl, Br, I; $R^{26}H$ and $OR^{26}H$, wherein $R^{26}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic 6-membered aromatic groups which can be substituted by a linear or branched $C_1$-$C_4$ alkyl group; —($CH_2$—O—$CH_2$)$_x$$CH_2$— wherein x is an integer from 1 to 20;

b) $R^{26}L$ and $OR^{26}L$ wherein $R^{26}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic $C_6$ aromatic rings which can be substituted by a linear or branched $C_1$-$C_4$ alkyl group; —($CH_2$—O—$CH_2$)$_x$$CH_2$— wherein x is an integer from 1 to 20; and L is a linker which can form a covalent bond with a targeting agent; and c) $R^{26}U$ and $OR^{26}U$, wherein $R^{26}$ is a single bond; or wherein $R^{26}$ is selected from the group: linear, non-cyclic, substituted and unsubstituted $C_{1-12}$ alkyl, wherein the said alkyl group can be single or multiple substituted by a homocyclic 6-membered aromatic group which can be substituted by a linear or branched $C_1$-$C_4$ alkyl group; homocyclic $C_6$ aromatic rings which can be substituted by a linear or branched $C_1$-$C_4$ alkyl group; —($CH_2$—O—$CH_2$)$_x$$CH_2$— wherein x is an integer from 1 to 20; and U is a physiochemistry modifying group selected from the group consisting of: —($CH_2$)$_m$$SO_3^-$, —($CH_2$)$_m$C(O)$O^-$, —($CH_2$)$_m$P(O)$O_2^{2-}$ —($CH_2$)$_m$$NR_2$ —($CH_2$)$_m$$NH_2$; —($CH_2$)$_m$$NHR^{32}$; ($CH_2$)$_m$$NR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl; and wherein $OR^{26}H$, $OR^{26}L$ and $OR^{26}U$ are present only when O is attached to a C atom;

In a more preferred embodiment of the application, $A_6$, $A_7$, $A_8$, $A_9$, and $A_{10}$, $A_{11}$, $A_{12}$, $A_{13}$ are C, N, or $^+$N, and either

A)

form a 6-membered aromatic ring which together with the pyrrolin derived ring to which they are attached form an indol or an azaindol system, which indol system can comprise a total of 1 N atoms and which azaindol system can comprise a total of 2 N atoms;

$R^3$, $R^4$, $R^5$, $R^6$, $R^7$, $R^8$ $R^9$ $R^{10}$ are independently H or selected from the group consisting of:

a) Halide selected from Cl, Br, I; $R^{25}H$ and $OR^{25}H$, wherein $R^{25}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic groups; —($CH_2$—O—$CH_2$)$_x$$CH_2$— wherein x is an integer from 1 to 12;

b) $R^{25}L$ and —$OR^{25}L$, wherein $R^{25}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic groups; —($CH_2$—O—$CH_2$)$_x$$CH_2$— wherein x is an integer from 1 to 12; and L is a linker which can form a covalent bond with a targeting agent; and c) $R^{25}U$ and —$OR^{25}U$, wherein $R^{25}$ is a single bond; or wherein $R^{25}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic group; —($CH_2$—O—$CH_2$)$_x$$CH_2$— wherein x is an integer from 1 to 12; and U is a physiochemistry modifying group selected from the group consisting of: —($CH_2$)$_m$$SO_3^-$; —($CH_2$)$_m$C(O)$O^-$, —($CH_2$)$_m$P(O)$O_2^{2-}$ —($CH_2$)$_m$$NR_2$ —($CH_2$)$_m$$NH_2$; —($CH_2$)$_m$$NHR^{32}$; ($CH_2$)$_m$$NR^{32}R^{33}$ wherein m is an integer from 0 to 6, and wherein $R^{32}$, $R^{33}$, is an alkyl group having from 1-12, preferably 1-8, more preferably 1-4 C atoms, in particular methyl or ethyl; and wherein $OR^{25}$, —$OR^{25}L$ and —$OR^{25}U$ are present only when O is attached to a C atom;

or

B)

$A_6$, $A_7$, $A_8$, $A_9$, and $A_{10}$, $A_{11}$, $A_{12}$, $A_{13}$ are C, N, or $^+$N and form a 6-membered aromatic ring which together with the pyrrolin derived ring to which they are attached form an indol or an azaindol system, and to which indol or azaindol system a further 6-membered ring is annulated which is formed by at least two of the substituents $R^3$, $R^4$, $R^5$, $R^6$, or $R^7$, $R^8$ $R^9$ $R^{10}$, resulting in a trinuclear ring in which 1 or 2 C atoms may be replaced by N, and which are substituted by $R^{11}$, $R^{12}$, $R^{13}$, $R^{14}$, and $R^{15}$, $R^{16}$, $R^{17}$;

$R^{11}$, $R^{12}$, $R^{13}$, $R^{14}$, and $R^{15}$, $R^{16}$, $R^{17}$ are independently H or selected from the group consisting of:

a) Halide selected from Cl, Br, I; $R^{26}H$ and $OR^{26}H$, wherein $R^{26}$ is selected from the group: linear, non-cyclic, substituted and unsubstituted $C_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 12;

b) R$^{26}$L and OR$^{26}$L, wherein R$^{26}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 12; and L is a linker which can form a covalent bond with a targeting agent; and c) R$^{26}$U, and OR$^{26}$U, wherein R$^{26}$ is a single bond; or wherein R$^{26}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 12; and U is a physiochemistry modifying group selected from the group consisting of: —(CH$_2$)$_m$SO$_3^-$, —(CH$_2$)$_m$C(O)O$^-$, —(CH$_2$)$_m$P(O)O$_2^{2-}$, —(CH$_2$)$_m$NR$_2$ —(CH$_2$)$_m$NH$_2$; —(CH$_2$)$_m$NHR$^{32}$; (CH$_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl and wherein OR$^{26}$H, OR$^{25}$L and OR$^{25}$U are present only when O is attached to a C atom;

In a still more preferred embodiment of the application, A$_6$, A$_7$, A$_8$, A$_9$, and A$_{10}$, A$_{11}$, A$_{12}$, A$_{13}$ are C, N, or $^+$N, and either.

A)
form a 6-membered aromatic ring which together with the pyrrolin derived ring to which they are attached form an indol or an azaindol system, which indol system can comprise a total of 1 N atoms and which azaindol system can comprise a total of 2 N atoms;

R$^3$, R$^4$, R$^5$, R$^6$, R$^7$, R$^8$ R$^9$ R$^{10}$ are independently H or selected from the group consisting of:

a) Halide selected from Cl, Br, I; R$^{25}$H and OR$^{25}$H, wherein R$^{25}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 6;

b) R$^{25}$L and —OR$^{25}$L, wherein R$^{25}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 6; and L is a linker which can form a covalent bond with a targeting agent; and c) R$^{25}$U and —OR$^{25}$U, wherein R$^{25}$ is a single bond; or wherein R$^{25}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic group; —(CH$_2$—O—CH$_2$)$_x$CH$_2$— wherein x is an integer from 1 to 6; and U is a physiochemistry modifying group selected from the group consisting of: —(CH$_2$)$_m$SO$_3^-$; —(CH$_2$)$_m$C(O)O$^-$, —(CH$_2$)$_m$P(O)O$_2^{2-}$ —(CH$_2$)$_m$NR$_2$ —(CH$_2$)$_m$NH$_2$; —(CH$_2$)$_m$NHR$^{32}$; (CH$_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl; and wherein OR$^{25}$H, —OR$^{25}$L and —OR$^{25}$U are present only when O is attached to a C atom;

or

B)
A$_6$, A$_7$, A$_8$, A$_9$, and A$_{10}$, A$_{11}$, A$_{12}$, A$_{13}$ are C, N, or $^+$N and form a 6-membered aromatic ring which together with the pyrrolin derived ring to which they are attached form an indol or an azaindol system, and to which indol or azaindol system a further 6-membered ring is annulated which is formed by at least two of the substituents R$^3$, R$^4$, R$^5$, R$^6$, or R$^7$, R$^8$ R$^9$ R$^{10}$, resulting in a trinuclear ring in which 1 or 2 C atoms may be replaced by N, and which are substituted by R$^{11}$, R$^{12}$, R$^{13}$, R$^{14}$, and R$^{15}$, R$^{16}$, R$^{17}$;

R$^{11}$, R$^{12}$, R$^{13}$, R$^{14}$, and R$^{15}$, R$^{16}$, R$^{17}$ are independently H or selected from the group consisting of:

a) Halide selected from Cl, Br, I; R$^{26}$H and OR$^{26}$H, wherein R$^{26}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 6;

b) R$^{26}$L and OR$^{26}$L, wherein R$^{26}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 6; and L is a linker which can form a covalent bond with a targeting agent; and c) R$^{26}$U, and OR$^{26}$U, wherein R$^{26}$ is a single bond; or wherein R$^{26}$ is selected from the group: linear, non-cyclic, substituted and unsubstituted C$_{1-8}$ alkyl, wherein the said alkyl group can be single substituted by a homocyclic 6-membered aromatic group; homocyclic 6-membered aromatic groups; —(CH$_2$—O—CH$_2$)$_x$CH$_2$— wherein x is an integer from 1 to 6; and U is a physiochemistry modifying group selected from the group consisting of: —(CH$_2$)$_m$SO$_3$, —(CH$_2$)$_m$C(O)O$^-$, —(CH$_2$)$_m$P(O)O$_2^{2-}$ —(CH$_2$)$_m$NR$_2$—(CH$_2$)$_m$NH$_2$; —(CH$_2$)$_m$NHR$^{32}$; (CH$_2$)$_m$NR$^{32}$R$^{33}$ wherein m is an integer from 0 to 6, and wherein R$^{32}$, R$^{33}$, is an alkyl group having from 1-12, preferably 1-8, more preferably 1-4 C atoms, in particular methyl or ethyl and wherein OR$^{26}$H, OR$^{25}$L and OR$^{25}$U are present only when O is attached to a C atom;

In the most general embodiment of the present application, X and Y are selected from the group consisting of: CR$^{29}$R$^{30}$, where R$^{29}$ and R$^{30}$ are each independently selected from H, unsubstituted and substituted linear or branched, cyclic or non-cyclic C$_1$-C$_6$ alkyl.

In a preferred embodiment of the application, X and Y are CR$^{29}$R$^{30}$, where R$^{29}$ and R$^{30}$ are each independently selected from H, unsubstituted and substituted non-cyclic linear and branched C$_1$-C$_4$ alkyl.

In a more preferred embodiment of the application, X and Y are CR$^{29}$R$^{30}$, where R$^{29}$ and R$^{30}$ are each independently selected from H, unsubstituted and substituted C$_1$-C$_2$ alkyl.

In the most general embodiment of the present application, E and E' are independently selected from H, unsubstituted and substituted linear or branched, cyclic or non-cyclic C$_1$-C$_6$ alkyl.

In a preferred embodiment of the application, E and E' are independently selected from H and unsubstituted and substituted linear or branched, cyclic or non-cyclic C$_1$-C$_4$ alkyl.

In a more preferred embodiment of the application, E and E' are independently selected from H and methyl and ethyl, preferably methyl.

The alkyleneoxy group —$(CH_2$—O—$CH_2)_x CH_2$— which is cited in the context with $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{23}$, $R_{24}$, $R_{25}$, $R_{26}$, has a length defined by x wherein x is an integer from 1 to 50, preferably from 1 to 20, more preferably from 1 to 12, still more preferably from 1 to 8, i.e. 1, 2, 3, 4, 5, 6, 7 or 8, or x may be an integer from 1 to 6.

In an embodiment, it is conceivable that in any alkyleneoxy group —$(CH_2$—O—$CH_2)_x CH_2$— which is cited in the context with $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{23}$, $R_{24}$, $R_{25}$, $R_{26}$, x is an integer from 1 to 2500.

$R^1$, $R^2$, $R^3$, $R^4$, $R^5$, $R^6$, $R^7$, $R$ $R^9$ $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, have the meanings as defined for the general, the preferred, the more preferred and the still more preferred embodiments for the formula A. In a further embodiment, and the case where the above residues can be H, an alkyl group, an aromatic group, an alkyleneoxy group, any of the above residues can have any of the following preferred meanings: H; a linear, non-cyclic, substituted and unsubstituted $C_{1-6}$ alkyl (methyl, ethyl, propyl, butyl, pentyl or hexyl) wherein the said alkyl group can be single substituted by a homocyclic 6-membered aromatic group, preferably phenyl; and homocyclic 6-membered aromatic groups, preferably phenyl, wherein preferably one of $R^{19}$ and $R^{20}$ is not aromatic in case of —$NR^{21}R^{12}$; —$(CH_2$—O—$CH_2)_x CH_2$— wherein x is an integer from 1 to 8, i.e. 1, 2, 3, 4, 5, 6, 7 or 8, or an integer from 1 to 6. For $R^{19}$ and $R^{20}$, and the case wherein $R^{19}$ and $R^{20}$, together with the N atom to which they are attached form a 5- or 6-membered heterocycle, this heterocycle can contain one further heteroatom selected from O and N, wherein the heterocycle can be substituted by a linear or branched, cyclic or non cyclic $C_1$-$C_6$ alkyl group, in particular 4-cyclohexylpiperazinyl Each of the above residues $R^1$-$R^{26}$ can have the above meanings in combination with any of the general, preferred, more preferred, still more preferred and most preferred meanings of any of the other substituents, i.e. that, for example, $R^{19}$ can have the above meaning, and any of the other substituents $R^1$-$R^{18}$ and $R^{20}$-$R^{26}$ can have the general, preferred, more preferred, still more preferred and most preferred meanings. This includes the cases that $R^{19}$ in —$OR^{19}$ is not H, in particular if the compound according to formula A does not contain at least 1 linker and/or 1 physiochemistry modifying group as defined in the context of the present application.

In the most general embodiment of the present application, linkers L are selected from the group consisting of: —$NH_2$, —OH, —SH, —$C(O)O^-$, —$C(O)Cl$, —$(CO)O(CO)R^{27}$, —$C(O)NHNH_2$, —$C(O)$, —$C(O)OR^{28}$, wherein $R^{27}$ is selected from the group consisting of H, alkyl and aryl; wherein $R^{28}$ is derived from substituted and unsubstituted N-hydroxysuccinimide, substituted and unsubstituted N-hydroxysulfosuccinimide, nitrophenol, fluorophenol each bound via —O—; azide $N_3^-$, —NCO, —NCS, —CHO, —$COCH_2I$, phosphoramidityl, phthalamidyl, maleimide, an alkyne group in particular —C≡$CR^{31}$ wherein $R^{31}$ is H or a $C_1$-$C_8$ alkyl group, sulfonate esters, alkyl halides, acyl halides, propargylglycine, a pentanoyl group, in particular pentanoyl chloride, pentynoic acid, propargylic acid, 6-aminobenzo[d]thiazole-2-carbonitrile, 6-hydroxybenzo[d]thiazole-2-carbonitrile, a 1,2-aminothiol group, in particular L-cysteine or D-cysteine.

In the most general embodiment of the present application, L has the following meaning: L is selected from the group consisting of: —$NH_2$, —OH, —SH, —$C(O)O^-$, —$C(O)Cl$, —$(CO)O(CO)R^{27}$, —$C(O)NHNH_2$, —$C(O)$ —$C(O)OR^{28}$, wherein $R^{27}$ is selected from the group consisting of H, alkyl and aryl; wherein $R^{28}$ is derived from substituted and unsubstituted N-hydroxysuccinimide, substituted and unsubstituted N-hydroxysulfosuccinimide, nitrophenol, fluorophenol each bound via —O—; azide $N_3^-$, —NCO, —NCS, —CHO, —$COCH_2I$, phosphoramidityl, phthalamidyl, maleimide, an alkyne group in particular —C≡$CR^{31}$ wherein $R^{31}$ is H or a $C_1$-$C_8$ alkyl group, preferably H or a $C_1$-$C_4$ alkyl group, sulfonate esters, alkyl halides, acyl halides, propargylglycine, a pentanoyl group, in particular pentanoyl chloride, pentynoic acid, propargylic acid, 6-aminobenzo[d]thiazole-2-carbonitrile, 6-hydroxybenzo[d]thiazole-2-carbonitrile, a 1,2-aminothiol group, in particular L-cysteine or D-cysteine, and the substituents Q, Z, E', E, X, Y, $R^1$-$R^{26}$ and $R^{29}$-$R^{33}$ and $A^6$-$A^{13}$ have the general, the preferred, the more preferred, the still more preferred or the most preferred embodiments as defined above. This includes the cases that $R^{19}$ in —$OR^{19}$ is not H, in particular if the compound according to formula A does not contain at least 1 linker and/or 1 physiochemistry modifying group as defined in the context of the present application.

In a preferred embodiment of the present application, L has the following meaning: L is selected from the group consisting of: —$NH_2$, —OH, —SH, —$C(O)O^-$, —$C(O)Cl$, —$C(O)OR^{28}$, wherein $R^{28}$ is derived from substituted and unsubstituted N-hydroxysuccinimide, substituted and unsubstituted N-hydroxysulfosuccinimide, nitrophenol, fluorophenol each bound via —O—; azide $N_3^-$, —NCO, —NCS, —CHO, phosphoramidityl, phthalamidyl, maleimide, an alkyne group in particular —C≡$CR^{31}$ wherein $R^{31}$ is H or a $C_1$-$C_8$ alkyl group, preferably H or a $C_1$-$C_4$ alkyl group, sulfonate esters, alkyl halides, acyl halides, pentynoic acid, propargylic acid, 6-aminobenzo[d]thiazole-2-carbonitrile, 6-hydroxybenzo[d]thiazole-2-carbonitrile, a 1,2-aminothiol group, in particular L-cysteine or D-cysteine, and the substituents Q, Z, E', E, X, Y, $R^1$-$R^2$ and $R^{29}$-$R^{33}$ and $A^6$-$A^{13}$ have the general, the preferred, the more preferred, the still more preferred or the most preferred embodiments as defined above. This includes the cases that $R^{19}$ in —$OR^{19}$ is not H, in particular if the compound according to formula A does not contain at least 1 linker and/or 1 physiochemistry modifying group as defined in the context of the present application.

In a more preferred embodiment of the present application, L has the following meaning: L is selected from the group consisting of: —OH, —SH, —$C(O)O^-$, —$C(O)OR^{28}$, wherein $R^{28}$ is derived from substituted and unsubstituted N-hydroxysuccinimide, substituted and unsubstituted N-hydroxysulfosuccinimide, nitrophenol, fluorophenol each bound via —O—; azide $N_3^-$, —NCS, —CHO, phosphoramidityl, phthalamidyl, maleimide, an alkyne group in particular —C≡$CR^{31}$ wherein $R^{31}$ is H or a $C_1$-$C_8$ alkyl group, preferably H or a $C_1$-$C_4$ alkyl group, sulfonate esters, alkyl halides, acyl halides, 6-aminobenzo[d]thiazole-2-carbonitrile, 6-hydroxybenzo[d]thiazole-2-carbonitrile, a 1,2-aminothiol group, L-cysteine, and the substituents Q, Z, E', E, X, Y, $R^1$-$R^{26}$ and $R^{29}$-$R^{33}$ and $A^6$-$A^{13}$ have the general, the preferred, the more preferred, the still more preferred or the most preferred embodiments as defined above. This includes the cases that $R^{19}$ in —$OR^{19}$ is not H, in particular if the compound according to formula A does not contain at least 1 linker and/or 1 physiochemistry modifying group as defined in the context of the present application.

With respect to the dyes of the application according to formula A, any of substituents Q, Z, E', E, X, Y, $R^1$-$R^{33}$, $A^6$-$A^{13}$ and L can have the general, the preferred, the more preferred or the still more preferred meaning, whereas any other of the substituents Q, Z, E', E, X, Y, $R^1$-$R^{33}$, $A^6$-$A^{13}$ and L as defined above can have any of the meanings as defined for the general, the preferred, the more preferred or the still more preferred embodiments. This includes the cases that $R^{19}$ in —$OR^{19}$ is not H, in particular if the compound according to formula A does not contain at least 1 linker and/or 1 physiochemistry modifying group as defined in the context of the present application. As an example, Q can have the still more preferred meaning, and any of the substituents Q, Z, E', E, X, Y, $R^1$-$R^{33}$, $A^6$-$A^{13}$ and L can have the general, the preferred, the more preferred, the still more preferred or the most preferred meaning. As another example, L can have the more preferred meaning, and any of the substituents Q, Z, E', E, X, Y, $R^1$-$R^{33}$, $A^6$-$A^{13}$ and L can have the general, the preferred, the more preferred, the still more preferred or the most preferred meaning.

In a more preferred embodiment of the application, $A^6$, $A^7$, $A^8$, $A^9$, and $A^{10}$, $A^{11}$, $A^{12}$, $A^{13}$ are such that they form together with the pyrrolin derived ring to which they are attached an aromatic system selected from

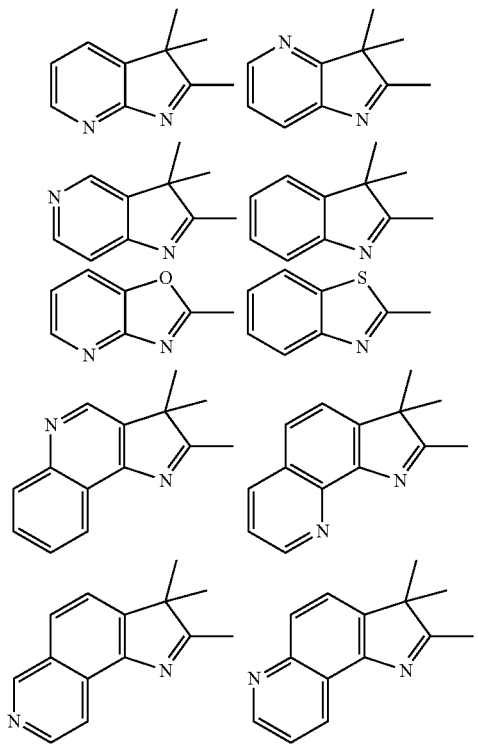

In the most general embodiment, X and Y are selected from the group consisting of: $CR^{29}R^{30}$, where $R^{29}$ and $R^{30}$ are each independently selected from H, unsubstituted and substituted linear or branched, cyclic or non-cyclic $C_1$-$C_6$ alkyl, and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In a preferred embodiment, X and Y are selected from the group consisting of: $CR^{29}R^{30}$, where $R^{29}$ and $R^{30}$ are each independently selected from H, unsubstituted and substituted non-cyclic linear and branched $C_1$-$C_4$ alkyl, and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In a more preferred embodiment, X and Y are $CR^{29}R^{30}$, where $R^{29}$ and $R^{30}$ are each independently selected from H, unsubstituted and substituted non-cyclic linear and branched $C_1$-$C_4$ alkyl, and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In a still more preferred embodiment, X and Y are $CR^{29}R^{30}$, where $R^{29}$ and $R^{30}$ are each independently selected from H and methyl and ethyl, preferably methyl, and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In the most preferred embodiment, X and Y are $CR^{29}R^{30}$, where $R^{29}$ and $R^{30}$ are each methyl, and the substituents Q, Z, E', E, X, Y, $R^1$-$R^{33}$ and $A^6$-$A^{13}$ and L have the general, the preferred the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In the most general embodiment, E and E' are independently selected from H, unsubstituted and substituted linear or branched, cyclic or non-cyclic $C_1$-$C_6$ alkyl, and the substituents Q, Z, E', E, X, Y, $R^1$-$R^{33}$ and $A^6$-$A^{13}$ and L have the general, the preferred the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In a preferred embodiment, E and E' are independently selected from H and linear and branched $C_1$-$C_6$ alkyl and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

In a more preferred embodiment, E and E' are independently selected from H and methyl and ethyl. In the most preferred embodiment, E and E' are both methyl, and the substituents Q, Z, E', E, X, Y, $R^1$-$R^{33}$ and $A^6$-$A^{13}$ and L have the general, the preferred, the more preferred or the still more preferred meanings as defined above. This includes the cases that $R^{19}$ in —$OR^{19}$ is not H, in particular if the compound according to formula A does not contain at least 1 linker and/or 1 physiochemistry modifying group as defined in the context of the present application.

Preferable points of attachment for the linkers are the nitrogen on (i) the heterocycles of the dyes according to formula A, through for example $R^{17}$ and/or $R^{18}$, $R^1$ and/or $R^2$; (ii) through any of the A6-A9 atoms when at least one of them is N; Preferably, the dyes and the targeting agents are linked through the N of the heterocycles, most preferably through $R^{17}$ and/or $R^{18}$, $R^1$ and/or $R^2$ or $R^1$ and/or $R^7$ if $A_6$ and/or $A_{10}$ are nitrogen.

In a preferred embodiment, the dyes of the application have 1, 2, 3 or 4 linkers, preferably 1, 2 or 3 linkers, more preferably 1 or 2 linkers, in particular 2 linkers. In general, the linkers are attached to the basic structure of the dye via a spacer group, which is thus preferred. It is also preferred to attach the linkers in the following positions: position $R^1$, $R^2$, or $R^1$ and $R^2$; in position $R^{17}$, $R^{18}$, or $R^{17}$ and $R^{18}$; or, if the ring annulated to the pyrrol structure contains a N atom, to this N atom, e.g., in positions $R^3$, $R^4$, $R^7$ and/or $R^6$, preferably $R^3$ and/or $R^7$.

The above-cited general, preferred, preferred, more preferred and still more preferred embodiments for the respective substituents also apply with respect to the below formulae B and C showing a bioconjugate imaging agent, respectively the precursor of a bioconjugate imaging agent, of the application.

The optical properties modulating group will in general be incorporated in the substituent Q.

The physiochemical properties modulating group can be attached to any position in the dye basic structure, in principle. However, the positions laid out above will often be occupied by linkers or the optical properties modulating group. As a consequence, the physiochemical properties modulating group will often be attached in position $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ and/or $R_{17}$. The number of physiochemical properties modulators is preferably 1, 2 or 3, more preferably 1 or 2. A physiochemical properties modulator can be attached with or without a spacer group, often without a spacer group.

Formula B and formula C each depict one embodiment of the variant denoted B in the definition of formula A. In formula B, Q, Z, E, E', X, Y, and $A^6$-$A^{15}$ have the meanings as set forth for formula A, including the general, the preferred, the more preferred and the still more preferred embodiments, including the cases that $R^{19}$ in —$OR^9$ is not H, in particular if the compound according to formula A does not contain at least 1 linker and/or 1 physiochemistry modifying group as defined in the context of the present application; $R^1$-$R^{14}$ and $R^1$-$R^{16}$, respectively, have the meanings as set forth for formula B, including the general, the preferred, the more preferred and the still more preferred embodiments, including the cases that $R^{19}$ in —$OR^9$ is not H, in particular if the compound according to formula A does not contain at least 1 linker and/or 1 physiochemistry modifying group as defined in the context of the present application, except that a further 6-membered ring which is formed by at least two of the substituents $R^3$, $R^4$, $R^5$, $R^6$, or $R^7$, $R^8$ $R^9$ $R^{10}$, resulting in a trinuclear ring which cannot be annulated. In formula C, Q, Z, E, E', X, Y, and $A^1$-$A^{19}$ have the meanings as set forth for formula A, including the general, the preferred, the more preferred and the still more preferred embodiments, including the cases that $R^9$ in —$OR^{19}$ is not H, in particular if the compound according to formula A does not contain at least 1 linker and/or 1 physiochemistry modifying group as defined in the context of the present application; $R^1$-$R^{17}$ have the meanings as set forth for formula A, including the general, the preferred, the more preferred and the still more preferred embodiments, including the cases that $R^{19}$ in —$OR^{19}$ is not H, in particular if the compound according to formula A does not contain at least 1 linker and/or 1 physiochemistry modifying group as defined in the context of the present application, except that a further 6-membered ring which is formed by at least two of the substituents $R^3$, $R^4$, $R^5$, $R^6$, or $R^7$, $R^8$ $R^9$ $R^{10}$, resulting in a trinuclear ring which cannot be annulated.

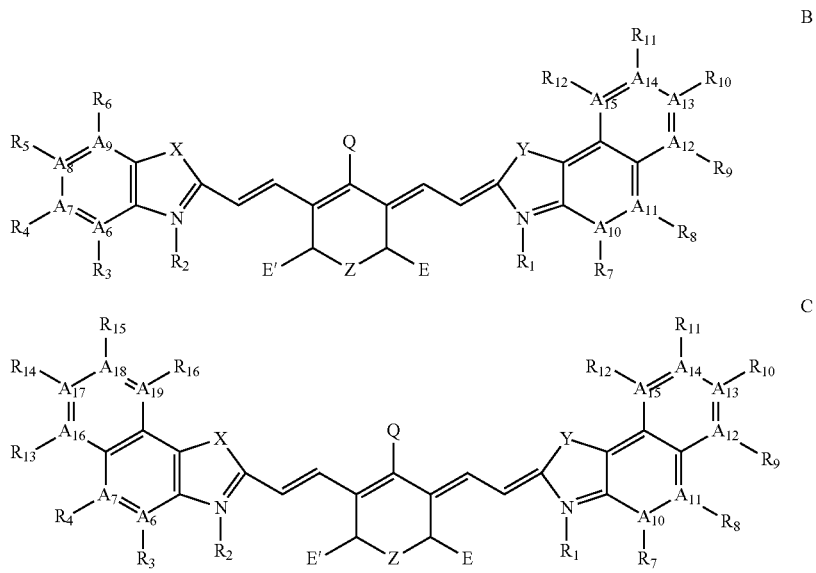

In a further aspect of the present application, the dyes according to the application are asymmetrical in the sense that they do not have a C2 symmetry. One example for a group of such asymmetric molecules is B. Asymmetry can also be caused by one or more substituents (linkers, optical properties modulating groups and physiochemistry properties modulating groups) which are present only on one side of the molecule (i.e. on one side of the axe/defined by Q and Z).

In another aspect, the application provides a bioconjugate imaging agent comprising a fluorescent dye of the application linked to at least one targeting agent, see for example formula D below. The targeting agent is, in general, attached to the dye via a linking group, i.e. a group that is formed in a reaction with a complementary reactive group on the targeting agent. In an embodiment of the application, the targeting agent may comprise an "anchor group" (having been attached to it prior to the reaction with the dye), which anchor group comprises functional groups capable of reacting with the linker functional group, or of more easily reacting with the linker functional group than the functional groups present on the targeting agent. Non-limiting examples of anchor groups comprise amino acids and bifunctional polyethylene glycols. In the bioconjugate imaging agents of the invention, the case that $R^{19}$ in —$OR^{19}$ is not H does not apply. Precise examples will be cited later on.

A skilled artisan would understand that the net charge of a compound should be zero. So when a compound is depicted to have one or more negative or positive ions, counter-ions, even if not shown, exist to make the net charge of the compound zero.

In another aspect, the subject matter of the present application provides a use of the fluorescent dyes of the application as pH sensors.

In another aspect, the fluorescent dyes can be used as a contrast reagents for optical acoustic/optoacoustic and for "shortwave infrared II (SWIR-II)" range (wavelengths from 0.9 to 1.7 microns) that has only recently been made practical by the development of Indium Gallium Arsenide (InGaAs) detectors.

In another aspect, the application provides a compound that can be used as both fluorescent probe (novel aza-cyanine dye) linked to targeted moiety such as fatty acid and a probe that can be detected with another imaging modality such as 19F-MRI. This can be accomplished by obtaining a compound as disclosed herein which comprises both a fatty acid moiety and a fluorine moiety.

In another aspect, the application provides an in vitro imaging method, the method comprising
(a) contacting a sample with the bioconjugate imaging agent of the present subject matter;
(b) allowing the agent to bind to a biological target;
(c) optionally removing unbound agent; and
(d) detecting signal emitted from the agent thereby to determine whether the agent has been activated by or bound to the biological target.

In another aspect, the application provides the bioconjugate imaging agent of the application for use in a method of in vivo imaging, the method comprising:
(a) administering to a subject the bioconjugate imaging agent of the application;
(b) allowing the agent to distribute within the subject; and
(c) detecting a signal emitted by the bioconjugate imaging agent.

In another aspect, the application provides the bioconjugate imaging agent of the application for use in a method of in vivo optical imaging, the method comprising:

(a) administering to a subject a bioconjugate imaging agent of the application;
(b) allowing the agent to distribute within the subject;
(c) exposing the subject to light of a wavelength absorbable by the fluorescent dye; and
(d) detecting a signal emitted by the agent.

As used herein, the term "effective amount" refers to the amount of a compound sufficient to effect beneficial or desired results. Unless stated otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and new born individuals are intended to be covered. The term 'preclinical' usually is used to describe tests carried out on such laboratory animals predominantly on rodents.

As used herein, the terms "patient" and "subject" refer to organisms to be subjected to, or treated by, the methods of the subject matter of the present application. Such organisms preferably include, but are not limited to, mammals (e.g., murines, simians, equines, bovines, porcines, canines, felines, and the like), and most preferably includes humans. The term 'clinical' is usually tests carried out on larger vertebrate mammals and predominantly on humans.

"Alkyne" refers to straight chain or branched hydrocarbon groups having from 2 to 10 carbon atoms, e.g., from 2 to 4 carbon atoms; and having at least 1, e.g., from 1 to 2, sites of double or triple bond unsaturation. This term includes, by way of example, bi-vinyl, allyl, and but-3-en-1-yl. Included within this term are the cis and trans isomers or mixtures of these isomers.

"Haloalkyl" or "alkyl halide" refers to a substituted alkyl group, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

"Acyl" refers to the groups H—C(O)—, alkyl-C(O)—, substituted alkyl-C(O)—, "Carboxyl," "carboxy" or "carboxylate" refers to —$CO_2H$ or salts thereof derived from $CO_2^-$ "Heteroaryl" refers to an aromatic group of from 2 to 15 carbon atoms, such as from 3 to 10 carbon atoms and 1 to 10 heteroatoms selected from the group consisting of oxygen, nitrogen (referred to as aza in the application) and sulfur within the ring. Such heteroaryl groups can have a single ring (such as, pyrrole, pyridyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen (referred to as aza in application), sulfur, or oxygen, The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3', 5,5'-tetraiodothyronine. Modified or unusual amino acids which can be used to practice the subject matter of the application include, but are not limited to, those derived from post translational modifications like phosphorylation and glycation, such as phosphoserine, phosphothreonine, phosphotyrosine, and others such as hydroxyproline, gamma-carboxyglutamate; hippuric acid, indole acetic acid, statine, penicillamine, ornithine, citruline and selenocysteine, D-amino acids, hydroxylysine, dehydroalanine, pyrrolysine, 2-aminoisobutyric acid, gamma aminobutyric acid, 5-hydroxytryptophan, S-adenosyl methionine, S-adenosyl homocysteine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methyl-aminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid. Protected amino acids are also covered and representative protecting groups such as carbobenzyloxy, (CbZ) at the amino terminus and others can be found and are known to those skilled in the art (See for example, Greene, T. W.; Wuts, P. G. M., *Protecting Groups In Organic Synthesis*, 3rd edition, John Wiley & Sons, Inc., New York (1999)

The term "peptide" describes a sequence of 2 to 50 amino acids, preferably 3 to 20 amino acids or peptidyl residues. The sequence may be linear, branched, cyclic such as resulting from intramolecular disulfide bonds from cysteinyl residues. Peptide sequences specifically recited herein are written or drawn out with the amino terminus on the left and the carboxy terminus on the right. D and L amino acids are both covered as well as protective groups like acetyl, acetoxymethyl, carbobenzyloxy, tert butyloxy and post translational modifications like methylation of arginine and lysine, phosphorylation and glycation of serine, threonine and tyrosine "OH" groups are also covered.

As used herein, a "pseudopeptide" or "peptidomimetic" is a compound which mimics the structure of an amino acid residue or a peptide, for example, by using linkers other than via amide linkages (pseudopeptide bonds) and/or by using non-amino acid substituents and/or a modified amino acid residue. A "pseudopeptide residue" means that portion of a pseudopeptide or peptidomimetic that is present in a peptide.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following conventional three-letter amino acid abbreviations are used herein: Ala=alanine; Aca=aminocaproic acid, Ahx=6-aminohexanoic acid, Arg=arginine; Asn=asparagines; Asp=aspartic acid; Cha=cyclohexylalanine; Cit=citrulline; Cys=cysteine; Dap=diaminopropionic acid; Gln=glutamine; Glu=glutamic acid; Gly=glycine; H is =histidine; Ile=isolenucine; Leu=leucine; Lys=lysine; Met=methionine; NaI=naphthylalanine; Nle=norleucine; Orn=ornithine; Phe=phenylalanine; Phg=phenylglycine; Pro=praline; Sar=sarcosine; Ser=serine; Thi=Thienylalanine; Thr=threonine; Trp=tryptophan; Tyr=tyrosine; and Val=valine. Use of the prefix D-indicates the D-isomer of that amino acid; for example D-lysine is represented as D-Lys.

The term "saccharide" refers to a sugar or other carbohydrate that could be derived or can be the result from the reduction and/or oxidation of a simple sugar. The saccharide can be a C6-polyhydroxy compound, with 2-6 hydroxy groups per unit, which could by cyclic or acyclic. Saccharides include inositols and their phosphorylated derivatives, Saccharides include simple sugars, i.e. C6 units (monomeric sugars) and their derivatives, as well as polysaccharides with two or more monosaccharide residues. The saccharide can include protecting groups on the hydroxyl groups, as described above in the definition of amino acids. The hydroxyl groups of the saccharide can be replaced with one or more halo or amino groups. Additionally, one or more of the carbon atoms can be oxidized, e.g., to keto or carboxyl groups. The term glycation and glycosylation refer to the addition of saccharide molecules to appropriate residues such as hydroxyl and amino groups in peptides and proteins.

As is known to those of skill in the art, "salts" of the compounds of the present application may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, formic, benzoic, malonic, naphthalene-2-sulfonic, benzenesulfonic acid, and the like. Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Throughout the description, where compositions and kits are described as having, including, or comprising specific components, or where processes and methods are described as having, including, or comprising specific steps, it is contemplated that, additionally, there are compositions and kits of the present application that consist essentially of, or consist of, the recited components, and that there are processes and methods according to the present application that consist essentially of, or consist of, the recited processing steps.

Certain compounds described herein may exist in particular geometric or stereoisomeric forms. The present application contemplates all such compounds, including cis- and trans-isomers, R- and S-enantiomers, diastereomers, (D)-isomers, (L)-isomers, the racemic mixtures thereof, and other mixtures thereof, as falling within the scope of the application. Additional asymmetric carbon atoms may be present in a substituent such as an alkyl group. All such isomers, as well as mixtures thereof, are intended to be included in this application.

The cyanine dyes derived from polymethine linked heterocycles such as Indocyanine Green (ICG) imaging agents are suitable chemicals which are used to provide the contrast or signal in fluorescence and that is detectable by optical imaging techniques. The use of NIR fluorescent cyanine dyes for in vivo imaging started with the dye indocyanine green (ICG) because of its ready availability with good purity plus it had desirable NIR optical properties. Importantly, this is the only known NIR fluorescent dye approved by the US Food and Drug Administration (FDA) for monitoring cardiac output, hepatic function, and retinal angiography in humans. For optical imaging, various studies have shown that ICG accumulates in tumors through enhanced permeability and retention effects and it has also successfully been used to image tumors and lymph nodes. Many ICG derivatives or analogues have been designed and synthesized for different purposes, such as improving aqueous solubility or adding reactive functions for further bio-conjugation. For example, a hydrophilic glucamide-derivatized indocyanine exhibited increased hydrophilicity and showed improved tumor-to-normal tissue contrast relative to ICG. A new class of fluorophores that incorporate multiple nitrogens exemplified by PPCy dyes has been synthesized via the reaction of diketopyrrolpyrrole with heteroarylacetonitriles. Although classified as cyanine dyes they are structurally different from the cyanine dyes. However they exhibit features for optical imaging, such as high quantum yields (>0.50), low photobleaching, and long fluorescence lifetimes (2.5 to 3.8 ns).

The application provides cyanine compounds that incorporate additional nitrogen atoms, also referred to as aza, in the heterocycles bridging the polymethine as well as the polymethine linkage for appending additional charges and linkers as modifications that are used to modulate photochemical, biological, solubility as well as amenable to other modes of interrogation such as optoaccoustic methods. The incorporation of aza moiety (nitrogen) in the additional benzene rings besides the indole nitrogen also enables under appropriate substitution pH sensitive compounds. A ratiometric measurement of the spectroscopic behavior of dyes that are differentially sensitive to acidic or basic environments can be exploited to indicate pH values. Advantages of ratiometric methods are accrued because several parameters such as path length, local probe concentration, photobleaching and leakage from the cells are not important. For these reasons, stable cyanine dyes are needed for use in labeling biomolecules as well as in vivo imaging for the diagnosis and prognosis of diseases such as cancer, infectious disease imaging and metabolic activity. Such compositions and methods would aid in the analysis of responses to various therapies. The present subject matter satisfies these and other needs.

The application provides novel class of fluorescent dyes belonging to the cyanine family (aza cyanine dyes), their derivatives for bioconjugation and imaging agents derived there from. The fluorescent dyes serve as labels and comprise aza substitution in the heterocycles as well as the bridging polymethine linkage.

Synthesis

The fluorescent dyes of the application generally comprise two to eight nitrogen atoms in the heterocycles as well as the polymethine linkage connecting the heterocycles. The nitrogen substitution instead of the CH moiety provides a heteroatom that improves aqueous solubility, enables easier appending of groups through alkylation of the said nitrogen, reduces the π stacking that lowers the quantum yield in the corresponding CH analogues. The nitrogen henceforth referred to as aza provide charge based derivatives that can be tuned to the biological specificity. Prior art with azabenzolium cyanines developed as nucleic acid intercalating agents has also shown a concomitant shift in wavelength to the red compared to their CH analogues (Scheme 1).

Scheme 1 -Typical NIR dye synthesis

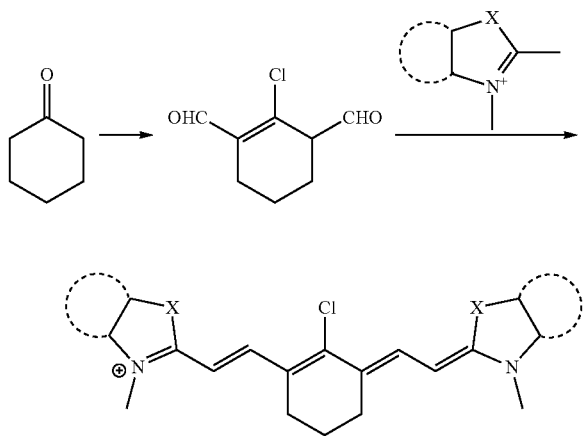

Optical techniques that need designer molecular probes for detecting and tracking molecular processes or biomarkers of interest are facilitated by the availability of the aza moiety for appending different chemical modifiers. The development of new molecular probes has attracted the attention of researchers for many decades because of their diverse applications in chemistry, biology, and medicine. In recent years, optical imaging of molecular processes in living organisms has stimulated interest in the development of numerous molecular probes for use in the near-infrared (NIR) region (700-900 nm) and there are about 6100 and more in the MICAD database.

NIR molecular probes offer two major advantages over those that emit at visible wavelengths. First, biological tissues have lower absorption of NIR light than visible light. This allows NIR light to penetrate deeper into tissue than light at visible wavelengths, thus enabling the assessment of information from deeper structures. Second, less autofluorescence is present at the NIR compared to visible wavelengths, enabling higher signal-to-background ratios. Molecular probes that emit light in the NIR region are expected to be suitable for in vivo imaging and with the substitution of the CH moiety with N provides structurally similar dyes with different photophysical, photochemical and biocompatibility that are superior to the carbon analogues. Prior art derivatives are usually derived from benzindolelinium and naphthindolelinium derivatives with the bridging methine linkages usually all carbon (Scheme 1), the current application is from pyridoindolelinium and quinolinoindolinium derivatives that contain within the bridge a hetero atom preferably nitrogen (Scheme 2).

Scheme 2 - Aza in heterocycle and methine chain (compounds of the application)

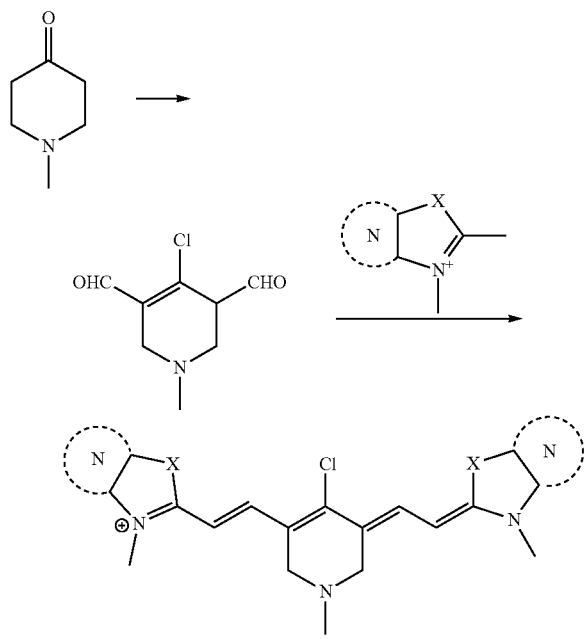

In general, the compounds as described herein can be synthesized as follows. First, a quaternized heterocycle (per example pyridoindolelinium and quinolinoindolinium) is prepared by attaching a solubilizing groups or linkers. The quaternized heterocylic species is then coupled with a bisimine (bridge), which is an electrophilic reagent, obtained from Vilsmeier-Haack-Amold formylation of a piperidone derivative. A substituent is then attached to the nitrogen atom in the central heterocycle (bridge), the resulting central heterocycle formed is then quaternized. The bisimine is reacted with a different quaternary heterocycle with the final result of a symmetric or asymmetric compound.

Bisimines are displayed in the formula below and can also be described as PhNH-PMB-CH=NHPh.HCl.

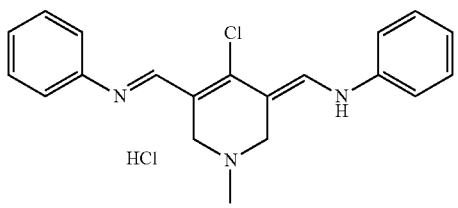 [SMILES: CN1CC(/C=N/c2ccccc2)=C(Cl)C(=C/Nc2ccccc2)/C1 ; Cl]

In some embodiments, a salt of the fluorescent dyes of the application can be formed by any suitable counter ion. In some preferred embodiments, the counter ion selected from the group comprising but are not limited to chloride, bromide, iodide, triflate, tosylate, formate, acetate, trifluoro acetate, benzoate, oxalate, cyanide, cyanate, thiocyanate, hydrogen carbonate, carbonate, arsenate, arsenite, phosphate, hydrogen phosphate, dihydrogen phosphate, nitrite, nitrate, sulfate, hydrogen sulfate, thiosulfate, sulphite, perchlorate, chlorate, bromate, iodate, chlorite, hypochlorite, hypobromite, chromate, dichromate, permanganate, hexafluorophophate, tetraphenylborate, tetrafluoroborate.

In some preferred embodiments, the fluorescent dyes of the application absorb in the region of 530 nm to 880 nm and have fluorescence emission in the region of 540-900 nm when excited in between 530-880 nm.

In further embodiments, Q is Cl.

When the indolelinium heterocycle, with a 6,5 fused system, is not fused to additional rings and with one double bond, the resulting "indocarbocyanine" dye typically exhibits an absorption maximum near 550 nm. Where two double bonds are present, the "indodicarbocyanines" typically absorb maximally near 650 nm. The "indotricarbocyanine" dyes, where three double bonds are present, typically absorbs maximally near 750 nm. The addition of an extra ring as in 6,6,5 or benzindolenium heterocycle adds about 15-20 nm to the absorption of the base indolenium described previously. Azindocyanine green derivatives the preferred dye of the application have three double bonds and two benzindolenium heterocycles bridging the polymethine chain, typically absorption ranges from 750-850 nm depending on additional substituents referred to as chemical modifiers (CM), solvent polarity and pH.

The azacyanine dyes have a high solubility in PBS buffer pH 7.4. This is more than 20 mM greater than commercial dyes such as ICG, 1.2 mM (1 mg/mL) in water, but it is not readily soluble in saline.

In some embodiments, the fluorescent dye of the application is a compound of formula E:

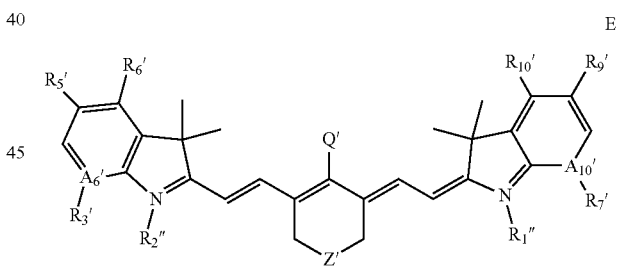

E wherein

Q' is Cl, Br, I, —$OR^{19'}$, —$SR^{19'}$, or —$NR^{19'}R^{20'}$, $R^{19'}$ and $R^{20'}$ are independently H or phenyl, wherein the phenyl can be substituted by $C_{1-6}$ alkyl, $C_{1-6}$ fluroalkyl, —$(CH_2)_{0-3}SO_3^-$, —$(CH_2)_{0-3}SO_3$— alkali metal, —$(CH_2)_{0-3}COOH$, —$(CH_2)_{0-3}COO$-alkali metal, —NCO, —NCS, —$(CH_2)_{0-3}NH_2$ or —$(CH_2)_{0-3}N^+H_3$, or $R^{19'}$ and $R^{20'}$ together with the nitrogen to which they are attached form a 5- or 6-membered heterocycle optionally containing one further heteroatom selected from O and N, wherein the heterocycle can be substituted by a linear or branched, cyclic or non-cyclic $Cl_6$ alkyl group;

$R_{1'''}$, $R_{2'''}$, $R_{3'}$, and $R_{7'}$ are independently absent, H, $C_{1-6}$ alkyl, or —$(CH_2)_{1-6}$ L', wherein L' is —COOH, —COO—

C$_{1-6}$alkyl, —NH2, —OH, —SH, —COO$^-$, SO$_3^-$, SO3-alkali metal, —COO-succinimide, —COO-sulfosuccininide, —NCO, —NCS, —COO-nitrophenyl, or —COO-fluorophenyl;

A$_{6'}$ and A$_{10'}$ are independently C, N, or N$^+$;

R$_{5'}$, R$_{6'}$, R$_{9'}$, and R$_{10'}$ are independently H, or R$_{5'}$ and R$_{6'}$ together with the carbons to which they are attached form a benzene, or R$_{9'}$ and R$_{10'}$ together with the carbons to which they are attached form a benzene, wherein the benzene can be substituted by —(CH$_2$)$_{0-3}$ SO$_3^-$, —(CH$_2$)$_{0-3}$ SO$_3$-alkali metal, —(CH$_2$)$_{0-3}$COOH, or —(CH$_2$)$_{0-3}$COO-alkali metal;

Z' is NR$^{17'}$ or $^+$NR$^{17'}$R$^{18'}$, wherein R$^{17'}$ and R$^{18'}$ are independently C$_{1-6}$ alkyl, —(CH$_2$)$_{1-3}$ ethynyl, —(CH$_2$)$_{1-6}$ L', wherein L' is —COOH, —COO—C$_{1-6}$alkyl, —NH$_2$, —OH, —SH, —COO$^-$, SO$_3^-$, SO$_3$-alkali metal, —COO-succinimide, —COO-sulfosuccininide, —COO-nitrophenyl, or —COO-fluorophenyl.

In some embodiments, a probe for multimodality imaging has a structure of the following formula F:

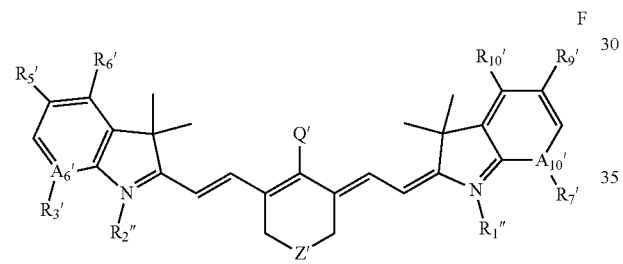

F

Wherein R$_{1''}$, R$_{2''}$, R$_{3'}$, R$_{5'}$, R$_{6'}$, R$_{7'}$, R$_{9'}$, R$_{10'}$, A$_{6'}$, A$_{10'}$, and Z' are defined as for formula E, Q' is —OR$^{19'}$ or —SR$^{19'}$, wherein R$^{19'}$ is phenyl substituted by —NHCSNH—R''' or —NHCONH—R''', wherein R''' is a phenyl or heterocyclic 5-, 6-, or 7-membered aromatic substituted by —(CH$_2$)$_{10-30}$ COOH and at least one group selected from F and C$_{1-6}$ fluoroalkyl.

In some embodiments, the fluorescent dyes of the application are selected from the group comprising

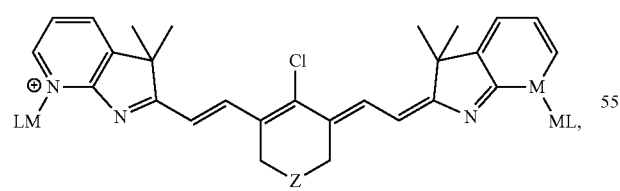

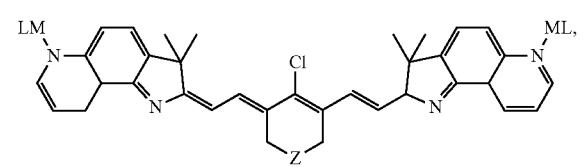

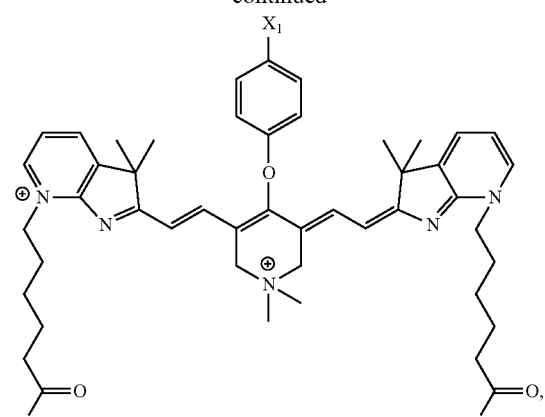

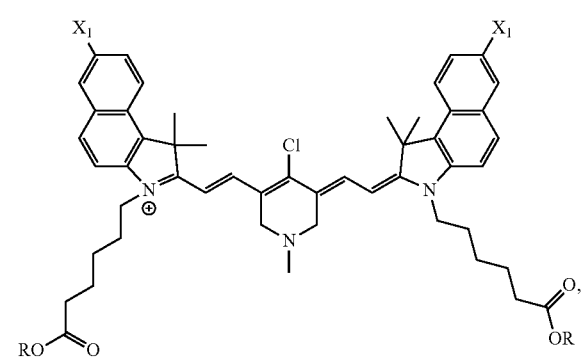

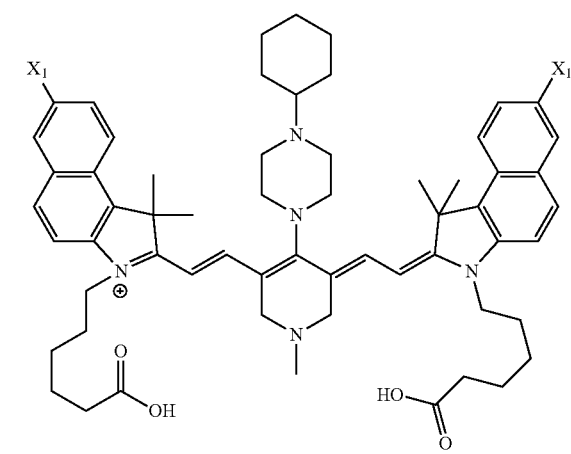

wherein

X$_1$ is selected from H, SO$_3$R, or CO$_2$R,

Z is selected from CH$_2$, N—C$_{1-6}$ alkyl (such as NMe), N$^+$ (C$_{1-6}$alkyl)$_2$ (such as N$^+$Me$_2$), N-ML, N$^+$Me-ML, ML is selected from (CH$_2$)$_{1-6}$COOR (such as (CH$_2$)$_5$COOR) and (CH$_2$)$_{1-5}$SO$_3$R (such as (CH$_2$)$_4$SO$_3$R), R is H, metal cation, ammonium, substituted or unsubstituted N-succinimide.

Examples for preferred dyes according to the application include the following compounds I-XIX, XXIII and XXV-XXVIII,

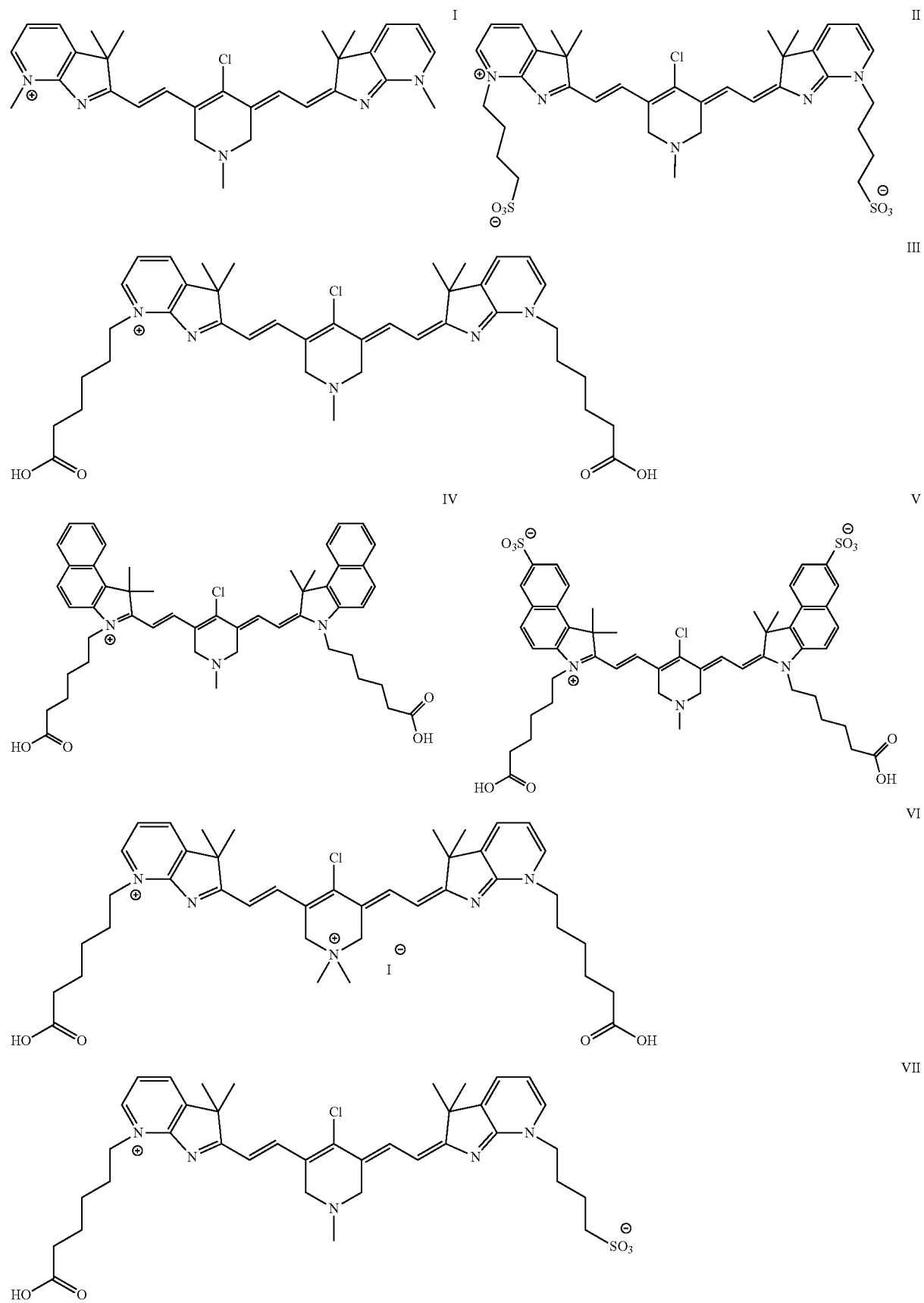

-continued
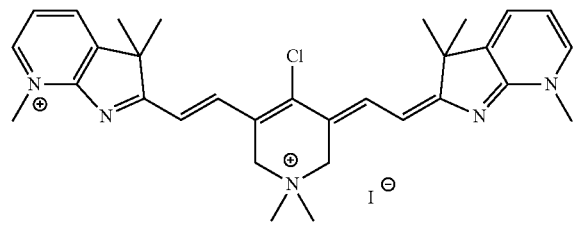
VIII
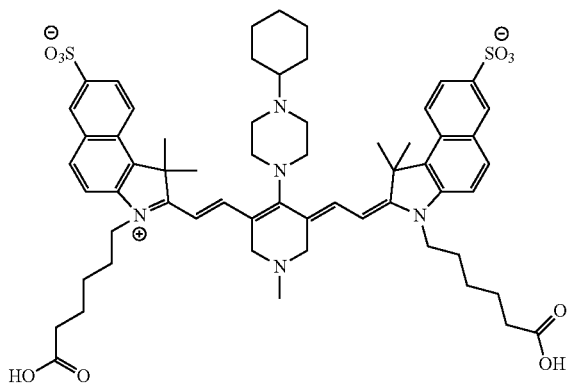
IX
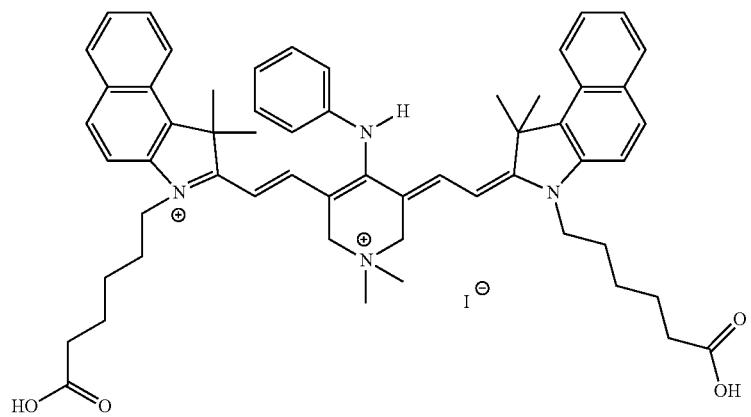
X
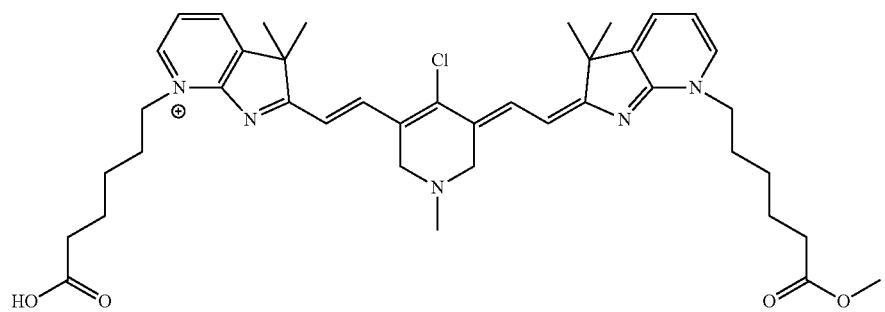
XI
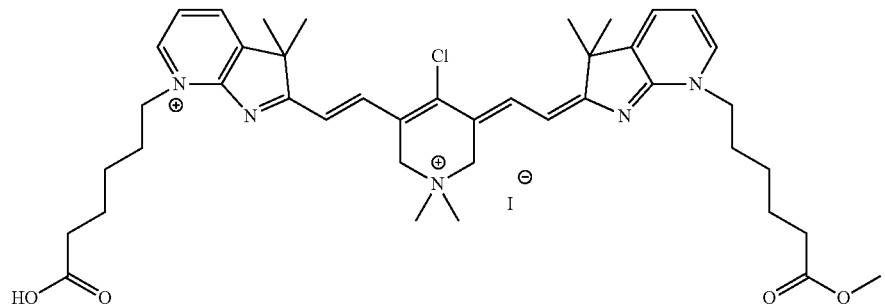
XII

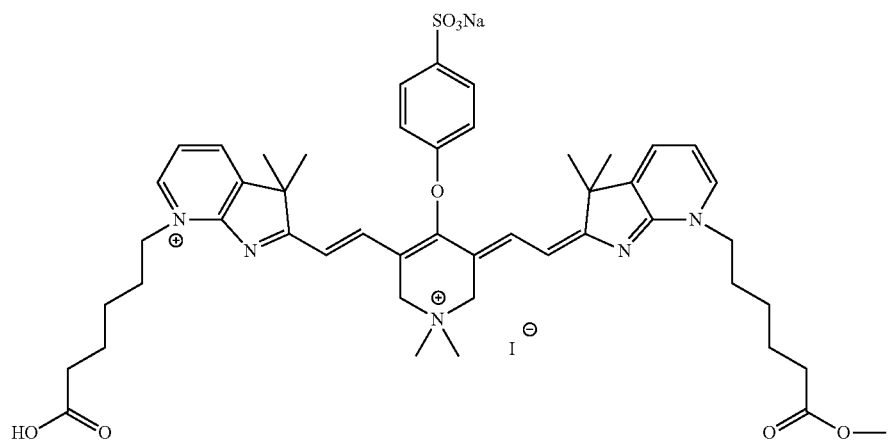
XIII
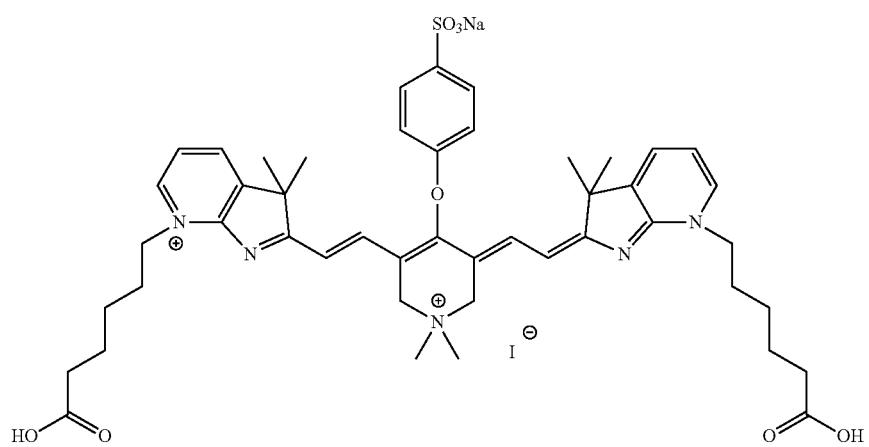
XIV
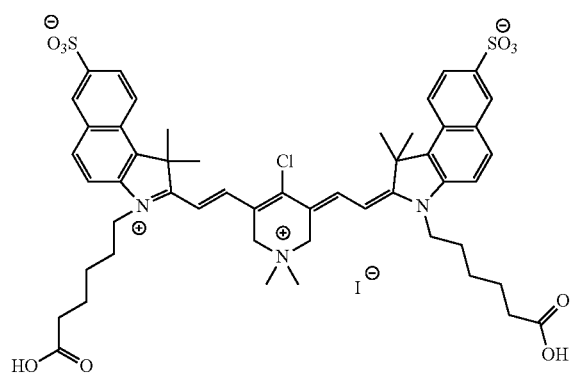
XV
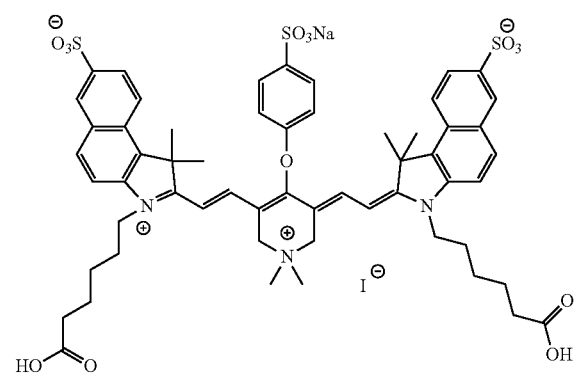
XVI

-continued
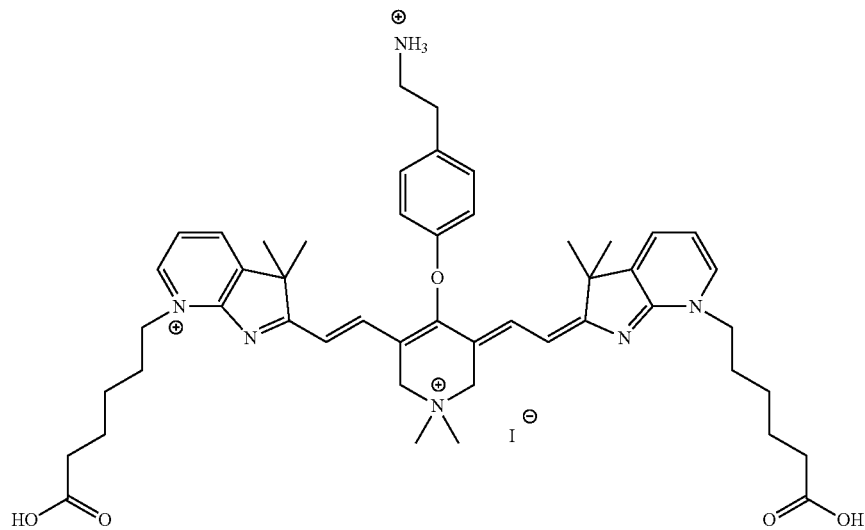
XVII
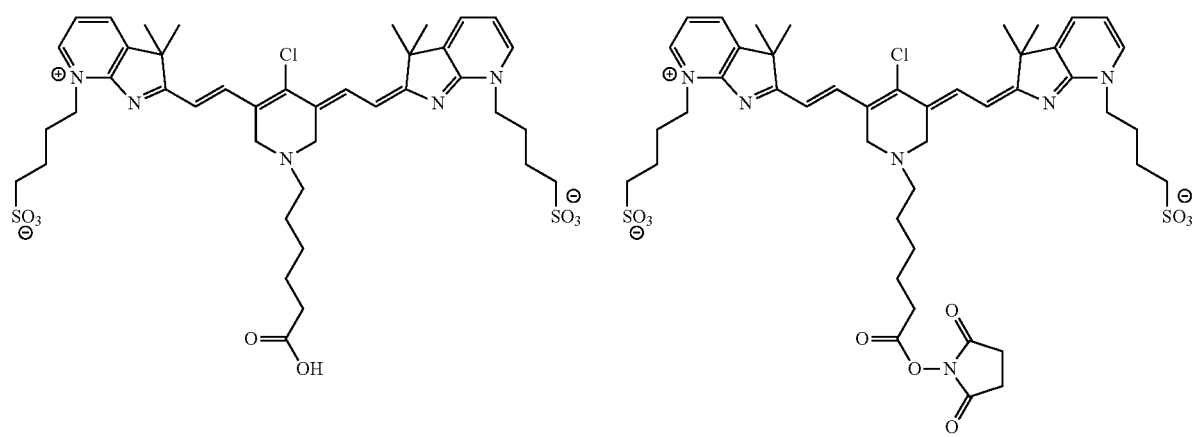
XVIII
XIX
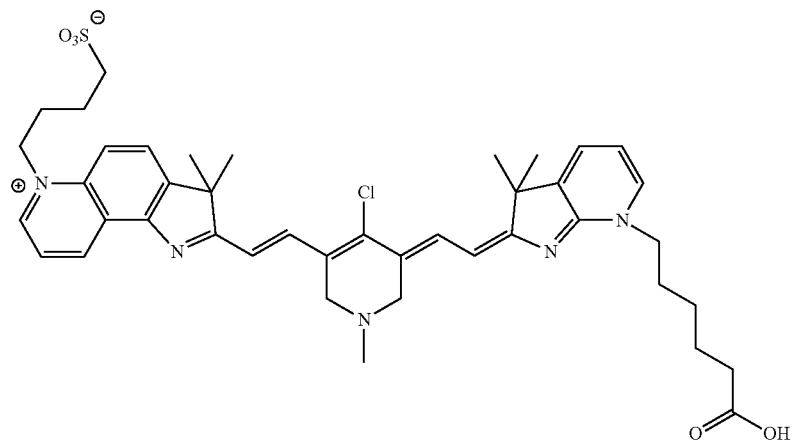
XXV

-continued

XXVI

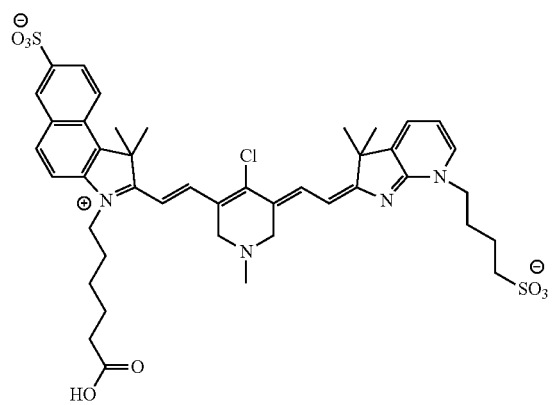

XXVII

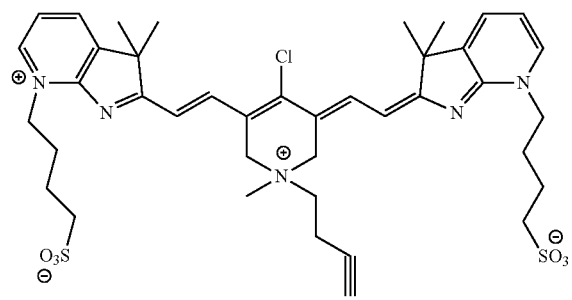

XXVI

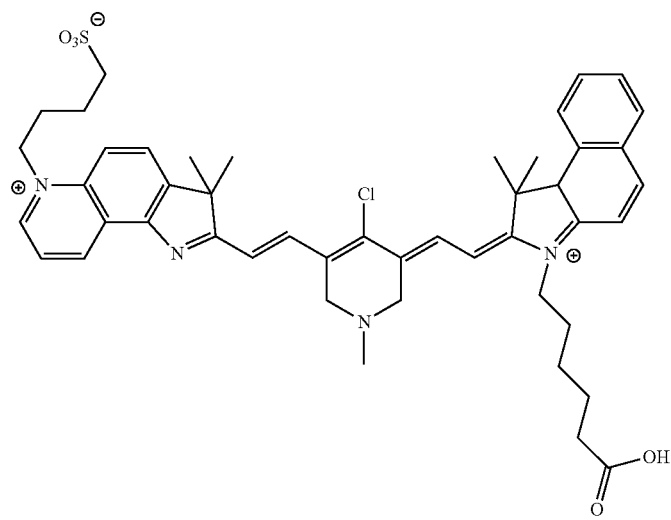

XXVII

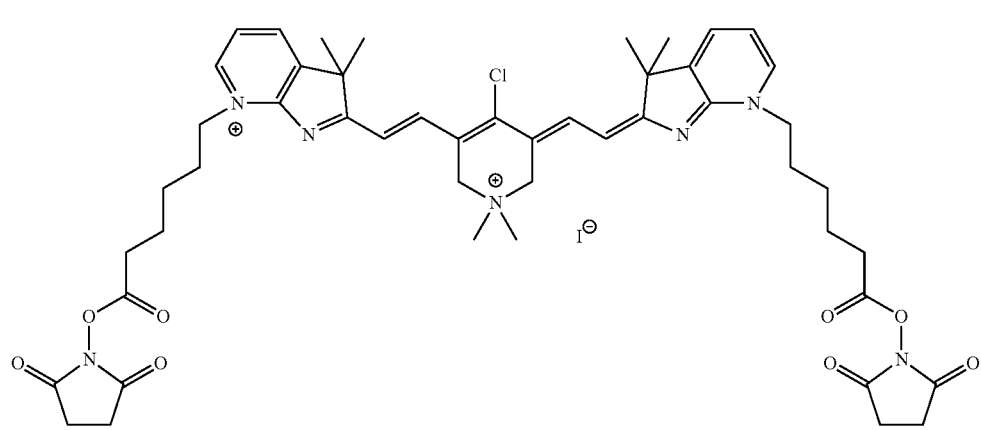

Another aspect of the application provides a bioconjugate imaging agent comprising the fluorescent dyes of the application. In an embodiment, a bioconjugate imaging agent comprises a fluorescent dye of the application linked to at least one targeting agent (optionally by an anchor group or various anchor groups, i.e. 2, 3, 4 or 5 anchor groups).

The term "linked" or "chemically linked"—in general via a linking group—is understood to mean a chemical bond between atoms. Chemical bonds are known to the skilled artisan. In the context of the present application, the chemical bond is preferably an ionic bond or a covalent bond, most preferably a covalent bond.

Properties of a bioconjugate imaging agent can be adjusted by modifying the charge and molecular weight of the fluorescent dye (fluorophore), targeting agents and, in some cases, the anchor group. In addition, properties of the bioconjugate imaging agent can be adjusted by the various substituents as defined above in the specification (physiochemistry properties modulators and optical properties modulators).

A targeting agent is a moiety that specifically recognizes a target, typically an in-vivo or an in-vitro biological target, such as a receptor or another cellular recognition moiety. In some embodiments, a targeting agent is selected from the group comprising peptides (e.g., RGD peptide, which specifically binds to $\alpha_v\beta_3$ integrin), small molecules, aptamers including peptide aptamers and DNA and RNA aptamers, antibodies, carbohydrates, saccharides, and nucleic acids. A further definition of targeting agents and preferred embodiments thereof is given below.

Frequently modification of the targeting agents compromises the binding avidity of the targeting moiety to its putative receptor on the target sample or disease causing organism or aberrant signalling cells.

In certain embodiments, the targeting agents comprise fluorophores of the current application linked to moieties that recognize cell surface receptors or report on the environment of the cell such as pH.

In certain embodiments, a targeting agent is a peptide that is an enzymatic substrate such that when conjugated to the fluorescent dye of the application provides substantially no fluorescence. Cleavage of the peptide by a particular enzyme dissociates the fluorescent dye causing an increase in fluorescence. The increase in fluorescence reports on the presence of the activating enzyme.

In some embodiments, targeting agents either all from the same grouping or combinations thereof are linked to the fluorescent dye either directly or through linking groups. Preferable points of attachment for the linking groups are the nitrogen on (i) the heterocycles of the dyes of the application, through for example $R^{17}$ and/or $R^{18}$ and/or $R^{20}$, $R^1$ and/or $R^2$; (ii) through any of the A6-A19 atoms when at least one of them is N. Preferred compounds are linked through the N of the heterocycles (most preferably through $R^{17}$ and/or $R^{18}$ or $R^{20}$, $R^1$ and/or $R^2$), or if the ring annulated to the pyrrol structure contains a N atom, to this N atom, e.g., in positions $R^3$, $R^4$, $R^7$ and/or $R^6$, preferably $R^3$ and/or $R^7$.

An anchor group is any functional group that can be used to link at least one targeting agent to the fluorescent dye of the application, in general via a linker. The anchor group will be attached to the targeting group, prior to linking it to the dye of the application.

Useful anchor groups include both natural and non-natural amino acids, oligopeptides, for example linear or cyclic oligopeptides, nucleic acids, peptides or peptides moieties, such as glycine, β-alanine, γ-aminobutyric acid or aminocaproic acid, as well as synthetic linker molecules such as aminoethyl maleimide or aminomethyl benzoic acid. In other embodiments, the anchor group is a polymer such as homobifunctional or heterobifunctional polyethylene glycol (PEG). Several PEG derivatives are commercially available from several suppliers (e.g., Quanta Biodesign, Merck). When the anchor group is a peptide, the peptide optionally may include proteolytic cleavage site that can be cleaved with a variety of agents, for example, an enzyme. It is understood that there is no particular structural, size or content limitation for a given linker. Anchor groups can include, for example, a variety of functional groups such as maleimide, dithiopyridyl, thiol, azide, alkene, or alkyne that permit the assembly of molecules of diverse architecture. Anchor groups can be homofunctional linkers or heterofunctional linkers. For example, amine ($NH_2$)-functionalized moieties can be reacted with bifunctional cross-linkers designed to react with amino groups. Particularly useful conjugation reagents that can facilitate covalent linkage between, for example, a fluorescent dye (a fluorophore), and an enzymatically cleavable oligopeptide can include a N-hydroxysuccinimide (NHS) ester and/or a maleimide. The NHS ester can react with the amine group of, for example, a peptide or fluorophore. The maleimide can react with the sulfhydryl group of another molecule. Other particularly useful anchor groups are bifunctional crosslinkers such as N-succinimidyl 3-(2-pyridyldithio)propionate (SPDP), long chain-SPDP, maleimidobenzoic acid-N-hydroxysuccinimide ester (MBS), succinimidyl trans-4-(maleimidylmethyl) cyclohexane-1-carboxylate (SMCC), succinimidyl iodoacetate (SIA).

In certain embodiments, an anchor group can be branched, for example glutamic acid or 5-(aminomethyl) isophthalic acid, or a dendrimer, such as a lysine or glutamic acid dendrimer, with multiple M groups linked to a single site on the fluorescent dye (fluorophore).

In certain embodiments, the biological modifier or physiochemistry modifier may be a PEG moiety that has a molecular weight, for example, from about 0.1 kDa to about 50 kDa, about 5 kDa to about 35 kDa, or about 10 kDa to about 30 kDa. Alternatively, the PEG may be dPEG, functionalized at a discrete molecular weight, for example, of about 1100 daltons. In certain embodiments, the PEG is methoxyPEG(5000)-succinimidylpropionate (mPEG-SPA), methoxyPEG(50000)-succinimidylsuccinate (mPEG-SS). Such PEGS are commercially available from Nektar Therapeutics SunBiowest or LaysanBio or NOF. The PEG moiety can be conjugated to reactive amines on the fluorescent dyes via a carboxyl functionality. Alternatively, the PEG modifier or physiochemistry modifier can be conjugated to the fluorescent dyes by using a thiol reactive cross linker and then reacting with a thiol group on the PEG. In one embodiment, the PEG may be branched, or Y-shaped, as available from Nektar Therapeutics Ca, JenKem USA, or Quanta Biodesign or comb-shaped, or synthesized by coupling two or more PEGs to a small molecule such as glutamic acid.

In another embodiment the chemical modifier or physiochemistry modifier may be dendrimers of various generations to provide multiple attachment points, such as those derived from polyamido(amine) PAMAM and characterized generationally by the number of functional groups and multiplicative radiating chains. The dendrimers are available from Merck, Dendritech and Polymer factory (Sweden).

In other embodiments, the biological chemical modifier or physiochemistry modifier can be polyvinylpyrrolidone (PVP)-type polymers. The biological or chemical modifier or physiochemistry modifier can be a functionalized polyvinylpyrrolidone, for example, carboxy or amine functionalized on one (or both) ends of the polymer (as available from Polymersource) or within the polymer chain. Alternatively, the biological chemical modifier or physiochemistry modifier can include Poly N-(2-hydroxypropyl)methacrylamide (HPMA), or functionalized HPMA (amine, carboxy, etc.), Poly(N-isopropyl acrylamide) or functionalized poly (N-isopropylacrylamide).

Accordingly, a further aspect of the present application is a bioconjugate imaging agent comprising a targeting agent as described above linked to a dye of the basic structure as depicted in formula A. The bioconjugate imaging agent has the formula D.

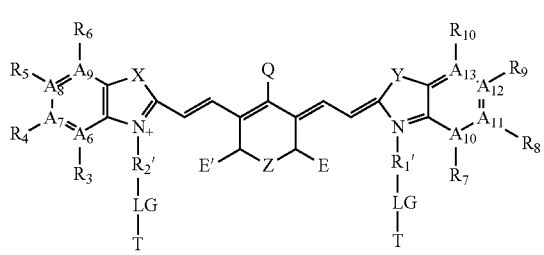

in which $R^3$-$R^{10}$, $A^6$-$A^{13}$, X, Y, Q, Z, E and E' have the general, preferred, more preferred, still more preferred and most preferred meanings as defined in connection with formula A, $R^{1'}$ and $R^{2'}$ independently of each other have the meaning of $R^{23}$ as defined in connection with $R^{23}L$ for formula A, in the general, preferred, more preferred, still more preferred and most preferred meanings as defined in connection with formula A; and wherein both of $R^{1'}$ and $R^{2'}$ are present; or only one of $R^{1'}$ and $R^{2'}$ is present as attached to T via LG, in which case the other substituent $R^{1'}$ or $R^{2'}$ is absent, H or has the meaning of $R^1$ or $R^2$ as defined in connection with formula A, in the general, preferred, more preferred, still more preferred and most preferred meanings as defined in connection with formula A.

The bioconjugate imaging agent may also have the formula G which has the same formula as formula A except that Q is $R^{21}$-LG-T, —O—$R^{21}$-LG-T, —S$R^{21}$-LG-T, or —N$R^{21}R^{22}$-LG-T, $R^{21}$ and $R^{22}$ has the same meaning of $R^{21}$ and $R^{22}$ as defined in connection with $R^{21}L$, —O$R^{21}L$, —S$R^{21}L$, and —N$R^{21}R^{22}L$ for formula A.

LG in both formula D and G is a linking group formed in the reaction of a linker as defined in the general, preferred, preferred, more preferred, still more preferred and most preferred meanings for formula A, with a complementary group on the targeting agent as defined in the general, preferred, more preferred and still more preferred meanings as defined in connection with formula A;

in both formula D and G is a targeting agent independently selected from receptors, ligands, antibodies, in particular monoclonal and polyclonal antibodies and fragments of these antibodies, antigens, peptides, (e.g., RGD peptide, which specifically binds to $α_ν β_3$ integrin), enzyme substrates, enzymes, (specific) proteins and protein fragments, biotin, avidin, streptavidin, anti-biotin, carbohydrates, saccharides, lectin, DNA and fragments thereof, RNA and fragments thereof, aDNA and fragments thereof, aRNA and fragments thereof, hormones, folate, aptamers including peptide aptamers and DNA and RNA aptamers, enzyme substrates, and small molecules such as a moiety comprising fatty acid (e.g., an amino substituted fatty acid) or a moiety comprising amino (e.g., an aniline substituted or unsubstituted). The targeting agent as shown in formula D is formed in the reaction of the respective linker as defined in the general, preferred, preferred, more preferred, still more preferred and most preferred meanings for formula A, with a complementary group on the targeting agent as defined in the general, preferred, more preferred and still more preferred meanings as defined in connection with formula A.

In the context of the present application, a targeting agent is, in a preferred embodiment of the invention, a ligand that is able to specifically interact with cell specific molecules via coordinative bonds in such a manner that results in a site-specific complex forming with the cell specific molecule. In the context of the present application, a coordinative bond is an intermolecular force, such as ionic bonds, hydrogen bonds and Van der Waals forces. Under physiological conditions the targeting agent typically acts as an inhibitor or an activator after it coordinatively bonds to the cell specific molecule.

Targeting agents that form those site-specific complexes with cell specific molecules are known to a person skilled in the art or may be available from recent articles. For example, these targeting agents are well described in "CourseSmart International E-Book for Principles of Biochemistry" (D. L. Nelson and M. M. Cox, Eds. Palgrave Macmillan, 13.02.2013) and "Illustrated Dictionary of Immunology. Third Edition" (J. M. Cruse and R. E. Lewis, Eds. CRC Press, 20.04.2009).

Depending on cell type and accessibility of the targeted cell specific molecule the targeting agent T is independently selected from the group cited above.

A small molecule is a low molecular weight <900 daltons organic compound that may help regulate a biological process, with a size on the order of $10^{-9}$ m. In a preferred embodiment, a small molecule is a molecule that binds to a specific biological target—such as a specific protein or nucleic acid—and acts as an effector, altering the activity or function of the target.

In the context of the present application, a receptor is a molecule, in general a protein, that receives chemical signals from a ligand binding to it. Classically, receptors are molecules which are embedded in the membrane of a cell and are known to the person skilled in the art. They can also be used without the transmembrane part. The term receptor here also includes other proteins which are drug-targets, in particular enzymes, transporters and ion-channels In the context of the present application, a ligand is a substance that forms a complex with a receptor, in general a protein, by binding to a site thereof by intermolecular forces, such as ionic bonds, hydrogen bonds and Van der Waals forces. The ligand can be a small molecule, ion, or protein, a substrate, an inhibitor, an activator, a neurotransmitter.

In the context of the present application, an antigen is a molecule that binds to Ag-specific receptors including antigens and is any molecule or molecule fragment that can be recognized by highly variable antigen receptors. Antigens are usually peptides, polysaccharides or lipids.

In the context of the present application, the term "antibody" refers to immunoglobulins which are a class of soluble proteins found in body fluids of humans and other vertebrates. They are also termed "antibodies" and play a key role in the processes of recognition, binding and adhesion of cells. Antibodies are oligomeric glycoproteins which have a paramount role in the immune system by the recognition and elimination of antigens, in general bacteriae and viruses.

The polymeric chain of antibodies is constructed such that they comprise so-called heavy and light chains. The basic immunoglobulin unit consists of two identical heavy and two identical light chains connected by disulfide bridges. There are five types of heavy chains (α, γ, δ, ε, μ), which determine the immunoglobulin classes (IgA, IgG, IgD, IgE, IgM). The light chain group comprises two subtypes, λ and κ. IgGs are soluble antibodies, that can be found in blood and other body fluids. They are built by B-cell derived plasma cells as response to and to neutralize bacterial or other pathogens. The two carboxy terminal domains of the heavy chains are forming the Fc fragment ("constant fragment"), the amino terminal domains of the heavy and light chains are recognizing the antigen and are named Fab fragment ("antigen-binding fragment"). Fc fusion proteins are created through a combination of an antibody Fc fragment and a protein or protein domain that provides the specificity for a given drug target. Other Fc fusion proteins are combinations of the Fc fragment with any type of therapeutic proteins or protein domains. The Fc part is considered to add stability and deliverability to the protein drug. Therapeutic antibodies and Fc fusion proteins are used to treat various diseases, prominent examples include rheumatoid arthritis, psoriasis, multiple sclerosis and many forms of cancer. Therapeutic antibodies can be monoclonal or polyclonal antibodies.

In the subject matter of the present application, all immunoglobulin (antibody) types IgA, IgG, IgD, IgE, IgM can be used. IgM is preferred, and this term comprises natural, monoclonal and polyclonal antibodies, Fc fusion proteins and therapeutic antibodies (polyclonal and monoclonal).

The general, preferred, more preferred and still more preferred embodiments cited in connection with formula A also apply with respect to the above formula (D). In the bioconjugate imaging agents of the invention according to (D), however, the case that $R^{19}$ in —$OR^{19}$ is not H does not apply.

With respect to the above formula D, the respective bioconjugate may contain two targeting groups attached to the dye skeleton via LG, $R^{1'}$ and $R^{2'}$, or only one of $R^{1'}$ and $R^{2'}$ is present to attach T via LG, meaning that the bioconjugate targeting agent contains only one targeting group. In this latter case, the other substituent $R^{1'}$ or $R^{2'}$ is absent, is H or has the meaning of $R^1$ or $R^2$ as defined in connection with formula A, in the general, preferred, more preferred still more preferred and most preferred meanings as defined in connection with formula A; or one of $R^{1'}$ and $R^{2'}$ has the meaning of $R^{23}L$ as defined in connection with formula A, in the general, preferred, more preferred, still more preferred and most preferred meanings, which means that a linker L is connected to the dye skeleton via $R^{23}$; or one of $R^{1'}$ and $R^{2'}$ has the meaning of $R^{23}U$ as defined in connection with formula A, in the general, preferred, more preferred and still more preferred meanings, which means that a physiochemistry modifying group U is connected to the dye skeleton via $R^{23}$.

Targeting agents are ligands that bind to receptors that are overexpressed on cancer cells, in a preferred embodiment. However, receptors overexpressed on cancer cells are also expressed on non-malignant cells in lower numbers. Therefore, ligand should have the affinity and specificity for overexpressed cell surfaced receptor. There are several targeting agents known biological targets. These targets include for example transferrin, monoclonal antibodies (MAbs), polyclonal antibodies, peptides, EGF (epidermal growth factor), folate and aptamers.

The targeting agents T can be the same or different. If T are different, the linking groups LG will preferably be different from each other, but may also be the same.

Irrespective of the fact if the targeting agents are different or not, the biomolecule imaging agents according to the above formula can be symmetrical, or asymmetrical in the sense that they do not have a C2 symmetry.

Examples of bioconjugate imaging agents of the application are compounds XX, XXI, XXII, and XXVIII as shown in Examples. Another example of image-rendering bioconjugates of the application is the following compound:

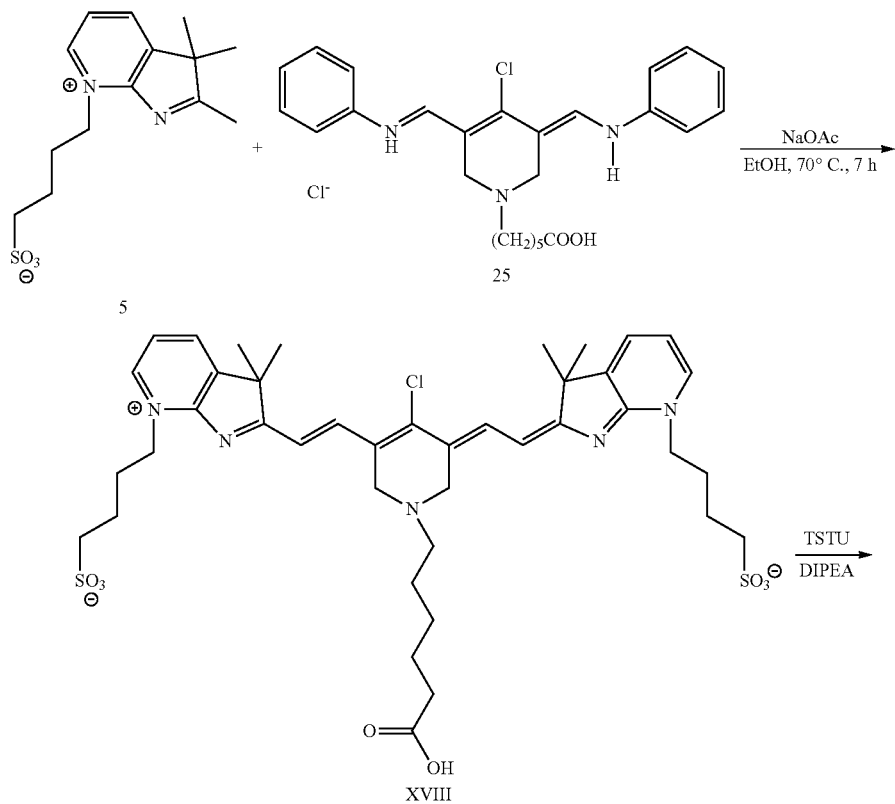

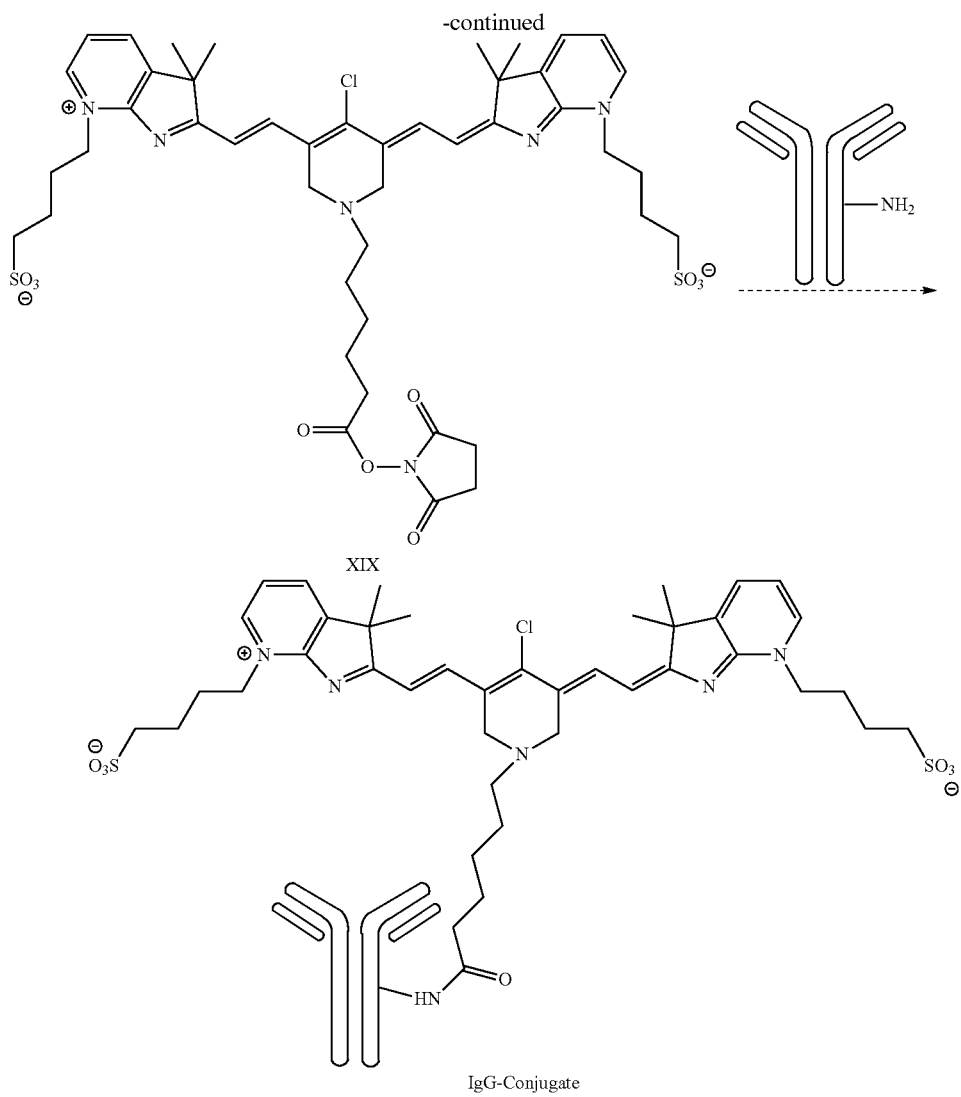

where the IgG molecule is a monoclonal or polyclonal antibody.

Examples are known in the art of groups reacting with each other under formation of a covalent bond used to link two molecules. In certain embodiments, the below reactions lend themselves for attaching the targeting group to the dye according to the application.

Electrophilic Group Nucleophilic Group Resulting Covalent Linkage

| | | |
|---|---|---|
| activated esters* | amines/anilines | carboxamides |
| acyl azides** | amines/anilines | Carboxamides |
| acyl halides | amines/anilines | Carboxamides |
| acyl halides | alcohols/phenols | Esters |
| acyl nitriles | alcohols/phenols | Esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | Esters |
| alkyl halides | thiols | thioethers |
| alkyl halides | alcohols/phenols | Ethers |
| alkyl sulfonates | thiols | thioethers |
| alkyl sulfonates | carboxylic acids | Esters |
| alkyl sulfonates | alcohols/phenols | Ethers |
| anhydrides | alcohols/phenols | Esters |
| anhydrides | amines/anilines | carboxamides |
| aryl halides | thiols | thiophenols |
| aryl halides | mines | ryl amines |
| aziridines | thiols | thioethers |
| boronates | glycols | boronate esters |
| carboxylic acids | amines/anilines | carboxamides |
| carboxylic acids | alcohols | Esters |
| carboxylic acids | hydrazines | hydrazides |
| carbodiimides | carboxylic acids | N-acylureas or anhydrides |
| diazoalkanes | carboxylic acids | Esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | Ureas |
| isocyanates | alcohols/phenols | urethanes |
| isothiocyanates | amines/anilines | thioureas |
| maleimides | thiols | thioethers |
| phosphoramidites | alcohols | phosphite esters |

| | | |
|---|---|---|
| silyl halides | alcohols | silyl ethers |
| sulfonate esters | amines/anilines | alkyl amines |
| sulfonate esters | thiols | thioethers |
| sulfonate esters | carboxylic acids | Esters |
| sulfonate esters | alcohols | ethers |
| sulfonyl halides | amines/anilines | sulfonamides |
| sulfonyl halides | phenols/alcohols | sulfonate esters |

Examples for preferred bioconjugate imaging agents according to the application include the following compound XX, XXI, XXII, and XXVIII. In bioconjugate XXVIII, the "dye" is XXVII.

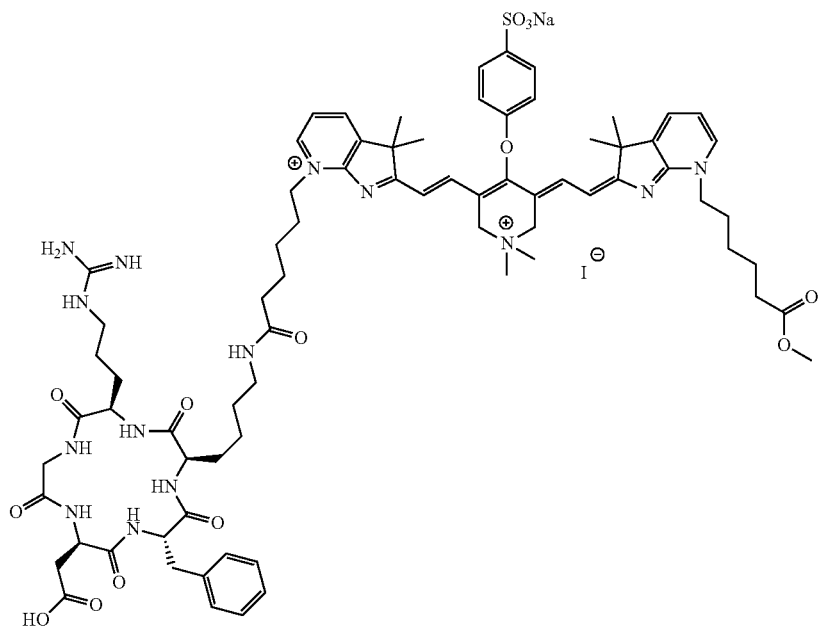

XX

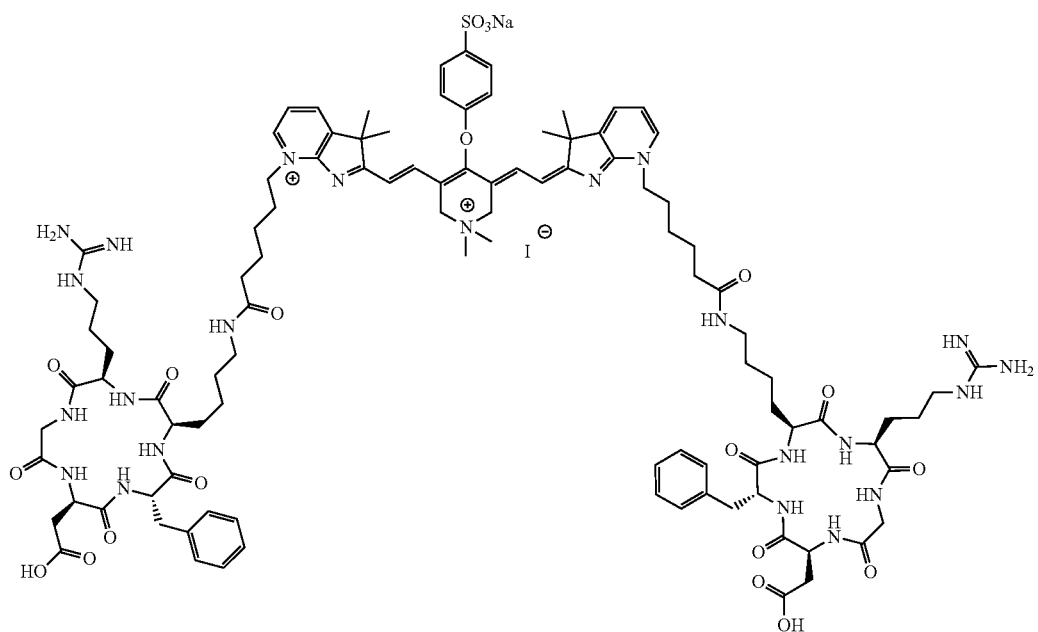

XXI

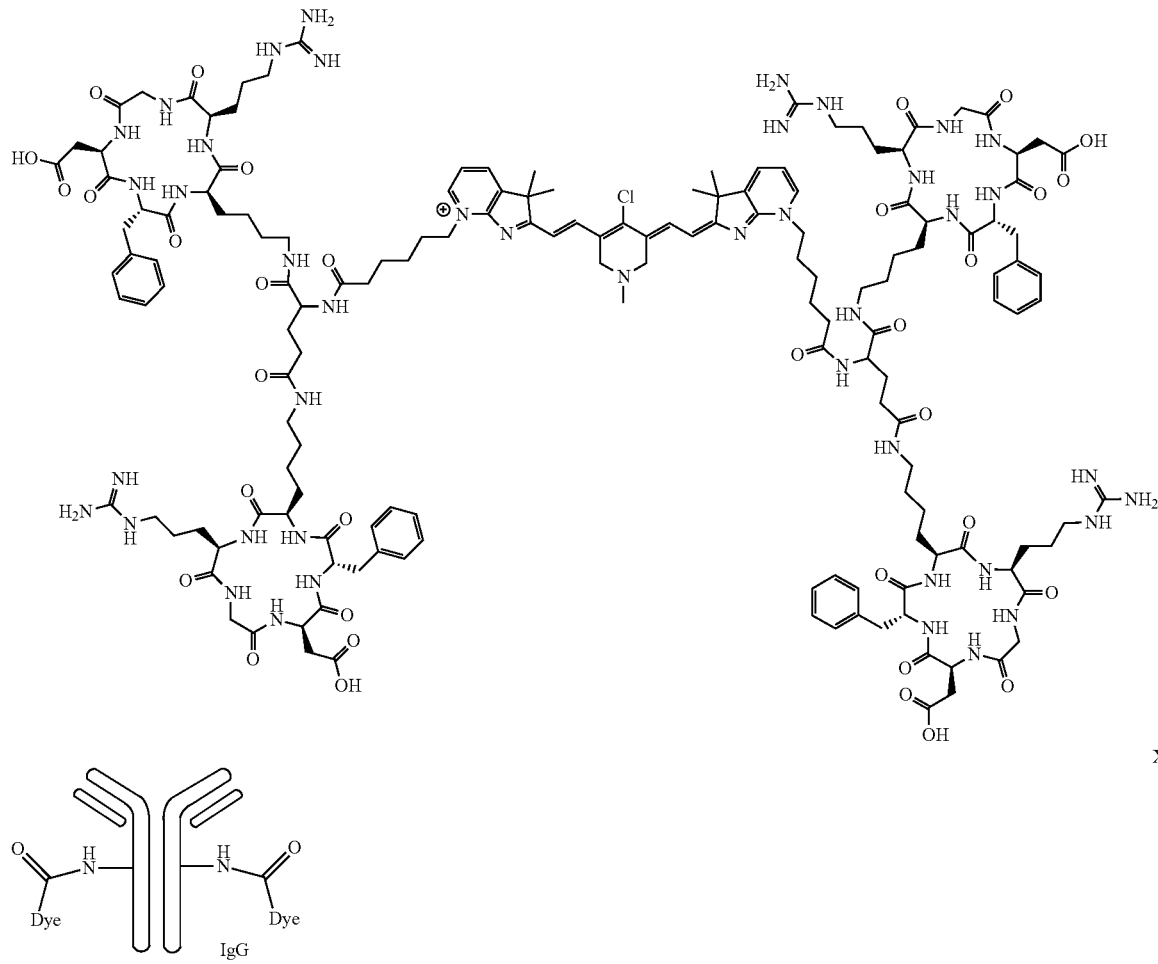

XXII

XXVIII

Another aspect of the subject matter of the application is the pH sensitivity of the fluorescent dyes of application when the nitrogen atom in the heterocycle is substituted and another N atom is available for protonation or deprotonation. The excitation and emission wavelengths are pH dependent, a feature that enables lysosomal tracking as the environment is acidic. At low pH the indole nitrogen is protonated and the dyes of the application shift to longer wavelengths upon deprotonation as the conjugation is extended. Such dyes are pH sensors as their absorbance and consequently fluorescence changes as a consequence of the pH of the environment. The fluorescent dyes of the application are pH sensors and are defined by their ability to change the fluorescence absorption and emission properties as a consequence of protonation of the non quaternized nitrogen in the system. Thus, the application provides a use of the fluorescent dyes of the application as pH sensors. The application also provides a method for measuring a pH of a solution, wherein the fluorescent dyes of the application are used.

In a further embodiment of the application, the bioconjugate imaging agent according to the application binds to a biological target. In this embodiment, the bioconjugate imaging agent permits detection of the presence of the biological target, preferably by visualisation, and of the disease or the diseased tissue expressing or presenting the biological target.

The resulting bioconjugate imaging agent can have a high binding affinity to a target, for example, due to an interaction between the biomolecule and the target, for example, via receptor-ligand interaction, an antibody-antigen interaction, peptide-peptide receptor interaction, enzyme substrate-enzyme interaction, protein-protein receptor interaction, biotin-avidin (or streptavidin or anti-biotin) interaction, carbohydrate-lectin (or carbohydrate receptor) interaction, DNA (RNA)-aDNA (aRNA) interaction, hormone-hormone receptor interaction.

T is a targeting agent independently selected from receptors, ligands, monoclonal and polyclonal antibodies and fragments of these antibodies, antigens, peptides, enzyme substrates, enzymes, (specific) proteins and protein fragments, biotin, avidin, streptavidin, anti-biotin, carbohydrates, saccharides, lectin, DNA and fragments thereof, RNA and fragments thereof, aDNA (antisense DNA) and fragments thereof, aRNA (antisense RNA) and fragments thereof, hormones, folate, aptamers, and enzyme substrates.

In an embodiment of the application, the targeting agent binds to targets that are overexpressed on cancer cells. However, targets overexpressed on cancer cells are also expressed on non-malignant cells in lower numbers. Therefore, the targeting agent used according to the application has affinity and specificity for overexpressed cell surface targets. Non-limiting examples include folate, transferrin, monoclonal antibodies (MAbs), peptides, EGF (epidermal growth factor) and aptamers.

Accordingly, the targeting agent can be a receptor, a ligand, an antibody, preferably a monoclonal antibody, an antigen, a peptide, an enzyme substrate, an enzyme, a protein, biotin, avidin, streptavidin, anti-biotin, a carbohydrate, a saccharide, lectin, a carbohydrate, DNA, RNA, aDNA, aRNA, a hormone.

One advantage of the bioconjugate imaging agents of the invention is that they do not demonstrate any binding to or uptake by live cells and selectively only binds to necrotic cells. This is shown by the examples.

In a further embodiment of the present invention, the fluorescent dyes and the bioconjugate imaging agents of the invention are modified such that they carry a chelating agent (hereinafter denoted as "CA"). The chelating agent lends itself for various purposes, e.g. for binding to a metal, preferably a radioactive metal. The binding of the metal to the chelate in general occurs via coordinate bonds (chelate effect), in which 2 or more atoms in the chelating agent bind to a single atom, in general a metal atom, Coordinative bonds are generally formed in a reaction between the metal atom (ion) and a free electron pair on an atom in the chelating agent.

Chelating agents are well known to the person skilled in the art. In the context of the present invention, the use of chelating agents which bind to metals, preferably radioactive metals and/or known radioactive isotopes of known metals, in particular radioactive metals or radioactive isotopes of metals which lend themselves as tumor imaging agent and/or as MRI contrast agent, is preferred.

The present invention preferably makes use of in particular 1,4,7,10-Tetraazacyclododecane-1,4,7,10-tetraacetic acid (DOTA), 1,4,7-Triazacyclononane-1,4,7-triacetic acid (NOTA), Triethylenetetramine (TETA), Ethylenediaminetetraacetic acid (EDTA), 1,4,7-triazacyclononane-1-glutaric acid-4,7-diacetic acid (NODAGA), and Diethylenetriaminepentaacetic acid (DTPA).

Chelating agents used in the present invention, in particular the above chelating agents, can be used to bind radioactive metals or radioactive isotopes metals, preferably as $^{68}$Gallium (68Ga), $^{64}$Copper (64Cu) for tumor imaging using PET or $^{111}$Indium (111In), or any other metal, preferably $Gd^{3+}$ for gadolinium-based MRI contrast agent, making this conjugate useful for various types of imaging modalities such as PET, SPECT, and MRI.

Chelating agents, preferably the chelating agents cited above, can be attached to any appropriate position in the dye molecules of the invention, i.e. the chelating agent can be in the position of any of the substituents Q, E, E' and $R^1$-$R^{16}$. "Being in the position of any" in the present context means that the chelating agent can replace the respective substituent, or it can be attached to the respective substituent. "Attached to" here means that chelating agent is attached to the chemical entity as defined relative to the respective substituent, in the preferred, the more preferred, the still more preferred or the most preferred embodiments as defined above. For example, this means that in case the chelating agent CA is in the position of Q, $R^1$ and/or, $R^2$, CA can be attached (in the most general embodiment) to a group selected from a linear and branched, non-cyclic and cyclic, substituted and unsubstituted $C_{1\text{-}20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- and 7-membered aromatic rings which can be substituted by a linear of branched $C_1$-$C_6$ alkyl group; and —($CH_2$—O—$CH_2$)$_x$$CH_2$— wherein x is an integer from 1 to 50. "Attached to" here also refers to the embodiment that CA is attached to a group U or L or even an optical properties modifying group. Here, CA may be attached to the respective group in a reaction transforming the reactive entities into different functionalities. In this embodiment, it may be necessary to provide a further group U, L or an optical properties modifying group in the fluorescent dye or the bioconjugate imaging agent, in order to reach the desired properties of the resulting dye and the bioconjugate imaging agent according to the invention.

In case the chelating agent replaces the respective substituent in the respective position, then the chelating agent can be attached to the respective atom directly. In the first embodiment, CA is attached to the respective atom on the dye via an atom previously present in the chelating agent, or via an atom in a functional group which has previously been attached to the CA. This is shown in the examples.

In the second embodiment, CA is attached to a chemical entity linking it to the respective atom in the respective site of the fluorescent dye. In general, these chemical entities are those defined for Q, alternative b) in connection with Formula A, in the general, preferred, more preferred, still more preferred and most preferred meanings as defined throughout the present application. The said chemical entities can, before the chelating agent is attached, be connected to the chelating agent or to the fluorescent dye, before linking the chelating agent to the dye.

Accordingly, in the general meaning, and in case CA is attached to a chemical entity linking it to the respective atom being part of the fluorescent dyes of the invention, the entity comprising CA is, in the most general meaning, defined as: $R^{35}$CA, —O$R^{35}$CA, —S$R^{35}$CA and —N$R^{35}$$R^{36}$CA wherein $R^{33}$ and $R^{36}$ d are independently selected from the group consisting of: H, linear and branched, non-cyclic and cyclic, substituted and unsubstituted $C_{1\text{-}20}$ alkyl, wherein the said alkyl group can be single or multiple substituted by a homocyclic or heterocyclic 5-, 6- or 7-membered aromatic group which can be substituted by a linear or branched $C_1$-$C_6$ alkyl group; homocyclic and heterocyclic 5-, 6- or 7-membered aromatic rings which can be substituted by a linear or branched $C_1$-$C_6$ alkyl group, wherein preferably one of $R^{35}$ and $R^{36}$ is not aromatic in case of —N$R^{35}$$R^{36}$; —($CH_2$—O—$CH_2$)$_x$$CH_2$-L wherein x is an integer from 1 to 50; and CA is a chelating agent as defined therein.

The above groups having $R^{33}$ and $R^3$ may each be an optical properties modifying group.

The preferred, more preferred, still more preferred and most preferred meanings for CA attached to a chemical entity are, accordingly, those defined for Q b) in each of the preferred, more preferred, still more preferred and most preferred embodiments, with $R^{21}$ and $R^{22}$ being replaced by $R^{35}$ and $R^{36}$.

The chelating agent can be in any position Q, E, E' and $R^1$-$R^{16}$, as stated above. Preferably, the chelating agent is in position Q, $R^1$ and/or $R^2$. Most preferably, CA is in position Q.

The number of chelating groups attached to the fluorescent dyes (and, therefore, also to the bioconjugate imaging agents) of the invention may vary from 1 to 4, preferably from 1 to 3, more preferably from 1 to 2. In one particular preferred embodiment, this number is 1. In another preferred embodiment, this number is 2.

Table 1 below cites various preferred chelating agents and the respective radioactive metals/isotopes which are bound by the agent. The table below is not meant to be limiting

| Chelation agent | Metals chelated |
| --- | --- |
| 1,4,7,10-Tetraazacyclododecane-1,4,7,10-tetraacetic acid (DOTA) | Indium-111, gallium-67/68, Copper-64, Yttrium-86 |
| 1,4,7-Triazacyclononane-1,4,7-triacetic acid (NOTA) | Indium-111, gallium-67/68 |
| Triethylenetetramine (TETA) | Copper-64 |
| Ethylenediaminetetraacetic acid (EDTA) | gallium-68, Copper-64 |
| 1,4,7-triazacyclononane-1-glutaric acid-4,7-diacetic acid (NODAGA) | gallium-68, Indium-111, Copper-64 |
| Diethylenetriaminepentaacetic acid (DTPA) | Indium-111, gallium-67/68, Copper-64, Yttrium-86, Zirconium-89 |

Below is shown the synthesis of a fluorescent dye of the invention to which a chelating agent (here: DOTA) is attached in a chemical reaction. The reaction starts from Compound VIII Reaction diagram 1 Substitution of central chlorine atom with S-R

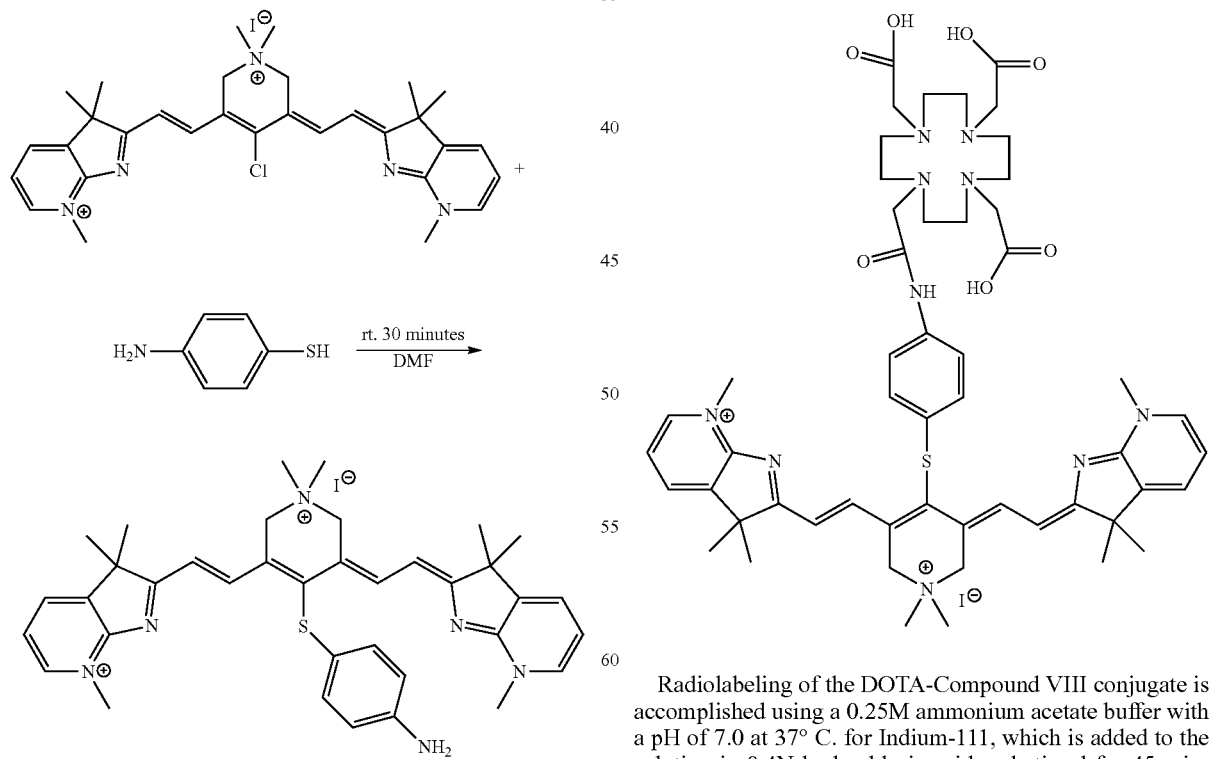

The amine-functionalized Compound VIII can then be coupled to a variety of chelating agents such as 1,4,7,10-Tetraazacyclododecane-1,4,7,10-tetraacetic acid (DOTA) that have been modified to contain a N-Hydroxysuccinimide functional group as shown in reaction diagram 2. This reaction is completed by using the functionalized Compound VIII and the N-hydroxysuccinimide ester form of DOTA, which is commercially available, in the presence of 4 equivalents of N,N-Diisopropylethylamine (DIPEA) at room temperature in a nitrogen atmosphere.

Reaction diagram 2 Conjugation of Compound VIII to DOTA

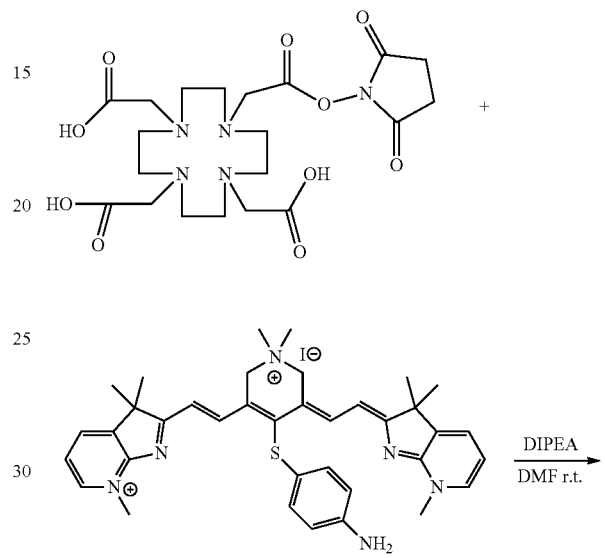

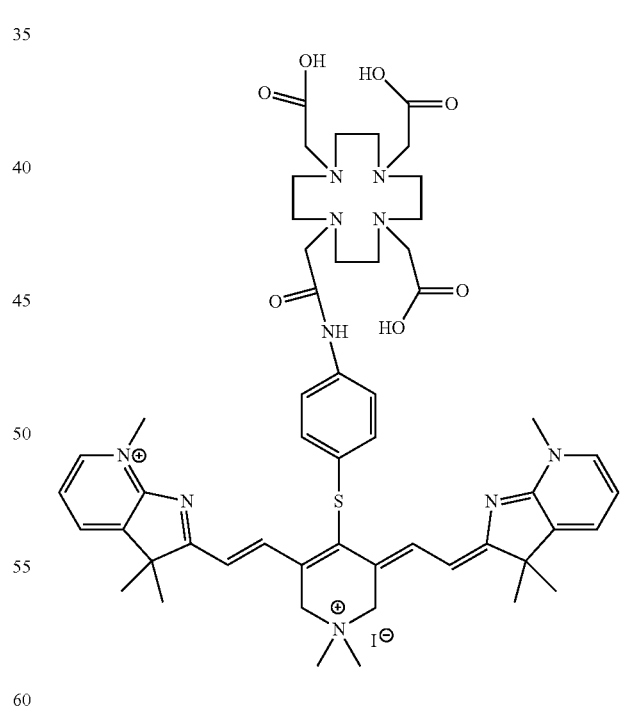

Radiolabeling of the DOTA-Compound VIII conjugate is accomplished using a 0.25M ammonium acetate buffer with a pH of 7.0 at 37° C. for Indium-111, which is added to the solution in 0.4N hydrochloric acid and stirred for 45 minutes. Other metal chelates behave in a similar fashion for chelation procedures. The reaction with Indium-111 is shown in reaction diagram 3.

Reaction diagram 3 Indium-111 chelation into DOTA-Compound VIII
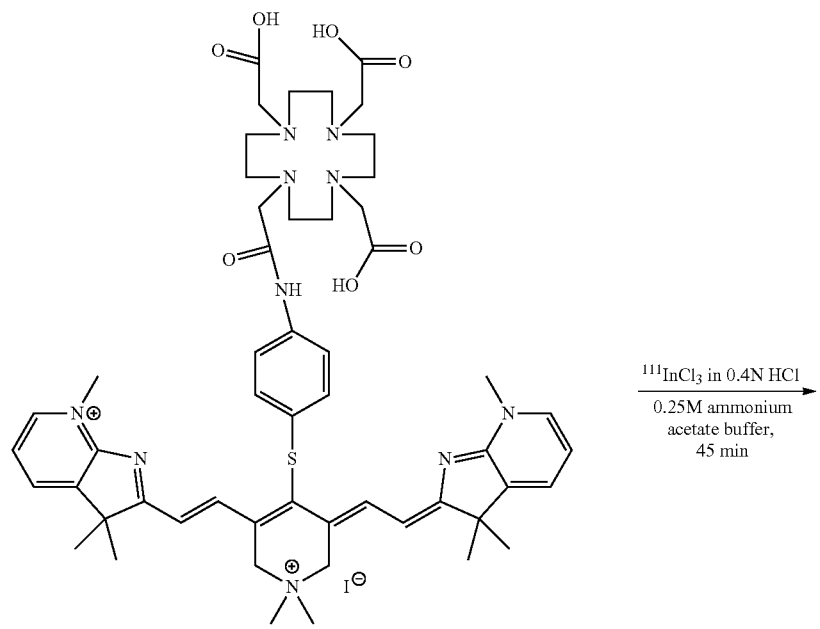
$^{111}InCl_3$ in 0.4N HCl
0.25M ammonium acetate buffer,
45 min
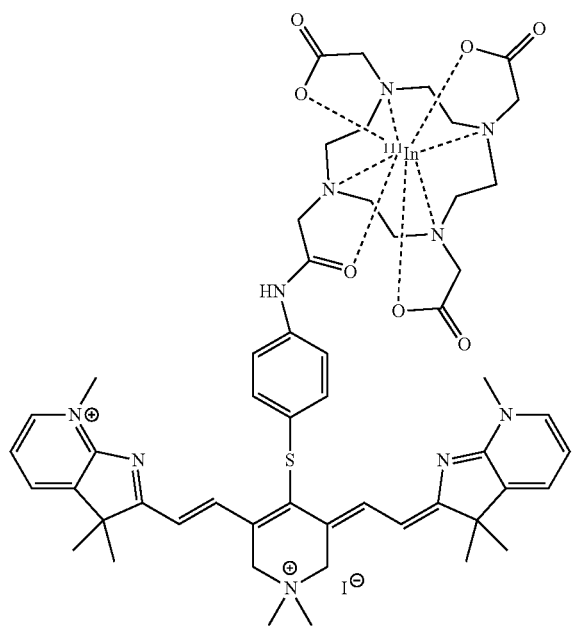

In the reaction diagram 4 is shown an alternative starting structure for conjugation and chelation of compound VIII In reaction diagram 5 is shown an alternative starting structure (carboxylic) for conjugation and chelation of compound VIII Reaction diagram 4

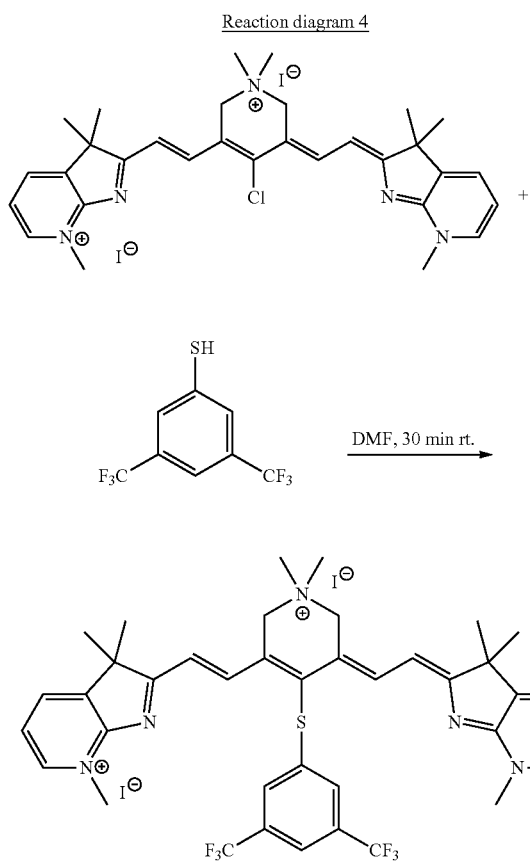

Reaction diagram 5

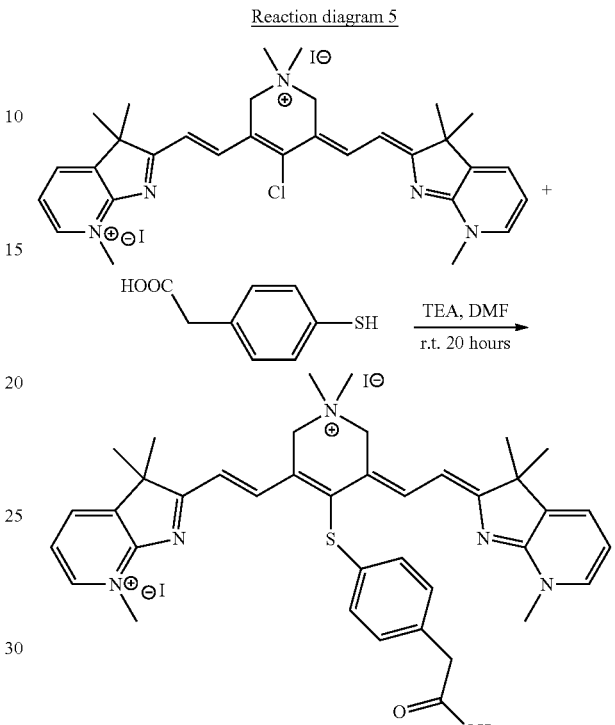

In reaction diagram 6 is shown an alternative structure of compound VIII with a functional group of isothiocyanat for a conjugation with a modified DOTA compound Reaction diagram 6

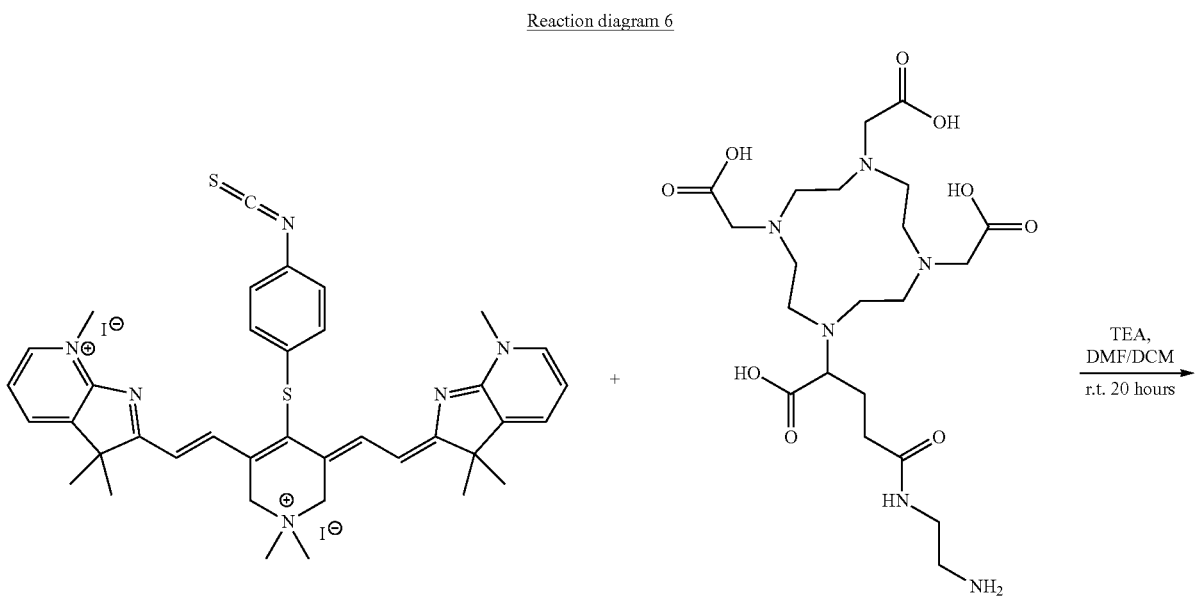

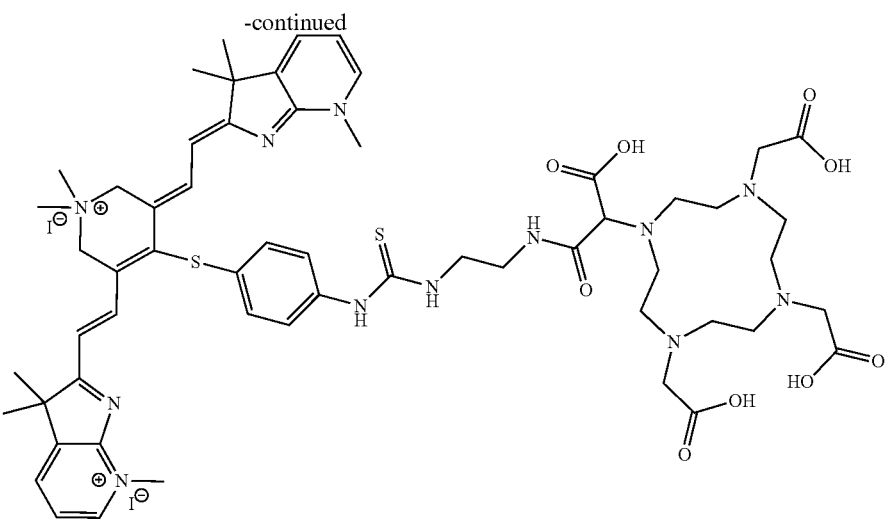
In reaction diagram 7 is shown a further structure of compound VIII with the isothiocyanat group as the starting compound for conjugation with a modified DOTA compound.
Reaction diagram 7
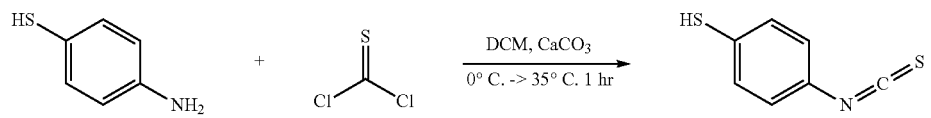
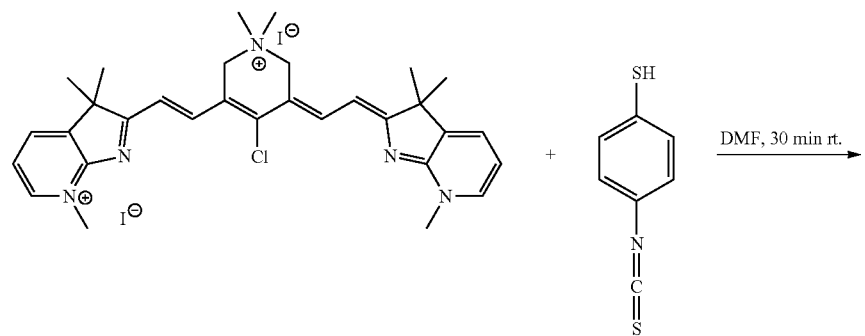
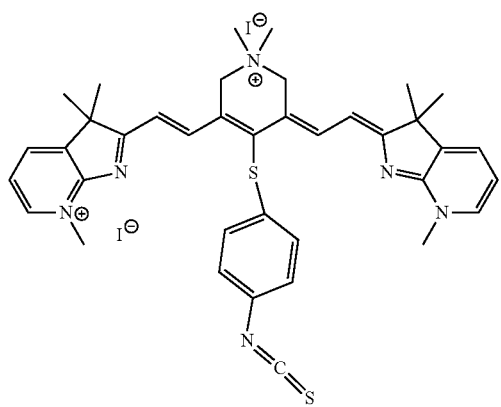

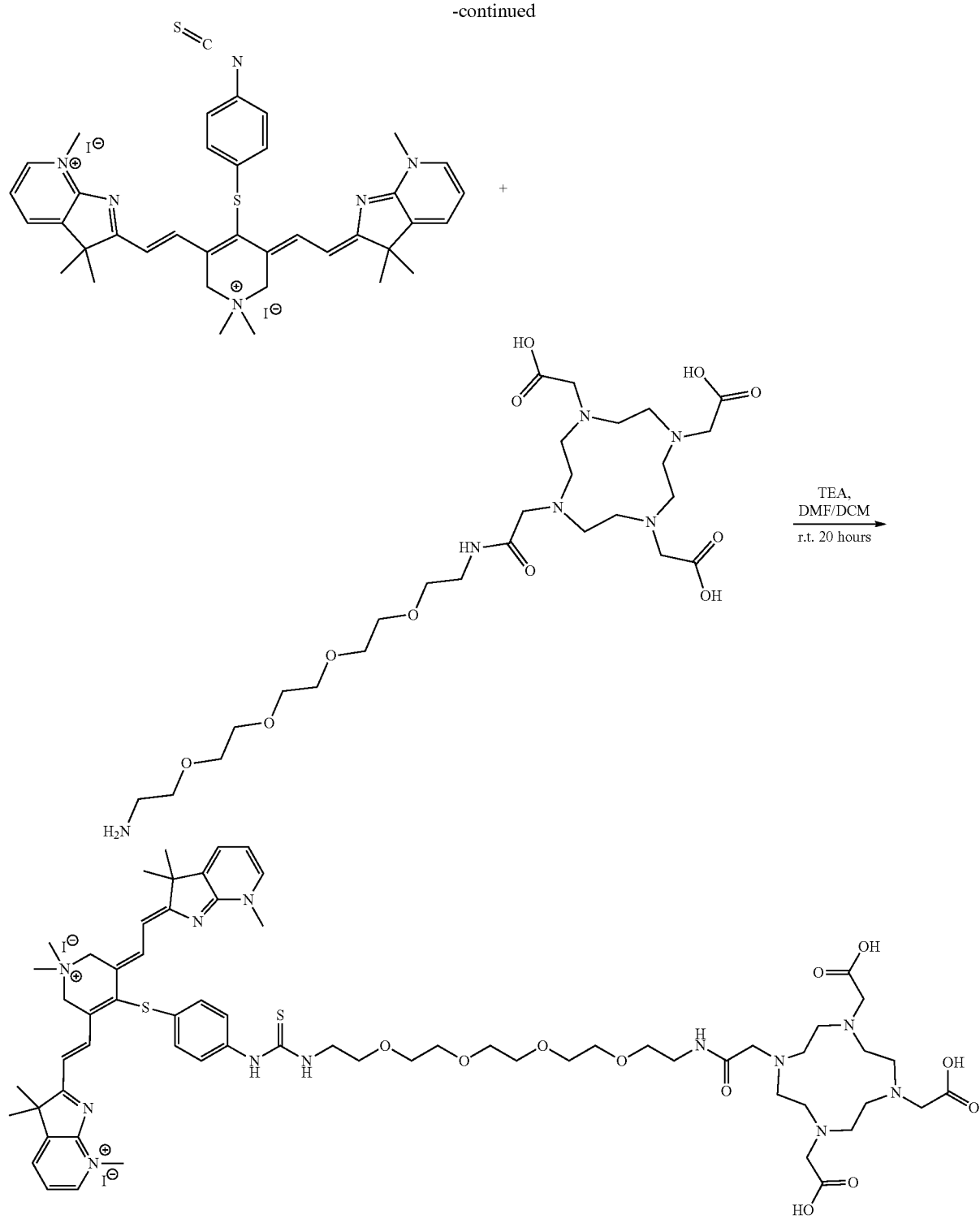

DOTA (and other chelating agents) are known to bind radioactive isotopes such as [68]Gallium (68Ga), [64]Copper (64Cu) for tumor imaging using PET or [111]Indium (111In) or any other metal such as $Gd^{3+}$ for gadolinium-based MRI contrast agent, making this conjugate useful for various types of imaging modalities such as PET, SPECT, and MRI. Corresponding compounds are also efficient fluorescent reagents, the conjugates can be used for optoacoustic, near-infrared imaging (600-900 nm) and shortwave infrared (SWIR II) range of wavelengths from 0.9 to 1.7 microns (see more details below). The molecule could also be envisioned for radiotherapy applications for local tumor irradiation when chelated to radioisotopes such as Lutetium or Yttrium ($^{177}$Lu, $^{90}$Y).

The carboxylic acid moiety on this molecule can also be used to couple to any other targeting ligand such as folic acid, cyclic RGD peptides (for alpha-v beta-3 receptor targeting) or antibody of choice (ex. Trastuzumab or TEM-1) or any other types of antibodies such as probodies ("masked" antibodies), nano-bodies, etc.

In reaction diagram 8 is shown an aza-fatty acid probe which can be used for image-guided surgery as some tumors show preferential uptake of fatty acids by comparison to normal tissue:

Reaction diagram 8

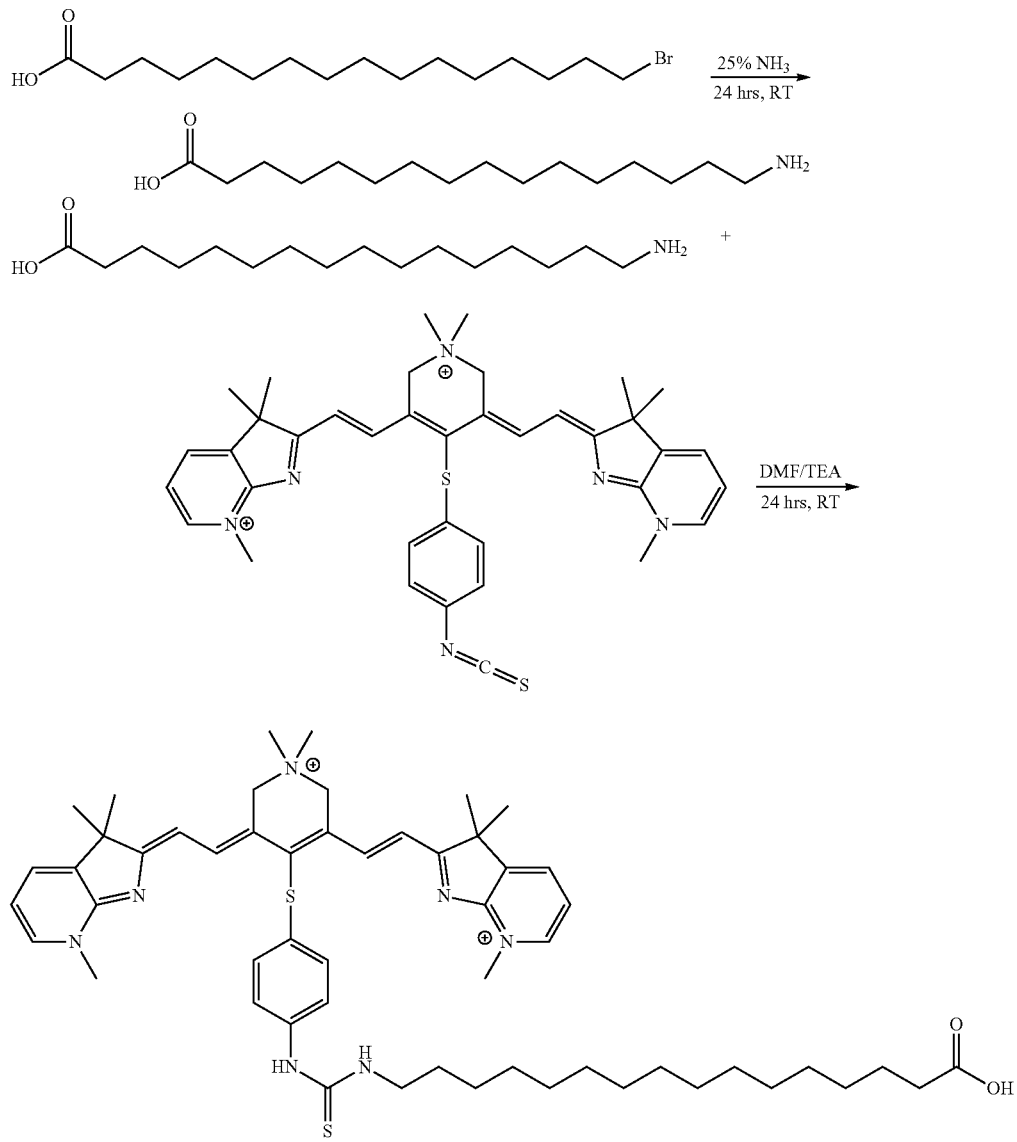

In reaction diagram 9 is shown a probe for multimodality imaging:

Reaction diagram 9

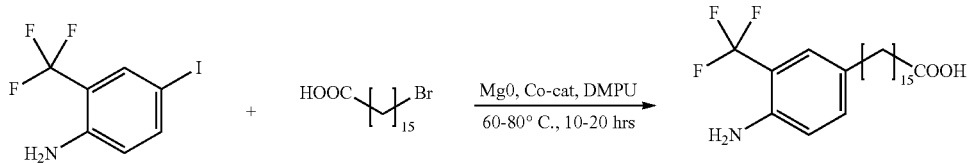

-continued

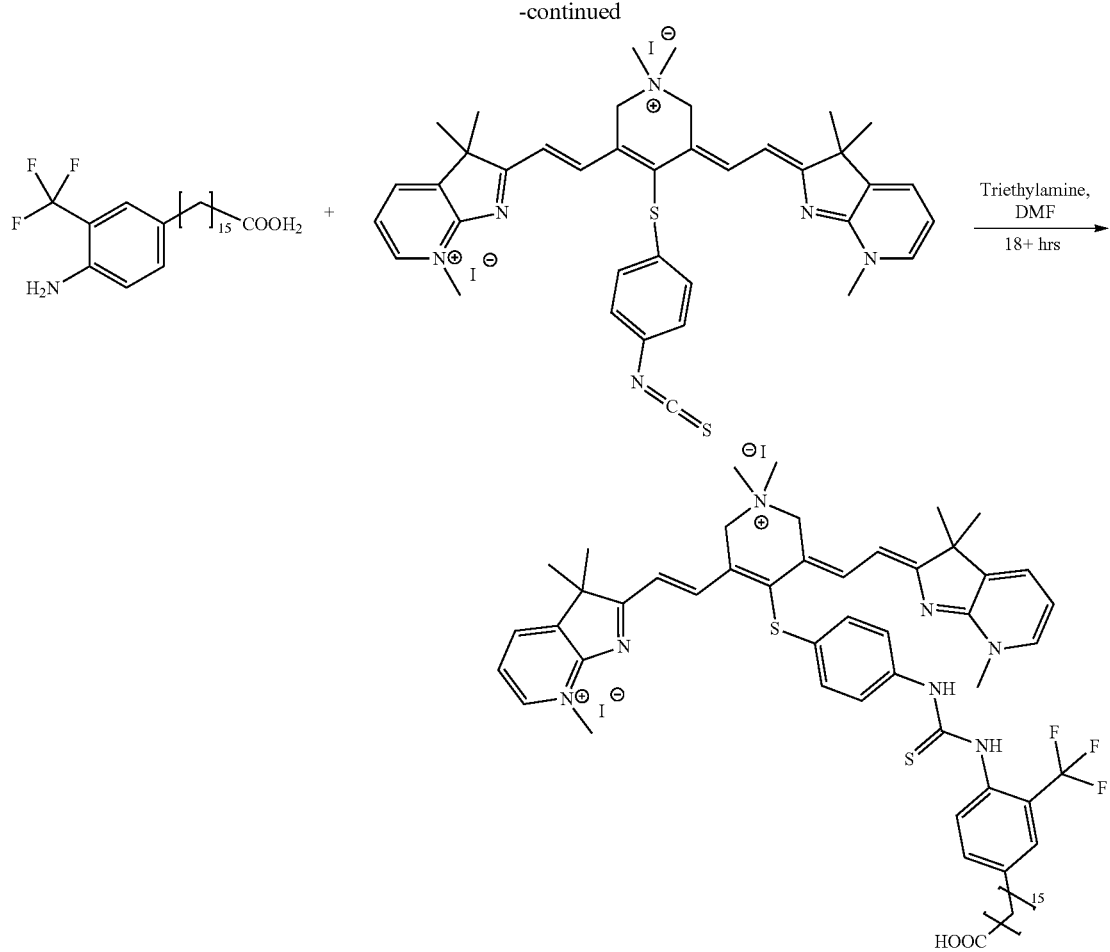

The final compound in reaction diagram 9 can be both a fluorescent probe and an imaging probe via imaging modality such as 19F-MRI.

The above-described embodiment of the invention in which the fluorescent dyes and the bioconjugate imaging agents of the invention are modified such that they carry a chelating agent, and in which the said chelating agent binds to a metal ion, preferably a radioactive metal/isotope can be used in all embodiments of the invention as disclosed hereinbefore and hereinafter, which are directed toward the fluorescent dyes and/or the bioconjugate imaging agents, including the respective kits.

Another aspect of the present invention is drawn towards a kit for fluorescence labelling of a biological sample, comprising a dye as described above or a salt thereof, preferably a solution of the dye or the salt, or a bioconjugate imaging agent according to any of claims 7-9, and optionally a suitable buffer.

Another aspect of the application provides methods for in vitro and in vivo imaging using the fluorescent dyes of the application including the dyes functionalized with a chelating agent including the embodiment with chelated metals in bioconjugate imaging agents. Optical imaging includes all methods from direct visualization without use of any device and use of devices such as various scopes, catheters and optical imaging equipment, for example computer based hardware for tomographic presentations. The imaging agents are useful with optical imaging modalities. Measurement techniques are known to the person skilled in the art and include, for example, endoscopy fluorescence endoscopy and further techniques which are known to the person skilled in the art; An imaging system useful in the practice of the application typically includes three basic components: (1) an appropriate light source for inducing excitation of the imaging agent, (2) a system for separating or distinguishing emissions from light used for fluorophore (fluorescent dye) excitation, and (3) a detection system. Exemplary detection systems include an endoscope, catheter, tomographic system, hand-held imaging system, an intraoperative microscope or a fluorescent microscope.

Another aspect of the application provides a method of in vivo imaging, the method comprising: (a) administering to a subject a bioconjugate imaging agent of the application comprising the fluorescent dye of the application; (b) allowing the agent to distribute within the subject; and (c) detecting a signal emitted by the bioconjugate imaging agent.

Another aspect of the application provides a method of in vivo optical imaging, the method comprising: (a) administering to a subject a bioconjugate imaging agent of the application comprising the fluorescent dye of the application; (b) allowing the agent to distribute within the subject; (c) exposing the subject to light of a wavelength absorbable by the fluorescent dye and (d) detecting a signal emitted by the agent.

Another aspect of the application provides a method of in vivo imaging, wherein the signal emitted by the bioconjugate imaging agent is used to construct an image. In other embodiments, the image is a tomographic image. In certain embodiments, the subject matter of the present application is a method of in vivo optical imaging, wherein steps (a)-(c) are repeated at predetermined time intervals thereby to permit evaluation of the emitted signals of the targeting agent in the subject over time. In certain embodiments, the subject matter of the present application is a method of in vivo optical imaging, wherein steps (a)-(d) are repeated at predetermined time intervals thereby to permit evaluation of the emitted signals of the bioconjugate imaging agents in the subject over time. In certain embodiments, the subject matter of the present application is a method of in vivo imaging, wherein the subject is an animal or a human. In certain embodiments, the subject matter of the present application is a method of in vivo imaging, wherein in step (a) two or more bioconjugate imaging agents whose signal properties are distinguishable from one another are administered to a subject, wherein at least one of the bioconjugate imaging agents has a targeting agent. In certain embodiments, the subject matter of the present application is a method of in vivo optical imaging, wherein the illuminating and detecting steps are performed using an endoscope, catheter, tomographic system, hand-held optical imaging system, or an intraoperative microscope.

Another aspect of the application provides a method of in vivo imaging, wherein the presence, absence, or level of emitted signal is indicative of a disease state. In certain embodiments, the subject matter of the present application is a method of in vivo imaging, wherein the method is used to detect and/or monitor a disease. In certain embodiments, the disease is selected from the group consisting of bone disease, cancer, cardiovascular disease, a neurogenerative disease, environmental disease, dermatological disease, a bone disease, trauma (e.g., injury), cell death, an autoimmune disease, immunologic disease, inherited disease, infectious disease, inflammatory disease, metabolic disease, and ophthalmic disease. Any cell type, tissue or organ can be monitored including for example, liver, kidney, pancreas, heart, blood, urine, plasma, eyes, CNS (brain), PNS, skin, solid tumours, etc In all the above aspects/embodiments of the invention, the terms "fluorescent dyes of the application" and "bioconjugate imaging agents" include dyes and bioconjugate imaging systems functionalized with a chelating agent including the embodiment in which metal as are chelated by chemically attached. chelating agent. The above also applies with respect to any of the following embodiments.

In a preferred embodiment of the application, the above method of the application can be uses to detect the degree of cell death. In this embodiment, it is even more preferred if the cell death results from a mechanism selected from apoptosis, necrosis, and necroptosis.

In the methods of the application, the subject is a human or an animal. In case of an animal, the animal is preferably a mammal.

In a further preferred embodiment of the above methods of the application, a compound, a dye according to the application is coupled to one or more of:
(a) a radio-active tracer,
(b) an MRI contrast agent,
(c) nanoparticle and,
(d) a biologically active compound Another aspect of the application provides a method of in vivo imaging, wherein, in step (a), cells labelled by a bioconjugate imaging agent are administered to the subject. In other embodiments, the signal emitted by the agent is used to monitor trafficking and localization of the cells.

With respect to optical in vivo imaging, such a method typically comprises (a) administering to a subject one or more of the bioconjugate imaging agents described herein, (b) allowing sufficient time to permit the agent to distribute with the subject, and (c) detecting a signal emitted by the bioconjugate imaging agents. The signal emitted by the agent can be used to construct an image, for example, a tomographic image. The foregoing steps can be repeated at predetermined time intervals thereby to permit evaluation of the emitted signals of the targeting agents in the subject over time. The subject may be a vertebrate, for example, a mammal, for example, a human. The subject may also be a non-vertebrate.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, and ophthalmic disease.

In addition, in vivo imaging can be used to assess the effect of a compound or therapy by using the bioconjugate imaging agents, wherein the subject is imaged prior to and after treatment with the compound or therapy, and the corresponding signal/images are compared.

In an embodiment of the application, the dyes and the conjugates with the targeting agent and the conjugates with the target molecules may be used in optoacoustic imaging application.

The dyes of the application may also be used as quenchers.

The methods and compositions (fluorescent dyes and/or bioconjugate imaging agents) of the application can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, 1, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosus, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer, bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein can, therefore, be used, for example, to detect and/or quantify the presence and/or localization of elevated positively charged cell surfaces in a subject, including humans, for instance in infectious or apoptotic cells, and to detect and/or quantify the presence and/or localization of infection and cell death, including the presence of infectious or apoptotic areas within an organ. The methods and compositions described herein can also be used to detect and/or quantify apoptosis associated with diseases, disorders and conditions, including but not limited to preneoplastic/neoplastic disease including areas at risk for acute occlusion (i.e. vulnerable plaques) in coronary and peripheral arteries, regions of expanding aneurysms, unstable plaque in carotid arteries, and ischemic areas. The methods and compositions of the application can also be used in identification and evaluation of cell death, injury, apoptosis, necrosis, and hypoxia. The methods and compositions can also be used for drug delivery and to monitor drug delivery, especially when drugs or drug-like molecules are chemically attached to the fluorescent probes. Exemplary drug molecules include chemotherapeutic and cytostatic agents and photodynamic agents including but not limited to Photofrin, Lutrin, Antrin, aminolevulinic acid, hypericin, benzoporphyrin derivative, and porphyrins.

In addition, the methods and compositions described herein can be used to image an infection in a subject. The method comprises administering to a subject (for example, a human or animal) an amount of one or more of the bioconjugate imaging agents described herein sufficient to facilitate in vivo and ex vivo imaging. After sufficient time to permit the agent to distribute within the animal or distribute within the area to be imaged, the presence and/or amount of the agent is determined. The presence and/or amount of the agent can then be used to create an image, for example, a tomographic image, representative of elevated positively charged cell surfaces within the tissues of the subject.

In addition, the methods and compositions described herein can be used to image infections in a subject such as tuberculosis, Lyme disease, brucellosis, whooping cough, pneumonia, tetanus, diphtheria, typhoid fever, meningitis, cellulitis, impetigo, botulism, psittacosis, urethritis, enteritis, colitis, anthrax, Legionnaire's Disease, syphilis, tularemia, bronchitis, ulcers, boils, leptospirosis, listeriosis, gonorrhea, shigellosis, *salmonellosis*, cholera, cystitis, septicemia, txinoses, endocarditis, toxic shock syndrome, scarlet fever, rheumatic fever, and Rocky Mountain Spotted Fever.

Another aspect of the application provides an in vitro imaging method, the method comprising: (a) contacting a sample with the bioconjugate imaging agent of the subject matter of the present application; (b) allowing the agent to bind to a biological target; (c) optionally removing unbound agent; and (d) detecting signal emitted from the agent thereby to determine whether the agent has been activated by or bound to the biological target. In other embodiments, the sample is a biological sample.

With respect to in vitro imaging, the imaging agents can be used in a variety of in vitro assays. After an imaging agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

Another aspect of the application provides clinical applications of the compounds (fluorescent dyes and bioconjugate imaging agents) of the application. Certain of the bioconjugate imaging agents described herein, for example, agents containing the optical or radiolabel and drug molecule, can be used to ameliorate a symptom of, or treat, a particular disease or disorder. The method comprises (a) administering an amount of one or more the agents described herein sufficient to impart a therapeutic effect in the subject; and (b) permitting sufficient time for the agent to distribute within the subject or otherwise localize in a region of the subject to be treated and then, (c) depending on the therapeutic agent, optionally activating the agent to impart a therapeutic effect. For example, when the therapeutic agent is a radiolabel, no subsequent activation is required. However, when the therapeutic agent is a photoreactive agent, for example, a dye used in photodynamic therapy, exposing the agent to light having a wavelength that activates the agent may activate the agent. As a result, the agents can be used to treat a condition of interest, for example, a cancer, immune disorder, inflammatory disorder, vascular disorder and the like. Furthermore the agents can be used to reduce tumor burden, to inhibit infection in an organ, or other region of interest in the subject, or reduce apoptotic cell proliferation within a subject.

Another aspect of the application provides probes that are molecular imaging agents, the molecular agents could be the fluorescent dyes of the application themselves in a particular environment such as solvent or vehicle in which it is administered or bioconjugates defined agents consisting of a fluorochrome (fluorescent dye) of the application conjugated through the linking group to a targeting agent as defined earlier. The molecular imaging agents are usually administered or delivered to a subject wherein the signal emitted by the agent is used to construct an image as described below.

Bioconjugate imaging agents described herein may be formulated with one or more pharmaceutically acceptable carriers (additives) and/or diluents to provide a pharmaceutical composition. Exemplary pharmaceutical compositions comprise one or more agents and one or more pharmaceutically acceptable carriers. As described in detail below, the pharmaceutical compositions may be specially formulated for administration in solid or liquid form. Examples for administration include oral administration, parenteral administration, topical application, and transdermal administration.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically-acceptable carriers include a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Wetting agents, emulsifiers and lubricants, as well as coloring agents. release agents, coating agents, sweetening, flavoring and perfuming agents, preservatives and antioxidants may also be present. Materials which can serve as pharmaceutically-acceptable carriers are known to the skilled artisan and include the typical materials.

In certain embodiments, the application provides a pharmaceutically acceptable composition suitable for administration to a subject comprising a bioconjugate imaging agent and a pharmaceutically acceptable excipient.

In some embodiments of the application, the fluorescent dyes of the application can be prepared as follows:

Scheme 3

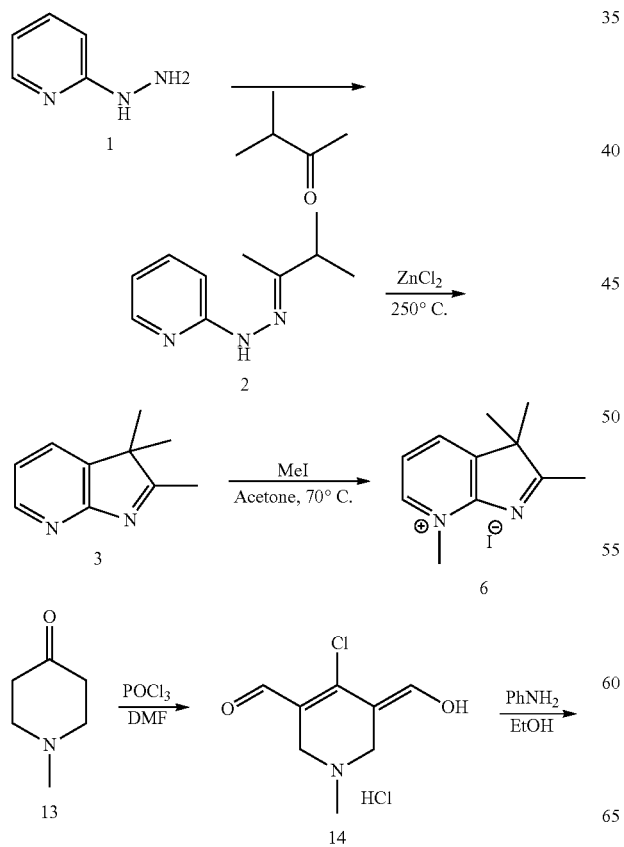

-continued

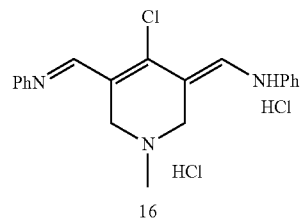

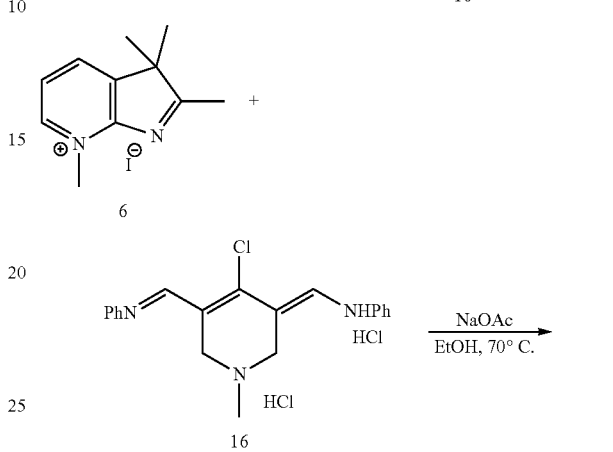

Scheme 4

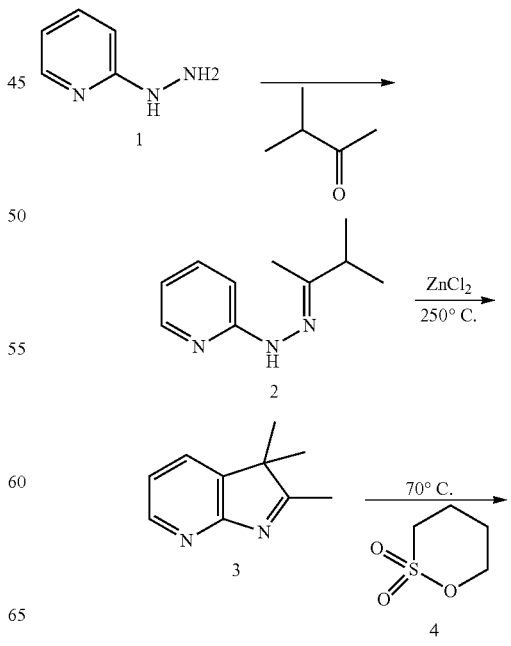

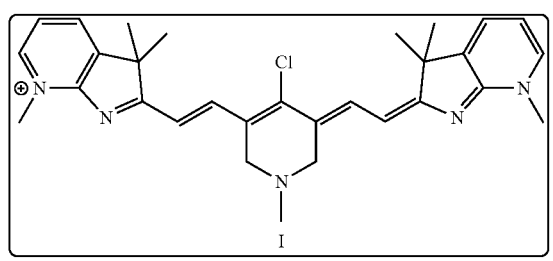

-continued
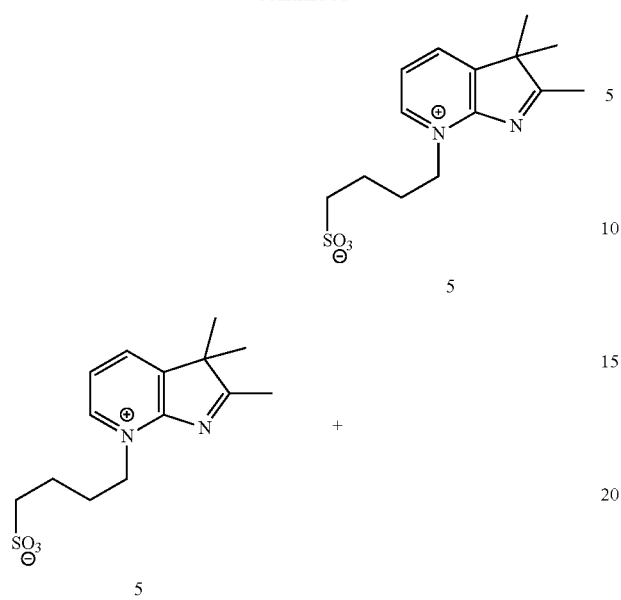
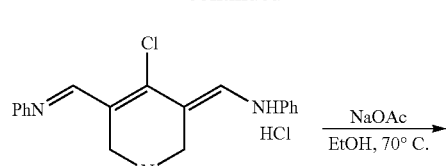
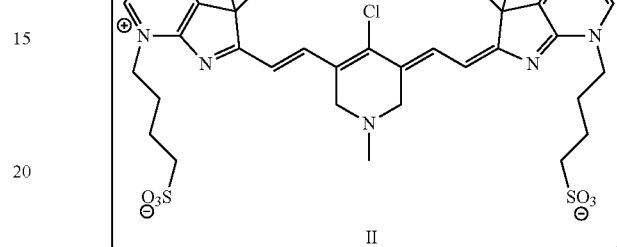
Scheme 5
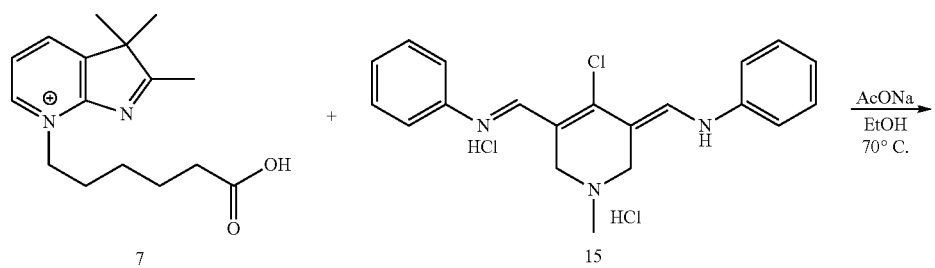
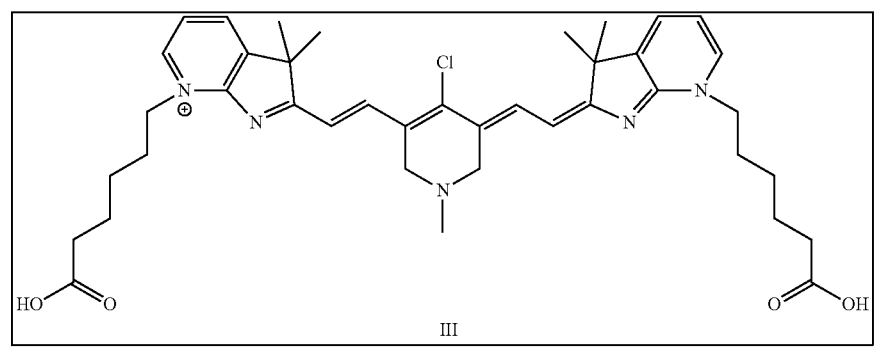

Scheme 6
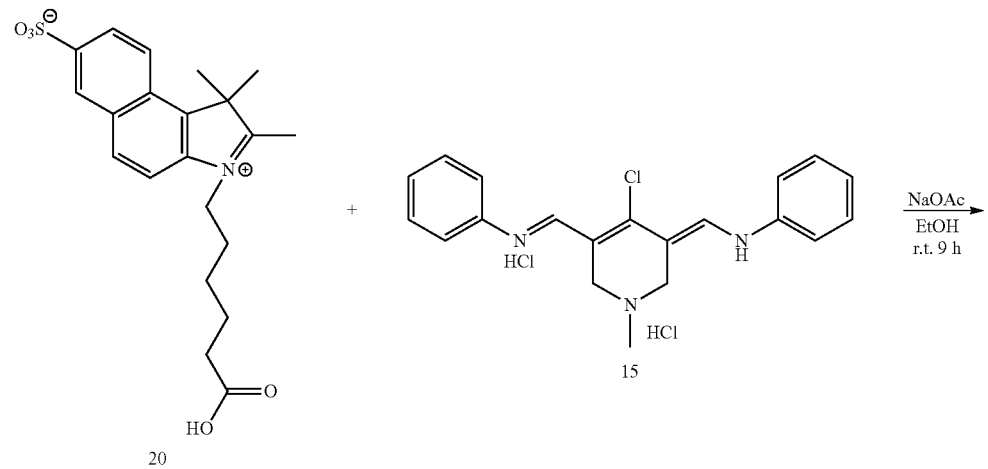
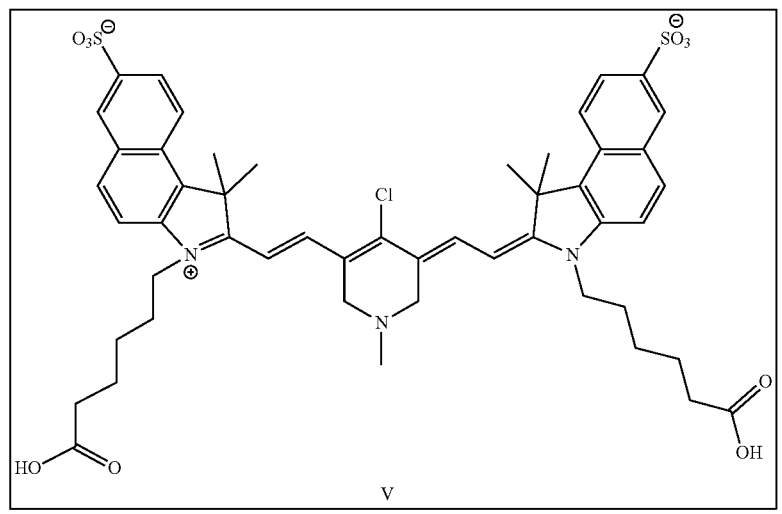

Scheme 7
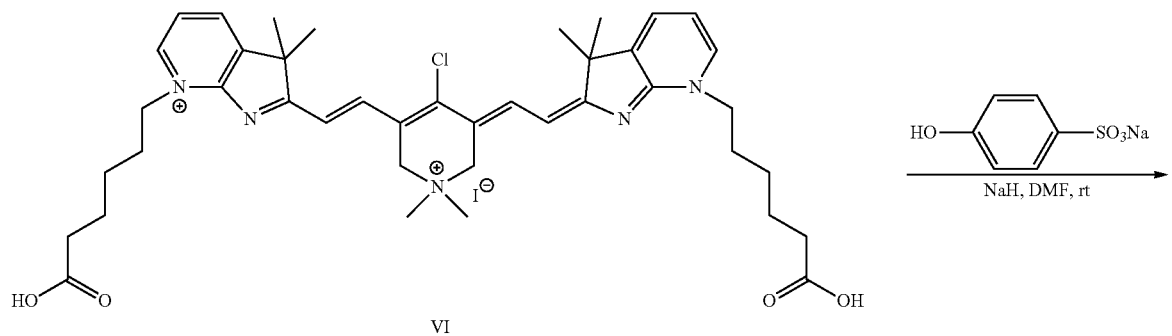
VI
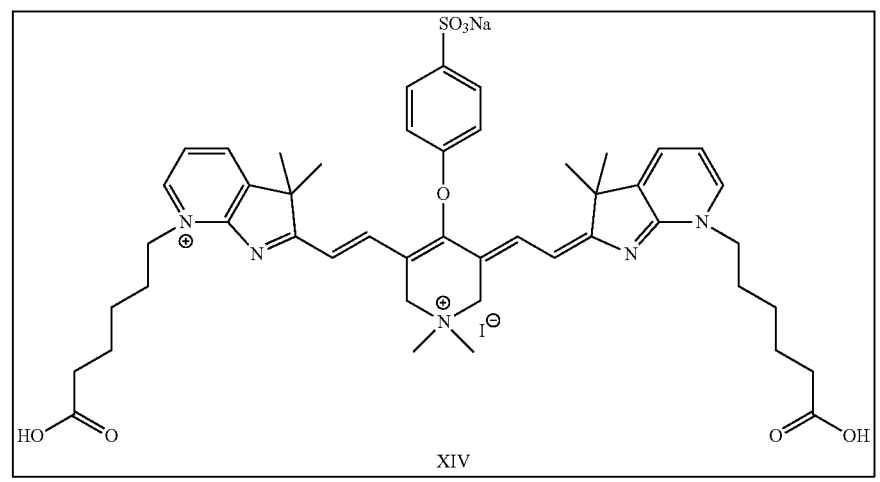
XIV
The bioconjugate imaging agents comprising fluorescent dyes of the application are derived according to the following scheme
Scheme 8
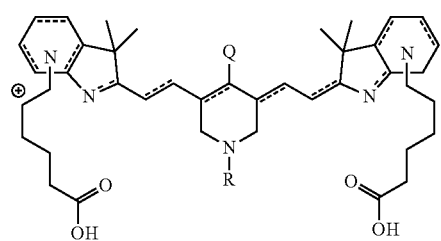
-continued
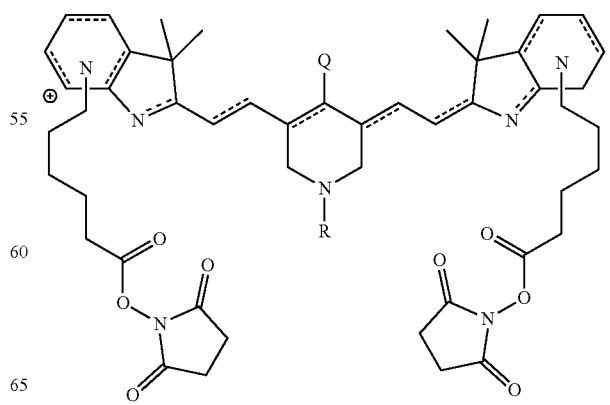

Scheme 9
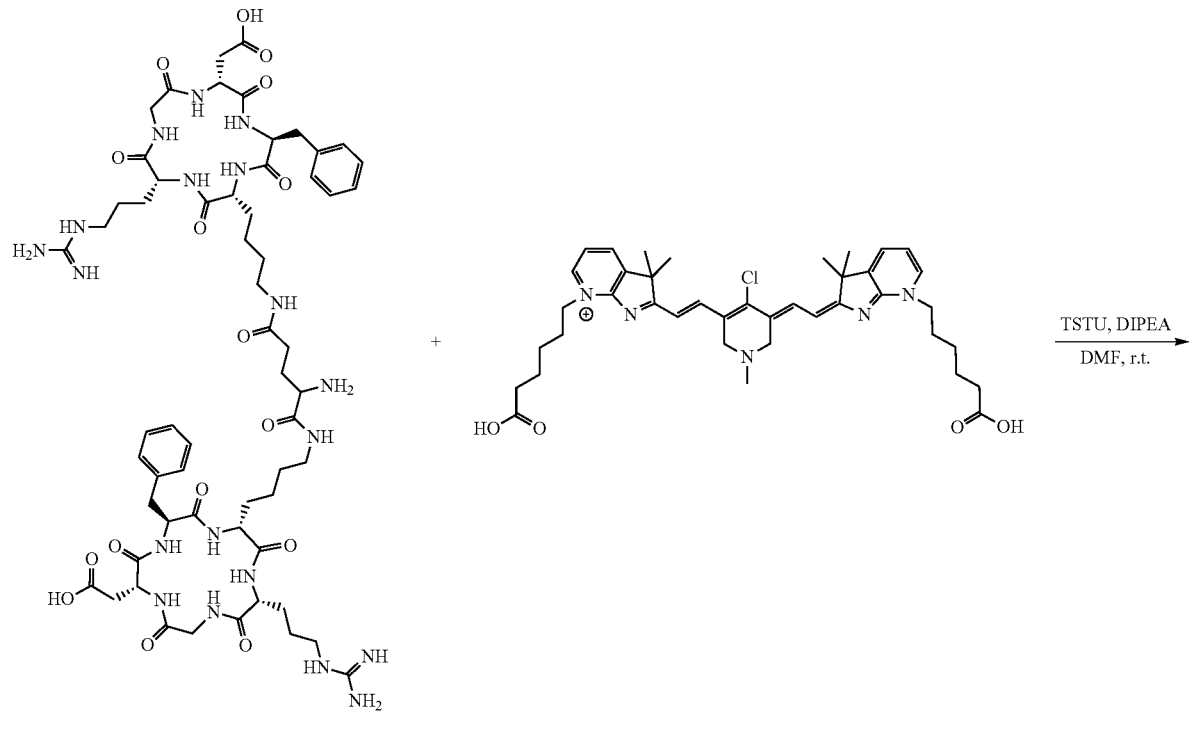
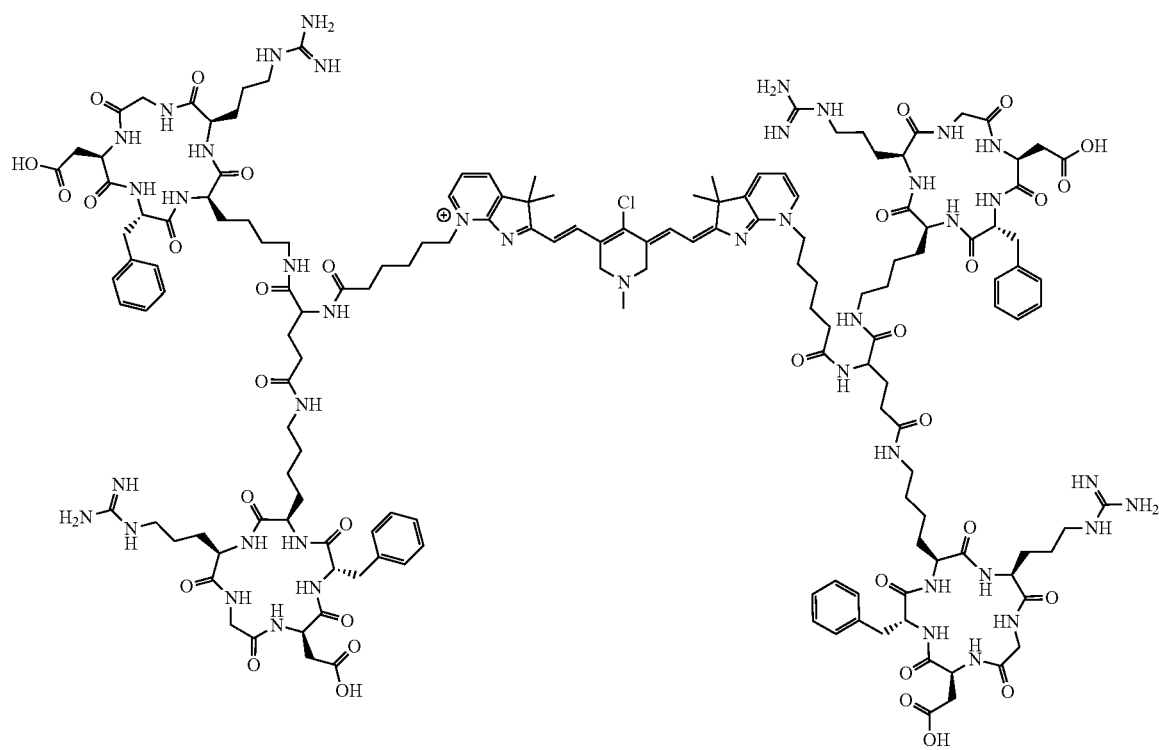

Scheme 10
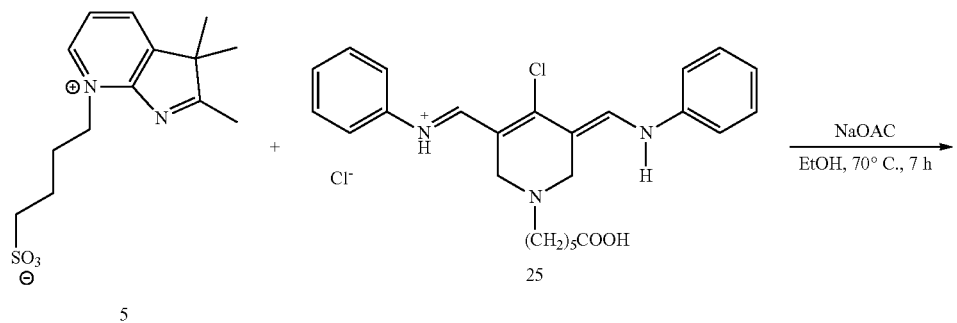
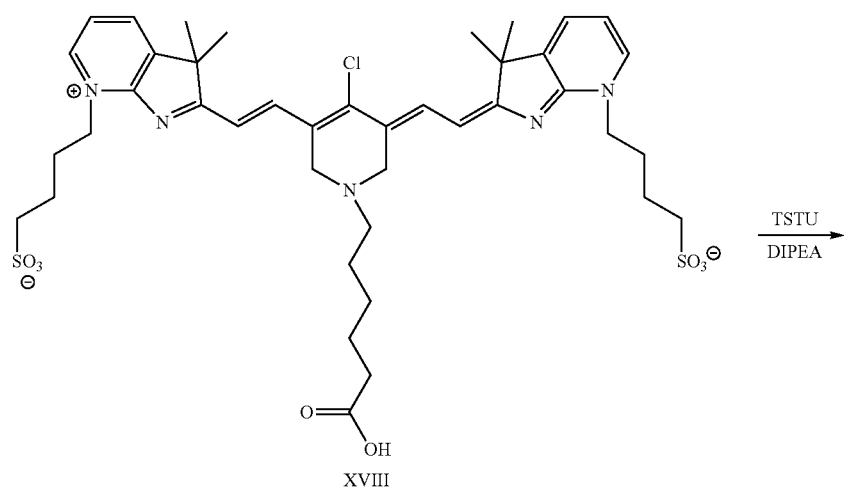
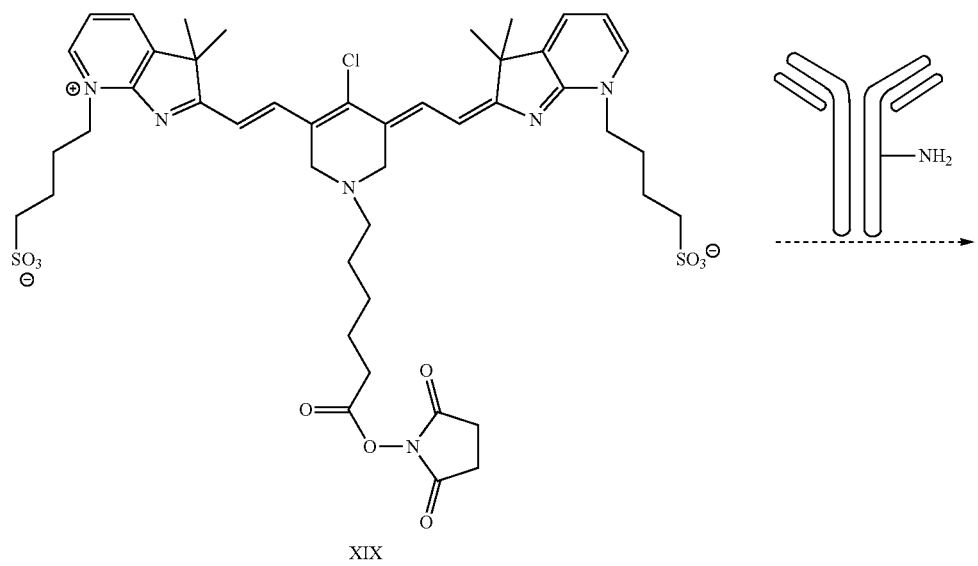

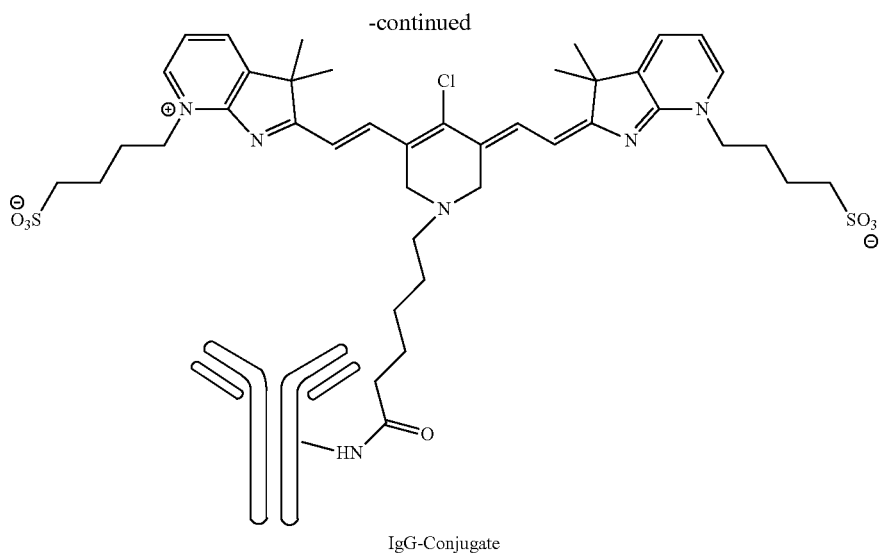

IgG-Conjugate

This application relates to new azacyanine dyes derived from pyridoindolelinium containing a heteroatom bridge preferably nitrogen. Incorporation of pyridoindolelinium into these cyanine dyes results in significantly increased solubility in both phosphate-buffered saline and water solutions over existing commercially available cyanine dyes ICG and IRDye800. The new azacyanine dyes XIII, XIV, XV, and II have cLogP values of −2.423, −3.545, −6.518, and −13.277 respectively, showing much greater hydophilicity than the commercially available ICG and IRDye800 dyes with cLogP values of 5.74 and −1.86.

Several cyanine dyes including probe XXI, RGD-ICG conjugate and InegriSense™750 (Perkin Elmer) were evaluated for targeting subcutaneous tumors in mice. Probe XXI exhibits faster and more specific tumor uptake with the optimal background to noise ratio achieved in 2 hours post injection. In comparison IntegriSense™750, a successful commercially available small molecule integrin □v□3 antagonist NIR probe shows optimal background to noise ratio in 24 hours. RGD-ICG conjugate exhibited tumor uptake kinetics similar to probe XXI, but it also generated a lot of non-specific binding to various animal tissues, possible due to random precipitation of the hydrophobic ICG dye. Faster tumor binding kinetics of probe XXI was also observed in bigger animals like dogs where highest accumulation in the tumor tissue was detected within 6 hours post injection compared with 36 hours for IntegriSense™750 (See FIG. 11 and FIGS. 12A and 12B).

Those skilled in the art will appreciate that the subject matter described herein is susceptible to variations and modifications other than those specifically described. It is to be understood that the application includes all such variations and modifications without departing from the spirit or essential characteristics thereof. The application also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the subject matter being indicated by the appended Claims, and all changes which, come within the meaning and range of equivalency are intended to be embraced therein.

The foregoing description will be more fully understood with reference to the following Examples. Such Examples, are, however, exemplary of methods of practising the present subject matter and are not intended to limit the scope of the application.

EXAMPLES

Synthesis of Compound 3

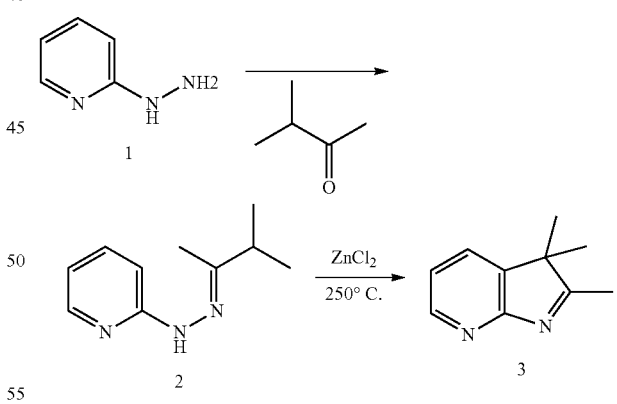

2-Hydrazinopyridine (1) (10.0 g), isopropyl methyl ketone (10 ml), were placed at 80° C. and stirred for 2 h. Excess of isopropyl methyl ketone was evaporated along with water under reduced pressure. The hydrazone 2 was heated at 250° C. with anhydrous zinc chloride (250 mg) until ammonia evolution ceased (1 hr). The dark brown product was fractionated under reduced pressure to give 3. Repeated recrystallisation from cyclohexane gave 3 as colourless needles. Yield over 2 steps: 19% HRMS calc: 161.1079; found 161.1085.

Synthesis of Compound 5

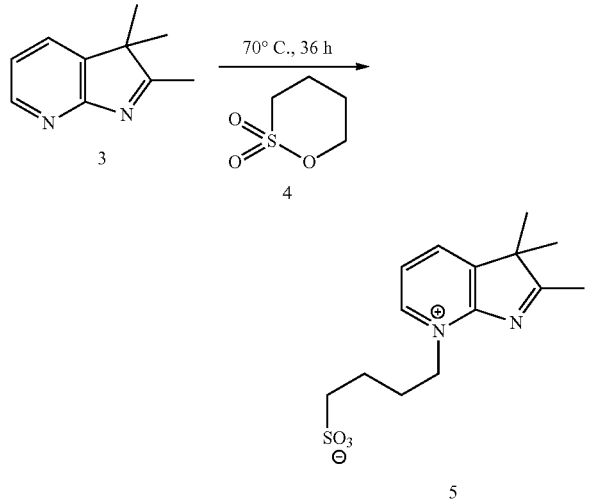

Compound 3 (130 mg) and 4 (500 uL), were placed in a sealed tube at 70° C. and stirred for 36 h. The reaction mixture was cooled down and ethyl acetate was added to give rise to a precipitate. The solid was separated by centrifugation. The solid was resuspended by means of sonication and centrifuged to isolated the solid. The procedure was repeated 3 times to obtain a pale pink solid. Yield 77%. HRMS calc: 297.1273; found 297.1281.

Synthesis of Compound 6

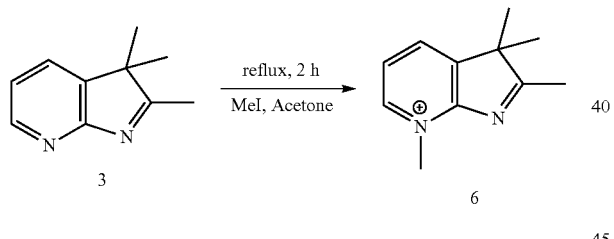

Compound 3 (180 mg) and methyl iodide (210 uL), were placed in acetone in a two necks flask under reflux and stirred for 2 h. The reaction mixture was cooled down and ethyl acetate was added to give rise to a precipitate. The solid was separated by centrifugation. The solid was resuspended by means of sonication and centrifuged to separate the solid. The procedure was repeated 3 times to obtain a pale yellow solid 6. Yield 93%. HRMS calc: 175.1235; found 175.1236.

Synthesis of Compound 7

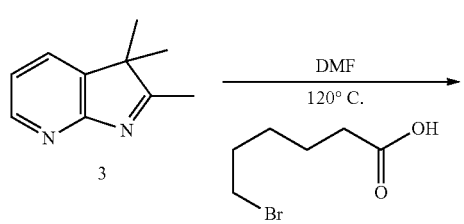

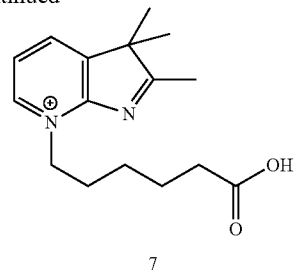

Compound 3 (200 mg) and 6-bromo hexanoic acid (731 mg), were dissolved in DMF (1 ml) in a sealed tube and warmed up to 120° C. for 2 h. The reaction mixture was cooled down and ethyl acetate was added to give rise to a precipitate. The solid was separated by centrifugation. The solid was resuspended by means of sonication and centrifuged to isolate the solid. The procedure was repeated 3 times to obtain a red solid. Yield 95%. HRMS calc: 275.1760; found 275.1766.

Synthesis of Compound 10

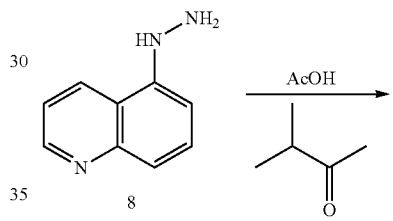

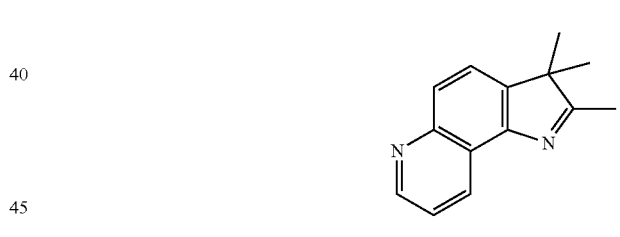

Hydrazin derivative (8) (1.0 g), isopropyl methyl ketone (540 mg), were placed at 130° C. and stirred for 4 h under nitrogen. Dilute the mixture with water and decant. Add NaOH 1M until ph 8 and formation of a brownish precipitate. Extract the solid with ethyl acetate 3 times. Yield 37%, HRMS calc: 211.1235; found 211.1236.

Synthesis of Compound 11

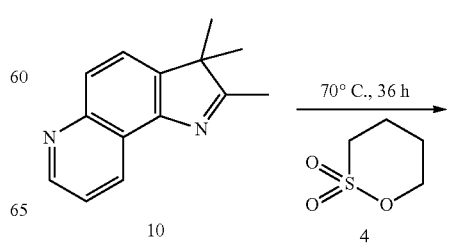

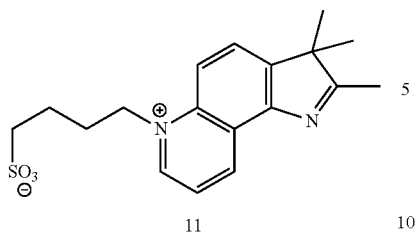

Compound 10 (130 mg) and 4 (500 uL), were placed in a sealed tube at 70° C. and stirred for 36 h. The reaction mixture was cooled down and ethyl acetate was added to give rise to a precipitate. The solid was separated by centrifugation. The solid was resuspended by means of sonication and centrifuged to isolated the solid. The procedure was repeated 3 times to obtain a pale grey solid. Yield 55%. HRMS calc: 347.1431; found 347.1431.

Synthesis of Compound 12

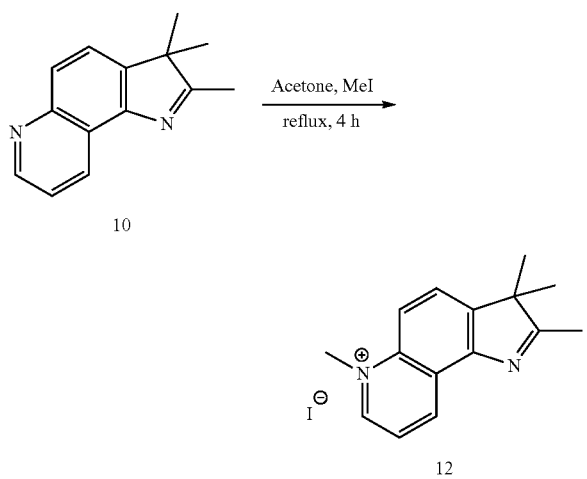

Compound 10 (180 mg) and methyl iodide (210 uL), were placed in acetone in a two necks flask under reflux and stirred for 4 h. The reaction mixture was cooled down and ethyl acetate was added to give rise to a precipitate. The solid was separated by centrifugation. The solid was resuspended by means of sonication and centrifuged to separate the solid. The procedure was repeated 3 times to obtain the red solid 12. Yield 71%. HRMS calc: 225.1392; found 225.1394.

Synthesis of Compound 15

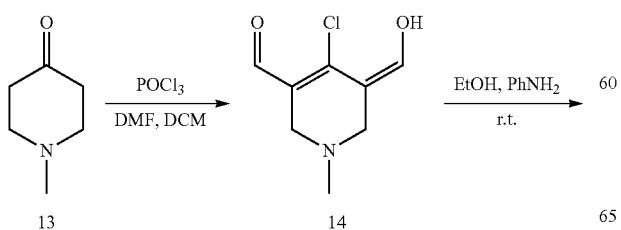

A solution of DMF (1.8 ml, 23.39 mmol) and dichloromethane (1.8 ml) was cooled in ice with stirring under nitrogen. Phosphorous oxychloride (2.68 g, 17.50 mmol) in dichloromethane (1.8 ml) was added dropwise over 10 min. 1-Methylpiperidin-4-one 13 (0.5 g, 4.41 mmol) was added dropwise over 10 min. The solution turned yellow. The mixture was heated at 70° C. for 3 h and become orange. The reaction mixture was cooled down and poured over cold water (10 ml). Solution was concentrated under vacuum and the yellow residue was washed twice with ether and air dried to obtain compound 14. Yield: 0.52 g, (62%). $^1$H NMR (400 MHz, Deuterium Oxide) 8.89 (s, 1H), 5.38 (s, 1H), 4.30 (d, J=14.9 Hz, 2H), 3.83 (d, J=14.9 Hz, 2H), 2.94 (s, 3H).

An ethanol solution (2.8 ml) of aniline (0.56 ml, 6.11 mmol) was slowly added into a solution of 14 (0.5 g, 2.66 mmol) in DMF (1.84 ml) and HCl (0.69 ml). The reaction temperature was maintained around 10-15° C. with an ice-water bath during the addition of aniline. After the reaction mixture was stirred for an additional 20 minutes, it was poured, with stirring, into 75 ml of diethyl ether. The deep-purple solid was collected by filtration and washed twice with cold water, washed twice with ether and then dried under vacuum at ambient temperature overnight. Product 15 was obtained as purple solid in 75% yield (0.79 g). $^1$H NMR (400 MHz, Deuterium Oxide) δ: 8.08 (s, 1H), 7.77-6.87 (m, 10H), 4.42 (d, J=13.7 Hz, 1H), 4.23 (d, J=15.0 Hz, 1H), 3.98 (d, J=13.8 Hz, 1H), 3.80 (d, J=14.9 Hz, 1H), 2.98 (s, 3H). ESI-QTOF MS m/z (C20H21Cl2N3) calculated: 373.1113, found: [M−Cl]$^-$=338.1424. HRMS calc: 338.1424; found 338.1422.

Synthesis of Compound 16

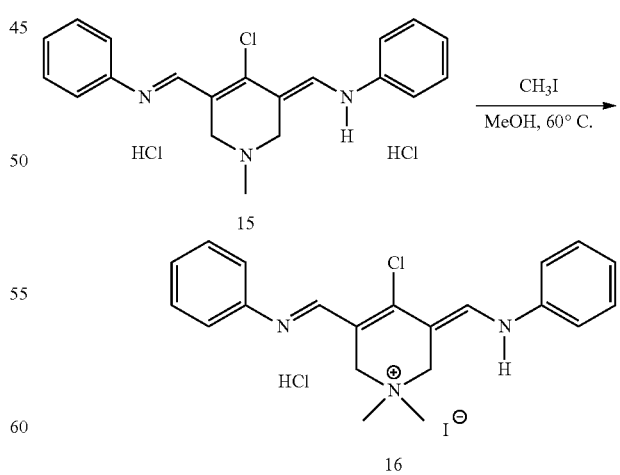

15 (0.075 g, 0.20 mmol) and methyl iodide (0.433 g, 3.05 mmol) were placed into a seal tube in dry methanol (6 ml) under N$_2$. The reaction mixture was heated at 40° C. for 28 h. The solvent was removed under vacuum and the product was washed twice with ether, and precipitated from methanol/ether. Product 16 was obtained as a red burgundy solid in 84% yield (0.086 g). ESI-QTOF MS m/z (C21H24Cl2IN3) calculated: 515.0392, found $C_{21}H_{22}N_3Cl$ [M]+=352.1581.

Synthesis of Compound 18

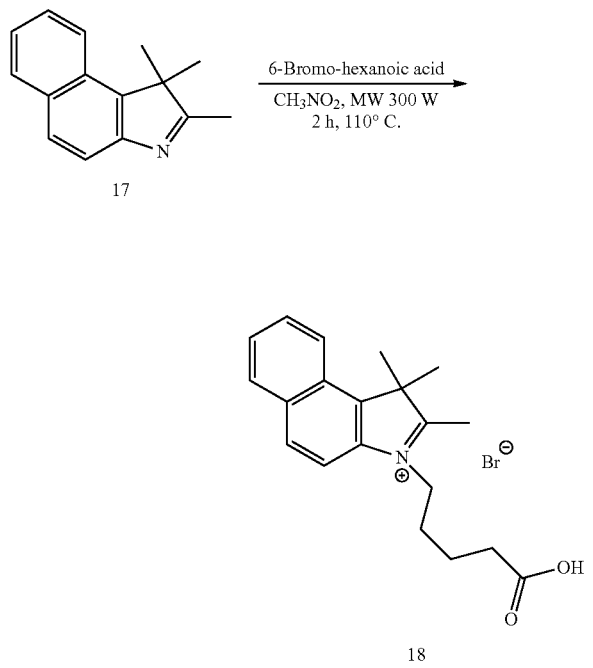

Compound 17 (1 g) and 6-bromo-hexanoic acid (1 g), were placed under nitrogen in a microwave flask and dissolved in nitromethane (2 ml). The reaction mixture was microwave for 2 hours at 110° C., 300 W. Ethyl acetate was added to give rise to a precipitate. The solid was separated by centrifugation. The solid was resuspended by means of sonication and centrifuged to separate the solid. The procedure was repeated 3 times to obtain a grey solid 18. Yield 95%. $^1$H NMR (400 MHz, Methanol-$d_4$) δ: 8.35 (d, J=8.5 Hz, 1H), 8.27 (d, J=9.0 Hz, 1H), 8.19 (d, J=8.3 Hz, 1H), 8.03 (d, J=8.9 Hz, 1H), 7.79 (dt, J=34.2, 7.5 Hz, 2H), 4.66 (t, J=7.8 Hz, 2H), 2.38 (t, J=7.1 Hz, 2H), 2.19-1.96 (m, 2H), 1.87 (s, 6H), 1.75 (p, J=7.3 Hz, 2H), 1.60 (tt, J=9.7, 6.1 Hz, 2H). HRMS calc: 324.1985; found 324.1983.

Synthesis of Compound 20

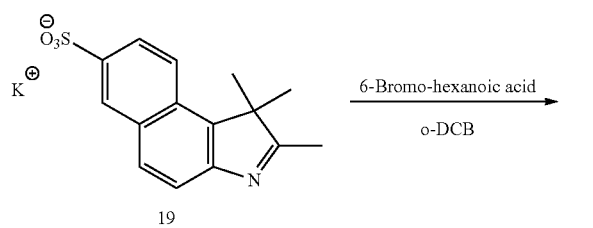

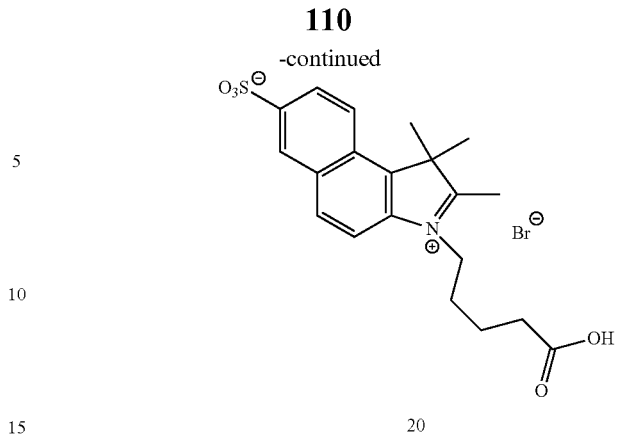

Compound 19 (0.5 g, 1.72 mmol) was dissolved in methanol (45 ml), then a solution of KOH (0.145 g, 2.59 mmol) in 2-propanol was added to the mixture. The reaction mixture was stirred for 2 hours at r.t. under $N_2$. Solvent was evaporated under reduced pressure without dryness and the solid was filtered off and dried under vacuum providing a pinkish solid (0.5 g, 90%). Product was used to the next step without further purification.

1,1,2-Trimethyl-1H-benzo[e]indole-7-sulfonate potassium salt (0.5 g, 1.52 mmol) and 6-bromohexanoic acid (0.38 g, 1.98 mmol) in 1,2-dichlorobenzene (5 ml) were heated at 110° C. under nitrogen atmosphere for 48 h. After the mixture was cooled down, solvent was decanted and the solid was triturated with 2-isopropanol (50 ml). The solid was collected through filtration, washed with EtOAc (3×25 ml) and dried under vacuum overnight to give 0.48 g of a grey solid (78%) of compound 20. $^1$H NMR (400 MHz, DMSO-$d_6$) δ: 8.54-8.25 (m, 3H), 8.13 (d, J=8.8 Hz, 1H), 7.96 (d, J=8.8 Hz, 1H), 4.57 (t, J=7.6 Hz, 2H), 2.93 (s, 3H), 2.24 (t, J=7.2 Hz, 2H), 1.91 (p, J=7.8 Hz, 2H), 1.75 (s, 6H), 1.66-1.36 (m, 4H).

Synthesis of Compound 22

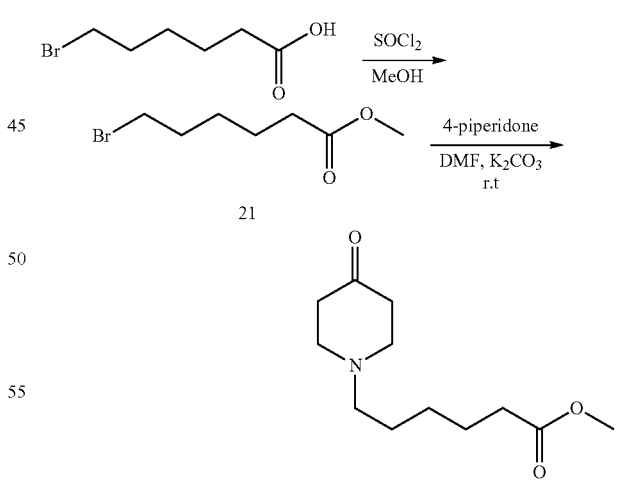

Thionyl chloride (2.8 ml, 38.45 mmol) was slowly added to methanol in an ice bath. A solution of bromohexanoic acid (1.5 g, 7.69 mmol) in methanol was added to the solution of thionyl chloride. The reaction mixture was stirred at 40° C. for 6 h. The solvent was evaporated giving the methyl-6-bromohexanoate (1.5 g, 94%) as yellow oil. Product was used without further purification to the next step. $^1$H NMR (400 MHz, Chloroform-d) δ: 3.69 (s, 3H), 3.42 (t, J=6.7 Hz, 2H), 2.35 (t, J=7.4 Hz, 2H), 1.89 (p, J=7.0 Hz, 2H), 1.68 (p, J=7.5 Hz, 2H), 1.58-1.39 (m, 2H).

To a solution of 4-piperidone (0.125 g, 1.26 mmol) in anhydrous DMF (2 ml), $K_2CO_3$ (0.2 g, 1.51 mmol), 21 (0.52 g, 2.48 mmol) and KI (0.015 g, 0.090 mmol) were added to the mixture. The reaction mixture was stirred at r.t. for 36 hours under $N_2$. The reaction mixture was filtered off and filtrate was concentrated and dried under vacuum providing a white solid (0.29 g, 98%) of compound 22. Product was used without further purification to the next step. $^1$H NMR (400 MHz, Chloroform-d) δ: 3.64 (d, J=2.0 Hz, 3H), 3.38 (t, J=6.7 Hz, 2H), 2.70 (t, J=6.2 Hz, 2H), 2.42 (t, J=6.8 Hz, 4H), 2.30 (t, J=7.4 Hz, 4H), 1.85 (p, J=7.0 Hz, 2H), 1.70-1.56 (m, 4H).

Synthesis of Compound 24

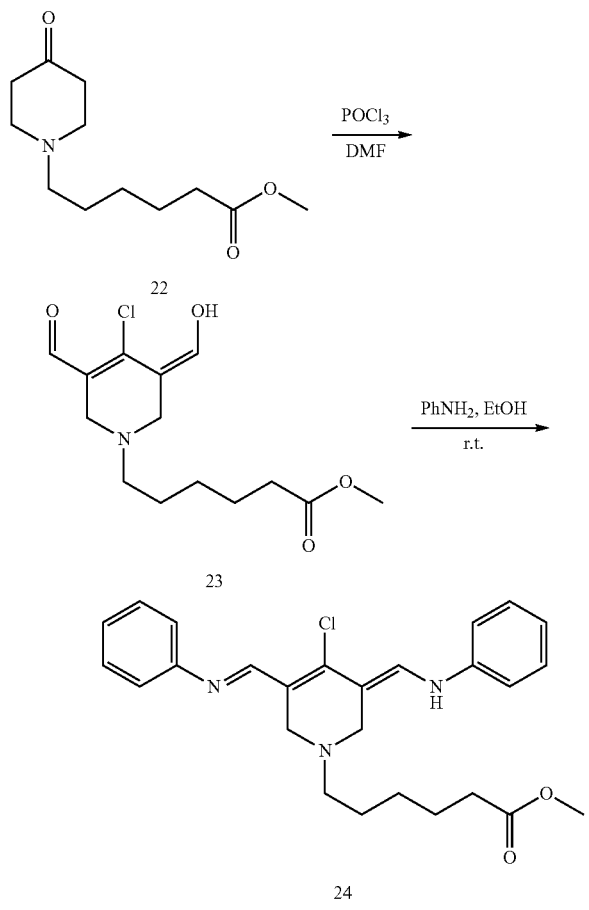

Phosphorus oxychloride (0.1 ml) was added to cooled N,N-dimethylformamide (0.12 ml) at 0° C. The temperature was maintained at 0° C. Stirring was continued for another 30 minutes before the addition of 22 (0.12 g, 0.52 mmol). The mixture was then stirred at room temperature for 4 hours before it was poured into water (5 ml), concentrated and washed twice with ether affording a yellow oil (0.16 g, 88%). After dried under vacuum overnight the crude product was used directly in the next reaction without further purification.

A solution containing aniline (0.062 g, 0.66 mmol) was dissolved in ethanol (0.32 ml) was slowly added into a solution containing 23 (0.09 g, 0.29 mmol) in DMF (0.2 ml) and concentrated hydrochloric acid (0.075 ml). The reaction temperature was maintained around 10-15° C. with an ice-water bath during the addition of aniline. After the reaction mixture was stirred for an additional 30 minutes, it was poured, with stirring, into 75 ml of ether. The deep-brown solid was collected by filtration and washed twice with cold water, and then dried under vacuum at ambient temperature overnight. Yield: 0.12 g, 80%. ESI-QTOF MS m/z ($C_{26}H_{31}Cl_2N_3O_2$) calculated: 487.1793 found: [M−Cl]+=452.2104.

Synthesis of Compound 25

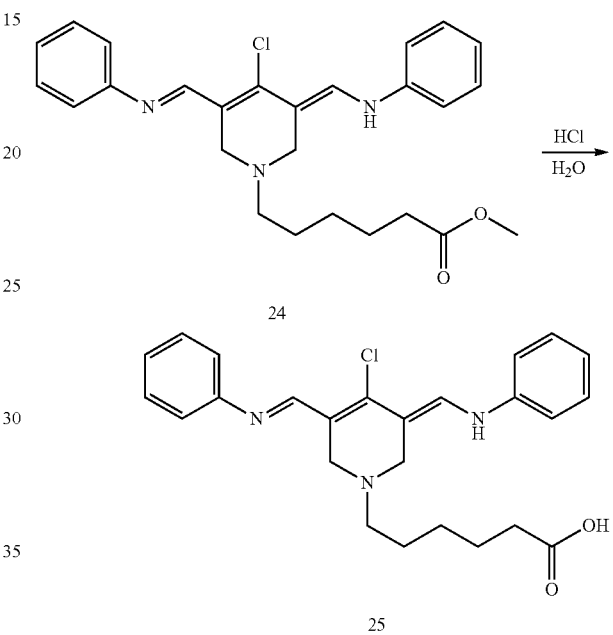

Compound 24 was (0.07 g, 0.137 mmol) dissolved in water, and HCl was added to the mixture. Reaction was stirred at room temperature for 18 hours. The solution was concentrated to dryness, and residue was washed several times with acetone to provide a red solid of compound 25. ESI-QTOF MS m/z (C25H29Cl2N3O2) calculated: 473.1637, found [M−Cl]−=438.1956. Yield: 0.045 g.

Synthesis of Dye I

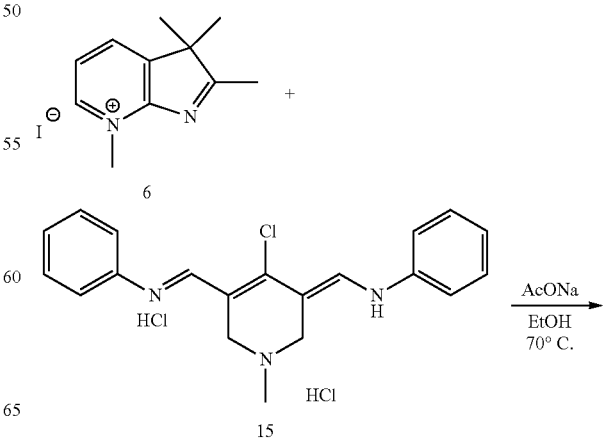

113

-continued

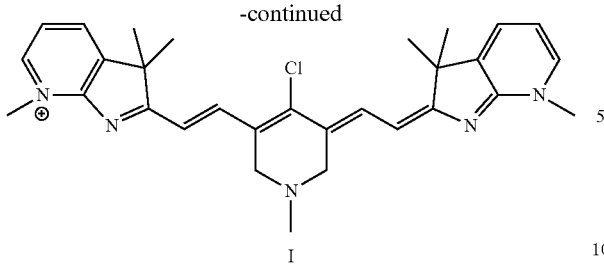

I

Compound 6 (10 mg) and 15 (2.8 mg), were placed in a sealed tube and dissolved in ethanol. Sodium acetate (5.4 mg) was added and the reaction stirred for 4 h at 70° C. The solvent was removed by rotavap and the crude separate by C4 column HPLC Agilent semi-prep. A dark blue-green precipitate was isolated. Compound I obtained in 91% yield. HRMS calc: 500.2579; found 500.2576.

Synthesis of Dye II

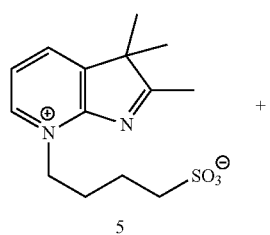

5

+

114

-continued

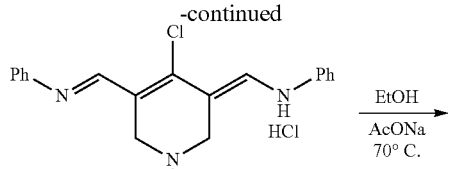

15

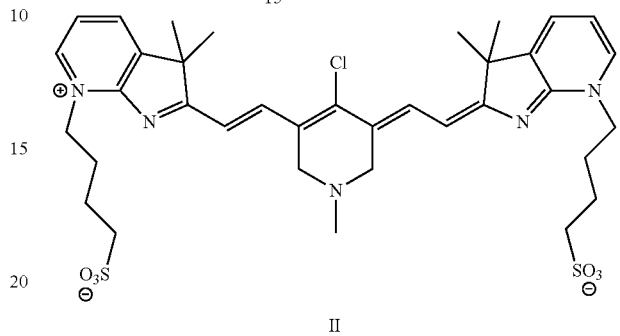

II

Compound 5 (10 mg) and 15 (2.8 mg), were placed in a sealed tube and dissolved in ethanol. Sodium acetate (5.4 mg) was added and the reaction stirred for 4 h at 70° C. The solvent was removed by rotavap and the crude separate by C18 HPLC Agilent semi-prep. A dark blue-green precipitate was isolated. Compound II obtained in 83% yield. HRMS calc: 742.2500; found 742.2515.

Synthesis of Dye III

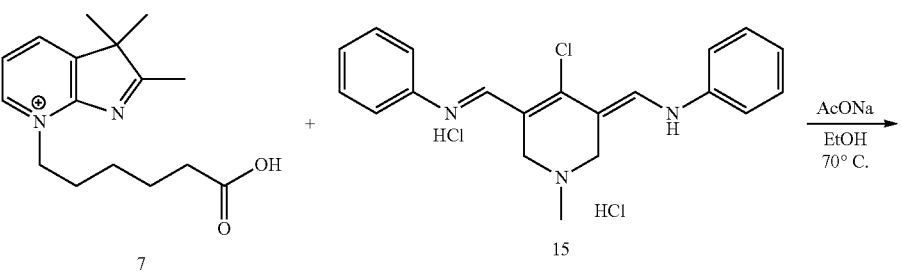

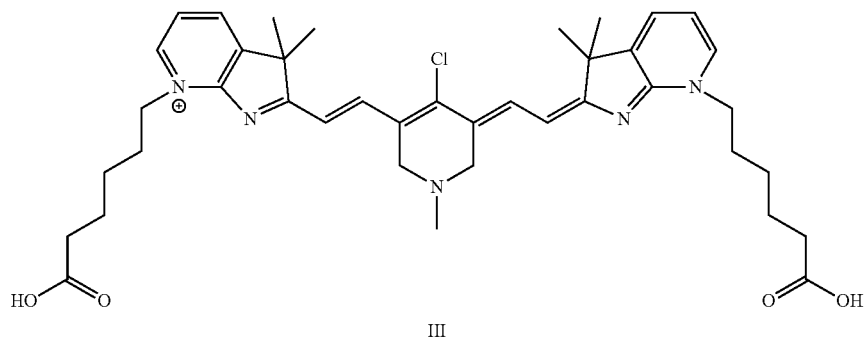

III

Compound 7 (16.7 mg) and 15 (5 mg), were placed in a sealed tube and dissolved in ethanol. Sodium acetate (9.8 mg) was added and the reaction stirred for 4 h at 70° C. The solvent was removed by rotavap and the crude separate by C4 HPLC Waters semi-prep. A dark blue solid was isolated. Compound m obtained in 75% yield. HRMS calc: 700.3641; found 700.3624.

Synthesis of Dye IV

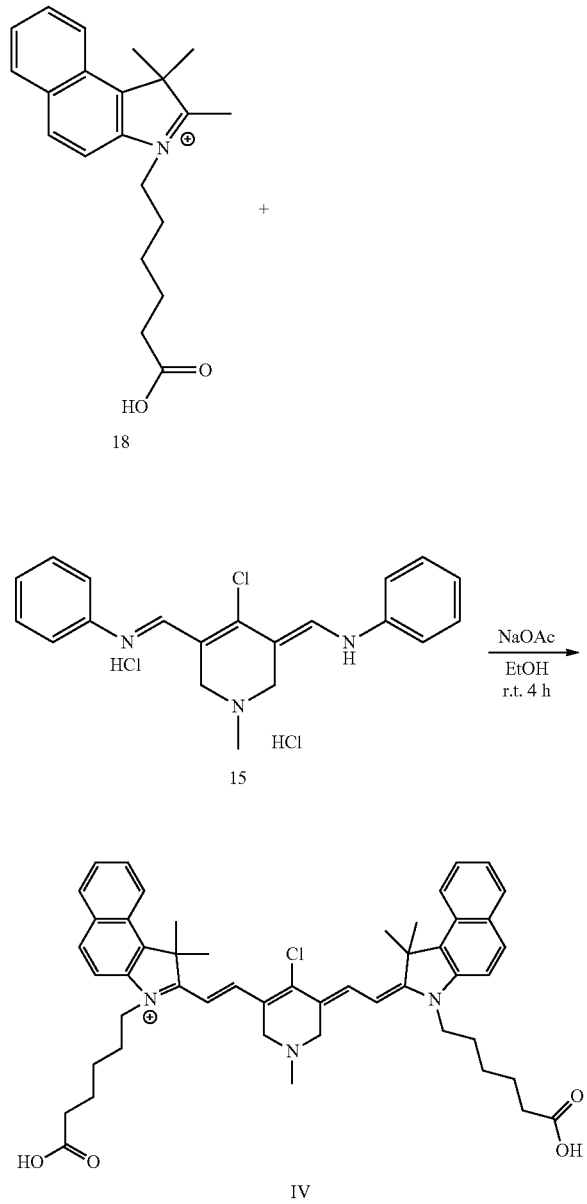

IV

A mixture of 18 (43 mg, 0.10 mmol), 15 (20 mg, 0.053 mmol) and sodium acetate (15 mg, 0.19 mmol) was dissolved in 6 ml of ethanol. After stirring at room temperature for 4 hours under $N_2$, the solvent was removed under reduced pressure. The residue was dissolved in dichloromethane and filtered to remove the excess of sodium acetate affording a dark green solid. Crude product was purified by HPLC (Waters RP-C18) to afford the corresponding compound IV as green solid (10 mg, 25%). ESI-QTOF MS m/z (C50H57ClN3O4) calculated: 798.4032, found: [M]+=798.4037.

Synthesis of Dye V

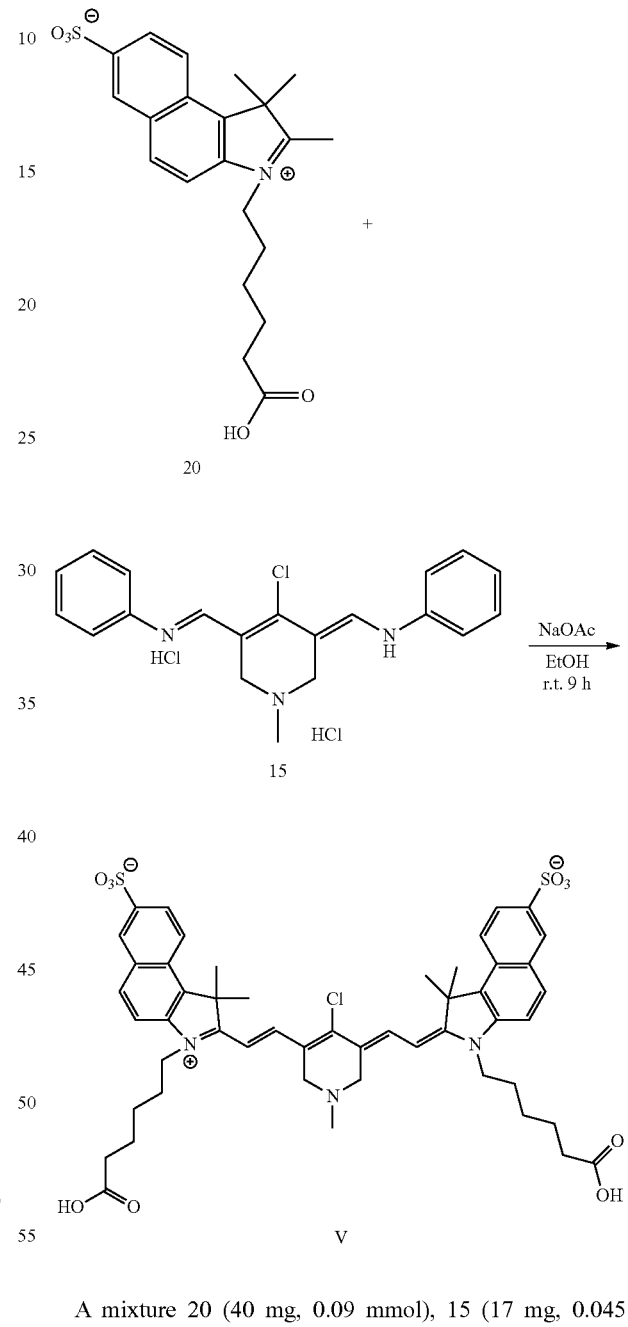

V

A mixture 20 (40 mg, 0.09 mmol), 15 (17 mg, 0.045 mmol) and sodium acetate (18 mg, 0.22 mmol) was dissolved in 6 ml of ethanol. After stirring at room temperature for 9 hours under $N_2$, the solvent was removed under reduced pressure. Crude product was purified by HPLC (Waters RP-C18) to afford the corresponding compound V as green solid (9 mg, 25%). ESI-QTOF MS m/z (C50H55ClN3O10S2) calculated: 956.3023, found: [M]+=956.2997.

Synthesis of Dye VI

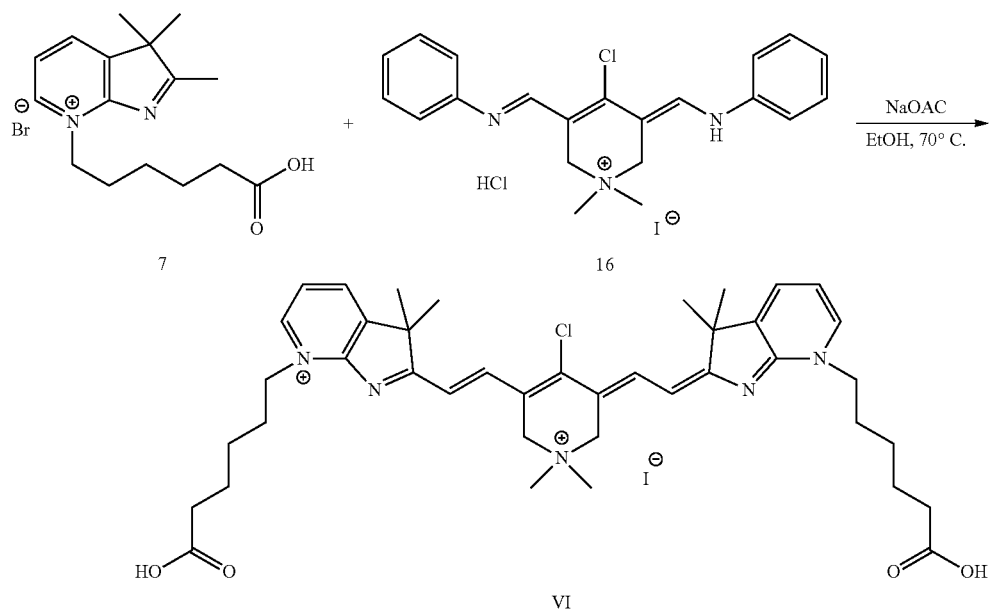

A mixture of 7 (40 mg, 0.11 mmol), 16 (15 mg, 0.029 mmol) and sodium acetate (24 mg, 0.28 mmol) was dissolved in ethanol (5 ml). Reaction mixture was stirred at 70° C. for 7 hours under $N_2$, the solvent was removed under reduced pressure. Crude product was purified by HPLC (Waters RP-C18) to afford the corresponding compound VI as green solid (6 mg, 25%). ESI-QTOF MS m/z (C41H54ClN5O4) calculated: 842.2904, found: $[M-I/2]^+=357.6933$.

Synthesis of Dye VII

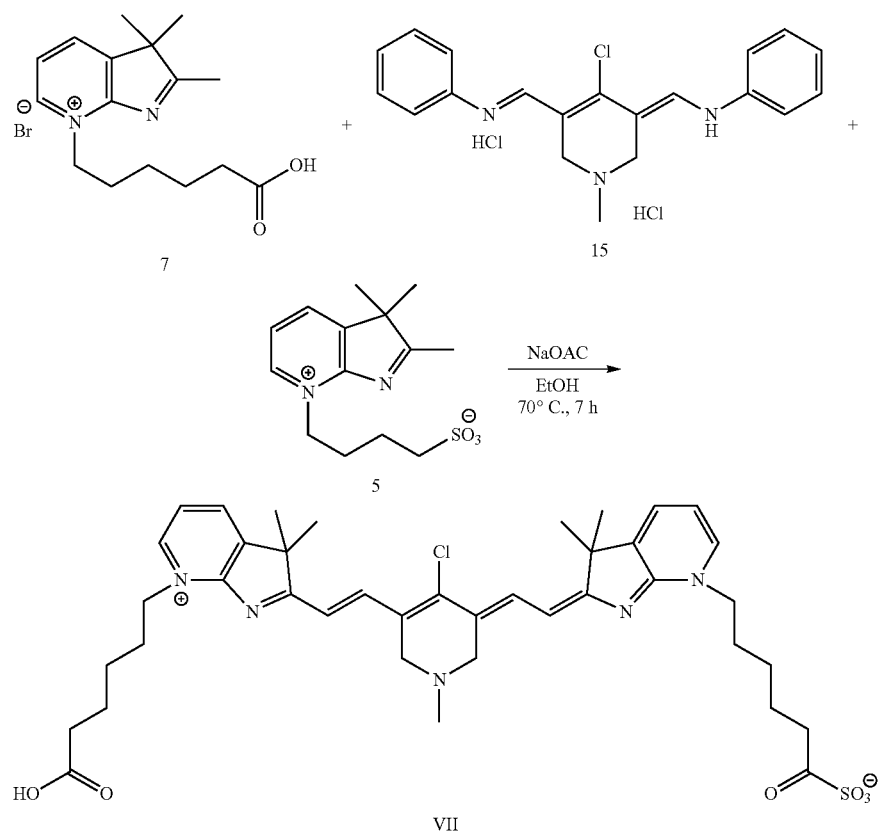

7 (42 mg, 0.12 mmol), and 5 (35 mg, 0.12 mmol) were first dissolved in ethanol (5 ml) under $N_2$ and stirred for 5 min, then 15 (20 mg, 0.048 mmol) and sodium acetate (39 mg, 0.48 mmol) were added into the solution. Reaction mixture was stirred at 70° C. for 7 hours under $N_2$, the solvent was removed under reduced pressure. Crude product was purified by HPLC (Waters RP-C18) to afford the corresponding compound VII as green solid (8 mg, 24%). Formation of symmetric dyes was observed but they were not isolated. ESI-QTOF MS m/z ($C_{38}H_{48}ClN_5O_5S$) calculated: 721.3065, found: $[M]^+$=722.3134.

Synthesis of Dye VIII

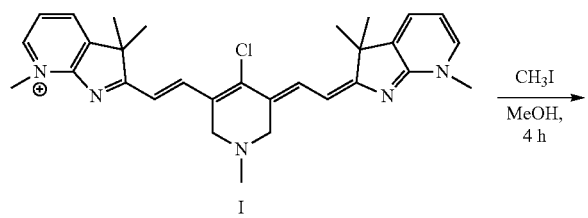

I

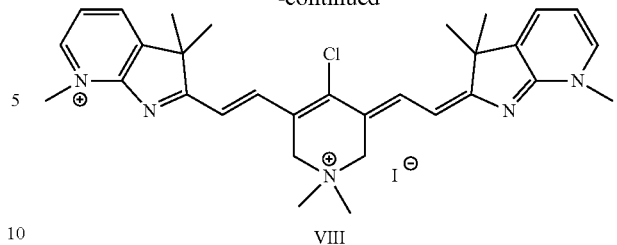

VIII

Dye I (20 mg, 0.038 mmol) and methyl iodide (0.22 g, 1.6 mmol) were placed into a seal tube in dry methanol (4 ml) under $N_2$. The reaction mixture was heated at 40° C. for 3 h. The solvent was removed under vacuum and the product was washed twice with ether. Crude product was purified by HPLC (Waters RP-C18) to afford the corresponding compound as green solid (6.5 mg, 29%). ESI-QTOF MS m/z (C31H38ClN5) calculated: 642.1855, found: [M−I/2]+=257.6408.

Synthesis of Dye IX

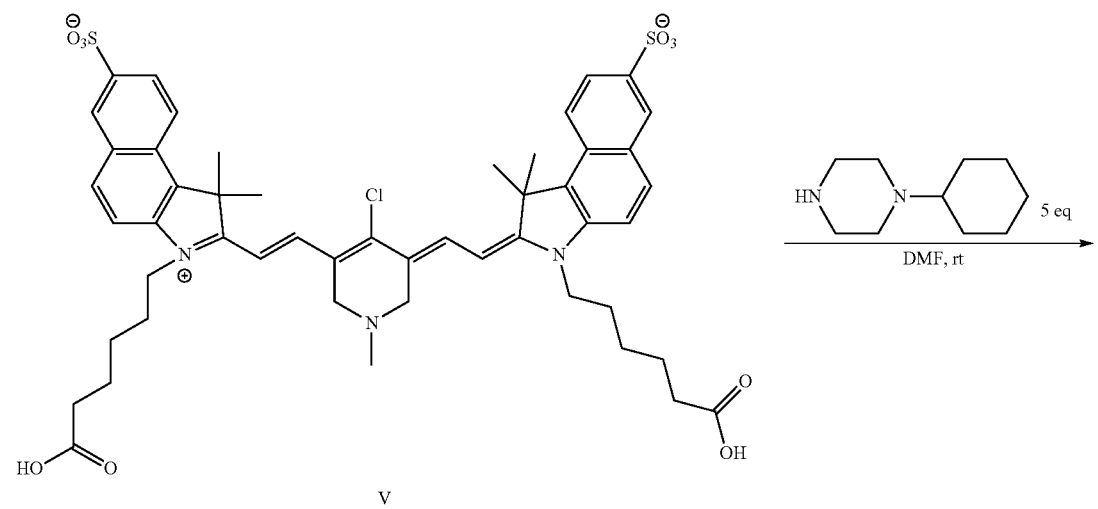

V

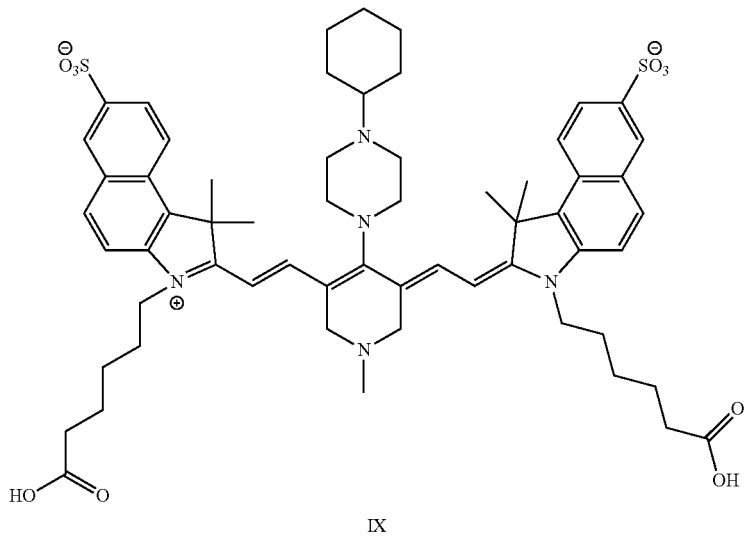

IX

Dye V (5 mg, 0.005 mmol) and 1-cyclohexylpiperazine (4.5 mg, 0.026 mmol) were dissolved in dry DMF (0.5 mL) and the solution was stirred at room temperature for 16 h. The solution color gradually changed from green to deep blue. The solvent was removed under vacuum and the product was washed twice with diethyl ether, and precipitated from methanol/ether. Purification was carried out by C8 HPLC (Agilent) to afford compound IX as dark blue solid (2.2 mg, 39%). ESI-QTOF MS m/z ($C_{60}H_{74}N_5O_{10}S_2$) calculated: 1088.4883 915.5783, found: $[M]^+$=1088.5243.

Synthesis of Dye X

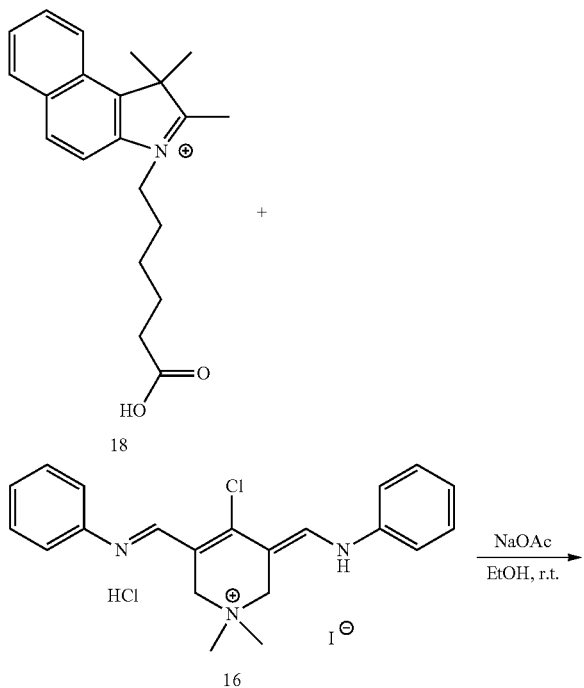

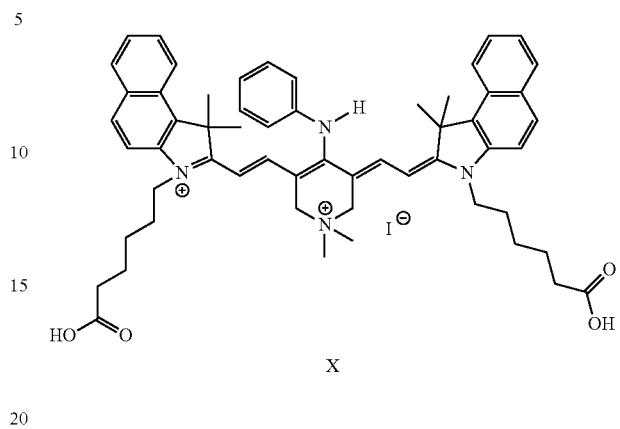

A mixture of 18 (40 mg, 0.099 mmol), 16 (20 mg, 0.048 mmol) and sodium acetate (20 mg, 0.24 mmol) were dissolved in 6 ml of ethanol. After stirring at room temperature for 2 hours under $N_2$, the solvent was removed under reduced pressure. The residue was dissolved in dichloromethane and filtered to remove the excess of sodium acetate affording a dark green solid. Crude product was purified by HPLC (Waters RP-C18) to afford the corresponding compound as green solid (8 mg, 21%). ESI-QTOF MS m/z (C57H66IN4O4) calculated: 997.4123, found: [M−I]+=871.1780.

Synthesis of Dye XI

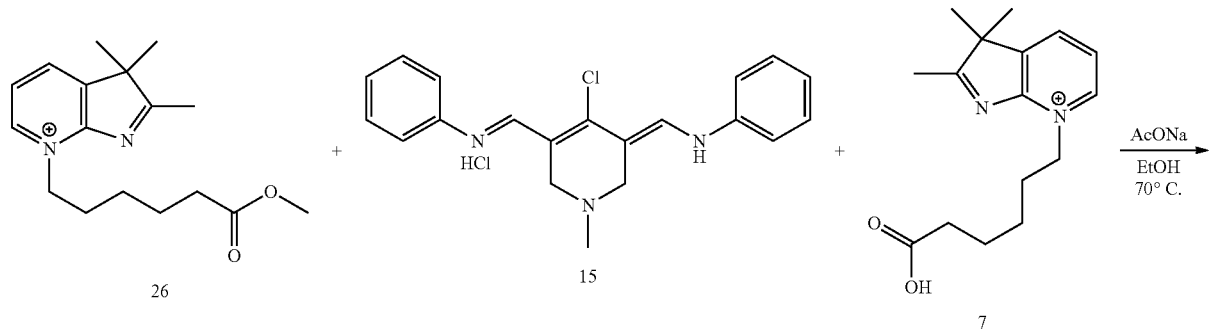

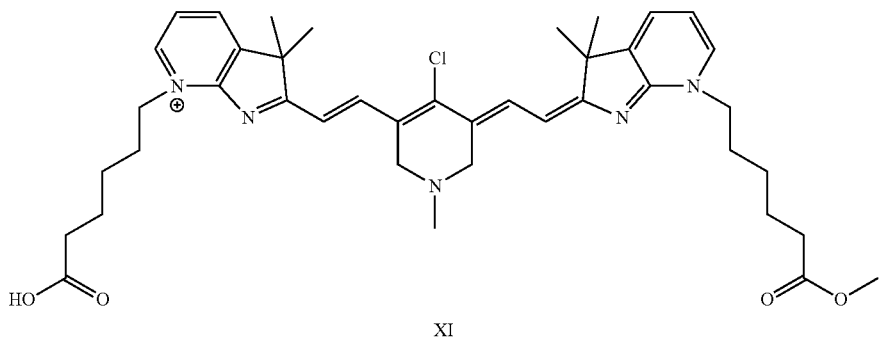

Compound 26 (365 mg, 1.33 mmol) and 15 (100 mg, 0.2.65 mmol) and sodium acetate (209 mg, 2.65 mmol) were placed into a sealed tube in dry ethanol (8 mL) under N₂. The reaction mixture was heated at 110° C. during 30 min. Solvent was removed under reduced pressure and the crude product was separated by HPLC (Waters 2998, Photodiode Array Detector, column: XTerra® Prep MS C₁₈OBD™ Column, 5 μm, 19×50 mm). Compound XI, was obtained in 20% yield (26 mg). HRMS calc: 714.3781; found 357.185.

Synthesis of Dye XII

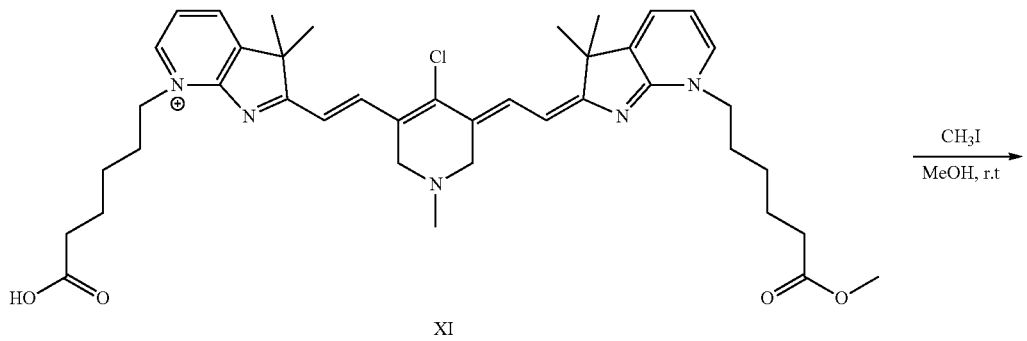

XI

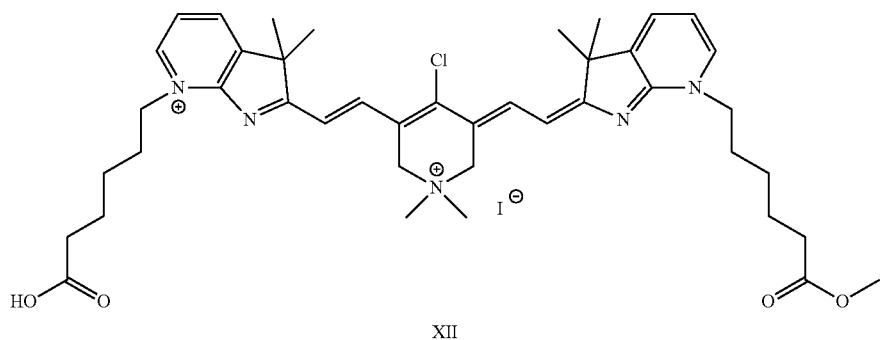

XII

Dye XI (13 mg, 0.018 mmol) and methyl iodide (0.1 mL, 1.6 mmol) were placed into a seal tube in dry methanol (2 ml) under N₂. The reaction mixture was stirred at rt. for 2 h. The solvent was removed under vacuum and the product was washed twice with ether affording a green solid. LCMS confirm the purity and formation of compound XII. Crude product was used to the next step without further purification. LRMS m/z ($C_{42}H_{56}ClIN_5O_4$) calculated: 856.306, found: [M-I/2]⁺=364.70.

Synthesis of Dye XIII

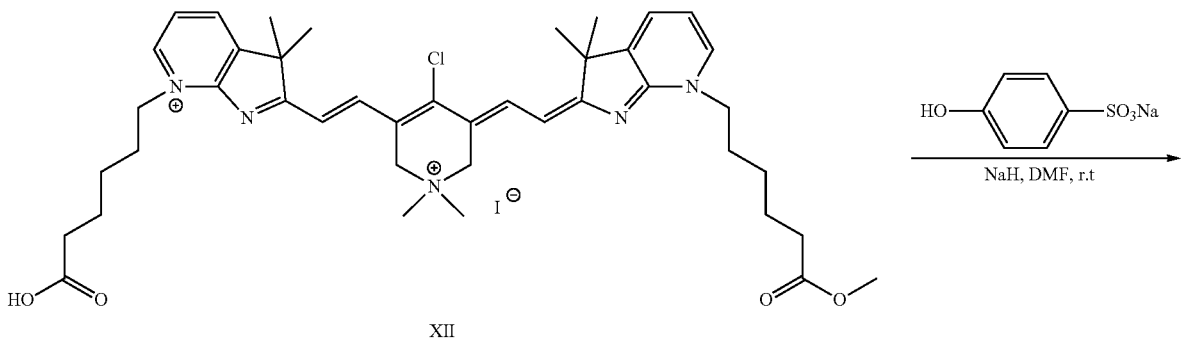

XII

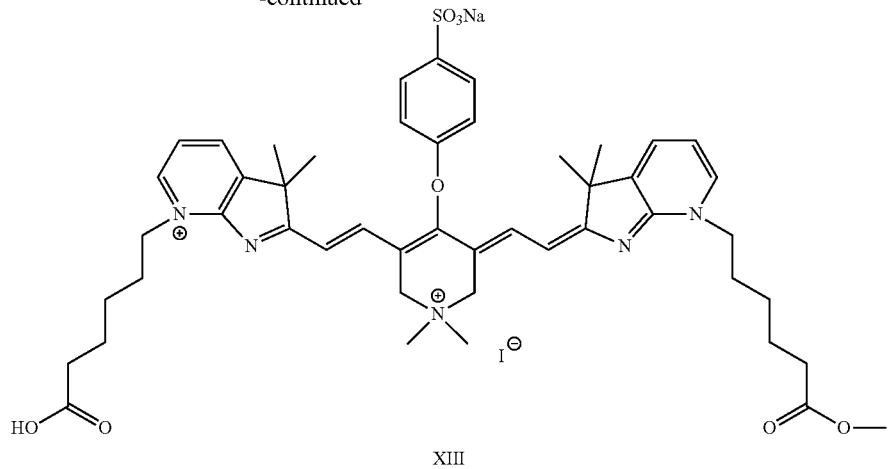

XIII

In a dry 25 mL flask under N₂ was added 4-hydroxybenzene sulfonate (17.2 mg, 0.087 mmol) and sodium hydride (4.2 mg, 0.175 mmol) in anhydrous DMF (0.8 mL). The reaction mixture was stirred at room temperature for 1.5 h under N₂. Chloro dye XII (15.0 mg, 0.017 mmol) dissolved in anhydrous DMF (1.0 mL) was then added to the reaction mixture, and stirred overnight under N₂. Reaction progress was monitored by LC-MS. Solvent was removed under reduced pressure. The crude product was purified by HPLC (Waters 2998, Photodiode Array Detector, column: XTerra® Prep MS C₁₈OBD™ Column, 5 μm, 19×50 mm) to obtain dye 5.09 mg of the pure dye XIII (32% yield). FTMS m/z (C48H60IN5NaO8S) calculated: 1016.3099, found: [M−I/2]+=444.7026.

Synthesis of Compound XIV

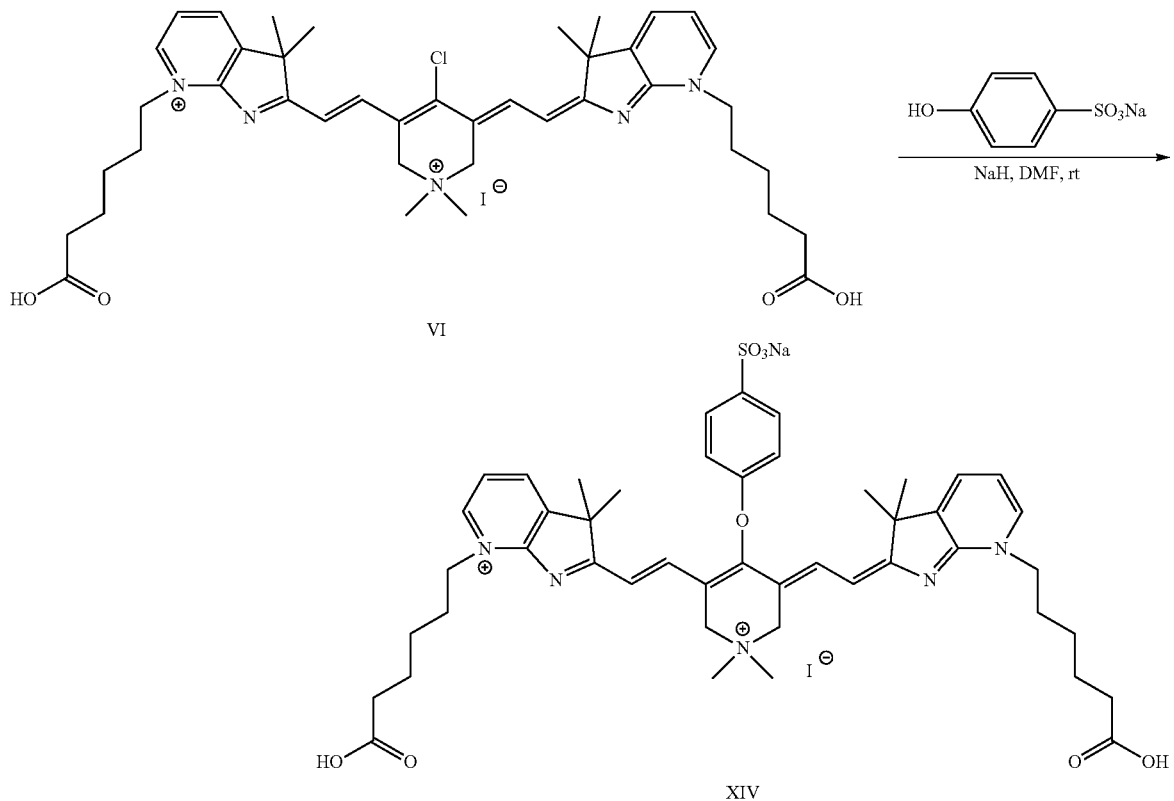

In a dry 25 mL flask under N₂ was added 4-hydroxybenzene sulfonate (18 mg, 0.094 mmol) and sodium hydride (4.5 mg, 0.188 mmol) in anhydrous DMF (1 mL). The reaction mixture was stirred at room temperature for 1.5 h under N₂. Chloro dye VI (16.0 mg, 0.018 mmol) dissolved in anhydrous DMF (1.5 mL) was then added to the reaction mixture, and stirred for 3 days under N₂. Reaction progress was monitored by LC-MS. Solvent was removed under reduced pressure. The crude product was purified by HPLC (Waters 2998, Photodiode Array Detector, column: XTerra® Prep MS C$_{18}$OBD™ Column, 5 μm, 19×50 mm) to obtain dye 6.5 mg of the pure dye XIV (32% yield). ESI-QTOF-MS m/z (C47H58IN5NaO8S) calculated: 1002.29, found: [M−I−Na/2]+=426.7054.

Synthesis of Dye XV

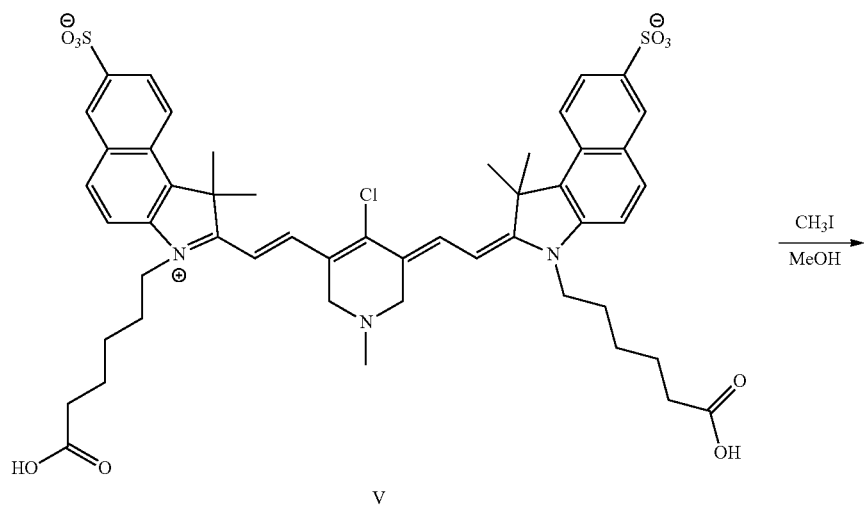

V

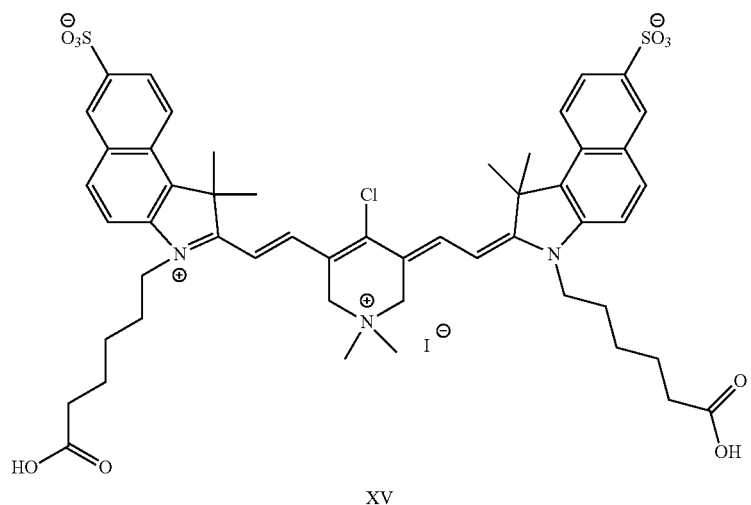

XV

Dye V (8 mg, 0.0083 mmol) and methyl iodide (0.05 mL) were placed into a seal tube in dry methanol (2 ml) under N$_2$. The reaction mixture was stirred at rt. for 4 h. The solvent was removed under vacuum and the product was washed twice with ether affording a green solid. LCMS confirm the purity and formation of compound XV. Crude product was used to the next step without further purification. LRMS m/z (C$_{51}$H$_{58}$ClIN$_3$O$_{10}$S$_2$) calculated: 1098.230, found: [M−I/2]+=971.33.

Synthesis of Dye XVI

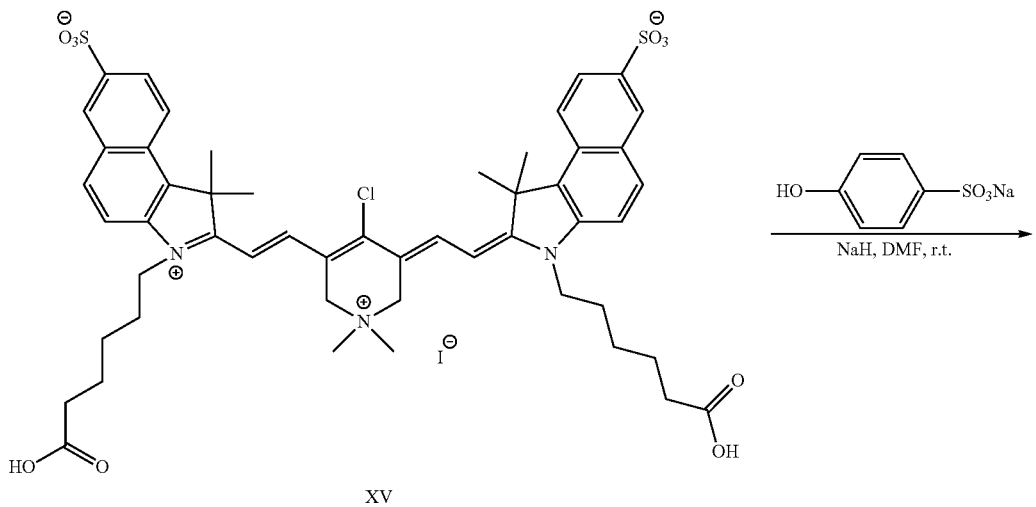

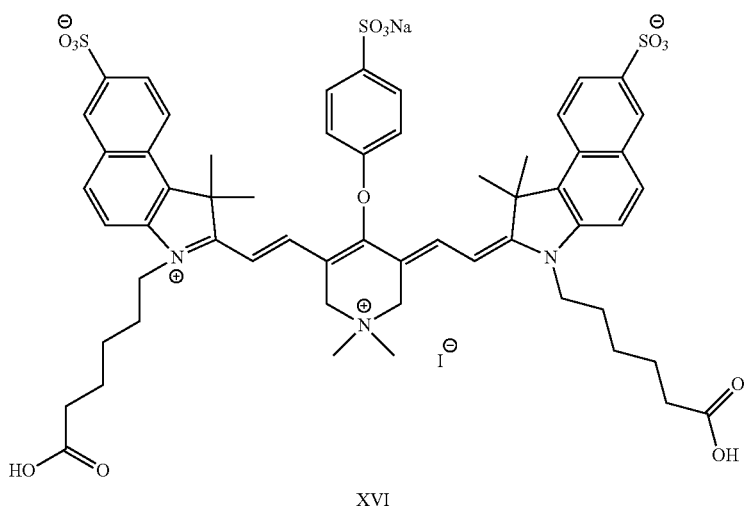

In a dry 25 mL flask under $N_2$ was added 4-hydroxybenzene sulfonate (30 mg, 0.152 mmol) and sodium hydride (7.4 mg, 0.308 mmol) in anhydrous DMF (1 mL). The reaction mixture was stirred at room temperature for 1.5 h under $N_2$. Chloro dye VI (17.0 mg, 0.015 mmol) dissolved in anhydrous DMF (1.5 mL) was then added to the reaction mixture, and stirred overnight under $N_2$. Reaction progress was monitored by LC-MS. Solvent was removed under reduced pressure. The crude product was purified by HPLC (Waters 2998, column: XTerra® Prep MS $C_{18}$OBD™ Column, 5 μm, 19×50 mm) to obtain dye 5.8 mg of the pure dye XVI (30% yield). LRMS m/z ($C_{57}H_{62}IN_3NaO_{14}S_3$) calculated: 1258.23, found: [M−I−Na]=1109.33.

Synthesis of Dye XVII

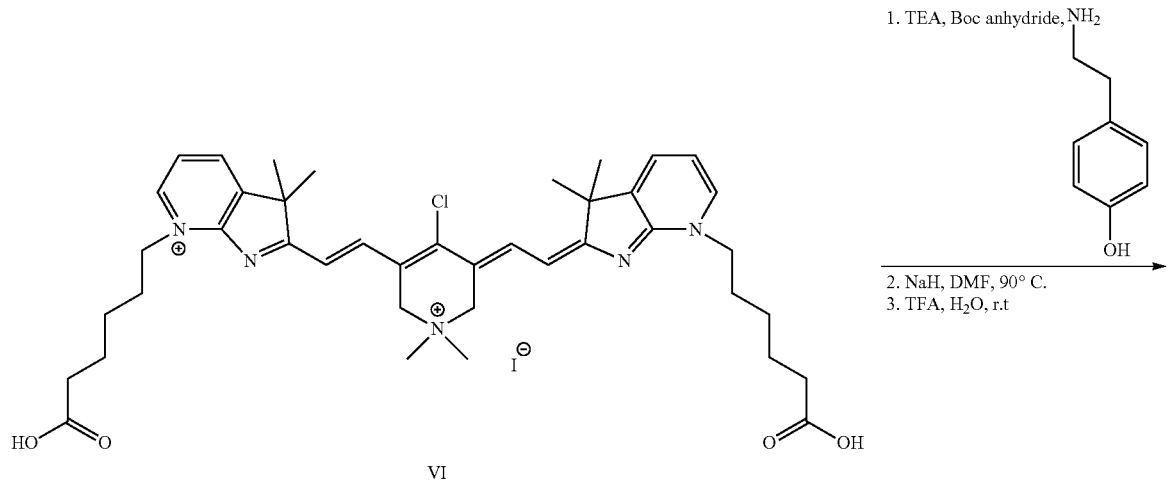

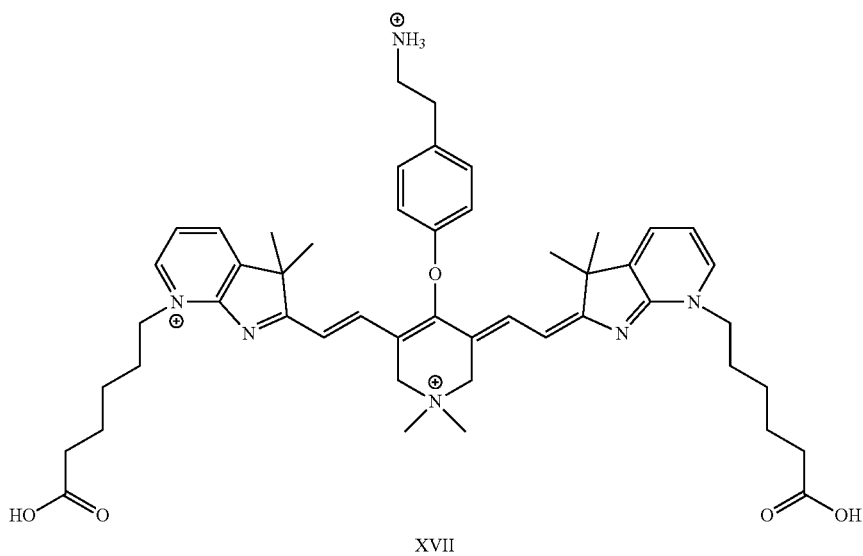

To a solution of tyramine (15 mg, 0.1 mmol) in DMF (1 mL) under $N_2$, was added TEA (22 mL, 0.159 mmol) followed by Boc anhydride (35 mg, 0.159 mmol), and the reaction mixture was stirred for 2 h. To the above solution under $N_2$, was then added NaH (2.4 mg, 0.1 mmol) and the mixture was stirred for 1 h. Finally the chloro dye VI was added to the reaction mixture under $N_2$, and the mixture was stirred for 48 h. Reaction was monitored by LCMS until disappearance of the chloro dye. The solvents were evaporated from the reaction mixture at 60° C., and the residue was redissolved in a mixture of DCM/TFA (0.6 mL, 1:1). The reaction mixture was stirred for 2.5 h, and then concentrated under reduced pressure. Crude sample was purified by HPLC (Waters RP-C18) to obtain 3 mg of XVII as green solid (44 yield). LRMS m/z ($C_{49}H_{65}IN_6O_5$) calculated: 944.4050, found: [M−I/2]=408.70.

Synthesis of Dye XVIII

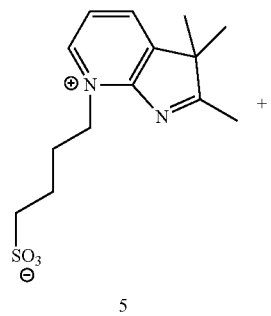

5

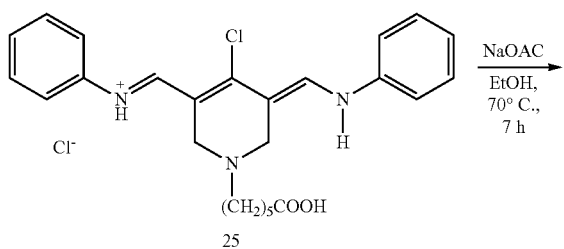

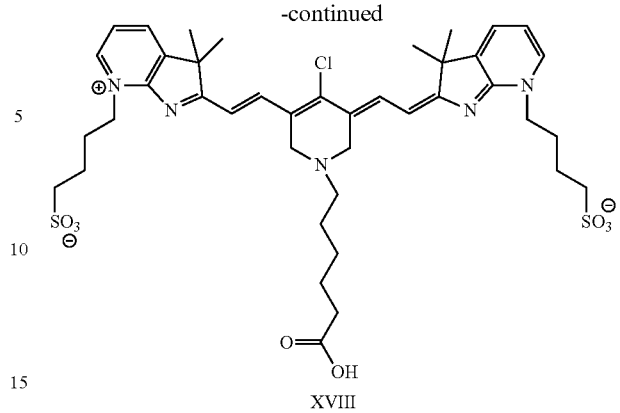

5 (46 mg, 0.158 mmol) was dissolved in ethanol (3 ml) under $N_2$ and stirred for 5 min, then 25 (15 mg, 0.031 mmol) and sodium acetate (25 mg, 0.31 mmol) were added into the solution. Reaction mixture was stirred at 70° C. for 7 hours under $N_2$, the solvent was removed under reduced pressure. Crude product was purified by HPLC (Waters RP-C18) to afford the corresponding compound as dark green solid (6 mg, 25%). ESI-QTOF MS m/z ($C_{41}H_{53}ClN_5O_8S_2$) calculated: 842.3030, found: $[M]^+$=843.3156.

Synthesis of Dye XIX

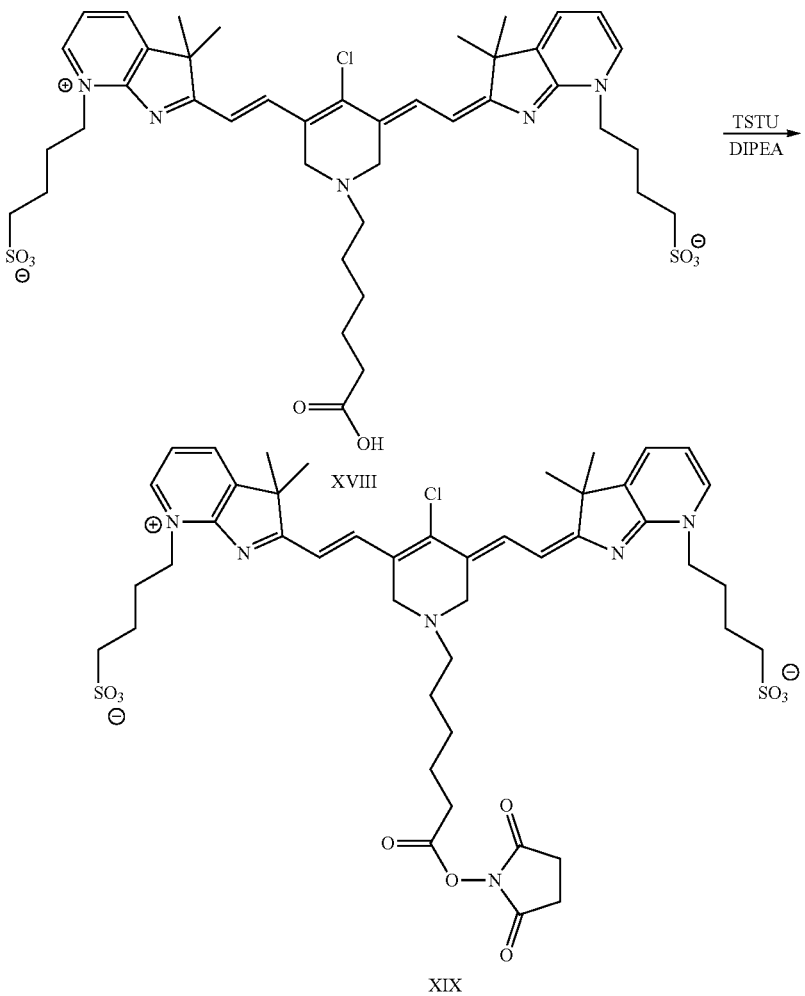

Dye XVIII (3 mg, 0.0035 mmol), dry DMF (1 mL), and DIPEA (1.5 μl, 0.0070 mmol) were added and mixture stirred at room temperature under $N_2$, then TSTU (1.6 mg, 0.0053 mmol) was added, and the resulting mixture was protected from light and stirred at room temperature for 3 h. The reaction was checked for completion by RP-HPLC (Waters), and the resulting succinimidyl ester XIX. LRMS= ($C_{45}H_{56}ClN_6O_{10}S_2$) calculated: 939.3193, found MS: 939.4.

Synthesis of Dye XX

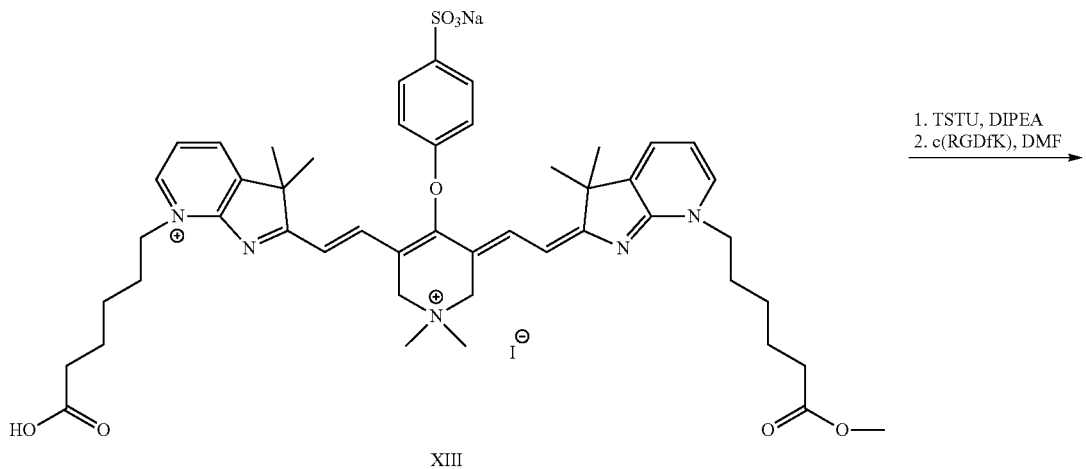

XIII

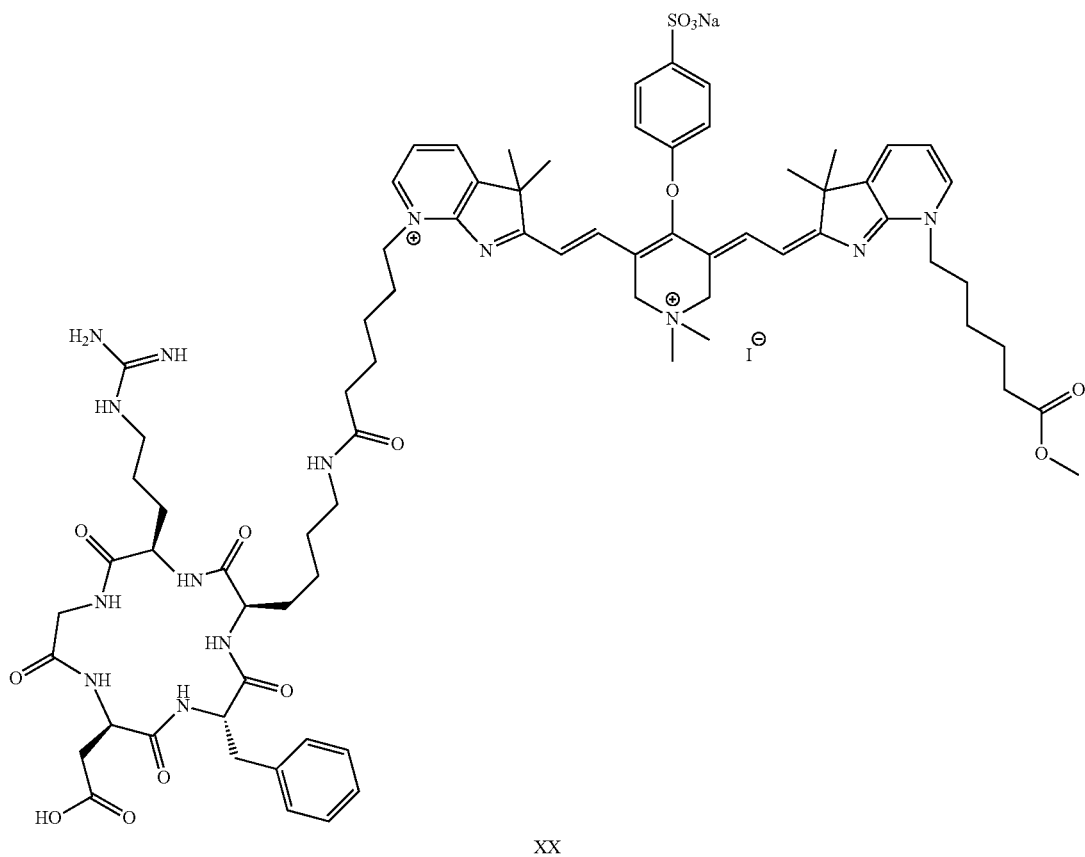

XX

Dye XIII (3.0 mg, 0.0029 mmol) was dissolved in dry DMF (1 mL) under $N_2$, and DIPEA (2.52 µL, 0.014 mmol) was added to the solution. The mixture was stirred at room temperature for 30 min. To the above solution under $N_2$ was then added TsTU (2.27 mg, 0.0074 mmol). The reaction mixture was stirred for 3 h and monitored by LC-MS to confirm formation of NH-ester. After 3 h, peptide c(RGDfK) (6.24 mg, 0.01 mmol) in DMF (0.4 mL) and DIPEA were added to the reaction mixture. The reaction was stirred for 18 h, while monitoring by LC-MS. Solvent was removed by reduced pressure and the product was purified by HPLC (Waters 2998, Photodiode Array Detector, column: XTerra® Prep MS $C_{18}$OBD™ Column, 5 µm, 19×50 mm) to obtain a pure target product XX in 60% yield (2.48 mg). FTMS m/z ($C_{75}H_{99}IN_{14}NaO_{14}S$) calculated: 1601.6123, found: [M–I–Na+H/2]+=726.3640.

Synthesis of Dye XXI

Dye XIV (3.0 mg, 0.003 mmol) was dissolved in dry DMF (1 mL) under $N_2$, and DIPEA (2.55 µL 3.5 equiv) was added to the solution. The mixture was stirred at room temperature for 30 min. To the above solution under $N_2$ was then added TsTU (3.1 mg, 0.01 mmol). The reaction mixture was stirred for 3 h and monitored by LC-MS to confirm formation of NH-ester. After 4.5 h, peptide derivative c(RGDfK) (9 mg, 0.015 mmol) in DMF (1 mL) were added to the reaction mixture. The reaction was stirred for 24 h, while monitoring by LC-MS. Solvent was removed by reduced pressure and the product was purified by HPLC (Waters 2998, Photodiode Array Detector, column: XTerra® Prep MS $C_{18}$OBD™ Column, 5 µm, 19×50 mm) to obtain a pure target product XXI in 62% yield (4 mg). FTMS m/z ($C_{101}H_{136}IN_{23}NaO_{20}S$) calculated: 2172.8990, found: [M–I–Na/2]+=1012.5097.

Synthesis of dye XXIIID

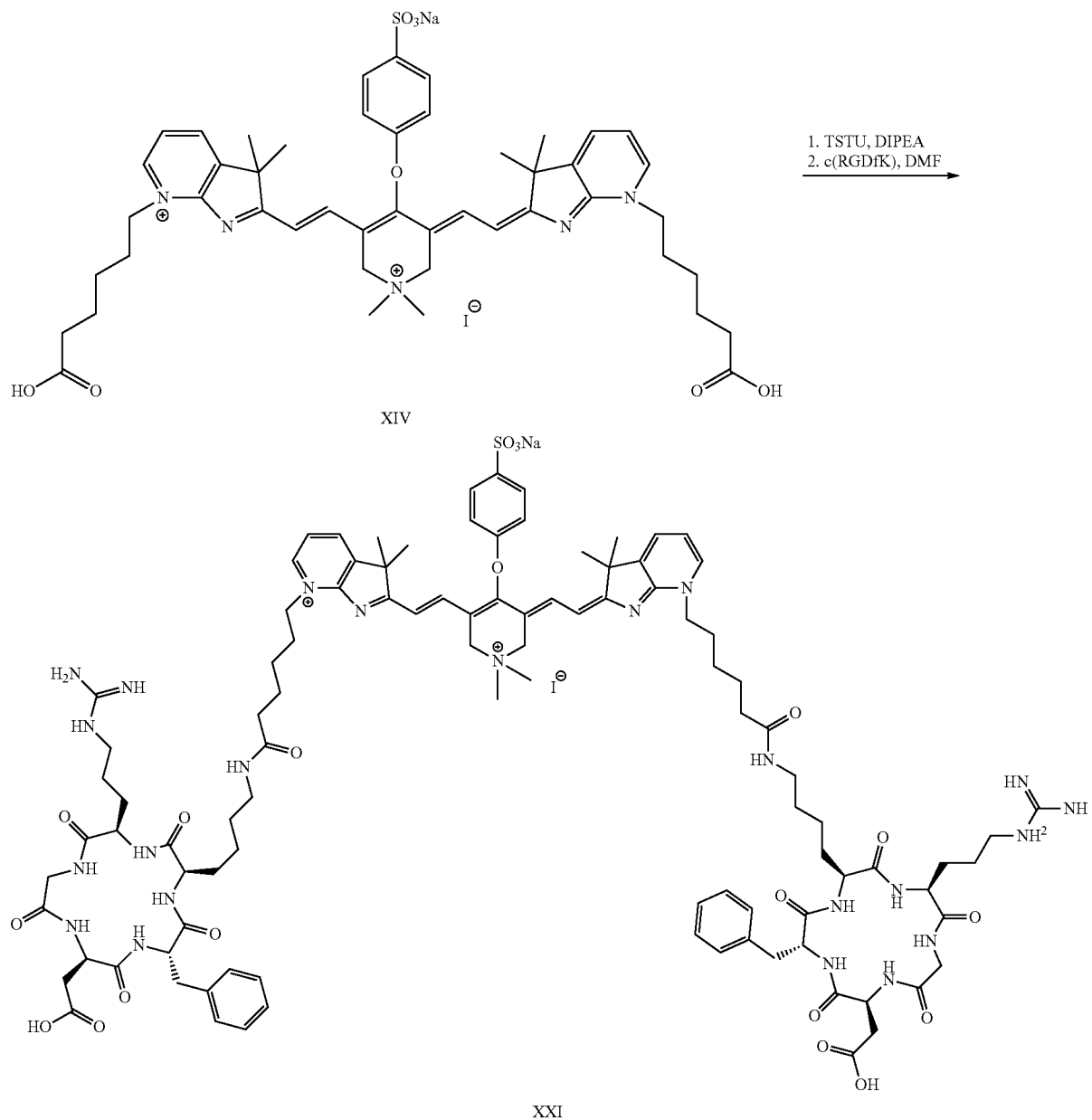

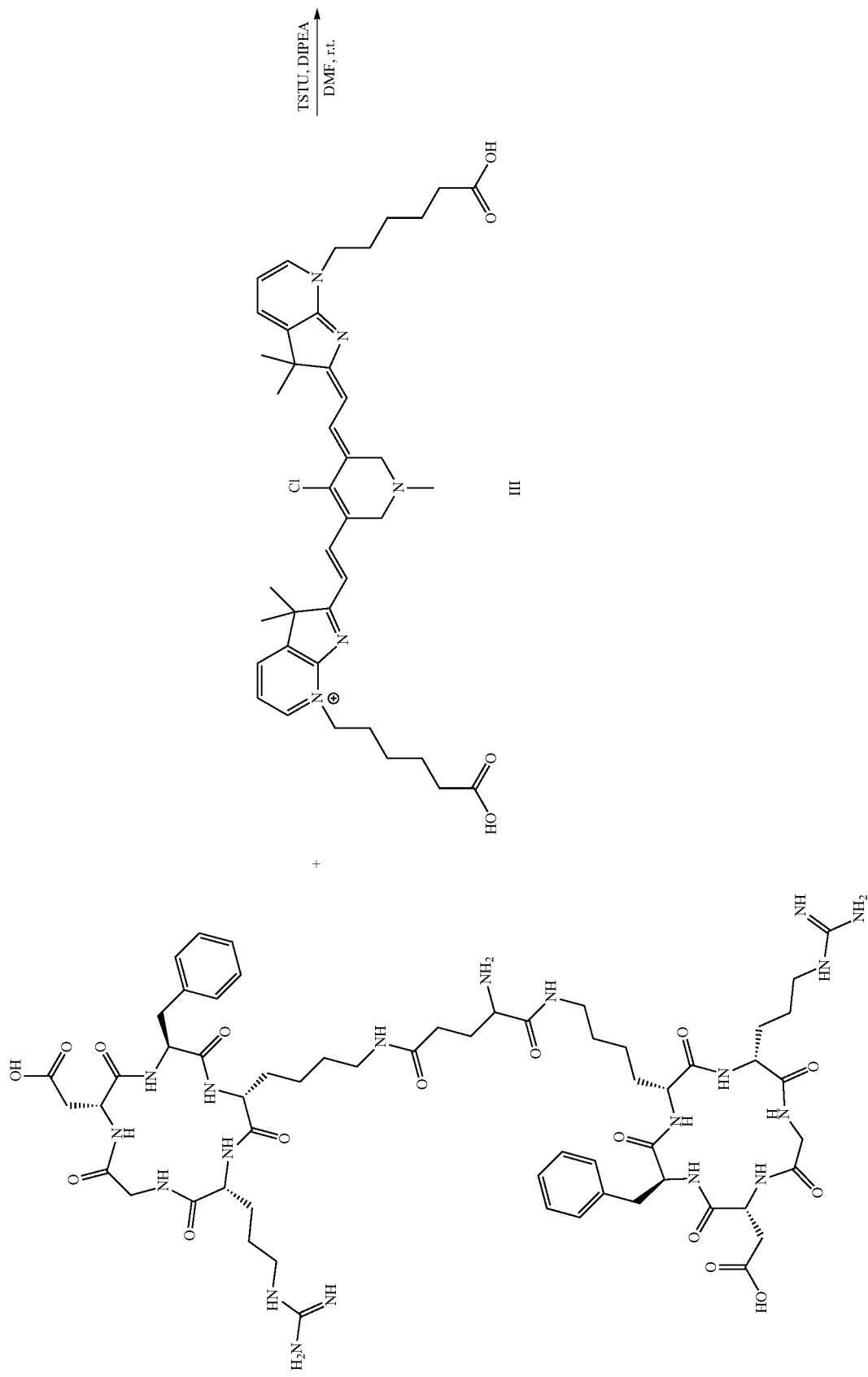

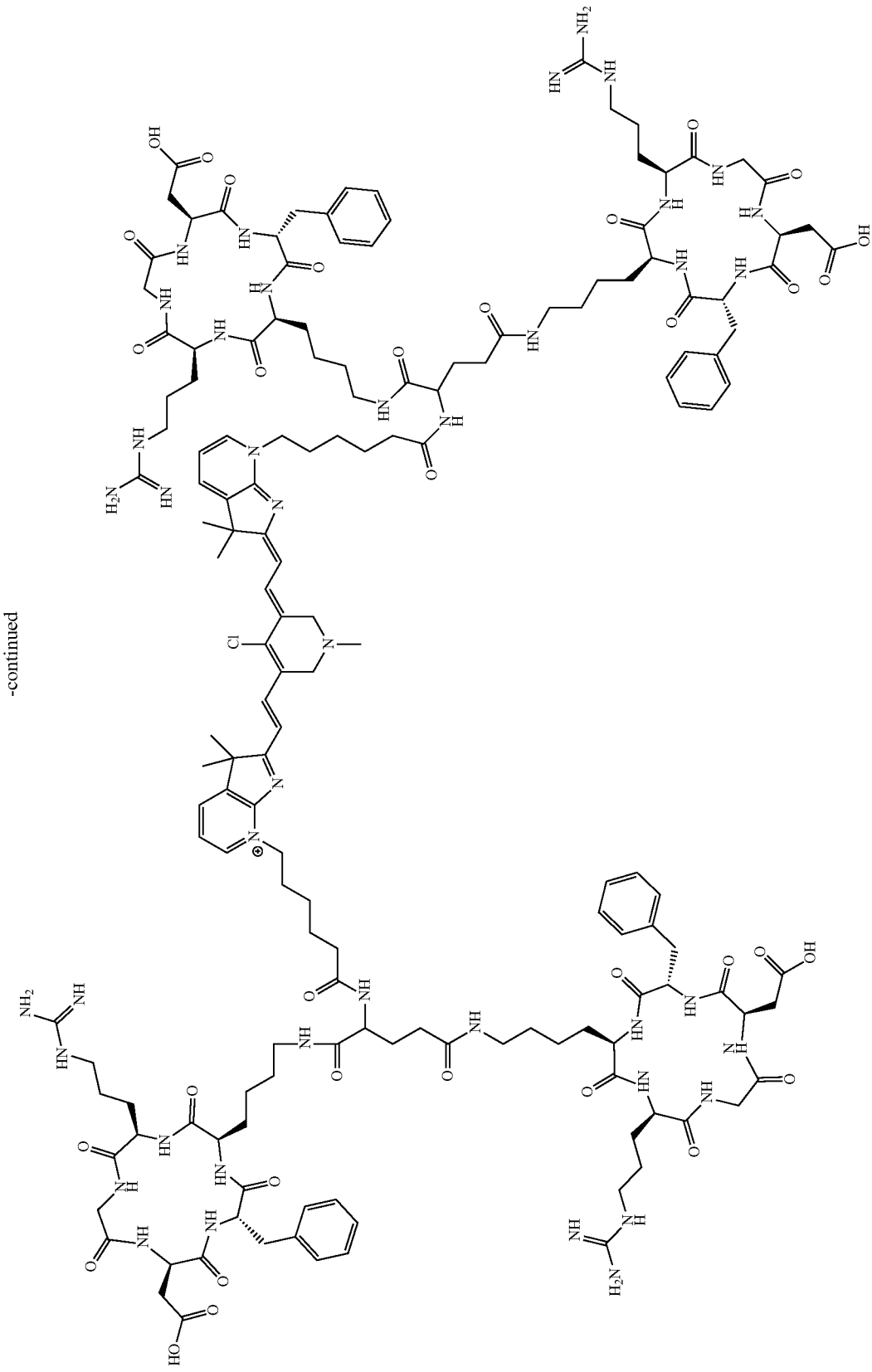
XXII

Dye III (2 mg, 0.0028 mmol) in dry DMF (1 mL), and DIPEA (3 d, 0.014 mmol) were added and mixture stirred at room temperature under N₂, then TSTU (1.9 mg, 0.0063 mmol) was added, and the resulting mixture was protected from light and stirred at room temperature for 3 h. The reaction was checked for completion by HPLC-MS (Agilent). 2RGD derivative (7.8 mg, 0.00589 mmol) and DIPEA (3 μl, 0.014 mmol) were added and mixture stirred at room temperature under N₂. The reaction was checked for completion by HPLC-MS (Agilent). The solvent was removed under reduced pressure. Crude product was purified by HPLC (Waters RP-C18) to afford the corresponding compound XXII as dark green solid (5 mg, 53%).

Synthesis of Compound XXIII

Synthesis of Compound XXIV

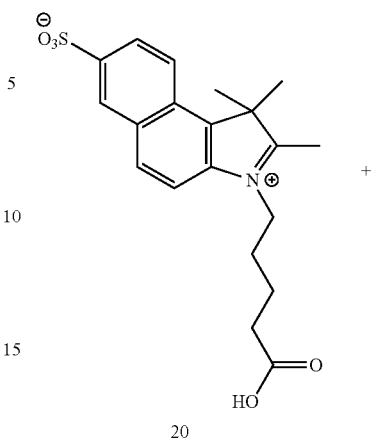

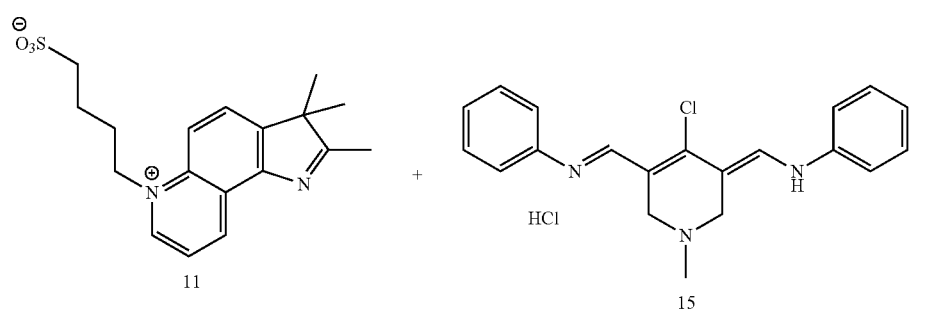

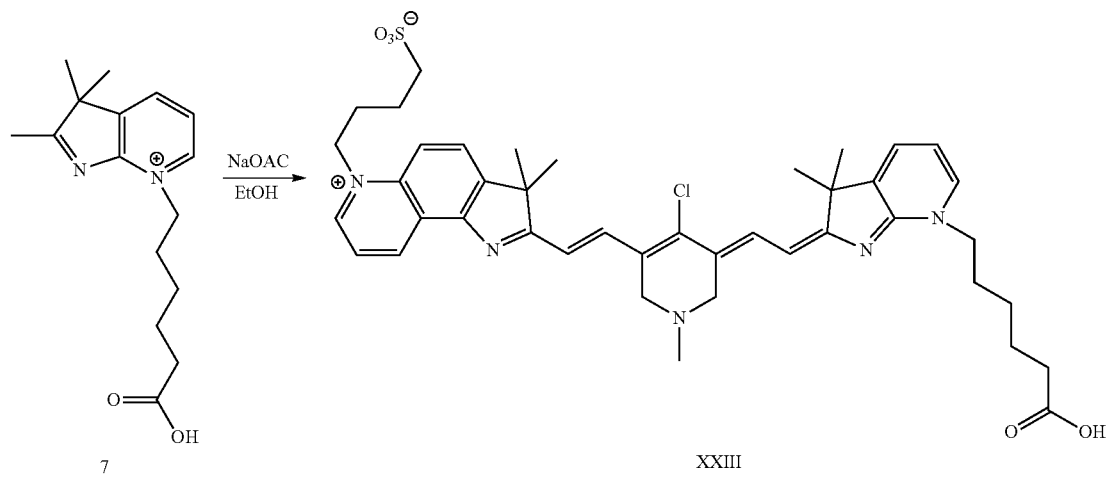

Compounds 11 and 7 are dissolved in ethanol under N₂, then compound 15 and sodium acetate are added into the solution. Reaction mixture is heated at 70° C. under N₂, The solvent is removed under reduced pressure, and crude product is purified by HPLC to afford the corresponding asymmetrical compound XXIII.

-continued

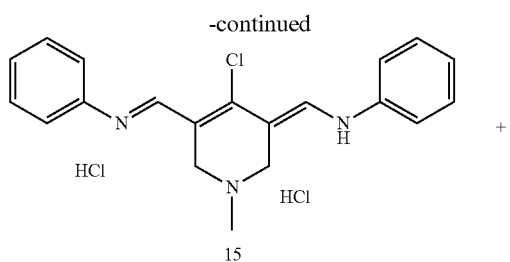

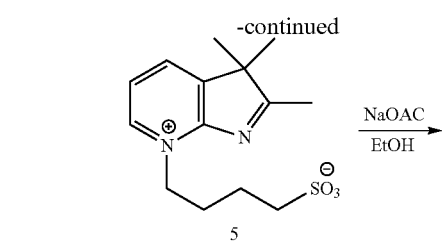

Compounds 20 and 5 are dissolved in ethanol under $N_2$, then compound 15 and sodium acetate are added into the solution. Reaction mixture is heated at 70° C. under $N_2$. The solvent is removed under reduced pressure, and crude product is purified by HPLC to afford the corresponding asymmetrical compound XXIV.

Synthesis of Compound XXV

Dye II and 4-iodobut-1-yne are placed into a seal tube in dry methanol under $N_2$. The reaction is stirred at r.t. The solvent is removed under vacuum and crude product is purified by HPLC to afford the corresponding compound XXV.

Synthesis of Compound XXVI

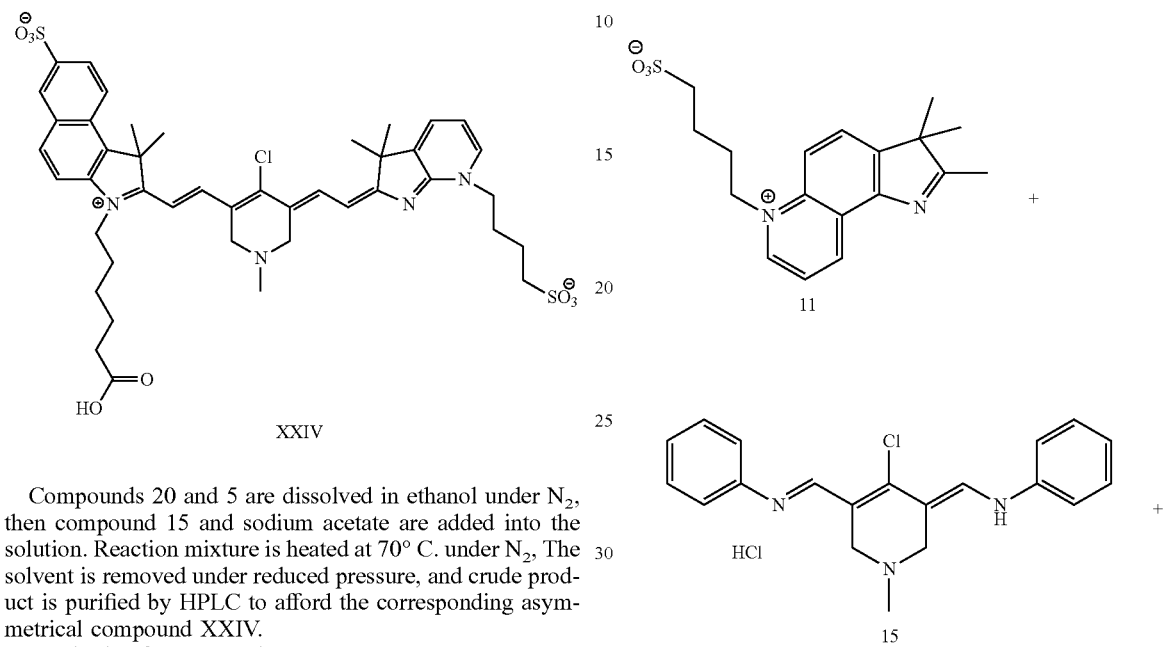

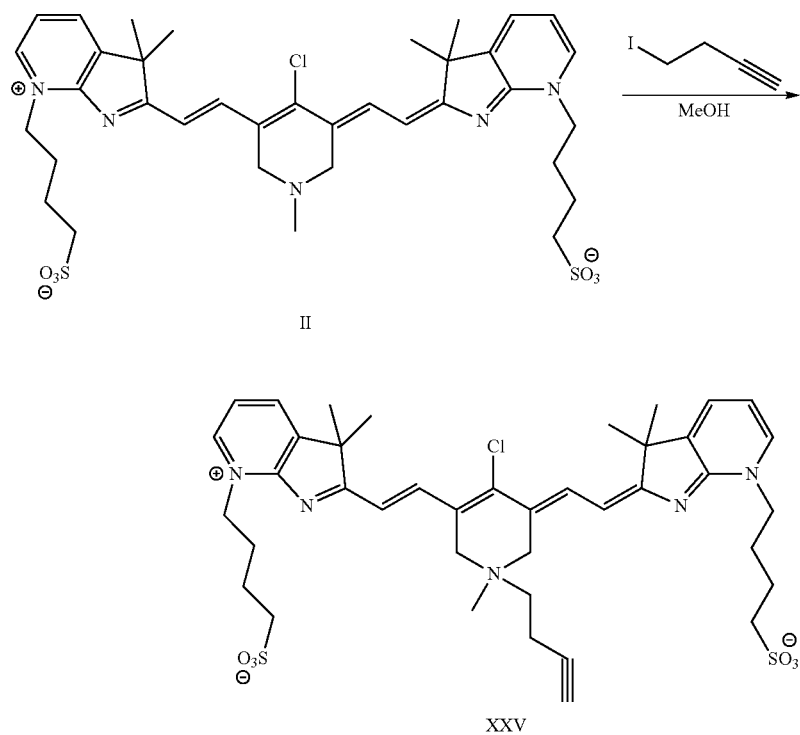

147
-continued

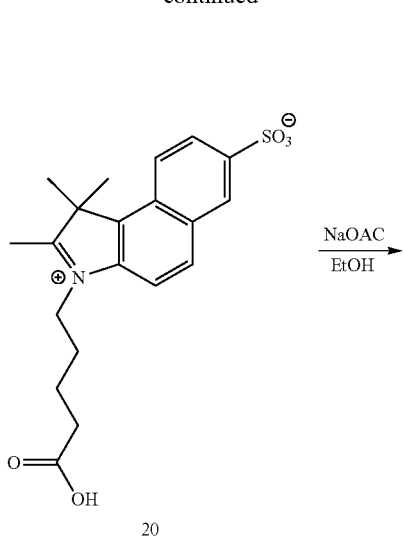

148
-continued

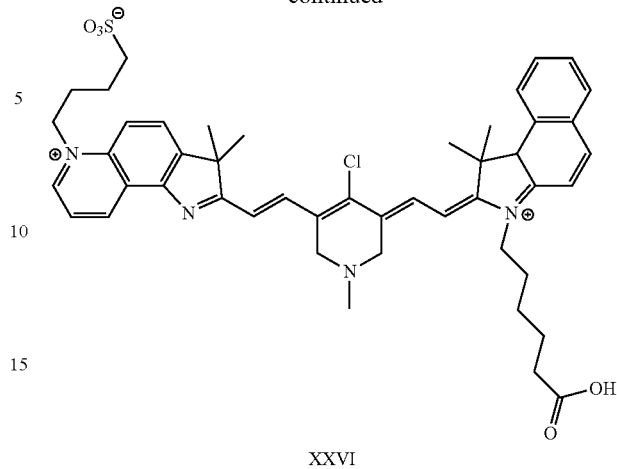

XXVI

Compounds 11 and 20 are dissolved in ethanol under $N_2$, and then compound 15 and sodium acetate are added into the solution. Reaction mixture is heated at 70° C. under $N_2$, The solvent is removed under reduced pressure, and crude product is purified by HPLC to afford the corresponding asymmetrical compound XXVI.

Preparation of IgG Bioconjugate XXVIII

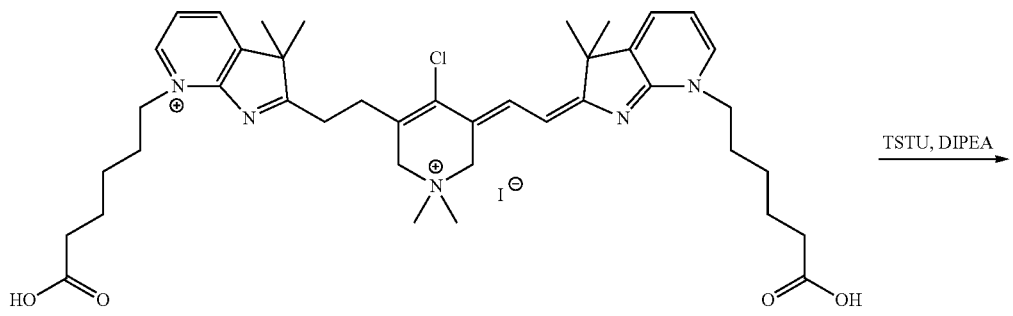

XIII

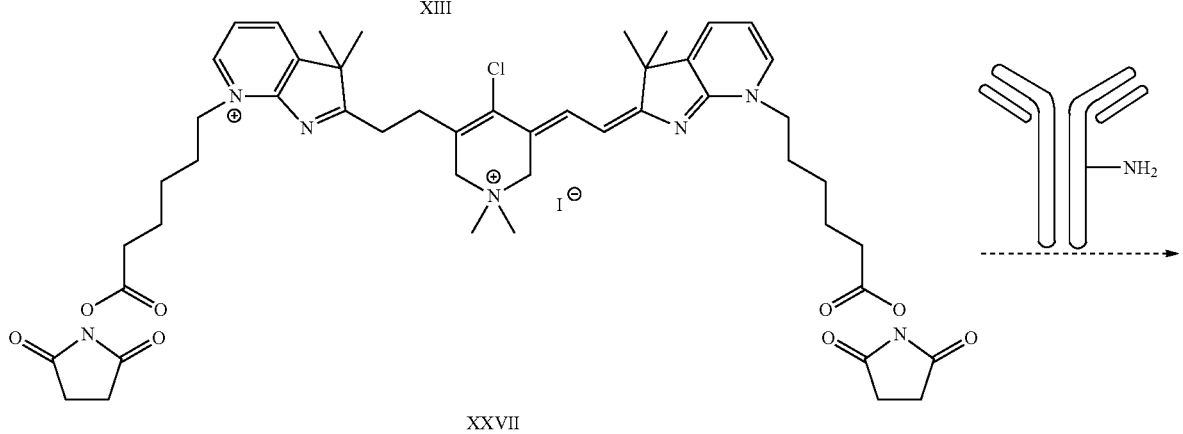

XXVII

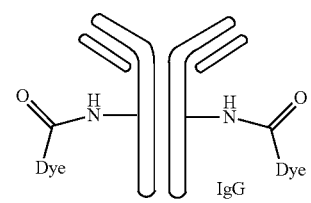

XXVIII

The corresponding antibody was diluted with 2× volume of 0.1 M NaHCO$_3$ (pH 8.5). 25 equivalents of fluorescent NHS dye XXVII (from 10 mM stock solution in DMSO) was added to the antibody solution and gently shacked in dark at room temperature for 2 hours. After incubation, antibody was purified by centrifuge filtration using desalting Zeba spin column 7K and stored in PBS at 4° C. affording bioconjugate XXVIII. The number of fluorophores per antibody was determined by spectrophotometric analysis and determined to be approximately 2-3 fluorescent dyes per antibody.

Synthesis of Compound XXVIX

DOTA is attached in a chemical reaction to compound VIII shown again below. The reaction starts from Compound VIII shown below.

Compound VIII

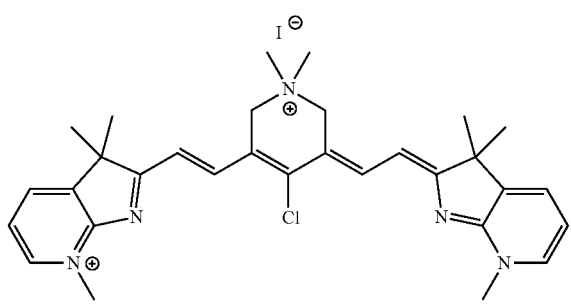

Compound VIII can be functionalized with a group containing a benzene thiol, such as 4-aminobenzenthiol, or 2-(4-mercaptophenyl)acetic acid, shown below.

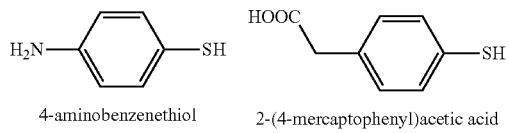

4-aminobenzenethiol    2-(4-mercaptophenyl)acetic acid

These compounds react readily in Dimethylformamide (DMF) at room temperature under a nitrogen atmosphere, as shown in the reaction diagram below. Dye A was dissolved in dry DMF and placed under nitrogen while stirring. The appropriate thiol was added to a dry vial, and dissolved in dry DMF before being added to the solution.[1] The resulting compounds were seen on an HPLC-MS to have m/z values of 302 and 324, corresponding to the values of [M$^+$/2] for the amine-functionalized and carboxylate compounds respectively.

Reaction Diagram 1

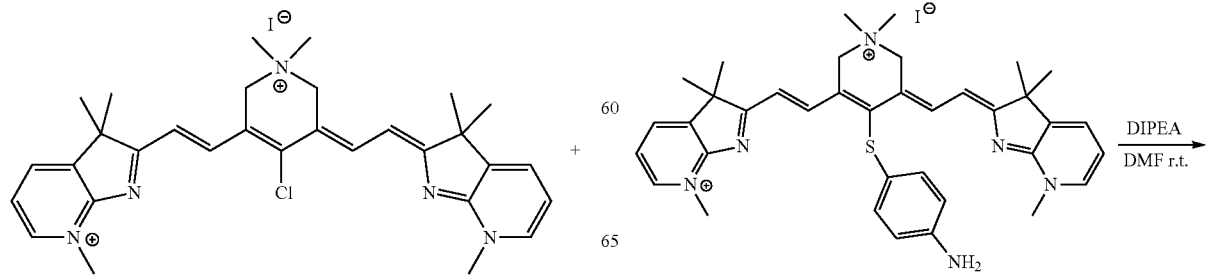

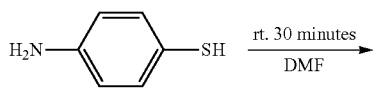

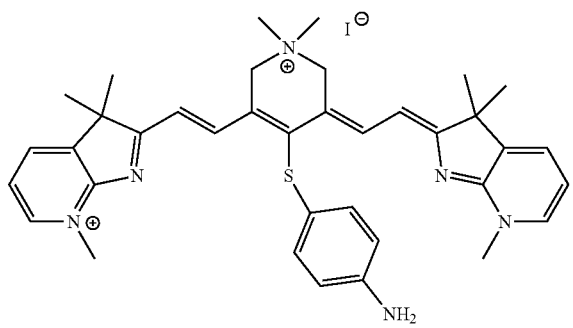

The amine-functionalized Compound VIII is coupled to 1,4,7,10-Tetraazacyclododecane-1,4,7,10-tetraacetic acid (DOTA) modified to contain a N-Hydroxysuccinimide functional group as shown in reaction diagram 2. This reaction is completed by using the functionalized Compound VIII and the N-hydroxysuccinimide ester form of DOTA, which is commercially available, in the presence of 4 equivalents of N,N-Diisopropylethylamine (DIPEA) at room temperature in a nitrogen atmosphere.

Reaction diagram 2 Conjugation of Compound VIII to DOTA

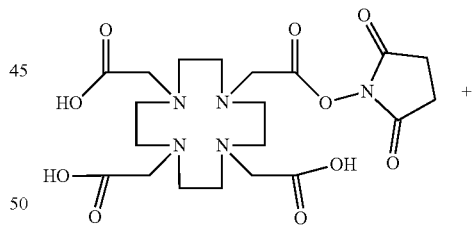

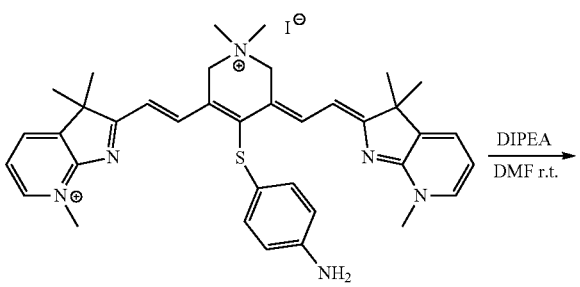

-continued

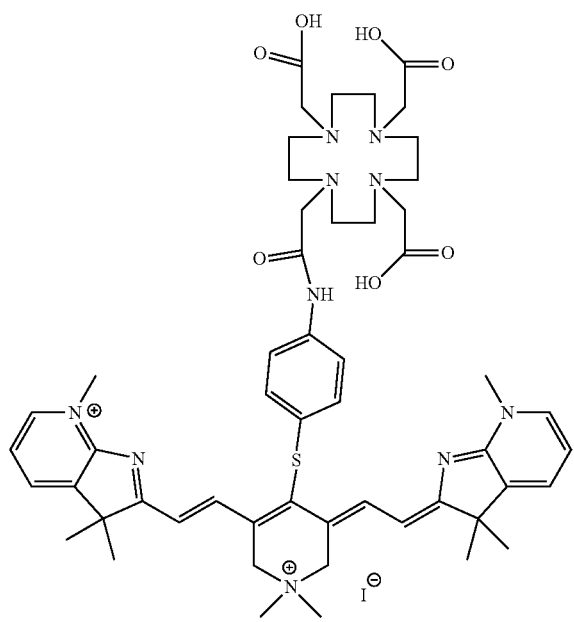

Radiolabeling of the DOTA-Compound VIII conjugate can be accomplished according to literature,[2] using a 0.25M ammonium acetate buffer with a pH of 7.0 at 37° C. for Indium-111, which is added to the solution in 0.4N hydrochloric acid and stirred for 45 minutes. Other metal chelates behave in a similar fashion for chelation procedures. The example of Indium-111 chelation is shown reaction diagram 3

Reaction diagram 3 Indium-111 chelation into DOTA-Compound VIII

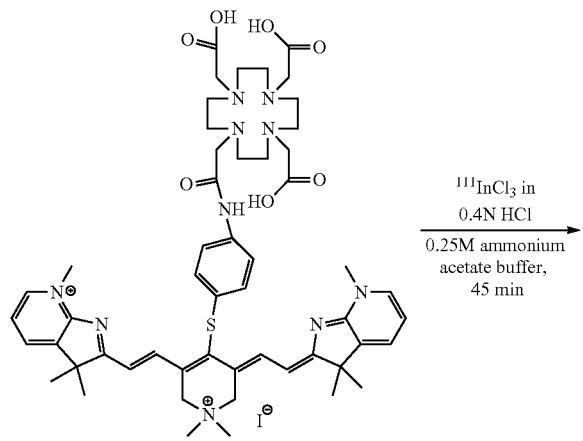

-continued

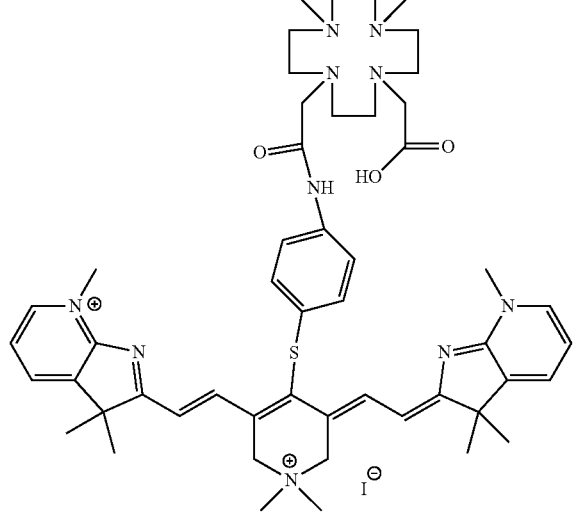

Since Compound VIII is also an efficient fluorescent reagent, this conjugate can be used for optoacoustic, near-infrared imaging (600-900 nm) and shortwave infrared (SWIR II) range of wavelengths from 0.9 to 1.7 microns (see more details below). This molecule could also be envisioned for radiotherapy applications for local tumor irradiation when chelated to radioisotopes such as Lutetium or Yttrium ($^{1777}$Lu, $^{90}$Y).

Optical Property Analyses

All optical measurements were performed at 37° C. in methanol in 10 mm spectrofluorometric quartz cuvettes with C ~$10^{-6}$ M. Perkin Elmer Lambda spectrophotometer was used to record UVN/Vis/NIR spectra. For fluorescence quantum yield (QY) measurements, ICG in methanol (QY 7.8%) was used as a calibration standard under conditions of matched absorbance at 770 nm. As shown in FIG. 1A-9B a range of compounds were found to exhibit substantial absorbance at the 800 nm wavelength. These compounds exhibited a variety of emission wavelengths ranging from about 800 to about 900 nm. Especially FIG. 1A and FIG. 1B show absorption and fluorescence spectra, and quantum yield QY of Compound I.

FIG. 2A and FIG. 2B show absorption and fluorescence spectra, and QY of Compound II.

Figures 3A, 3B:
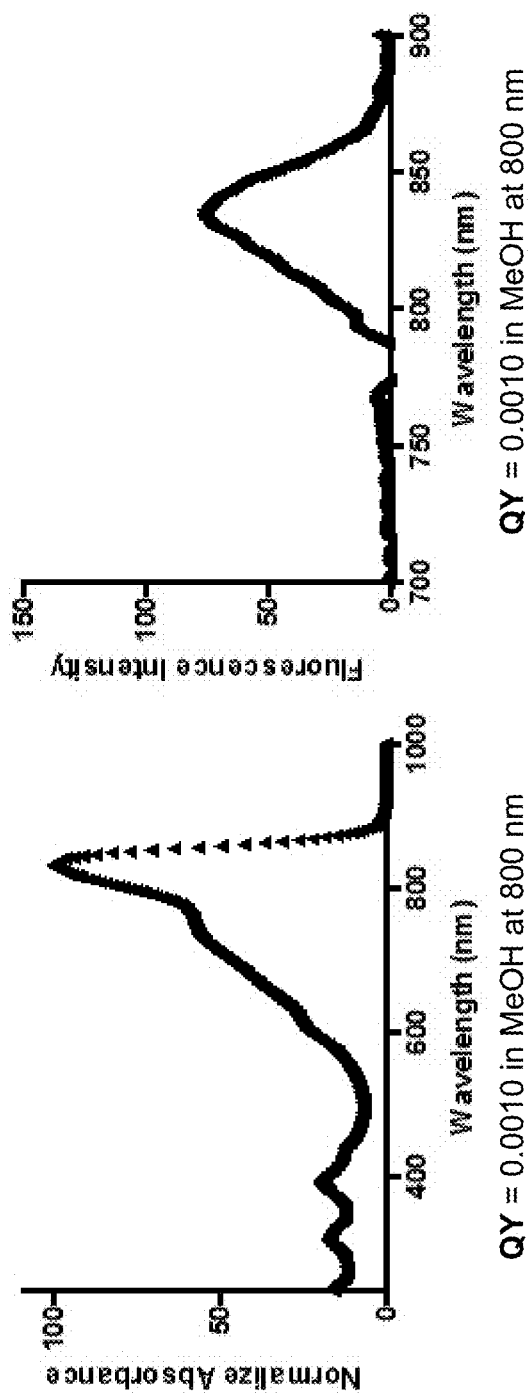
FIG. 3A shows absorption and quantum yield QY of Compound III.
FIG. 3B shows fluorescence spectra and quantum yield QY of Compound III.

FIG. 3A and FIG. 3B show absorption and fluorescence spectra, and QY of Compound II.

Figures 4A, 4B:
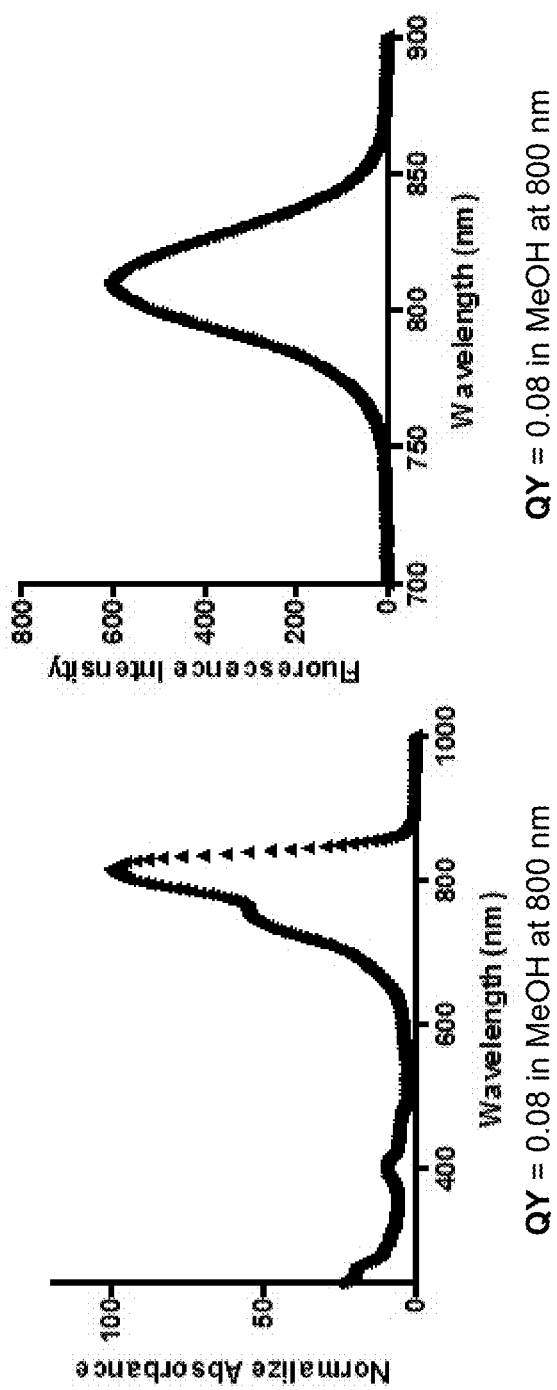
FIG. 4A shows absorption and quantum yield QY of Compound IV.
FIG. 4B shows fluorescence spectra and quantum yield QY of Compound IV.

FIG. 4A and FIG. 4B show absorption and fluorescence spectra, and QY of Compound IV.

Figures 5A, 5B:
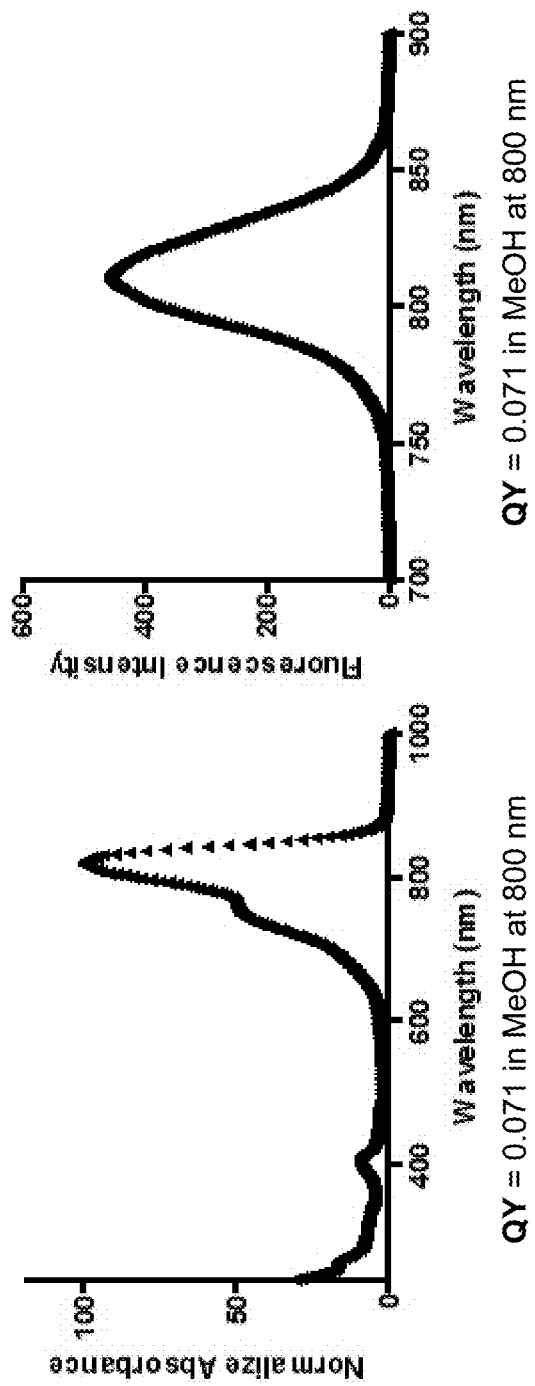
FIG. 5A shows absorption and quantum yield QY of Compound V.
FIG. 5B shows fluorescence spectra and quantum yield QY of Compound V.

FIG. 5A and FIG. 5B show absorption and fluorescence spectra, and QY of Compound V.

Figures 6A, 6B:
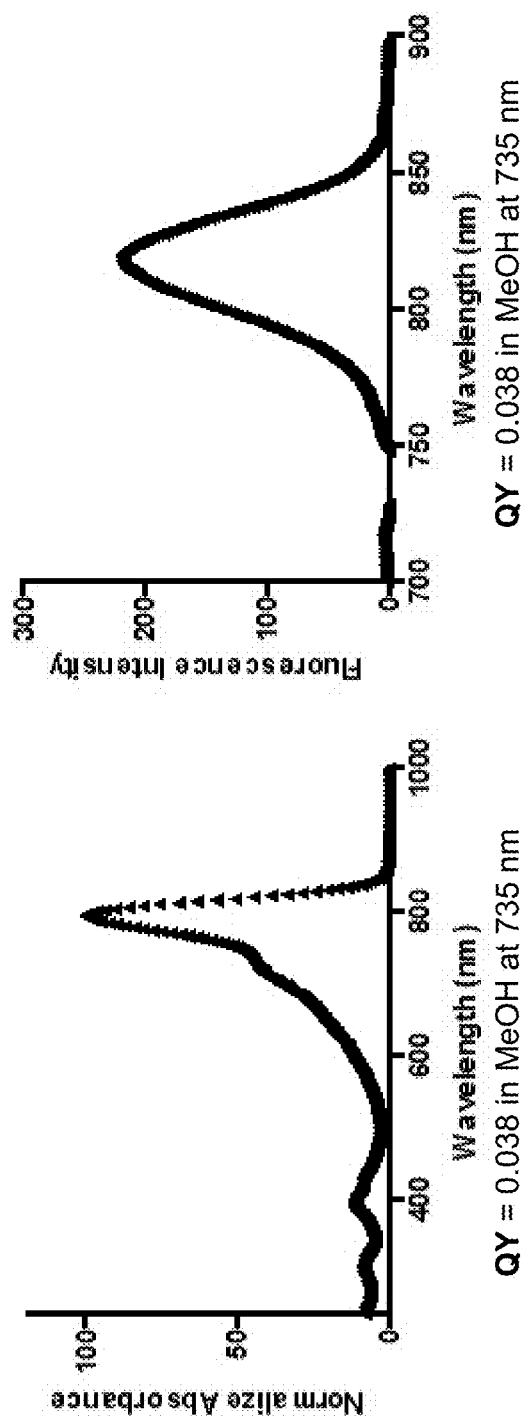
FIG. 6A shows absorption and quantum yield QY of Compound VI.
FIG. 6B shows fluorescence spectra and quantum yield QY of Compound VI.

FIG. 6A and FIG. 6B show absorption and fluorescence spectra, and QY of Compound VI.

Figures 7A, 7B:
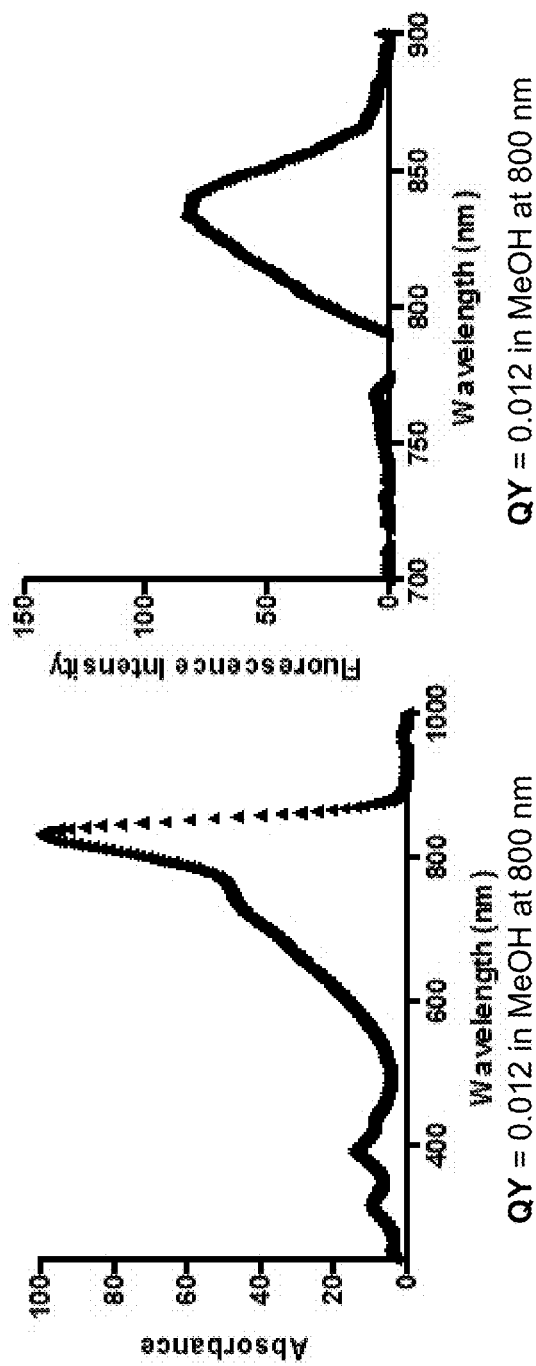
FIG. 7A shows absorption and quantum yield QY of Compound VII.
FIG. 7B shows fluorescence spectra and quantum yield QY of Compound VII.

FIG. 7A and FIG. 7B show absorption and fluorescence spectra, and QY of Compound VII.

Figures 8A, 8B:
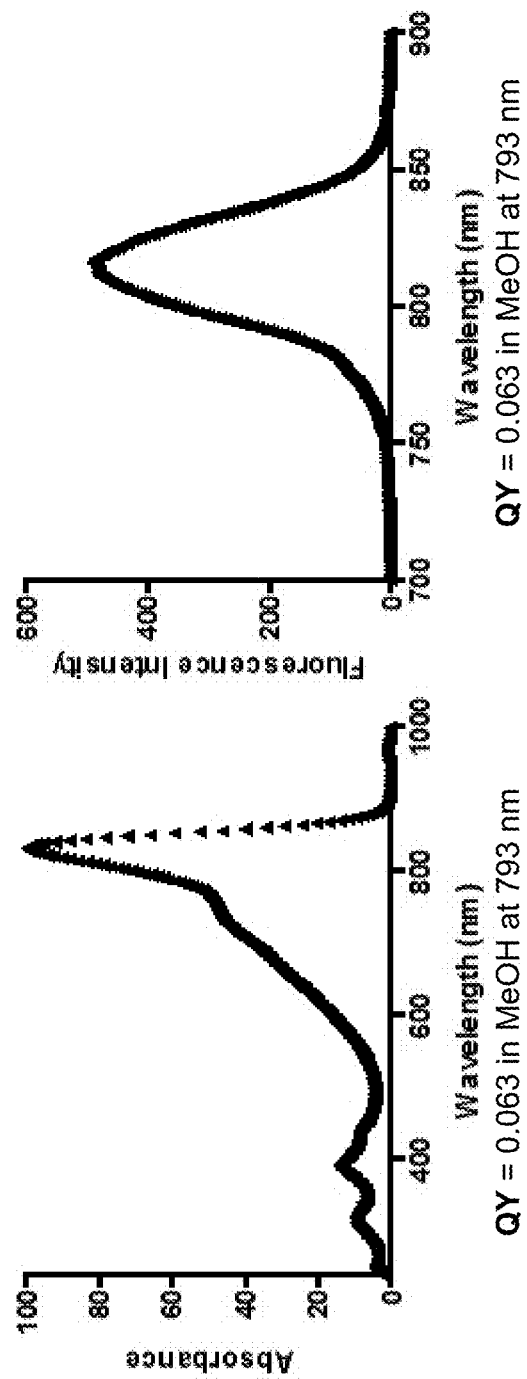
FIG. 8A shows absorption and quantum yield QY of Compound VIII.
FIG. 8B shows fluorescence spectra and quantum yield QY of Compound VIII.

FIG. 8A and FIG. 8B show absorption and fluorescence spectra, and QY of Compound VIII.

Figures 9A, 9B:
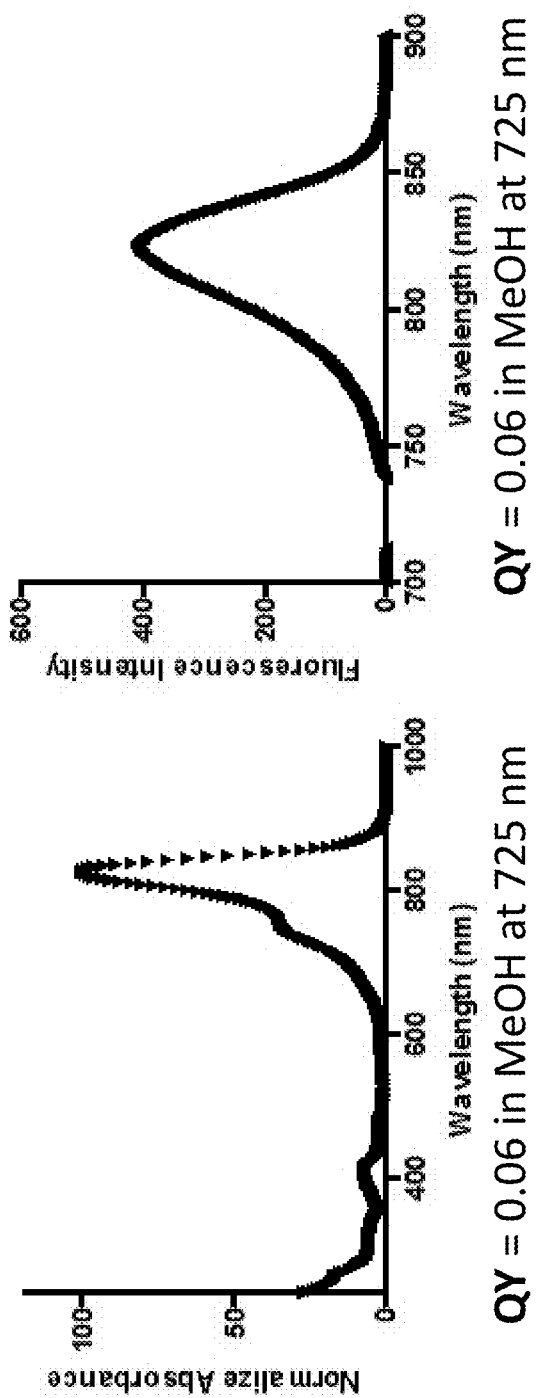
FIG. 9A shows absorption and quantum yield QY of Compound IX.
FIG. 9B shows fluorescence spectra and quantum yield QY of Compound IX.

FIG. 9A and FIG. 9B show absorption and fluorescence spectra, and QY of Compound IX.

Evaluation of XXVIII for In Vivo Fluorescence Imaging

Figure 10B:
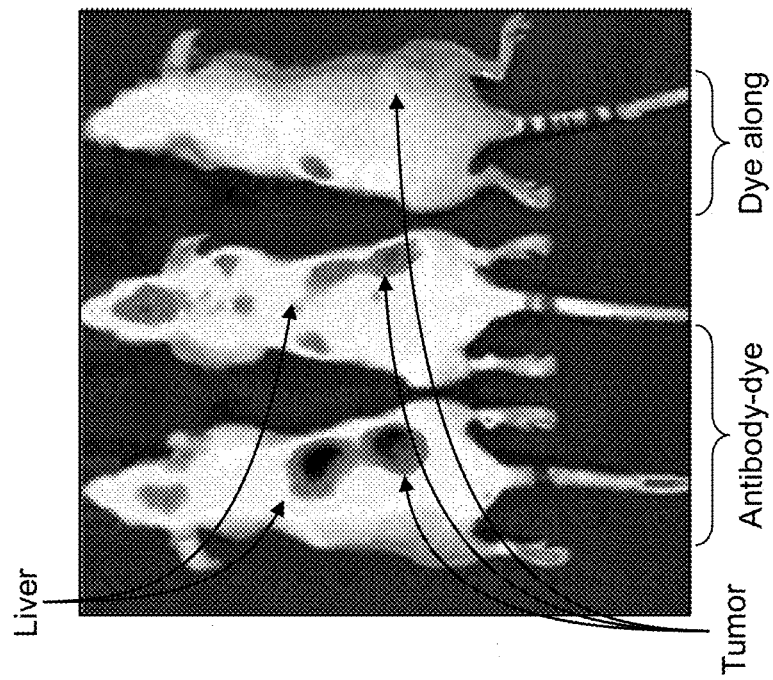
FIG. 10 A and FIG. 10B show three representative mice bearing an established 4T1-luc2 tumours implanted subcutaneously into the right flank were injected with the indicated imaging agent.
Figure 10A:
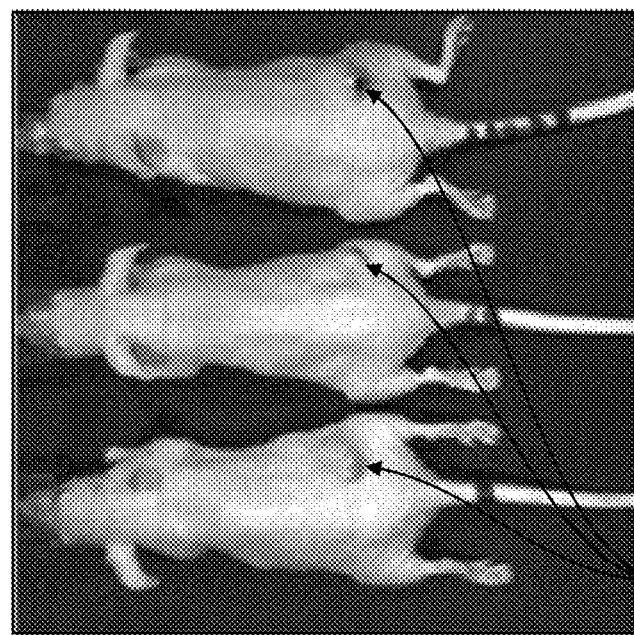

Female nude mice 6-8 weeks of age were injected with 1M of 4T1 cells in 100 ul of PBS subcutaneously into the right flank. Once the tumors reached approximately 0.5 cm³ in size, animals were injected with 0.7 nmol of antibody conjugate XXVIII intravenously in 100 ul of PBS. Mice were then imaged at different time points using IVIS Spectrum instrument (Perkin Elmer) at recommended settings 745/810 nm excitation/emission. Three representative mice bearing an established 4T1-luc2 tumours implanted subcutaneously into the right flank were injected with the indicated imaging agent. FIG. 10A: Mice were imaged by IVIS Spectrum to show tumour localization and FIG. 10B: NIR fluorescence images to show specific biomarker detection, after intravenously receiving 0.7 nmol of antibody conjugate XXVIII.

Evaluation of XXI for In Vivo Fluorescence Imaging

Figure 11:
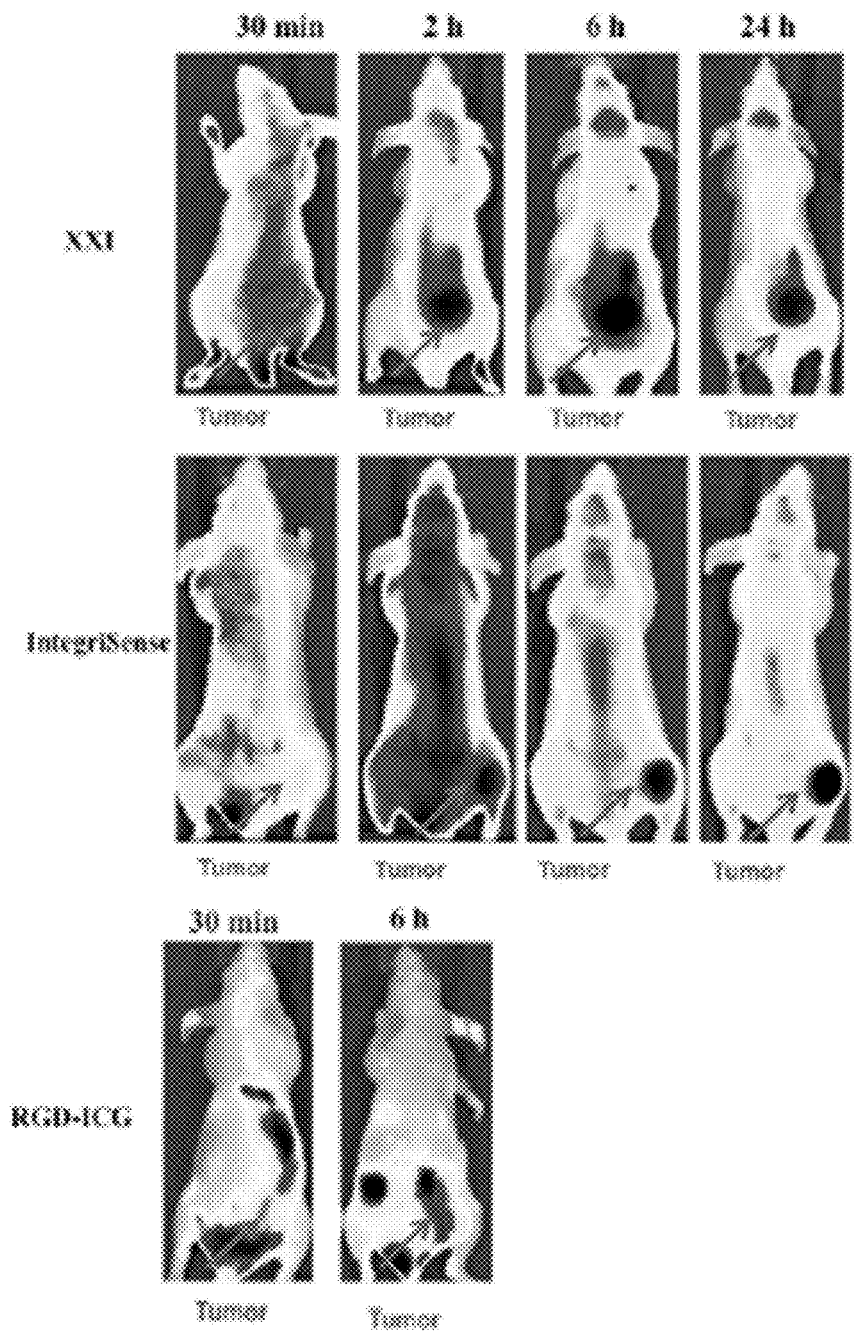
FIG. 11 shows NIR fluorescence images of 4T1-luc2 tumour bearing mice at the indicated time points after intravenous injection of probe XXI, IntegriSense™ 750, and RGD-ICG.
Figure 12A:
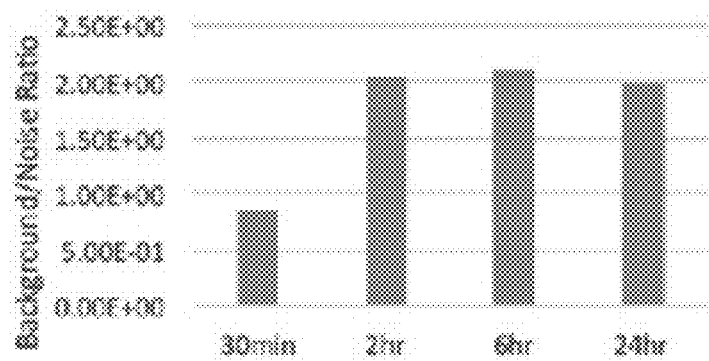
FIG. 12 A and FIG. 12 B show the optimal background/noise ratio calculated from the region of interest of 4T1 tumour bearing mice at 2 h post injection of probe XXI (FIG. 12A) and 24 h post injection of IntegriSense™ 750 (FIG. 12B).
Figure 12B:
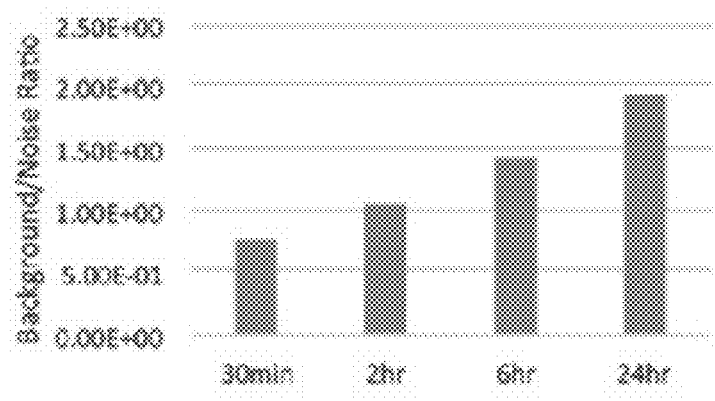

Female nude mice 6-8 weeks of age were injected with 1M of 4T1 cells in 100 ul of PBS subcutaneously into the right flank. Once the tumors reached approximately 0.5 cm³ in size, animals were injected with 20 nmol of the imaging probe XXI intravenously in 100 ul of PBS. Mice were then imaged at different time points using IVIS Spectrum instrument (Perkin Elmer) at recommended settings 745/810 nm excitation/emission. FIG. 11 shows NIR fluorescence images of 4T1-luc2 tumour bearing mice at the indicated time points after intravenous injection of probe XXI, IntegriSense™ 750, and RGD-ICG. FIGS. 12 A and 12 B show the optimal background/noise ratio calculated from the region of interest of 4T1 tumour bearing mice at 2 h post injection of probe XXI (FIG. 12A) and 24 h post injection of IntegriSense™ 750 (FIG. 12B).

Evaluation of XXI for Fluorescence Image-Guided Surgery

Example 1

Figures 14A, 14B:
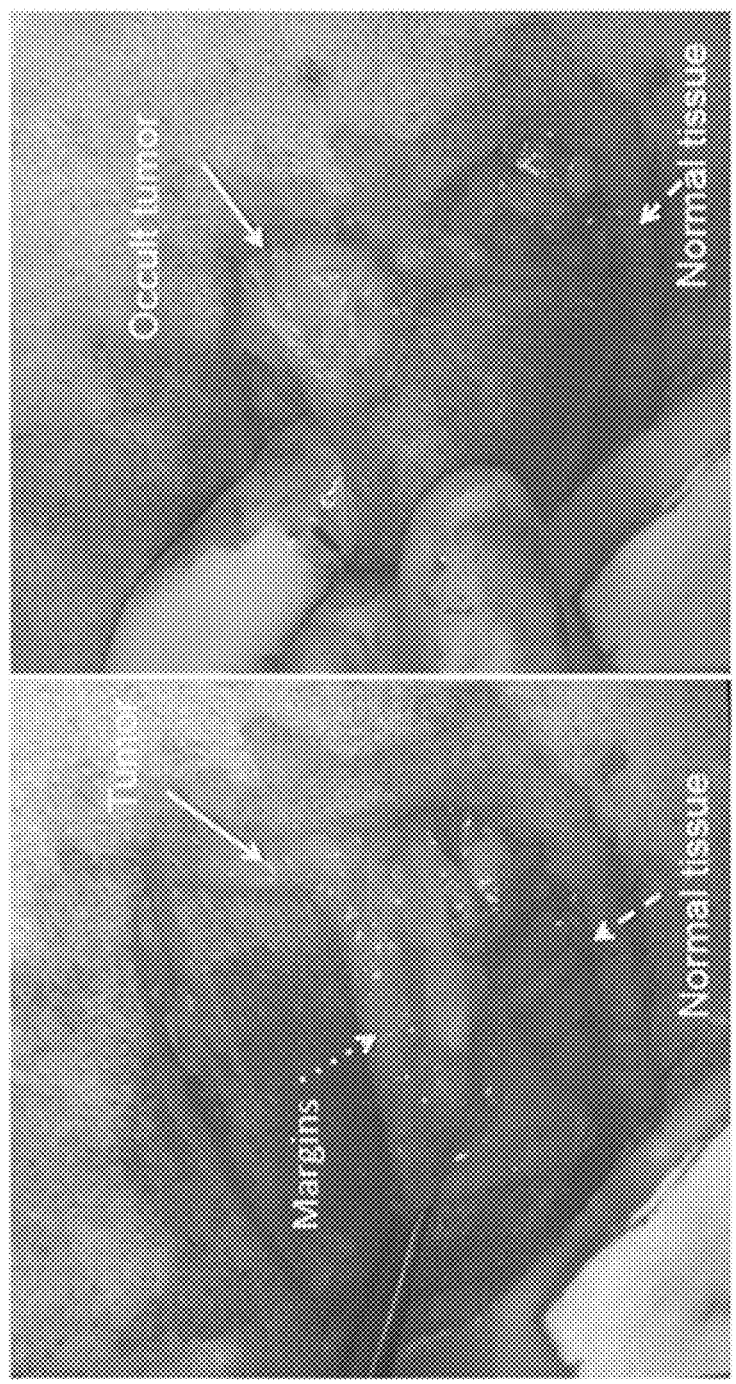
FIG. 14A shows fluorescence image-guided surgical procedure of mastocytoma tumour resection. A mastocytoma tumour (solid arrow) is clearly identified by a rim around the tumor in vivo, 6 h after injection of probe XXI. Normal tissue (dashed arrow) shows negligible background uptake of probe XXI. The enhanced ability to visualize tumor margins in fluorescence image-guided surgery led to more complete resection of the tumor (round dot arrow)
FIG. 14B shows occult malignant lesion.
Figures 15A, 15B:
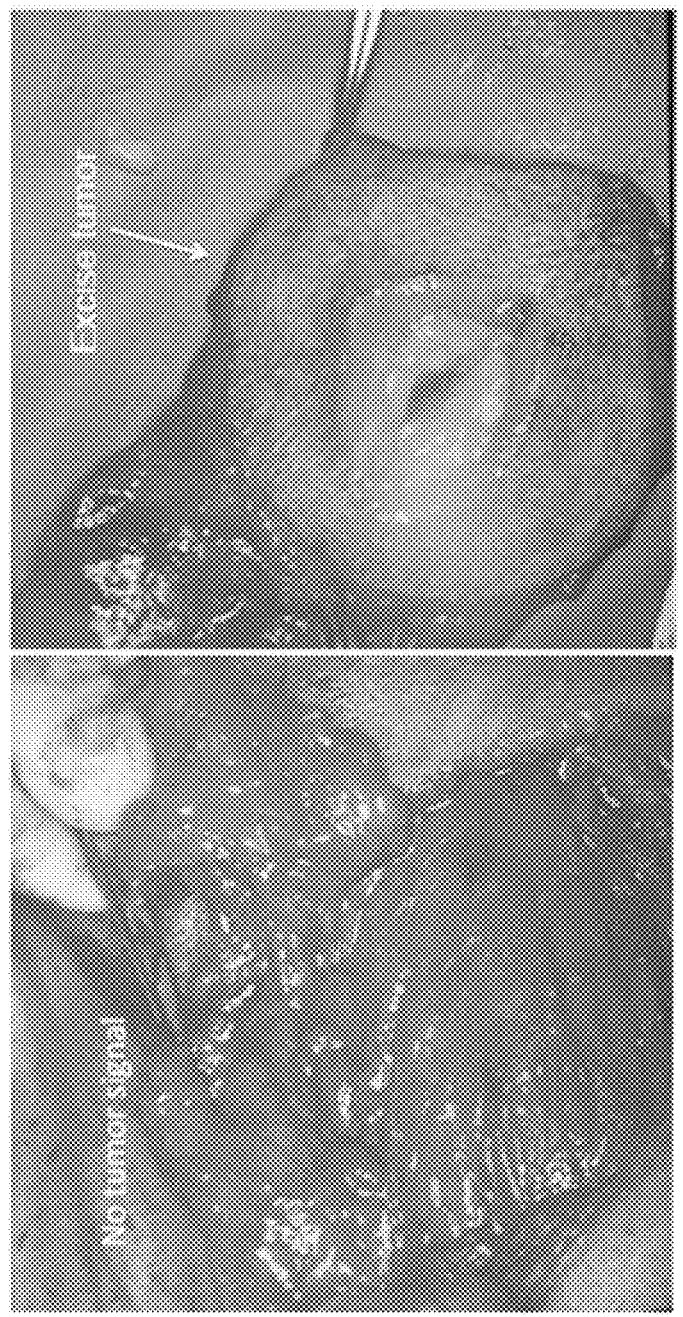
FIG. 15A shows no apparent fluorescence from residual tumour could be observed after the operation.
FIG. 15B shows after resection carried out under the guidance of fluorescent light and slicing of the same specimen, the rim around the tumor can be visualized ex vivo.

A kuvasz dog (male, 30 kg) diagnosed with mastocytoma tumor on his right leg was used for image guided surgery study. All canine studies were performed at Veterinair Verwijscentrum Gouda, Netherlands. Canine was injected intravenous catheterization into the cephalic vein with fluorescence probe XXI (180 nmol/kg) 6 h prior to surgery. Canine underwent to general anesthesia prior to surgery. Image guided cancer surgery was performed using Solaris Open-air Fluorescence Imaging System (Perkin Elmer), equipped with four fluorescent channels (470 nm, 660 nm, 750 nm and 800 nm) to obtain real-time visualization of tumor imaging in ambient light FIG. 13A shows I.V. catheter injection in a 30 kg dog 6 h before surgery with 180 nmol/kg of probe XXI, and FIG. 13B shows localization of mastocytoma tumour in dog's right leg. FIG. 14A shows fluorescence image-guided surgical procedure of mastocytoma tumour resection. A mastocytoma tumour (solid arrow) is clearly identified by a rim around the tumor in vivo, 6 h after injection of probe XXI. Normal tissue (dashed arrow) shows negligible background uptake of probe XXI. The enhanced ability to visualize tumor margins in fluorescence image-guided surgery led to more complete resection of the tumor (round dot arrow), and FIG. 14B shows occult malignant lesion. FIG. 15A shows no apparent fluorescence from residual tumour could be observed after the operation, and FIG. 15B shows after resection carried out under the guidance of fluorescent light and slicing of the same specimen, the rim around the tumor can be visualized ex vivo.

Example 2

Figures 17A, 17B:
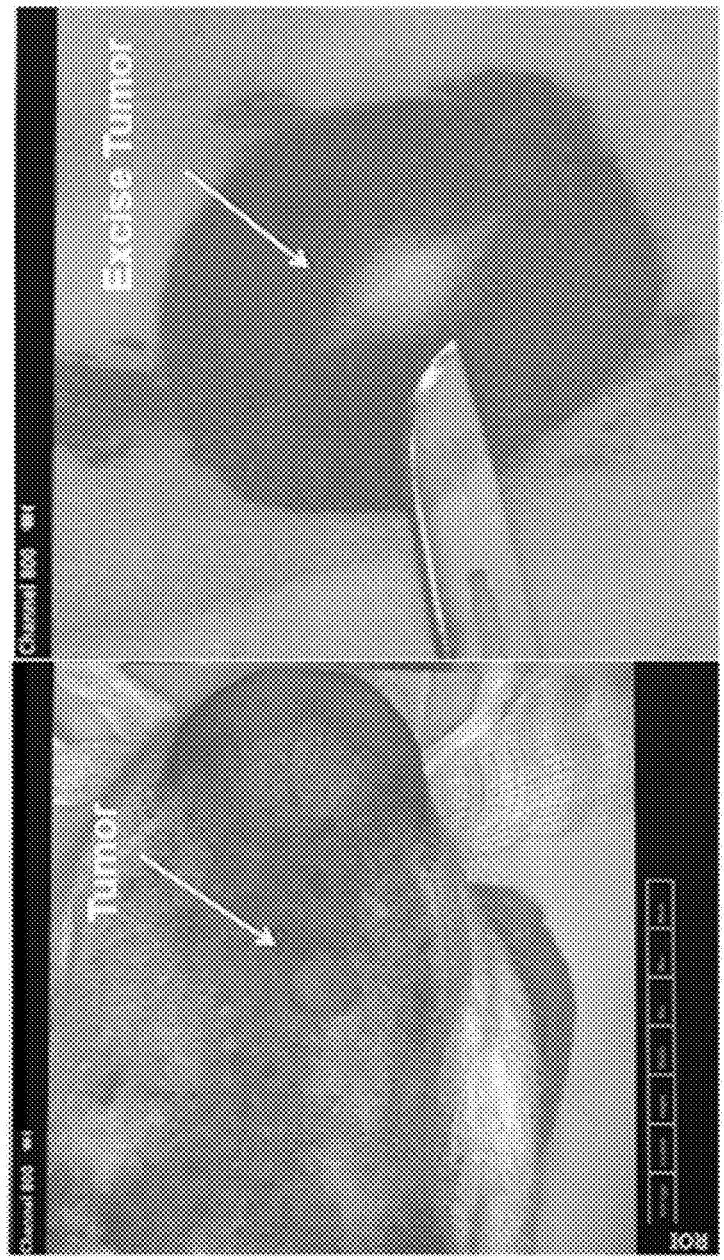
FIG. 17A show fluorescence image-guided surgical procedure of dog's mastocytoma tumour and FIG. 17B shows after resection carried out under the guidance of fluorescent light and slicing of the same specimen, the rim around the tumor can be visualized ex vivo.

A labrador dog (male, 33 kg) diagnosed with mastocytoma tumor on his nose was used for image guided surgery study. All canine studies were performed at Veterinair Verwijscentrum Gouda, Netherlands. Canine was injected intravenous catheterization into the cephalic vein with fluorescence probe XXI (92 nmol/kg) 10 h prior to surgery. Canine underwent to general anesthesia prior to surgery. Image guided cancer surgery was performed using Solaris Open-air Fluorescence Imaging System (Perkin Elmer), equipped with four fluorescent channels (470 nm, 660 nm, 750 nm and 800 nm) to obtain real-time visualization of tumor imaging in ambient light FIG. 16A shows I.V. catheter injection in a 33 Kg dog 10 h before surgery with 92 nmol/kg of probe XXI, and FIG. 16B shows localization of mastocytoma tumour in dog's nose FIG. 17A shows fluorescence image-guided surgical procedure of dog's mastocytoma tumour and FIG. 17B shows after resection carried out under the guidance of fluorescent light and slicing of the same specimen, the rim around the tumor can be visualized ex vivo.

Imaging Necrosis

Figure 18B:
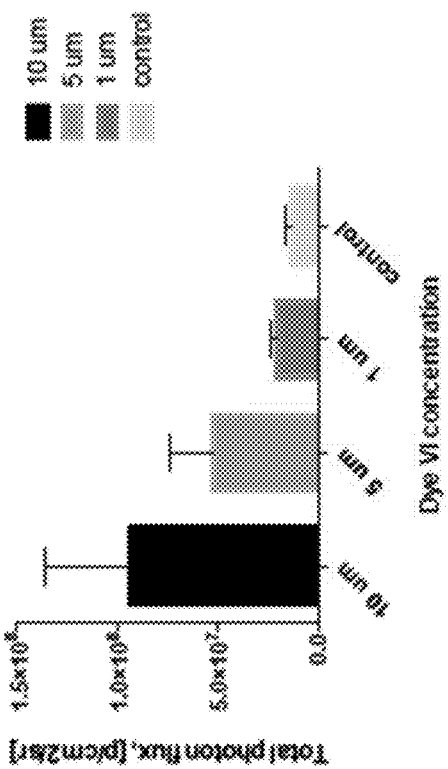
FIG. 18B shows total photon flux of treated cells at different concentrations.
Figure 18A:
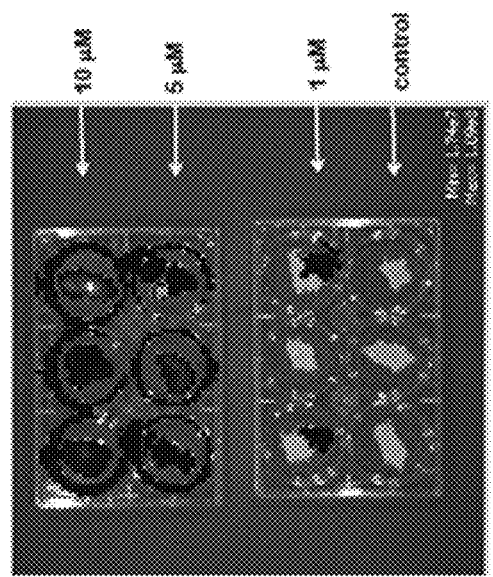
FIG. 18A shows cryogenic tissue damage with dye VI, the cells at the site of focal dry-ice treatment showed strong fluorescence signal whereas no signal was obtained from the viable cells.
Figures 19A, 19B:
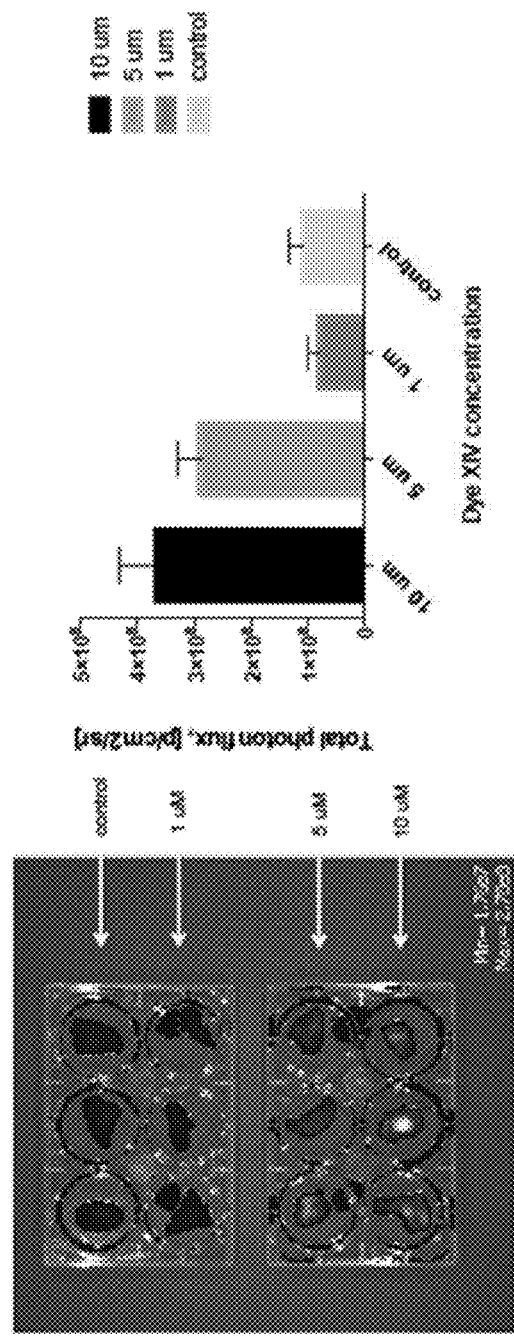
FIG. 19A shows cryogenic tissue damage with dye XIV, fluorescence of the dye XIV showed strong accumulation of fluorescence at the site of focal dry-ice treatment in the cryogenic tissue.
FIG. 19B shows total photon flux of treated tissue at different concentrations.

Ex vivo cell death assay for compounds, VI and XIV were studied using a method of cryogenic tissue damage. Briefly, a bar of a dry ice was applied to sliced skin tissue of a nude mouse recently sacrificed in a petri dish for a period of 60 sec. Subsequently, the skin tissue samples were incubated with different concentrations of dye VI and XIV (1 uM, 5 uM, and 10 uM) for 10 min at room temperature. After gentle washing with PBS, the samples were scanned for fluorescence using an IVIS Spectrum imaging system FIG. 18A shows cryogenic tissue damage with dye VI, the cells at the site of focal dry-ice treatment showed strong fluorescence signal whereas no signal was obtained from the viable cells, and FIG. 18B shows total photon flux of treated cells at different concentrations. FIG. 19A shows cryogenic tissue damage with dye XIV, fluorescence of the dye XIV showed strong accumulation of fluorescence at the site of focal dry-ice treatment in the cryogenic tissue, and FIG. 19B shows total photon flux of treated tissue at different concentrations.

Figure 20:
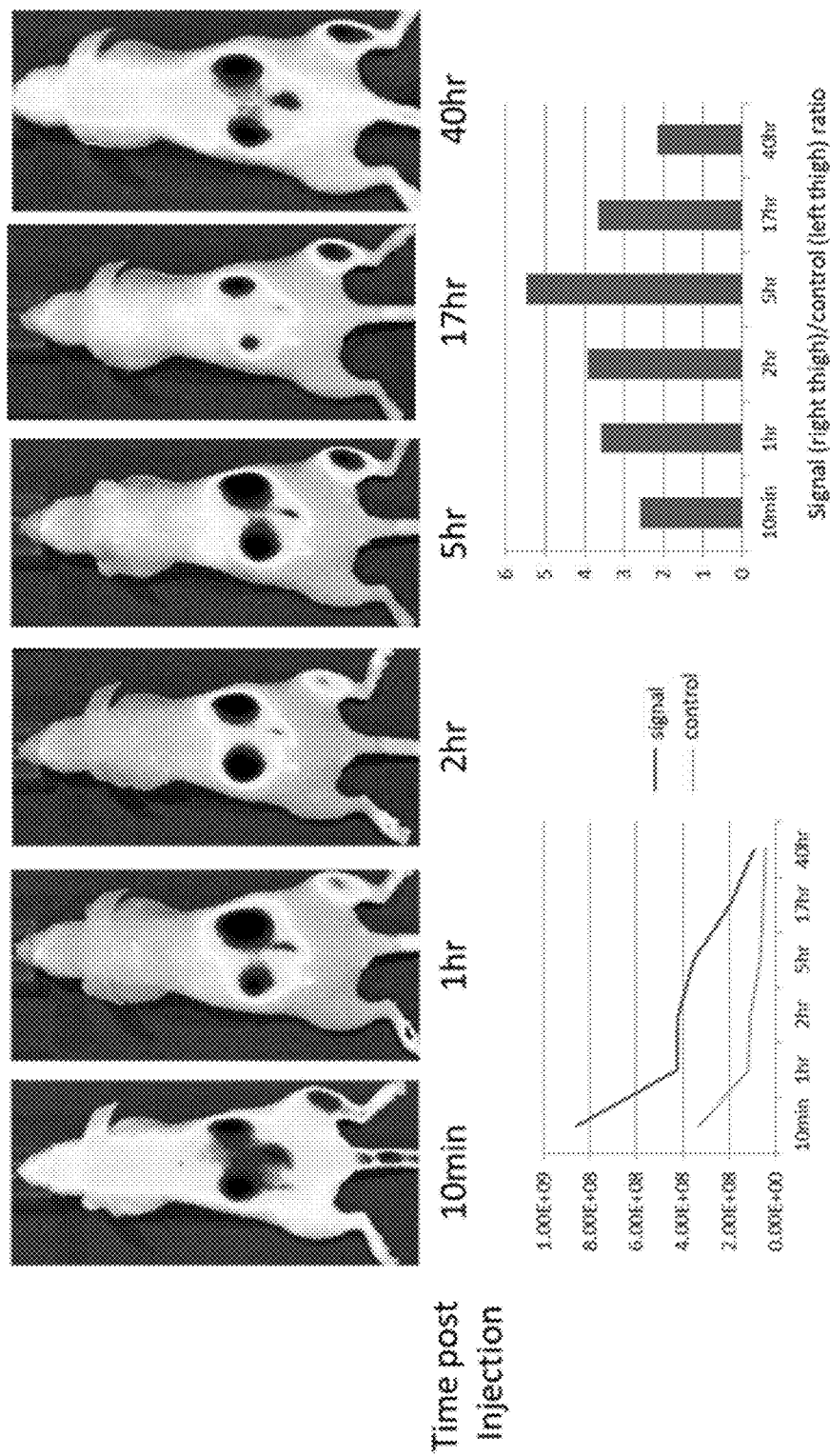
FIG. 20 shows the measured signal as a function of time post injection.
Figure 21:
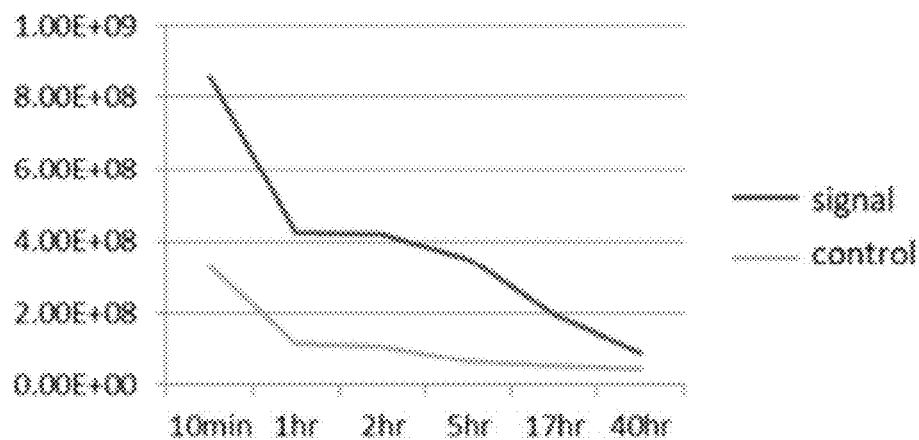
FIG. 21 shows the signal and the control as a function of time.
Figure 22:
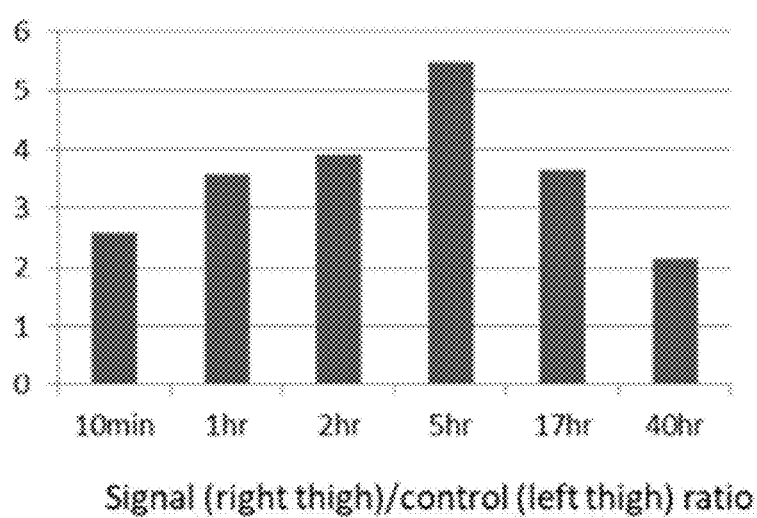
FIG. 22 shows the ratio of signal to control as a function of time.
Figure 23:
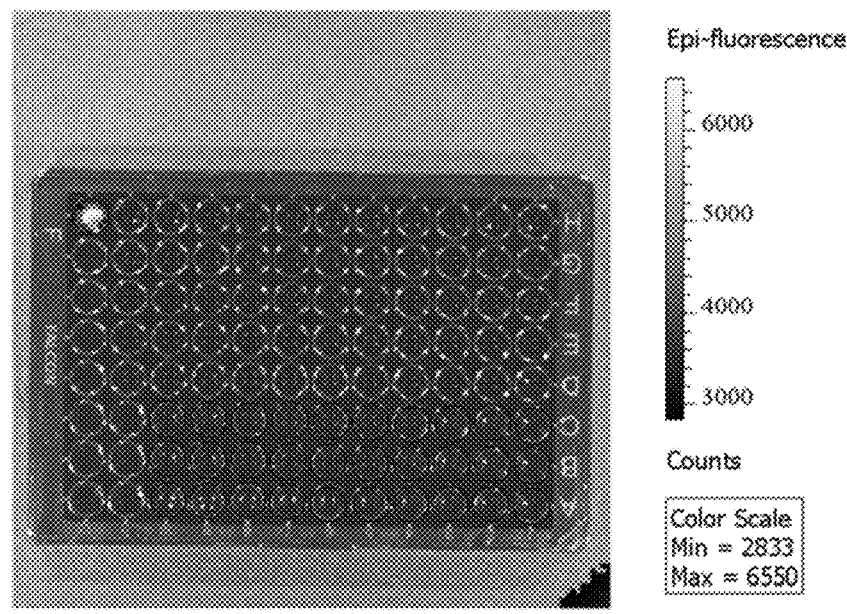
FIG. 23 shows the multi-well plate and the level of fluorescence.

Evaluation of VIII for Necrosis Imaging:

Compound VIII has been shown to selectively target necrotic tissue in vivo. Cardiotoxin (10 μM in 50 μL of PBS) was injected into the right thigh of the mouse and 50 μL of PBS was injected into the left thigh. 24 hours post-injection of toxin, Compound VIII (40 μmoles in 100 μL PBS) was injected intravenously into the tail of the mouse. The results show that the dye selectively targets the necrotic area and clears through the kidneys instead of accumulating in the liver. The results are shown below in FIG. 20-22. The brightnesses of the images are not on scale with one another. The quantification is shown on the same graph. Significant signal over-background ratios resulting from accumulation of the dye in necrosis areas observed as early as 10 min post-injection of the Compound VIII making it ideal for clinical translation.

Cell Uptake:

It is important that necrosis-targeting compound does not demonstrate any binding to or uptake by live cells and selectively only binds to necrotic cells. This should significantly minimize unwanted side effects when used in patients.

Therefore, we performed such experiments in live cells with Compound VIII compound. No uptake of Compound VIII was observed in live A431 cells even at long incubation periods (30 min) at rather high concentrations (25 uM). The following procedure was used:

Cells were grown in 96 well plates to confluent level. Media was removed, cells washed with PBS, incubated for a set time (5, 15, or 30 minutes) at varying concentrations of the dye (5 μM, 10 μM, and 25 μM) in PBS. Dye was removed, cells washed twice with PBS, then PBS added for imaging.

The values for each well were consistent with that of the control group of wells that were not exposed to the dye in wells A1-A3. The bright well at F12 is a solution of Compound VIII at 5 μM in PBS to insure imaging of the dye is occurring. The wells from B1-C10 are cells that were incubated with the dye; these wells were individually selected, and the radiance was compared to that of the control, with no significant difference between the groups. The image taken on the IVIS Spectrum is displayed below in FIG. 7.

The values for each well are also shown in the Table below.

TABLE 1

Incubation of Compound VIII in A431 cells

| Image | Avg Radiant Efficiency [p/s/cm$^2$/sr]/[μW/cm$^2$] | Average values[p/s/cm$^2$/sr]/[μW/cm$^2$] |
| --- | --- | --- |
| Control | 1.40E+07 | 1.46E+07 |
|  | 1.57E+07 |  |
|  | 1.42E+07 |  |
| 5 μM, 5 minutes | 1.64E+07 | 1.49E+07 |
|  | 1.47E+07 |  |
|  | 1.36E+07 |  |
| 10 μM, 5 minutes | 1.50E+07 | 1.39E+07 |
|  | 1.39E+07 |  |
|  | 1.28E+07 |  |
| 25 μM, 5 minutes | 1.39E+07 | 1.33E+07 |
|  | 1.34E+07 |  |
|  | 1.27E+07 |  |
| 5 μM, 15 minutes | 1.29E+07 | 1.24E+07 |
|  | 1.23E+07 |  |
|  | 1.19E+07 |  |
| 10 μM, 15 minutes | 1.24E+07 | 1.20E+07 |
|  | 1.18E+07 |  |
|  | 1.17E+07 |  |
| 25 μM, 15 minutes | 1.22E+07 | 1.20E+07 |
|  | 1.20E+07 |  |
|  | 1.19E+07 |  |
| 5 μM, 30 minutes | 1.18E+07 | 1.17E+07 |
|  | 1.16E+07 |  |
|  | 1.17E+07 |  |
| 10 μM, 30 minutes | 1.16E+07 | 1.15E+07 |
|  | 1.15E+07 |  |
|  | 1.13E+07 |  |
| 25 μM, 30 minutes | 1.20E+07 | 1.20E+07 |
|  | 1.20E+07 |  |
|  | 1.20E+07 |  |
| 5 μM solution of dye | 3.33E+07 | 3.33E+07 |

Using Aza-Dyes as Fluorescent Probe for Shortwave Infrared/NIR II:

Aza-dyes also have shown the potential to be used in the short wave infrared (SWIR) region located between 1000-2000 nm. This region is also known as near infrared II (NIR-II), although this region is usually defined as between 1000-1700 nm. It is important for in vivo imaging because tissue scattering and autofluorescence are significantly lower than in the NIR I (700-1000 nm) region. This has led SWIR/NIR-II to be called a "tissue transparent" zone.

Figure 24:
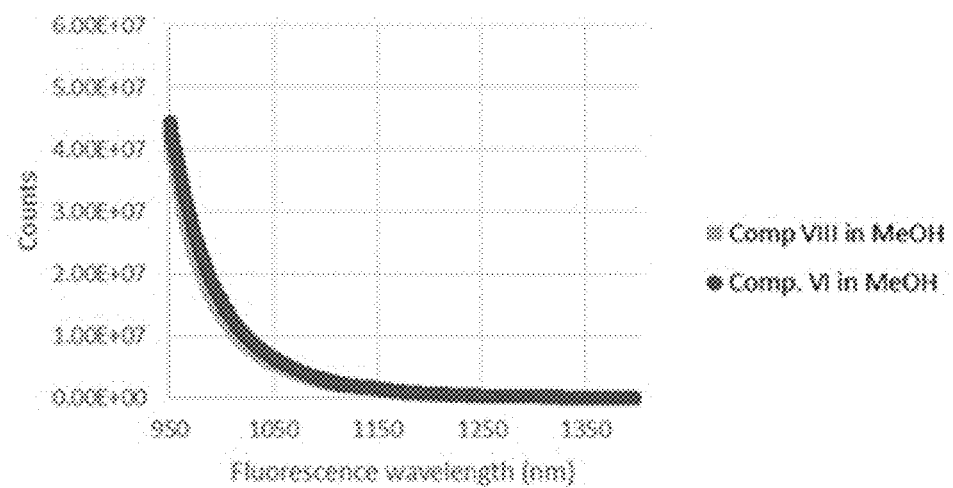
FIG. 24 shows the fluorescence spectra of Compound VIII and Compound VI.

Recently it has been shown that some cyanine dyes, including ICG and CW-800, also have emission in the SWIR region that is between 1000-1700 nm using an InGaAs SWIR camera system[3]. It was already shown that in the NIR-II region there is less absorption and no scattering enabling 2 times deeper imaging with much higher resolution respectively. Here we demonstrate that the new NIRF AZA-cyanine compounds such as Compound VIII and compound VI also absorbs in the NIR-II region and can be imaged with a commercial SWIR camera system. The results are shown on FIG. 24. The camera used for obtaining the data has the following specs: "Princeton NIRvana detector, IsoPlane SCT320 spectrometer, Nikon inverted microscope, 658 nm, 785 nm and Xenon lamp/monochromator illumination sources" The other derivatives of aza-cyanine analogs covered in the current invention are currently being tested to find the optimal SWIR imaging dye.

The invention claimed is:

1. A fluorescent dye of formula E:

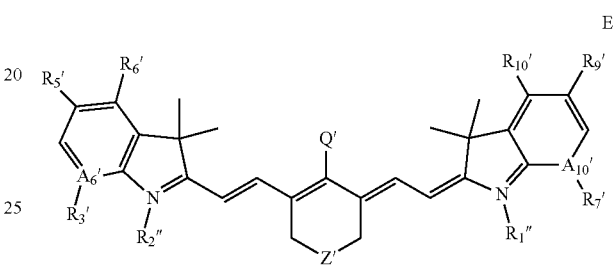

E wherein

Q' is Cl, Br, I, —OR$^{19'}$, —SR$^{19'}$, or —NR$^{19'}$R$^{20'}$, R$^{19'}$ and R$^{20'}$ are independently H or phenyl, wherein the phenyl can be substituted by $C_{1-6}$ alkyl, $C_{1-6}$ fluroalkyl, —(CH$_2$)$_{0-3}$SO$_3^-$, —(CH$_2$)$_{0-3}$SO$_3$-alkali metal, —(CH$_2$)$_{0-3}$COOH, —(CH$_2$)$_{0-3}$COO-alkali metal, —NCO, —NCS, —(CH$_2$)$_{0-3}$NH$_2$, or —(CH$_2$)$_{0-2}$N$^+$H$_3$, or R$^{19'}$ and R$^{20'}$ together with the nitrogen to which they are attached form a 5- or 6-membered heterocycle optionally containing one further heteroatom selected from O and N, wherein the heterocycle can be substituted by a linear or branched, cyclic or non-cyclic $C_{1-6}$ alkyl group;

R$_{1'''}$, R$_{2'''}$, R$_{3'}$, and R$_{7'}$ are independently absent, H, $C_{1-6}$ alkyl, or —(CH$_2$)$_{1-6}$ L', wherein L' is —COOH, —COO—$C_{1-6}$alkyl, —NH2, —OH, —SH, —COO$^-$, SO$_3^-$, SO3-alkali metal, —COO-succinimide, —COO-sulfosuccininide, —NCO, —NCS, —COO-nitrophenyl, or —COO-fluorophenyl;

A$_{6'}$ and A$_{10'}$ are independently C, N, or N$^+$;

R$_{5'}$, R$_{6'}$, R$_{9'}$, and R$_{10'}$ are independently H, or R$_{5'}$ and R$_{6'}$ together with the carbons to which they are attached form a benzene, or R$_{9'}$ and R$_{10'}$ together with the carbons to which they are attached form a benzene, wherein the benzene can be substituted by —(CH$_2$)$_{0-3}$ SO$_3^-$, —(CH$_2$)$_{0-3}$ SO$_3$-alkali metal, —(CH$_2$)$_{0-3}$COOH, or —(CH$_2$)$_{0-3}$COO-alkali metal;

Z' is NR$^{17'}$ or °NR$^{17'}$R$^{18'}$, wherein R$^{17'}$ and R$^{18'}$ are independently $C_{1-6}$ alkyl, —(CH$_2$)$_{1-3}$ ethynyl, —(CH$_2$)$_{1-6}$ L', wherein L' is —COOH, —COO —C$_{1-6}$alkyl, —NH$_2$, —OH, —SH, —COO$^-$, SO$_3^-$, SO$_3$-alkali metal, —COO-succinimide, —COO-sulfosuccininide, —COO-nitrophenyl, or —COO-fluorophenyl.

2. A probe for multimodality imaging having a structure of the following formula F:

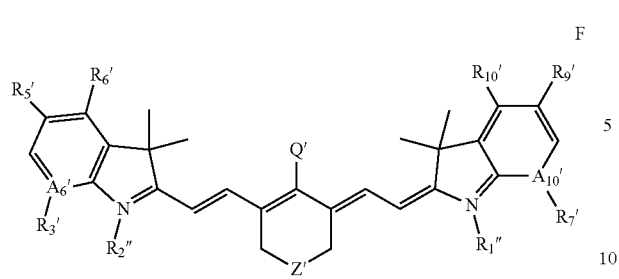

wherein $R_{1''}$, $R_{2''}$, $R_{3'}$, $R_{5'}$, $R_{6'}$, $R_{7'}$, $R_{10'}$, $A_{6'}$, $A_{10'}$, and $Z'$ are defined in claim 1, $Q'$ is —$OR^{19'}$ or —$SR^{19'}$, wherein $R^{19'}$ is phenyl substituted by —NHCSNH—R''' or —NHCONH—R''', wherein R''' is a phenyl or heterocyclic 5-, 6-, or 7-membered aromatic substituted by —$(CH_2)_{10-30}$ COOH and at least one group selected from F and $C_{1-6}$ fluoroalkyl.

3. A fluorescent dye selected from the group consisting of:

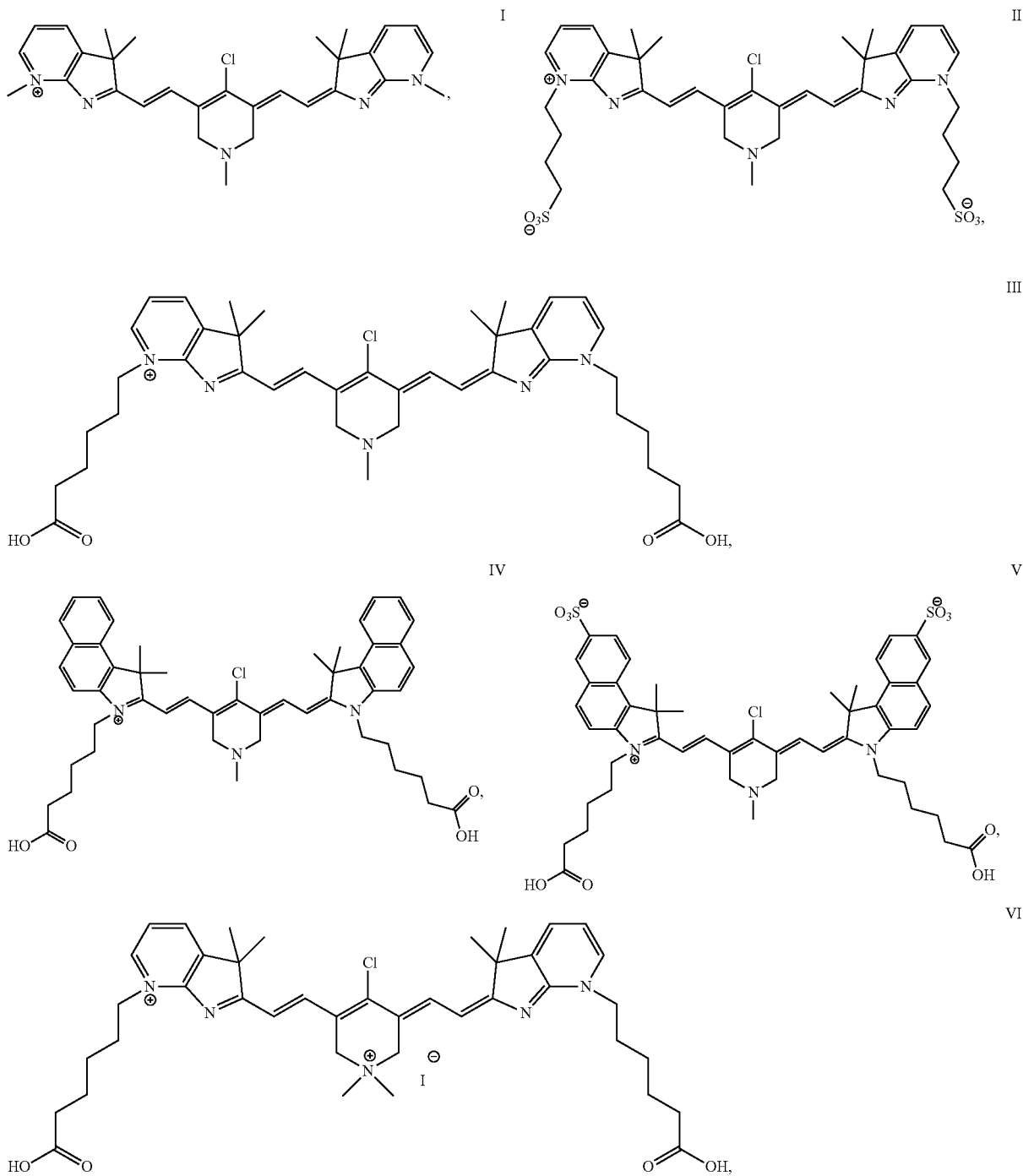

-continued
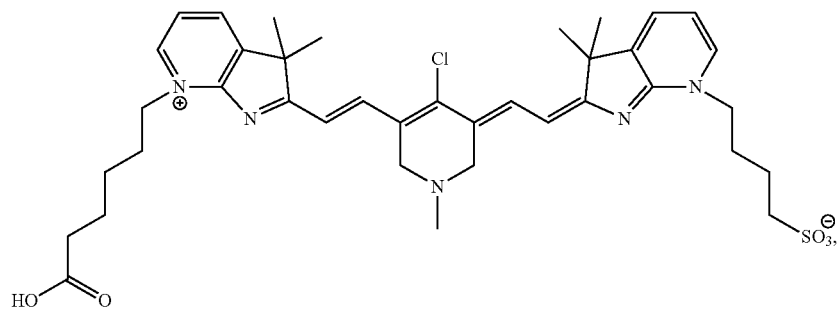
VII
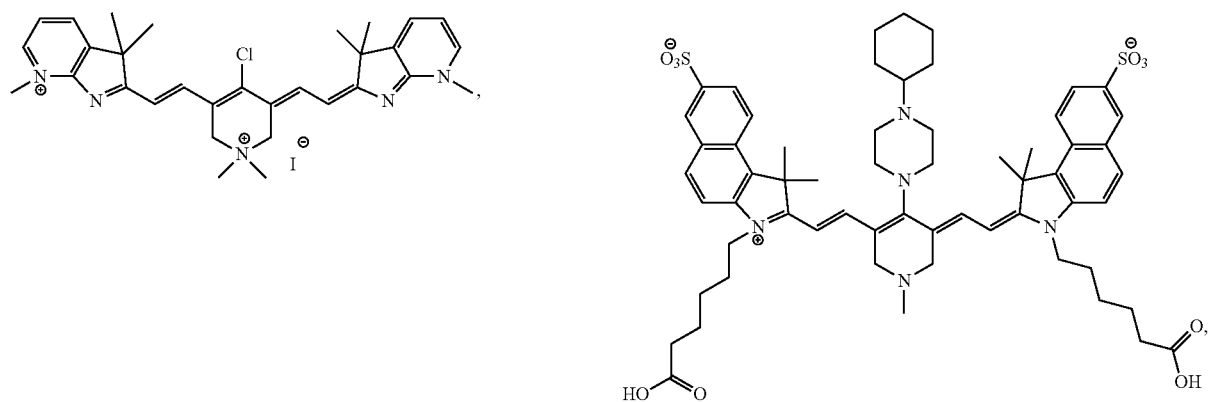
VIII
IX
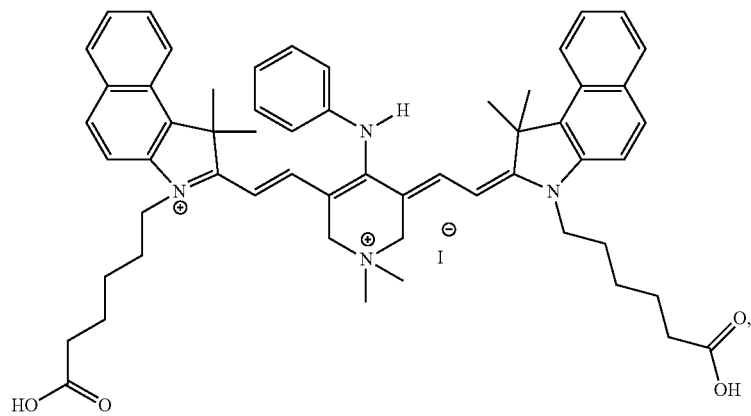
X
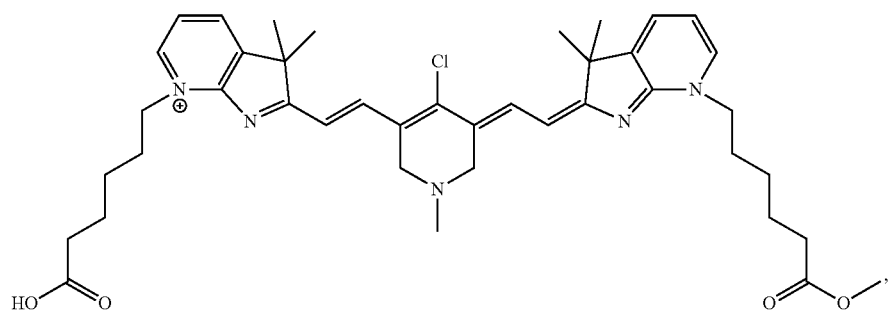
XI

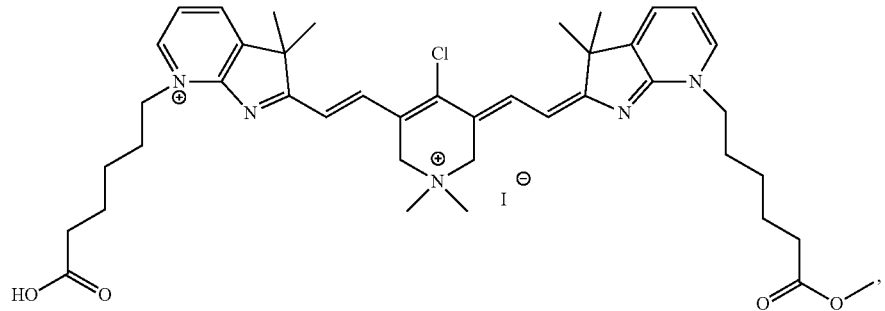
XII
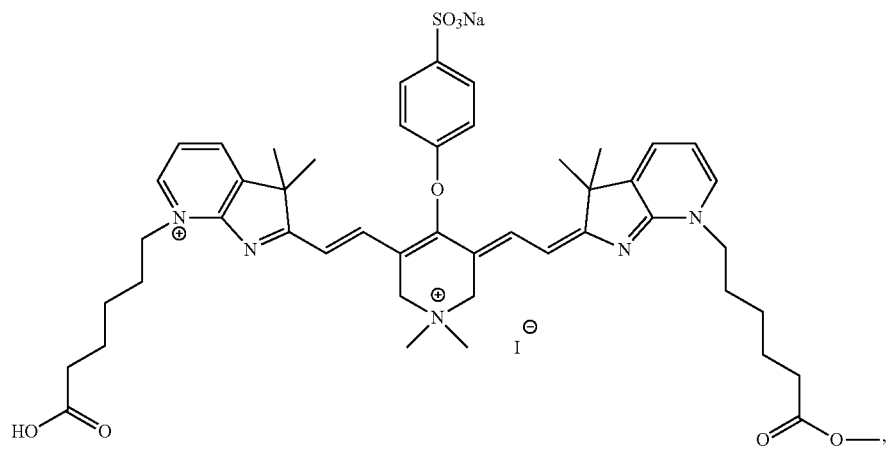
XIII
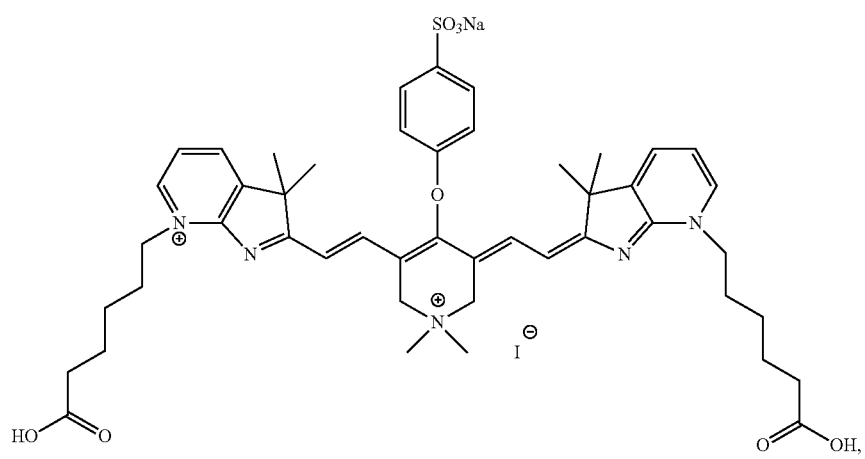
XIV

-continued
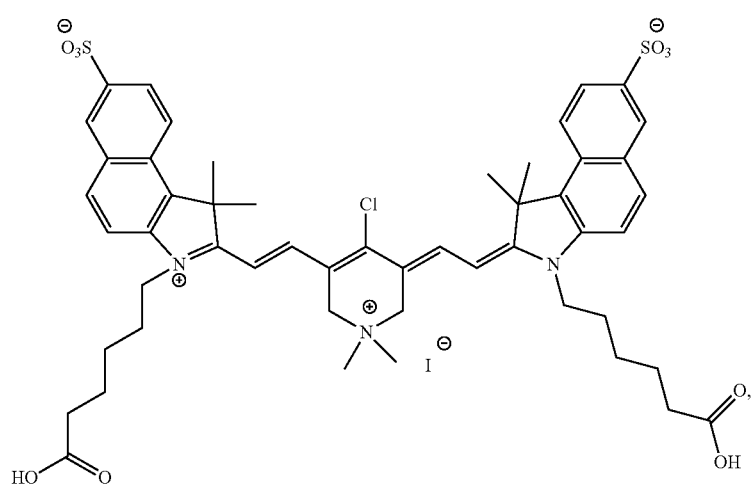
XV
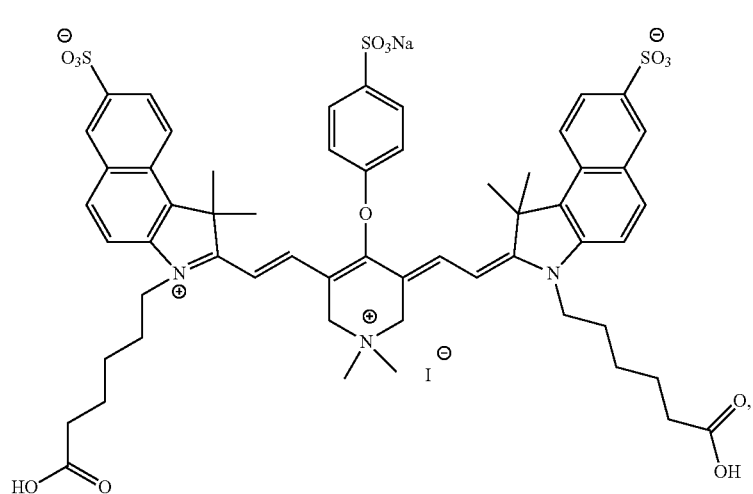
XVI
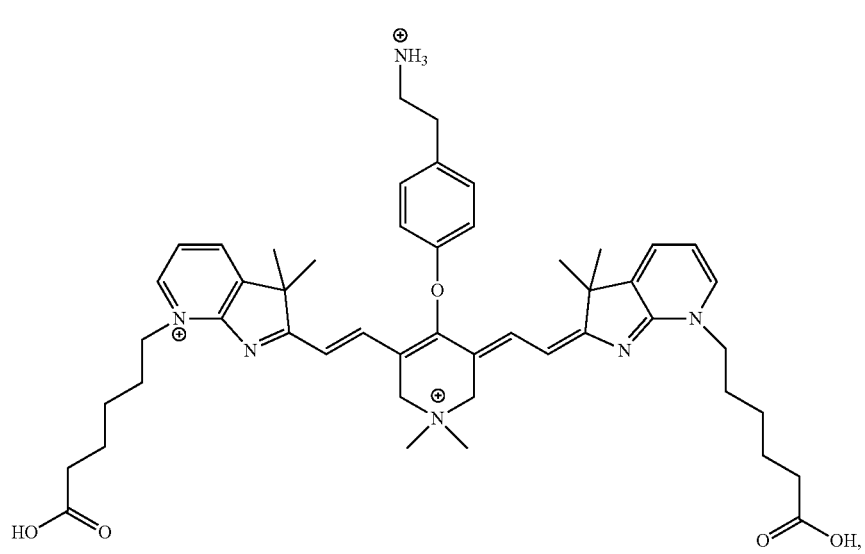
XVII

-continued
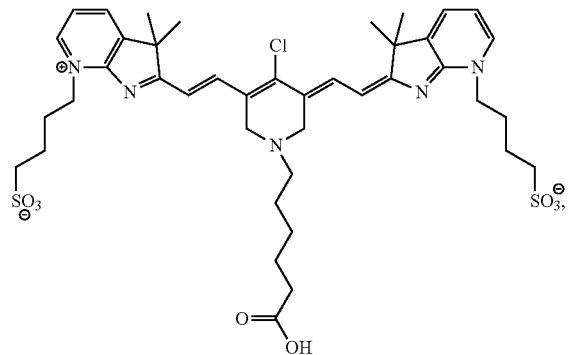 XVIII
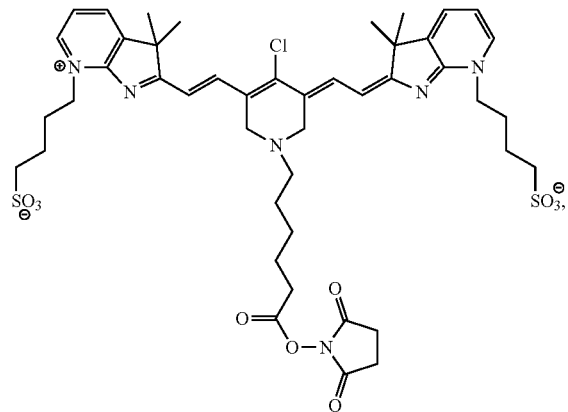 XIX
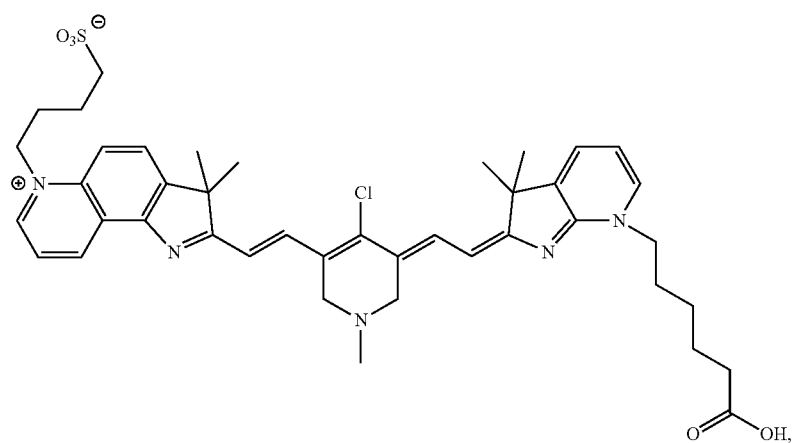 XXV
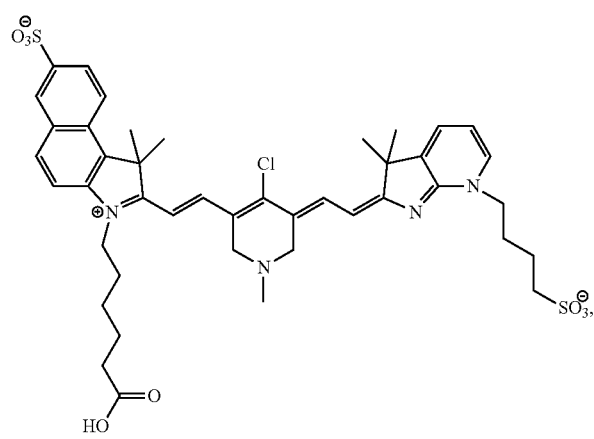 XXVI
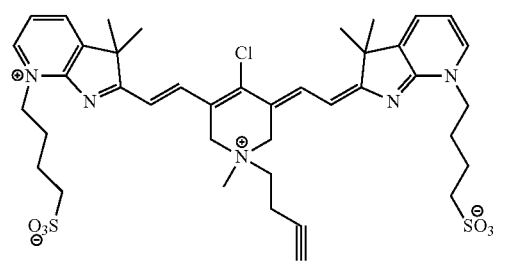 XXVII -continued
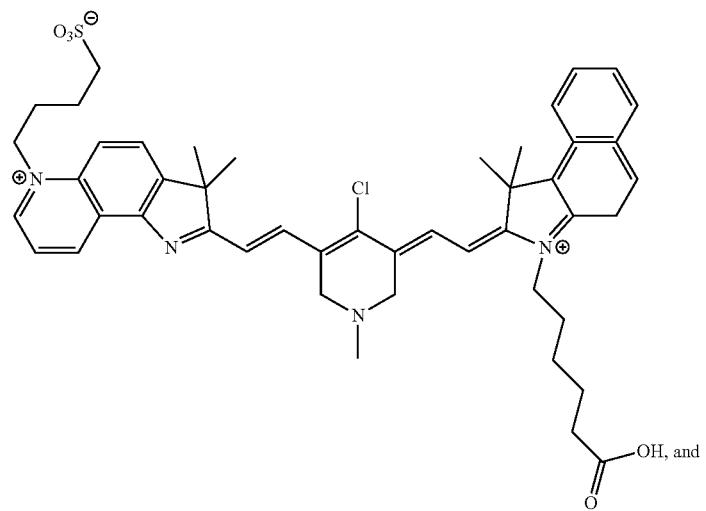
XXVIII
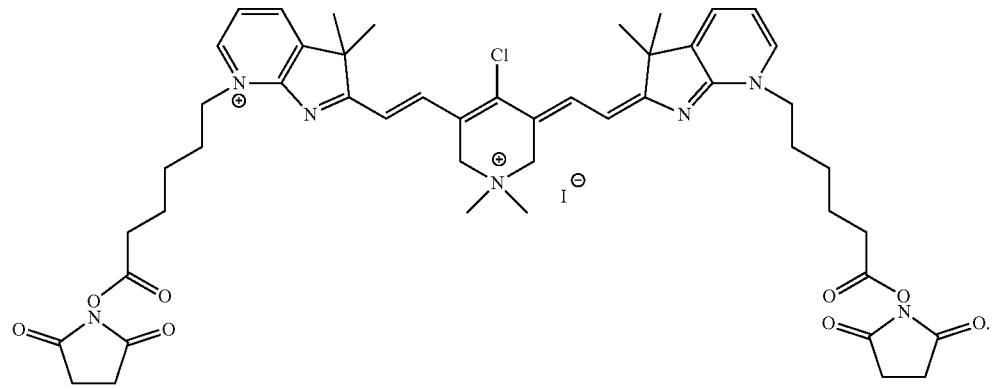
XXIX
* * * * *